(12) United States Patent
de Visser et al.

(10) Patent No.: US 10,179,912 B2
(45) Date of Patent: Jan. 15, 2019

(54) RNA MODULATING OLIGONUCLEOTIDES WITH IMPROVED CHARACTERISTICS FOR THE TREATMENT OF DUCHENNE AND BECKER MUSCULAR DYSTROPHY

(71) Applicant: BioMarin Technologies B.V., Leiden (NL)

(72) Inventors: Peter Christian de Visser, Leiden (NL); Judith Christina Theodora van Deutekom, Dordrecht (NL)

(73) Assignee: BioMarin Technologies B.V., Leiden (NL)

( * ) Notice: Subject to any disclaimer, the term of this patent is extended or adjusted under 35 U.S.C. 154(b) by 0 days.

(21) Appl. No.: 15/232,493

(22) Filed: Aug. 9, 2016

(65) Prior Publication Data

US 2017/0029818 A1 Feb. 2, 2017

Related U.S. Application Data

(63) Continuation of application No. 14/444,244, filed on Jul. 28, 2014, now abandoned, which is a continuation of application No. PCT/NL2013/050045, filed on Jan. 28, 2013.

(60) Provisional application No. 61/591,354, filed on Jan. 27, 2012, provisional application No. 61/612,467, filed on Mar. 19, 2012.

(30) Foreign Application Priority Data

Jan. 27, 2012 (EP) .................................... 12152934

(51) Int. Cl.
  *C12N 15/113* (2010.01)
  *A61K 31/7115* (2006.01)
  *A61K 31/712* (2006.01)
  *A61K 31/7125* (2006.01)

(52) U.S. Cl.
  CPC ........ *C12N 15/113* (2013.01); *C12N 2310/11* (2013.01); *C12N 2310/14* (2013.01); *C12N 2310/315* (2013.01); *C12N 2310/321* (2013.01); *C12N 2310/3231* (2013.01); *C12N 2310/3233* (2013.01); *C12N 2310/331* (2013.01); *C12N 2310/335* (2013.01); *C12N 2310/3341* (2013.01); *C12N 2320/33* (2013.01)

(58) Field of Classification Search
  None
  See application file for complete search history.

(56) References Cited

U.S. PATENT DOCUMENTS

| | | |
|---|---|---|
| 5,034,506 A | 7/1991 | Summerton et al. |
| 5,418,139 A | 5/1995 | Campbell |
| 5,541,308 A | 7/1996 | Hogan et al. |
| 5,593,974 A | 1/1997 | Rosenberg et al. |
| 5,608,046 A | 3/1997 | Cook et al. |
| 5,624,803 A | 4/1997 | Noonberg et al. |
| 5,627,263 A | 5/1997 | Ruoslahti et al. |
| 5,658,764 A | 8/1997 | Pergolizzi et al. |
| 5,741,645 A | 4/1998 | Orr et al. |
| 5,766,847 A | 6/1998 | Jaeckle et al. |
| 5,853,995 A | 12/1998 | Lee |
| 5,869,252 A | 2/1999 | Bouma et al. |
| 5,916,808 A | 6/1999 | Kole et al. |
| 5,962,332 A | 10/1999 | Singer et al. |
| 5,968,909 A | 10/1999 | Agrawal et al. |
| 5,976,879 A | 11/1999 | Kole et al. |
| 6,124,100 A | 9/2000 | Jin |
| 6,130,207 A | 10/2000 | Dean et al. |
| 6,133,031 A | 10/2000 | Monia et al. |
| 6,165,786 A | 12/2000 | Bennett et al. |
| 6,172,208 B1 | 1/2001 | Cook |
| 6,172,216 B1 | 1/2001 | Bennett et al. |
| 6,210,892 B1 | 4/2001 | Bennett et al. |
| 6,251,589 B1 | 6/2001 | Tsuji et al. |
| 6,280,938 B1 | 8/2001 | Ranum et al. |
| 6,300,060 B1 | 10/2001 | Kantoff et al. |
| 6,322,978 B1 | 11/2001 | Kahn et al. |
| 6,329,501 B1 | 12/2001 | Smith et al. |
| 6,355,481 B1 | 3/2002 | Li et al. |
| 6,355,690 B1 | 3/2002 | Tsuji |
| 6,369,038 B1 | 4/2002 | Blumenfeld et al. |
| 6,379,698 B1 | 4/2002 | Leamon |
| 6,399,575 B1 | 6/2002 | Smith et al. |
| 6,514,755 B1 | 2/2003 | Ranum et al. |
| 6,623,927 B1 | 9/2003 | Brahmachari et al. |
| 6,653,466 B2 | 11/2003 | Matsuo |
| 6,653,467 B1 | 11/2003 | Matsuo et al. |
| 6,670,461 B1 | 12/2003 | Wengel et al. |
| 6,727,355 B2 | 4/2004 | Matsuo et al. |
| 6,982,150 B2 | 1/2006 | Sheetz et al. |

(Continued)

FOREIGN PATENT DOCUMENTS

| | | |
|---|---|---|
| CA | 2319149 A1 | 10/2001 |
| CA | 2526893 A1 | 11/2004 |

(Continued)

OTHER PUBLICATIONS

U.S. Appl. No. 10/395,031, filed Mar. 21, 2003, issued Jul. 5, 2011 as U.S. Pat. No. 7,973,015.

(Continued)

*Primary Examiner* — Richard A Schnizer

(74) *Attorney, Agent, or Firm* — Jones Day

(57) ABSTRACT

The current invention provides an improved oligonucleotide and its use for treating, ameliorating, preventing and/or delaying DMD or BMD.

9 Claims, 11 Drawing Sheets

Figure 1A:
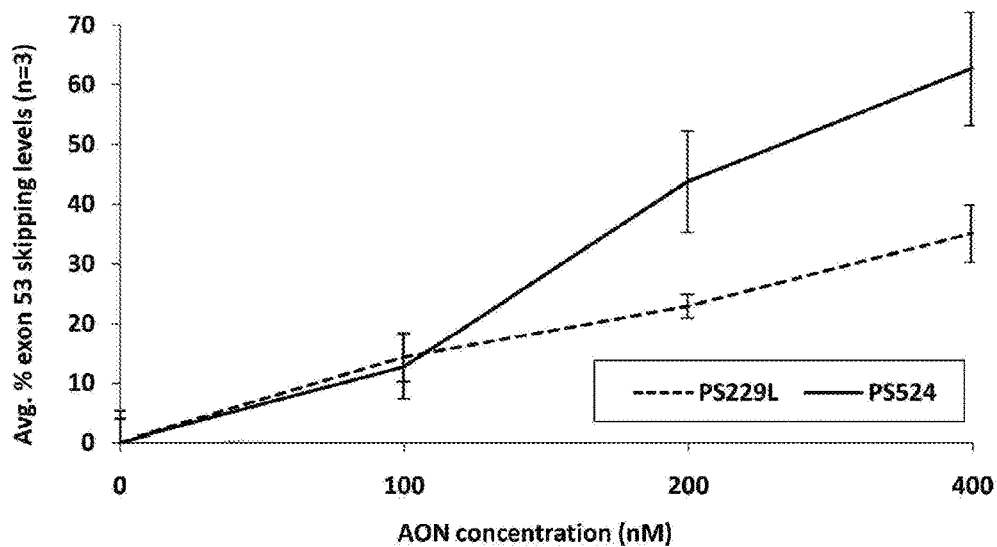

Specification includes a Sequence Listing.

(56) References Cited

U.S. PATENT DOCUMENTS

| | | | |
|---|---|---|---|
| 7,001,994 B2 | 2/2006 | Zhu | |
| 7,118,893 B2 | 10/2006 | Ranum et al. | |
| 7,189,530 B2 | 3/2007 | Botstein et al. | |
| 7,202,210 B2 | 4/2007 | Wolfman et al. | |
| 7,250,404 B2 | 7/2007 | Felgner et al. | |
| 7,355,018 B2 | 4/2008 | Glass | |
| 7,405,193 B2 | 7/2008 | Lodish et al. | |
| 7,442,782 B2 | 10/2008 | Ranum et al. | |
| 7,514,551 B2 | 4/2009 | Rabbani et al. | |
| 7,534,879 B2* | 5/2009 | van Deutekom | A61K 48/0016 435/325 |
| 7,589,189 B2 | 9/2009 | Ichiro et al. | |
| 7,655,785 B1 | 2/2010 | Bentwich | |
| 7,771,727 B2 | 8/2010 | Fuselier et al. | |
| 7,807,816 B2 | 10/2010 | Wilson et al. | |
| 7,902,160 B2 | 3/2011 | Matsuo et al. | |
| 7,960,541 B2 | 6/2011 | Wilton et al. | |
| 7,973,015 B2* | 7/2011 | van Ommen | A61K 48/005 514/44 R |
| 8,084,601 B2 | 12/2011 | Popplewell et al. | |
| 8,232,384 B2 | 7/2012 | Wilton et al. | |
| 8,263,760 B2 | 9/2012 | De Kimpe et al. | |
| 8,268,962 B2 | 9/2012 | Heemskerk et al. | |
| 8,304,398 B2 | 11/2012 | 'T Hoen et al. | |
| 8,324,371 B2 | 12/2012 | Popplewell et al. | |
| 8,361,979 B2 | 1/2013 | Aartsma-Rus et al. | |
| 8,455,636 B2 | 6/2013 | Wilton et al. | |
| 8,519,097 B2 | 8/2013 | Heemskerk et al. | |
| 8,609,065 B2 | 12/2013 | Kuik-Romeijn et al. | |
| 8,759,507 B2* | 6/2014 | Van Deutekom | A61K 48/0016 536/24.1 |
| 8,802,645 B2 | 8/2014 | Van Ommen et al. | |
| 9,035,040 B2* | 5/2015 | Wilton | C12N 15/113 536/24.5 |
| 9,079,934 B2 | 7/2015 | Watanabe et al. | |
| 9,139,828 B2 | 9/2015 | Platenburg et al. | |
| 9,243,245 B2* | 1/2016 | De Kimpe | A61K 31/56 |
| 9,499,818 B2 | 11/2016 | Van Deutekom et al. | |
| 9,528,109 B2* | 12/2016 | De Kimpe | A61K 31/56 |
| 2001/0056077 A1 | 12/2001 | Matsuo | |
| 2002/0049173 A1 | 4/2002 | Bennett et al. | |
| 2002/0055481 A1 | 5/2002 | Matsuo et al. | |
| 2002/0115824 A1 | 8/2002 | Engler et al. | |
| 2002/0165150 A1 | 11/2002 | Ben-Sasson | |
| 2003/0045488 A1 | 3/2003 | Brown et al. | |
| 2003/0073215 A1 | 4/2003 | Baker et al. | |
| 2003/0082763 A1 | 5/2003 | Baker et al. | |
| 2003/0082766 A1 | 5/2003 | Baker et al. | |
| 2003/0109476 A1 | 6/2003 | Kmiec et al. | |
| 2003/0124523 A1 | 7/2003 | Asselbergs et al. | |
| 2003/0134790 A1 | 7/2003 | Langenfeld | |
| 2003/0235845 A1 | 12/2003 | Van Ommen et al. | |
| 2003/0236214 A1 | 12/2003 | Wolff et al. | |
| 2004/0101852 A1 | 5/2004 | Bennett et al. | |
| 2004/0219565 A1* | 11/2004 | Kauppinen | C07H 19/06 435/5 |
| 2004/0226056 A1 | 11/2004 | Roch et al. | |
| 2005/0048495 A1 | 3/2005 | Baker et al. | |
| 2005/0096284 A1 | 5/2005 | McSwiggen | |
| 2005/0222009 A1 | 10/2005 | Lamensdorf et al. | |
| 2005/0246794 A1 | 11/2005 | Khvorova et al. | |
| 2005/0277133 A1 | 12/2005 | McSwiggen | |
| 2005/0288246 A1 | 12/2005 | Iversen et al. | |
| 2006/0024715 A1 | 2/2006 | Liu et al. | |
| 2006/0074034 A1 | 4/2006 | Collins et al. | |
| 2006/0099612 A1 | 5/2006 | Nakao et al. | |
| 2006/0099616 A1* | 5/2006 | van Ommen | C07H 21/02 435/6.11 |
| 2006/0147952 A1 | 7/2006 | Van Ommen et al. | |
| 2006/0148740 A1 | 7/2006 | Platenburg | |
| 2006/0160121 A1 | 7/2006 | Mounts et al. | |
| 2007/0082861 A1 | 4/2007 | Matsuo et al. | |
| 2007/0134655 A1 | 6/2007 | Bentwich | |
| 2007/0141628 A1 | 6/2007 | Cunningham et al. | |
| 2007/0275914 A1 | 11/2007 | Manoharan et al. | |
| 2007/0292408 A1 | 12/2007 | Singh et al. | |
| 2008/0015158 A1 | 1/2008 | Ichiro et al. | |
| 2008/0039418 A1 | 2/2008 | Freier | |
| 2008/0113351 A1 | 5/2008 | Naito et al. | |
| 2008/0207538 A1 | 8/2008 | Lawrence et al. | |
| 2008/0209581 A1 | 8/2008 | Van Ommen et al. | |
| 2008/0249294 A1 | 10/2008 | Haeberli et al. | |
| 2009/0099066 A1 | 4/2009 | Moulton et al. | |
| 2009/0228998 A1 | 9/2009 | Van Ommen et al. | |
| 2010/0081627 A1 | 4/2010 | Sampath et al. | |
| 2010/0099750 A1 | 4/2010 | McSwiggen et al. | |
| 2010/0130591 A1 | 5/2010 | Sazani et al. | |
| 2010/0168212 A1 | 7/2010 | Popplewell et al. | |
| 2010/0184833 A1 | 7/2010 | De Kimpe et al. | |
| 2010/0209487 A1* | 8/2010 | Quay | C12N 15/111 424/450 |
| 2010/0248239 A1 | 9/2010 | Highsmith, Jr. et al. | |
| 2011/0015258 A1 | 1/2011 | Wilton et al. | |
| 2011/0263682 A1 | 10/2011 | De Kimpe et al. | |
| 2011/0294753 A1 | 12/2011 | De Kimpe et al. | |
| 2012/0022134 A1 | 1/2012 | De Kimpe et al. | |
| 2012/0022145 A1 | 1/2012 | Wilton et al. | |
| 2012/0029057 A1 | 2/2012 | Wilton et al. | |
| 2012/0029058 A1 | 2/2012 | Wilton et al. | |
| 2012/0041050 A1 | 2/2012 | Wilton et al. | |
| 2012/0046342 A1 | 2/2012 | Van Deutekom et al. | |
| 2012/0046348 A1 | 2/2012 | Vaillant et al. | |
| 2012/0108652 A1 | 5/2012 | Popplewell et al. | |
| 2012/0122801 A1 | 5/2012 | Platenburg | |
| 2012/0202752 A1 | 8/2012 | Lu | |
| 2012/0270925 A1 | 10/2012 | Wilton et al. | |
| 2013/0072671 A1 | 3/2013 | Van Deutekom et al. | |
| 2013/0211062 A1 | 8/2013 | Watanabe et al. | |
| 2013/0302806 A1 | 11/2013 | Van Deutekom | |
| 2014/0045763 A1 | 2/2014 | Aguilera Diez et al. | |
| 2014/0113955 A1 | 4/2014 | De Kimpe et al. | |
| 2014/0128592 A1 | 5/2014 | De Kimpe et al. | |
| 2014/0213635 A1 | 7/2014 | Van Deutekom | |
| 2014/0221458 A1 | 8/2014 | De Kimpe et al. | |
| 2014/0275212 A1 | 9/2014 | Van Deutekom | |
| 2014/0298496 A1 | 10/2014 | Krainer et al. | |
| 2014/0343266 A1 | 11/2014 | Watanabe et al. | |
| 2014/0350076 A1 | 11/2014 | Van Deutekom | |
| 2014/0357698 A1 | 12/2014 | Van Deutekom et al. | |
| 2014/0357855 A1 | 12/2014 | Van Deutekom et al. | |
| 2014/0378527 A1 | 12/2014 | Van Deutekom | |
| 2015/0045413 A1 | 2/2015 | De Visser et al. | |
| 2015/0080563 A2 | 3/2015 | Van Deutekom et al. | |
| 2015/0148404 A1 | 5/2015 | De Visser et al. | |
| 2015/0191725 A1 | 7/2015 | Van Deutekom | |
| 2015/0203849 A1 | 7/2015 | Van Deutekom et al. | |
| 2015/0218559 A1 | 8/2015 | Van Deutekom et al. | |
| 2015/0322434 A1 | 11/2015 | Van Deutekom | |
| 2015/0361424 A1 | 12/2015 | Van Deutekom | |
| 2016/0053254 A1 | 2/2016 | De Kimpe et al. | |
| 2016/0053262 A1 | 2/2016 | Platenburg et al. | |
| 2016/0168570 A1 | 6/2016 | Van Deutekom et al. | |
| 2016/0194636 A1 | 7/2016 | Van Deutekom et al. | |
| 2016/0251658 A1 | 9/2016 | Van Deutekom et al. | |
| 2016/0264967 A1 | 9/2016 | Van Deutekom et al. | |
| 2016/0304864 A1 | 10/2016 | De Kimpe et al. | |
| 2016/0355810 A1 | 12/2016 | Van Deutekom | |
| 2017/0029820 A1 | 2/2017 | Aguilera Diez et al. | |
| 2017/0044534 A1 | 2/2017 | Van Deutekom | |
| 2017/0107512 A1 | 4/2017 | De Kimpe et al. | |

FOREIGN PATENT DOCUMENTS

| | | |
|---|---|---|
| EP | 0438512 A1 | 7/1991 |
| EP | 0558697 A1 | 9/1993 |
| EP | 0614977 A2 | 9/1994 |
| EP | 0850300 A1 | 7/1998 |
| EP | 1015628 A1 | 7/2000 |
| EP | 1054058 A1 | 11/2000 |
| EP | 1133993 A1 | 9/2001 |
| EP | 1160318 A2 | 12/2001 |
| EP | 1191097 A1 | 3/2002 |

(56) References Cited

FOREIGN PATENT DOCUMENTS

| | | |
|---|---|---|
| EP | 1191098 A2 | 3/2002 |
| EP | 1380644 A1 | 1/2004 |
| EP | 1487493 A2 | 12/2004 |
| EP | 1495769 A1 | 1/2005 |
| EP | 1501931 A2 | 2/2005 |
| EP | 1544297 A2 | 6/2005 |
| EP | 1567667 A1 | 8/2005 |
| EP | 1568769 A1 | 8/2005 |
| EP | 1619249 A1 | 1/2006 |
| EP | 1857548 A1 | 11/2007 |
| EP | 2119783 A1 | 11/2009 |
| JP | 2002-325582 A | 11/2002 |
| KR | 20030035047 A | 5/2003 |
| WO | WO-9301286 A2 | 1/1993 |
| WO | WO-9516718 A1 | 6/1995 |
| WO | WO-9521184 A1 | 8/1995 |
| WO | WO-9530774 A1 | 11/1995 |
| WO | WO-9712899 A1 | 4/1997 |
| WO | WO-9730067 A1 | 8/1997 |
| WO | WO-9818920 A1 | 5/1998 |
| WO | WO-9843993 A2 | 10/1998 |
| WO | WO-9849345 A1 | 11/1998 |
| WO | WO-9853804 A1 | 12/1998 |
| WO | WO-9916871 A2 | 4/1999 |
| WO | WO-9955857 A2 | 11/1999 |
| WO | WO-9963975 A2 | 12/1999 |
| WO | WO-0024885 A2 | 5/2000 |
| WO | WO-0076554 A1 | 12/2000 |
| WO | WO-0116312 A2 | 3/2001 |
| WO | WO-0159102 A2 | 8/2001 |
| WO | WO-0179283 A1 | 10/2001 |
| WO | WO-0183503 A2 | 11/2001 |
| WO | WO-0183695 A2 | 11/2001 |
| WO | WO-0224906 A1 | 3/2002 |
| WO | WO-0226812 A1 | 4/2002 |
| WO | WO-0229006 A2 | 4/2002 |
| WO | WO-0229056 A2 | 4/2002 |
| WO | WO-03002739 A1 | 1/2003 |
| WO | WO-03004511 A2 | 1/2003 |
| WO | WO-03013437 A2 | 2/2003 |
| WO | WO-03014145 A2 | 2/2003 |
| WO | WO-03037172 A2 | 5/2003 |
| WO | WO-03062258 A1 | 7/2003 |
| WO | WO-03095647 A2 | 11/2003 |
| WO | WO-2004011060 A2 | 2/2004 |
| WO | WO-2004015106 A1 | 2/2004 |
| WO | WO-2004016787 A1 | 2/2004 |
| WO | WO-2004037854 A1 | 5/2004 |
| WO | WO-2004047741 A2 | 6/2004 |
| WO | WO-2004048570 A1 | 6/2004 |
| WO | WO-2004083432 A1 | 9/2004 |
| WO | WO-2004083446 A2 | 9/2004 |
| WO | WO-2004101787 A1 | 11/2004 |
| WO | WO-2004108157 A2 | 12/2004 |
| WO | WO-2005019453 A2 | 3/2005 |
| WO | WO-2005023836 A2 | 3/2005 |
| WO | WO-2005035550 A2 | 4/2005 |
| WO | WO-2005085476 A1 | 9/2005 |
| WO | WO-2005086768 A2 | 9/2005 |
| WO | WO-2005105995 A2 | 11/2005 |
| WO | WO-2005115439 A2 | 12/2005 |
| WO | WO-2005115479 A2 | 12/2005 |
| WO | WO-2005116204 A1 | 12/2005 |
| WO | WO-2006000057 A1 | 1/2006 |
| WO | WO-2006007910 A1 | 1/2006 |
| WO | WO-2006017522 A2 | 2/2006 |
| WO | WO-2006031267 A2 | 3/2006 |
| WO | WO-2006054262 A2 | 5/2006 |
| WO | WO-2006083800 A2 | 8/2006 |
| WO | WO-2006108052 A2 | 10/2006 |
| WO | WO-2006112705 A2 | 10/2006 |
| WO | WO-2006121960 A2 | 11/2006 |
| WO | WO-2007002904 A2 | 1/2007 |
| WO | WO-2007044362 A2 | 4/2007 |
| WO | WO-2007089584 A2 | 8/2007 |
| WO | WO-2007089611 A2 | 8/2007 |
| WO | WO-2007123402 A2 | 11/2007 |
| WO | WO-2007135105 A1 | 11/2007 |
| WO | WO-2008011170 A2 | 1/2008 |
| WO | WO-2008018795 A1 | 2/2008 |
| WO | WO-2008021136 A2 | 2/2008 |
| WO | WO-2008039418 A2 | 4/2008 |
| WO | WO-2008043561 A2 | 4/2008 |
| WO | WO-2009005793 A2 | 1/2009 |
| WO | WO-2009008727 A2 | 1/2009 |
| WO | WO-2009015384 A1 | 1/2009 |
| WO | WO-2009054725 A2 | 4/2009 |
| WO | WO-2009101399 A1 | 8/2009 |
| WO | WO-2009144481 A2 | 12/2009 |
| WO | WO-2010048586 A1 | 4/2010 |
| WO | WO-2011057350 A1 | 5/2011 |
| WO | WO-2011078797 A2 | 6/2011 |
| WO | WO-2012029986 A1 | 3/2012 |
| WO | WO-2012150960 A1 | 11/2012 |
| WO | WO-2013100190 A1 | 7/2013 |
| WO | WO-2013170385 A1 | 11/2013 |

OTHER PUBLICATIONS

U.S. Appl. No. 11/233,495, filed Sep. 21, 2005.
U.S. Appl. No. 11/233,507, filed Sep. 21, 2005.
U.S. Appl. No. 11/919,248, filed Feb. 28, 2008.
U.S. Appl. No. 11/982,285, filed Oct. 31, 2007.
U.S. Appl. No. 12/198,007, filed Aug. 25, 2008, issued May 19, 2009 as U.S. Pat. No. 7,534,879.
U.S. Appl. No. 12/297,251, filed Nov. 25, 2009, issued Nov. 6, 2012 as U.S. Pat. No. 8,304,398.
U.S. Appl. No. 12/300,629, filed Mar. 24, 2009, issued Jan. 29, 2013 as U.S. Pat. No. 8,361,979.
U.S. Appl. No. 12/377,160, filed Feb. 24, 2010.
U.S. Appl. No. 12/383,897, filed Mar. 30, 2009.
U.S. Appl. No. 12/684,534, filed Jan. 8, 2010, issued Dec. 17, 2013 as U.S. Pat. No. 8,609,065.
U.S. Appl. No. 12/685,369, filed Jan. 11, 2010, issued Sep. 18, 2012 as U.S. Pat. No. 8,268,962.
U.S. Appl. No. 12/767,702, filed Apr. 26, 2010, issued Jan. 26, 2016 as U.S. Pat. No. 9,243,245.
U.S. Appl. No. 12/852,057, filed Aug. 6, 2010, issued Sep. 11, 2012 as U.S. Pat. No. 8,263,760.
U.S. Appl. No. 12/976,381, filed Dec. 22, 2010, issued Jun. 24, 2014 as U.S. Pat. No. 8,759,507.
U.S. Appl. No. 12/992,218, filed Nov. 11, 2010, issued Sep. 22, 2015 as U.S. Pat. No. 9,139,828.
U.S. Appl. No. 13/094,548, filed Apr. 26, 2011.
U.S. Appl. No. 13/094,571, filed Apr. 26, 2011.
U.S. Appl. No. 13/266,110, filed Oct. 24, 2011.
U.S. Appl. No. 13/349,198, filed Jan. 12, 2012.
U.S. Appl. No. 13/529,640, filed Jun. 21, 2012, issued Aug. 12, 2014 as U.S. Pat. No. 8,802,645.
U.S. Appl. No. 13/550,210, filed Jul. 16, 2012.
U.S. Appl. No. 13/568,866, filed Aug. 7, 2012, issued Aug. 27, 2013 as U.S. Pat. No. 8,519,097.
U.S. Appl. No. 13/718,666, filed Dec. 18, 2012.
U.S. Appl. No. 14/056,464, filed Oct. 17, 2013.
U.S. Appl. No. 14/097,210, filed Dec. 4, 2013.
U.S. Appl. No. 14/134,971, filed Dec. 19, 2013.
U.S. Appl. No. 14/198,992, filed Mar. 6, 2014.
U.S. Appl. No. 14/200,251, filed Mar. 7, 2014.
U.S. Appl. No. 14/248,279, filed Apr. 8, 2014.
U.S. Appl. No. 14/295,298, filed Jun. 3, 2014.
U.S. Appl. No. 14/295,311, filed Jun. 3, 2014.
U.S. Appl. No. 14/313,152, filed Jun. 24, 2014.
U.S. Appl. No. 14/331,934, filed Jul. 15, 2014.
U.S. Appl. No. 14/444,244, filed Jul. 28, 2014.
U.S. Appl. No. 14/522,002, filed Oct. 23, 2014.
U.S. Appl. No. 14/542,183, filed Nov. 14, 2014.
U.S. Appl. No. 14/581,633, filed Dec. 23, 2014.
U.S. Appl. No. 14/631,686, filed Feb. 25, 2015.
U.S. Appl. No. 14/678,517, filed Apr. 3, 2015.

(56) References Cited

OTHER PUBLICATIONS

U.S. Appl. No. 14/688,871, filed Apr. 16, 2015.
U.S. Appl. No. 14/712,753, filed May 14, 2015.
U.S. Appl. No. 14/809,483, filed Jul. 27, 2015.
U.S. Appl. No. 14/839,200, filed Aug. 28, 2015.
U.S. Appl. No. 14/859,598, filed Sep. 21, 2015.
U.S. Appl. No. 14/990,712, filed Jan. 7, 2016.
U.S. Appl. No. 15/047,233, filed Feb. 18, 2016.
U.S. Appl. No. 15/053,185, filed Feb. 25, 2016.
U.S. Appl. No. 15/057,861, filed Mar. 1, 2016.
U.S. Appl. No. 15/094,212, filed Apr. 8, 2016.
U.S. Appl. No. 15/098,589, filed Apr. 14, 2016.
U.S. Appl. No. 90/011,320, filed Nov. 9, 2010.
U.S. Appl. No. 15/168,662, filed May 31, 2016.
U.S. Appl. No. 15/289,053, filed Oct. 7, 2016.
Aartsma-Rus, A., et al., "Antisense Mediated Exon Skipping; A Versatile Tool with Therapeutic and Research Applications," RNA, vol. 13 (10), pp. 1609-1624, 2007.
Aartsma-Rus, A., et al., "Antisense-Induced Exon Skipping for Duplications in Duchenne Muscular Dystrophy," BMC Medical Genetics, vol. 8 (43), 9 pages, 2007.
Aartsma-Rus, A., et al., "Antisense-Induced Multiexon Skipping for Duchenne Muscular Dystrophy Makes More Sense," American Journal of Human Genetics, vol. 74, pp. 83-92, 2004.
Aartsma-Rus, A., et al., "Comparative Analysis of Antisense Oligonucleotide Analogs for Targeted DMD Exon 46 Skipping in Muscle Cells," Gene Therapy, vol. 11 (18), pp. 1391-1398, 2004.
Aartsma-Rus, A., et al., "Exonic Sequences Provide Better Targets for Antisense Oligonucleotides Than Splice Site Sequences in the Modulation of Duchenne Muscular Dystrophy Splicing," Oligonucleotides, vol. 20 (2), pp. 69-77, 2010.
Aartsma-Rus, A., et al., "Exploring the Frontiers of Therapeutic Exon Skipping for Duchenne Muscular Dystrophy by Double Targeting within One or Multiple Exons," Molecular Therapy, vol. 14 (3), pp. 401-407, Sep. 2006.
Aartsma-Rus, A., et al., "Functional Analysis of 114 Exon-Internal AONs for Targeted DMD Exon Indication for Steric Hindrance of SR Protein Binding Sites," Oligonucleotides, vol. 15, pp. 284-297, 2005.
Aartsma-Rus, A., et al., "Guidelines for Antisense Oligonucleotide Design and Insight Into Splice-Modulating Mechanisms," Molecular Therapy, vol. 17 (3), pp. 548-553, Mar. 2009.
Aartsma-Rus, A., et al., "Targeted Exon Skipping as a Potential Gene Correction Therapy for Duchenne Muscular Dystrophy," Neuromuscular Disorders, vol. 12, pp. S71-S77, 2002.
Aartsma-Rus, A., et al., "Theoretic Applicability of Antisense-Mediated Exon Skipping for Duchenne Muscular Dystrophy Mutations," Human Mutation, vol. 30 (3), pp. 293-299, 2009.
Aartsma-Rus, A., et al., "Therapeutic Antisense-Induced Exon Skipping in Cultured Muscle Cells from Six Different DMD Patients," Human Molecular Genetics, vol. 12 (8), pp. 907-914, 2003.
Aartsma-Rus, A., et al., "Therapeutic Modulation of DMD Splicing by Blocking Exonic Splicing Enhancer Sites with Antisense Oligonucleotides," Annals of the New York Academy of Sciences, vol. 1082, pp. 74-76, 2006.
Abbs, S., et al., "A Convenient Multiplex PCR System for the Detection of Dystrophin Gene Deletions: A Comparative Analysis with cDNA Hybridisation Shows Mistypings by Both Methods," Journal of Medical Genetics, vol. 28, pp. 304-311, 1991.
Academisch Ziekenhuis Leiden, "Sequences of Exon 53, Putative SES Fragments and Oligonucleotides," p. 1, Dec. 5, 2001.
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's List of Proposed Motions, 8 pages, filed Sep. 10, 2014 [Patent Interference No. 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Apr. 3, 2015) 18 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's List of Proposed Motions, 6 pages, Sep. 10, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Opposition 4 (To Not Exclude Evidence), 22 pages, May 5, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 2 (To Deny the Benefit of AU 2004903474), 11 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 3 (For Judgment of Unpatentability based on Myriad), 12 pages, Apr. 3, 2015, [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 4 (In Support of Responsive Motion 4 to Add Two New Claims), 17 pages, Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Request for Oral Argument, 3 pages, Apr. 10, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Responsive Motion 4 (to Add Two New Claims), 65 pages, filed Dec. 23, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 1 (For Judgment that UWA Claims are Unpatentable Under 35 U.S.C. §§ 102 and 103) 69 pages, Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Substantive Motion 2 (To Deny UWA the Benefit of AU 2004903474), 23 pages, Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 3 (For Judgment of Unpatentability based on Myriad), 19 pages, Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Feb. 17, 2015), 18 pages, Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's List of Exhibits (as of May 5, 2015) 18 pages, filed May 5, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 1 (35 U.S. C. § 112(a)), 93 pages, Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 2 (Indefiniteness), 31 pages, Feb. 17, 2015 [Patent Interference No. 106,007 (RES)].

(56) References Cited

OTHER PUBLICATIONS

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 3 (Standing Order ¶ 203.1 and 37 C.F.R. § 41.202(a) and (e)), 20 pages, Feb. 17, 2015 [Patent Interference No. 106,007 (RES)].

Academisch Ziekenhuis Leiden, *University of Western Australia* (U.S. Pat. No. 8,455,636) v. *Academisch Ziekenhuis Leiden* (U.S. Appl. No. 11/233,495) and *University of Western Australia* (U.S. Pat. Nos. 7,960,541 and 7,807,816) v. *Academisch Ziekenhuis Leiden* (U.S. Appl. No. 13/550,210), Declaration of Judith Van Deutekom, 45 pages, Feb. 17, 2015 [Patent Interference Nos. 106,007 and 106,008 (RES)].

Academisch Ziekenhuis Leiden, *University of Western Australia* (U.S. Pat. No. 8,486,907) v. *Academisch Ziekenhuis Leiden* (U.S. Appl. No. 14/198,992), Academisch Ziekenhuis Leiden List of Exhibits (as of Feb. 17, 2015) 3 pages, Feb. 17, 2015 [Patent Interference No. 106,013 (RES)].

Academisch Ziekenhuis Leiden, *University of Western Australia* (U.S. Pat. No. 8,486,907) v. *Academisch Ziekenhuis Leiden* (U.S. Appl. No. 14/198,992), Academisch Ziekenhuis Leiden Opposition 1 (Standing Order ¶ 203.1 and 37 C.F.R. § 41.202 (a) and (e)) 20 pages, Feb. 17, 2015 [Patent Interference No. 106,013 (RES)].

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 1 (For Judgment that UWA's Claims are Unpatentable Under 35 U.S.C. §§ 102 and 103), 17 pages, Apr. 3, 2015 [Patent Interference No. 106,007 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden List of Exhibits (as of Apr. 3, 2015), 18 pages, Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden List of Exhibits (as of Feb. 17, 2015), 18 pages, Feb. 17, 2015 [Patent Interference No. 106,008 (RES)].

Academisch Ziekenhuis Leiden, *University of Western Australia* (U.S. Pat. No. 7,960,541 and 7,807,816) v. *Academisch Ziekenhuis Leiden* (U.S. Appl. No. 13/550,210), Academisch Ziekenhuis Leiden Opposition 1 (35 U.S.C. § 112(a)), 83 pages, Feb. 17, 2015 [Patent Interference No. 106,008 (RES)].

Academisch Ziekenhuis Leiden, *University of Western Australia* (U.S. Pat. No. 7,960,541 and 7,807,816) v. *Academisch Ziekenhuis Leiden* (U.S. Appl. No. 13/550,210), Academisch Ziekenhuis Leiden Opposition 2 (Indefiniteness), 32 pages, Feb. 17, 2015 [Patent Interference No. 106,008 (RES)].

Academisch Ziekenhuis Leiden, *University of Western Australia* (U.S. Pat. No. 7,960,541 and 7,807,816) v. *Academisch Ziekenhuis Leiden* (U.S. Appl. No. 13/550,210), Academisch Ziekenhuis Leiden Opposition 3 (35 U.S.C. § 135(b)), 44 pages, Feb. 17, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 1 (For Judgment that UWA's Claims are Unpatentable Under 35 U.S.C. §§ 102 and 103), 17 pages, filed Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 2 (To Deny the Benefit of AU 2004903474), 12 pages, Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 3 (For Judgment of Unpatentability based on Myriad), 13 pages, Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 4 (In Support of Responsive Motion 4 to Add Two New Claims), 17 pages, filed Apr. 3, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Request for Oral Argument, 3 pages, Apr. 10, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Responsive Motion 4 (to Add Two New Claims), 57 pages, Dec. 23, 2014 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Second Declaration of Erik Sontheimer, Ph.D., 44 pages, Dec. 23, 2014 [Patent Interference No. 106,008 (RES)].

Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 2 (To Deny UWA the Benefit of AU2004903474, 24 pages, filed Nov. 18, 2014 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden's List of Exhibits (as of May 5, 2015), 18 pages, filed May 5, 2015 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden's Opposition 4 (To Not Exclude Evidence), 21 pages, filed May 5, 2015 [Patent Interference No. 106,008 (RES).

Academisch Ziekenhuis Leiden, *University of Western Australia* (U.S. Pat. Nos. 7,960,541, and 7,807,816) v. *Academisch Ziekenhuis Leiden* (U.S. Appl. No. 13/550,210), Academisch Ziekenhuis Leiden Substantive Motion 1 (for Judgment that UWA's Claims are Unpatentable Under 35 U.S.C. §§ 102 and 103), 69 pages, filed Nov. 18, 2014 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden's Substantive Motion 2 (To Deny UWA the Benefit of AU2004903474, 24 pages, Nov. 18, 2014 [Patent Interference No. 106,008 (RES)].

Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Substantive Motion 3 (For Judgment of Unpatentability Based on Myriad), 20 pages, Nov. 18, 2014 [Patent Interference No. 106,008 (RES)].

Agrawal, S., et al., "Antisense therapeutics: is it as simple as complementary base recognition?," Molecular Medicine Today, vol. 6, pp. 72-81, Feb. 2000.

Alter, J., et al., "Systemic delivery of morpholino oligonucleotide restores dystrophin expression bodywide and improves dystrophic pathology," Nature Medicine, 12(2), pp. 175-177, Feb. 2006.

Amalfitano, A., et al., "Dystrophin Gene, protein and cell biology: Structure and mutation of the dystrophin gene," Cambridge University Press, pp. 1-28, 1997.

Anderson, J., et al., "Correlated NOS-Iµ and myf5 expression by satellite cells in mdx mouse muscle regeneration during NOS manipulation and deflazacort treatment," Neuromuscular Disorders, vol. 13(5), pp. 388-396, Jun. 2003.

Arap, W., et al., "Steps toward mapping the human vasculature by phage display," Nature Medicine, vol. 8, No. 2, pp. 121-127, Feb. 2002.

Arechavala-Gomeza, V., et al., "Comparative Analysis of Antisense Oligonucleotide Sequences for Targeted Skipping of Exon 51

(56) References Cited

OTHER PUBLICATIONS

During Dystrophin Pre-mRNA Splicing in Human Muscle," Human Gene Therapy, vol. 18 (9), pp. 798-810, 2007.
Arruda, V.R., "The Role of Immunosuppression in Gene- and Cell-Based Treatments for Duchenne Muscular Dystrophy," Molecular Therapy, vol. 15, No. 6, pp. 1040-1041, Jun. 2007.
Arzumanov, A., et al., "Inhibition of HIV-1 Tat-Dependent Trans Activation by Steric Block Chimeric 2'-O-Methyl/LNA Oligoribonucleotides," Biochemistry, 2001, vol. 40 (48), pp. 14645-14654.
Austin, R.C., et al., "Cloning and Characterization of Alternatively Spliced Isoforms of Dp71," Human Molecular Genetics, 1995, vol. 4 (9), pp. 1475-1483.
Barabino, S.M., et al., "Antisense Probes Targeted to an Internal Domain in U2 snRNP Specifically Inhibit the Second Step of Pre-mRNA Splicing," Nucleic Acids Research, 1992, vol. 20 (17), pp. 4457-4464.
Barany, F., "The Ligase Chain Reaction in a PCR World," PCR Methods and Applications, 1991, vol. 1 (1), pp. 5-16.
Beggs, et al., "*Homo Sapiens* Dystrophin (DMD) Gene, Exon 55 and Partial CDS," National Center for Biotechnology Information, Database GenBank [Online], GenBank Accession No. AF213440.1, 2 pages, Jan. 27, 2002.
Bijvoet, A.G., et al., "Recombinant Human Acid α-Glucosidase: High Level Production in Mouse Milk, Biochemical Characteristics, Correction of Enzyme Deficiency in GSDII KO Mice.," Human Molecular Genetics, 1998, vol. 7 (11), pp. 1815-1824.
Board of Patent Appeals and Interferences, Ex parte Kimishige Ishizaka, Christine L. Martens and Kevin W. Moore, 24 U.S.P.Q.2d 1621, Appeal No. 91-2539, pp. 1-10, Apr. 30, 1992.
Board; of Patent Appeals and Interferences., "Ex parte Olav A. Kristense, 10 U.S.P.Q.2d 1701, Appeal No. 87-0697, pp. 1-5, Jan. 17, 1989", Board of Patent Appeals and Interferences, Jan. 17, 1989, 1-10.
Board; Of Patent Appeals and Interferences., "Ex parte Prebin M. Remark, 15 U.S.P.Q.2d 1498, Appeal No. 87-2422, pp. 1-12, Jan. 25, 1990", Board of Patent Appeals and Interferences, 1-12.
Bremmer-Bout, M., et al., "Targeted Exon Skipping in Transgenic hDMD Mice: A Model for Direct Preclinical Screening of Human-Specific Antisense Oligonucleotides," Molecular Therapy, vol. 10, No. 2, pp. 232-240, Aug. 2004.
Brett, D., et al., "EST Comparison Indicates 38% of Human mRNAs Contain Possible Alternative Splice Forms," FEBS Letters, vol. 474 (1), pp. 83-86, 2000.
Brolin, C., et al., "Antisense mediated exon skipping therapy for duchenne muscular dystrophy (DMD)," Artificial DNA, RNA & XNA, vol. 2, No. 1, pp. 6-15, Jan. 2011.
Brown, M.D., et al., "Gene Delivery with Synthetic (Non Viral) Carriers," International Journal of Pharmaceutics, vol. 229 (1-2), pp. 1-21, 2001 (Abstract).
Buck, G.A., et al., "Design Strategies and Performance of Custom DNA Sequencing Primers," BioTechniques, vol. 27 (3), pp. 528-536, 1999.
Burnett, R., et al., "DNA Sequence-Specific Polyamides Alleviate Transcription Inhibition Associated with Long GAA•TTC Repeats in Friedreich's Ataxia," Proceedings of the National Academy of Sciences of the United States of America, 2006, vol. 103 (31), pp. 11497-11502.
Caplen, N.J., et al., "Rescue of polyglutamine-mediated cytotoxicity by double-stranded RNA-mediated RNA Interference Human Molecular Genetics," Human Molecular Genetics, 2002, vol. 11 (2), pp. 175-184.
Cartegni, L., et al., "Correction of Disease-Associated Exon Skipping by Synthetic Exon-Specific Activators," Nature Structural Biology, vol. 10 (2), pp. 120-125, 2003.
Cartegni, L., et al., "Listening to Silence and Understanding Nonsense: Exonic Mutations that Affect Splicing," Nature Review Genetics, 2002, vol. 3 (4), pp. 285-298.
Case-Green, S.C., et al., "Studies on the Base Pairing Properties of Deoxyinosine by Solid Phase Hybridisation to Oligonucleotides," Nucleic Acids Research, vol. 22 (2), pp. 131-136, 1994.
Cavanaugh, D.L., Third-Party Submission Under 35 U.S.C. §122(e) and 37 C.F.R. § 1.290 for U.S. Appl. No. 11/233,495, 6 pages, filed Jun. 5, 2013.
Chamberlain, "Dystrophin Levels Required for Genetic Correction of Duchenne Muscular Dystrophy," Basic and Applied Myology, vol. 7 (3-4), pp. 251-255, 1997.
Chaubourt, E., et al., "Muscular Nitric Oxide Synthase (muNOS) and Utrophin," Journal of Physiology Paris, 2002, vol. 96 (1-2), pp. 43-52.
Coulter, L.R., et al., "Identification of a New Class of Exonic Splicing Enhancers by In Vivo Selection," Molecular and Cellular Biology, 1997, vol. 17 (4), pp. 2143-2150.
Crooke, S.T., "Basic Principles of Antisense Therapeutics, Handbook of Experimental Pharmacology: Antisense Research and Application," Springer-Verlag Berlin Heidelberg, 1998, vol. 131, pp. 1-50.
Dahlqvist, C., et al., "Functional Notch Signaling is Required for BMP4-Induced Inhibition of Myogenic Differentiation.," Development, 2003, vol. 130 (24), pp. 6089-6099.
De Angelis, F.G., et al., "Chimeric snRNA Molecules Carrying Antisense Sequences Against the Splice Junctions of Exon 51 of the Dystrophin Pre-mRNAInduce Exon Skipping and Restoration of a Dystrophin Synthesis in Δ48-50 DMD Cells," Proceedings of the National Academy of Sciences of the United States of America, Jul. 9, 2002, vol. 99 (14), pp. 9456-9461.
Denny, P., et al., "Oligo-Riboprobes. Tools for in Situ Hybridization," Histochemistry, 1988, vol. 89 (5), pp. 481-483.
Dickson, G., et al., "Screening for Antisense Modulation of Dystrophin Pre-mRNA Splicing," Neuromuscular Disorders, 2002, vol. 12 (Suppl 1), pp. S67-S70.
Dirksen, W.P., et al., "Mapping the SF2/ASF Binding Sites in the Bovine Growth Hormone Exonic Splicing Enhancer," The Journal of Biological Chemistry, 2000, vol. 275 (37), pp. 29170-29177.
Dorchies, O.M., et al., "Green Tea Extract and its Major Polyphenol (−)-Epigallocatechin Gallate Improve Muscle Function in a Mouse Model for Duchenne Muscular Dystrophy," American Journal of Physiology—Cell Physiology, vol. 290 (2), pp. C616-C625, 2006.
Duboc, D., et al., "Effect of Perindopril on the Onset and Progression of Left Ventricular Dysfunction in Duchenne Muscular Dystrophy," Journal of the American College of Cardiology, 2005, vol. 45 (6), pp. 855-857.
Dubowitz, V., "Foreword," Neuromuscular Disorders, 12, pp. S1-S2, 2002.
Dubowitz, V., "Special Centennial Workshop—101st ENMC International Workshop: Therapeutic Possibilities in Duchenne Muscular Dystrophy, Nov. 30-Dec. 2, 2001, Naarden, The Netherlands," Neuromuscular Disorders, vol. 12, pp. 421-431, 2002.
Dunckley, M.G., et al., "Modification of Splicing in the Dystrophin Gene in Cultured Mdx Muscle Cells by Antisense Oligoribonucleotides," Human Molecular Genetics, 1995, vol. 5 (1), pp. 1083-1090.
Dunckley, M.G., et al., "Modulation of Splicing in the DMD Gene by Antisense Oligoribonucleotides," Nucleosides & Nucleotides, 1997, vol. 16 (7-9), pp. 1665-1668.
El-Andaloussi, S., et al., "Induction of Splice Correction by Cell-Penetrating Peptide Nucleic Acids," The Journal of Gene Medicine, 2006, vol. 8 (10), pp. 1262-1273 (Abstract).
Erba, H.P., et al., "Structure, Chromosome Location, and Expression of the Human γ-Actin Gene: Differential Evolution, Location, and Expression of the Cytoskeletal β- and γ-Actin Genes," Molecular and Cellular Biology, 1988, vol. 8 (4), pp. 1775-1789.
Errington, S.J., et al., "Target Selection for Antisense Oligonucleotide Induced Exon Skipping in the Dystrophin Gene," The Journal of Gene Medicine, 2003, vol. 5 (6), pp. 518-527.
European Patent Office, Communication pursuant to Article 94(3) EPC, Application No. 10177969.2-1404, dated Aug. 22, 2013, 5 pages.
European Patent Office, Communication pursuant to Article 94(3) EPC, Application No. 10718717.1-1401, dated Dec. 19, 2013, 5 pages.

(56) References Cited

OTHER PUBLICATIONS

European Patent Office, Decision to refuse a European Patent application, Application No. 01979073.2-1402, dated Jan. 7, 2015, 10 pages.
European Patent Office, Extended European Search Report, Application No. 10177969.2-2401, dated Dec. 16, 2010, 7 pages.
Feener, C.A., et al., "Alternative Splicing of Human Dystrophin mRNA Generates Isoforms at the Carboxy Terminus," Nature, 1989, vol. 338 (6215), pp. 509-511.
Fluiter, K., et al., "In Vivo Tumor Growth Inhibition and Biodistribution Studies of Locked Nucleic Acid (LNA) Antisense Oligonucleotides," Nucleic Acids Research, 2003, vol. 31 (3), pp. 953-962.
Fu, Y.H., et al., "An Unstable Triplet Repeat in a Gene Related to Myotonic Muscular Dystrophy," Science, 1992, vol. 255 (5049), pp. 1256-1258.
Furling, D., et al., "Viral Vector Producing Antisense RNA Restores Myotonic Dystrophy Myoblast Functions," Gene Therapy, 2003, vol. 10 (9), pp. 795-802.
Galderisi, U., et al., "Myotonic Dystrophy: Antisense Oligonucleotide Inhibition of DMPK Gene Exression in Vitro," Biochemical and Biophysical Research Communications, 1996, vol. 221 (3), pp. 750-754.
Garcia-Blanco, M.A., et al., "Alternative Splicing in Disease and Therapy," Nature Biotechnology, May 2004, vol. 22 (5), pp. 535-546.
Ghosh, P., et al., "Mannose 6-Phosphate Receptors: New Twists in the Tale," Natural Reviews Molecular Cell Biology, Mar. 2003, vol. 4 (3), pp. 202-212.
Ginjaar, I.B., et al., "Dystrophin Nonsense Mutation Induces Different Levels of Exon 29 Skipping and Leads to Variable Phenotypes within One BMD Family," European Journal of Human Genetics, 2000, vol. 8 (10), pp. 793-796.
Goemans, N.M., et al., "Systemic Administration of PRO051 in Duchenne's Muscular Dystrophy," The New England Journal of Medicine, vol. 364 (16), pp. 1513-1522, 2011.
Gollins, H., et al., "High-Efficiency Plasmid Gene Transfer Into Dystrophic Muscle," Gene Therapy, 2003, vol. 10 (6), pp. 504-512.
Grady, D., "Early Drug Test Shows Promise in Treating Muscular Dystrophy," International Herald Tribune, Jan. 2008, Health and Science, p. 9.
Grady, D., Promising Dystrophy Drug Clears Early Test, The New York Times, 2 pages, Dec. 27, 2007.
Granchelli, J.A., et al., "Pre-Clinical Screening of Drugs Using the mdx Mouse," Neuromuscular Disorders, 2000, vol. 10 (4-5), pp. 235-239.
Gryaznov, S.M., "Oligonucleotide N3'-P5' Phosphoramidates as Potential Therapeutic Agents," Biochimica et Biophysica Acta, 1999, vol. 1489, pp. 131-140.
Habara, Y., et al., "In Vitro Splicing Analysis Showed that Availability of a Cryptic Splice Site is not a Determinant for Alternative Splicing Patterns Caused by +1G-A Mutations in Introns of the Dystrophin Gene," Journal of Medical Genetics, vol. 46 (8), pp. 542-547, 2009.
Hagiwara, Y., et al., "A Novel Point Mutation (G<sup>-1</sup>to T) in a 5' Splice Donor Site of Intron 13 of the Dystrophin Gene Results in Exon Skipping and is Responsible for Becker Muscular Dystrophy.," American Journal of Human Genetics, 1994, vol. 54 (1), pp. 53-61.
Handa, V., et al., "The AUUCU Repeats Responsible for Spinocerebellar Ataxia Type 10 Form Unusual RNA Hairpins," The Journal of Biological Chemistry, 2005, vol. 280 (32), pp. 29340-29345.
Hansen, S., "Product Development—Addition by subtraction," BioCentury, The Bernstein Report on BioBusiness, Jan. 7, 2008, p. A28.
Harding, P.L., et al., "The Influence of Antisense Oligonucleotide Length on Dystrophin Exon Skipping," Molecular Therapy, Jan. 2007, vol. 15 (1), pp. 157-166.
Hasholt, L., et al., "Antisense Downregulation of Mutant Huntingtin in a Cell Model," Journal of Gene Medicine, 2003, vol. 5 (6), pp. 528-538.
Hassan, A.B., "Keys to the Hidden Treasures of the Mannose 6-Phosphate/Insulin-Like Growth Factor 2 Receptor," American Journal of Pathology, Jan. 2003, vol. 162 (1), pp. 3-6.
Heemskerk, H., et al., "Development of Antisense-Mediated Exon Skipping as a Treatment for Duchenne Muscular Dystrophy," Annals of the New York Academy of Sciences, 2009, vol. 1175, pp. 71-79.
Heemskerk, H.A., et al., "In Vivo Comparison of 2'-O-Methyl Phosphorothioate and Morpholino Antisense Oligonucleotides for Duchenne Muscular Dystrophy Exon Skipping," The Journal of Gene Medicine, 2009, vol. 11 (3), pp. 257-266.
Heemskerk, H.A., et al., "Preclinical PK and PD Studies on 2'-O-Methyl-phosphorothioate RNA Antisense Oligonucleotides in the mdx Mouse Model," Molecular Therapy, Jun. 2010, vol. 18 (6), pp. 1210-1217.
Henderson, A.M., et al., "The Basic Helix-Loop-Helix Transcription Factor HESR1 Regulates Endothelial Cell Tube Formation," The Journal of Biological Chemistry, vol. 276 (9), pp. 6169-6176, 2001.
Hoffman, E.P., et al., "Somatic Reversion/Suppression of the Mouse mdx Phenotype in Vivo," Journal of the Neurological Sciences, 1990, vol. 99 (1), pp. 9-25.
Hoffman, E.P., "Skipping Toward Personalized Molecular Medicine," The New England Journal of Medicine, Dec. 2007, vol. 357 (26), pp. 2719-2722.
Hua, Y., et al., "Antisense Correction of SMN2 Splicing in the CNS Rescues Necrosis in a Type III SMA Mouse Model," Genes and Development, 2010, vol. 24 (15), pp. 1634-1644.
Hussey, N.D., et al., "Analysis of Five Duchenne Muscular Dystrophy Exons and Gender Determination Using Conventional Duplex Polymerase Chain Reaction on Single Cells," Molecular Human Reproduction, 1999, vol. 5 (11), pp. 1089-1094.
Iezzi, S., et al, "Deacetylase Inhibitors Increase Muscle Cell Size by Promoting Myoblast Recruitment and Fusion through Induction of Follistatin," Developmental Cell, May 2004, vol. 6 (5), pp. 673-684.
Ikezawa, M., et al., "Dystrophin Gene Analysis on 130 Patients with Duchenne Muscular Dystrophy with a Special Reference to Muscle mRNA Analysis," Brain & Development, 1998, vol. 20 (3), pp. 165-168.
Ito, T., et al., "Purine-Rich Exon Sequences are Not Necessarily Splicing Enhancer Sequence in the Dystrophin Gene," The Kobe Journal of Medical Sciences, Oct. 2001, vol. 47 (5), pp. 193-202.
Jou, C., et al., "Deletion Detection in the Dystrophin Gene by Multiplex Gap Ligase Chain Reaction and Immunochromatographic Strip Technology," Human Mutation, 1995, vol. 5 (1), pp. 86-93.
Karras, J.G., et al., "Deletion of Individual Exons and Induction of Soluble Murine Interleukin-5 Receptor-α Chain Expression through Antisense Oligonucleotide-Mediated Redirection of Pre-mRNA Splicing," Molecular Pharmacology, 2000, vol. 58 (2), pp. 380-387.
Kendall, G.C., et al., "Dantrolene Enhances Antisense-Mediated Exon Skipping in Human and Mouse Models of Duchenne Muscular Dystrophy," Science Translational Medicine, vol. 4 (164), 26 pages, Dec. 12, 2012.
Kerr, K., et al., "BMP Regulates Skeletal Myogenesis at Two Steps," Molecular and Cellular Proteomics, 2003, vol. 2 (9), pp. 976.
Kinali, M., et al., "Local Restoration of Dystrophin Expression With the Morpholino Oligomer AVI-4658 in Duchenne Muscular Dystrophy: A Single-Blind, Placebo-Controlled, Dose-Escalation, Proof-of-Concept Study," The Lancet. Neurology, 2009, vol. 8 (10), pp. 918-928.
Kurreck, J., et al., "Design of Antisense Oligonucleotides Stabilized by Locked Nucleic Acids," Nucleic Acids Research, 2002, vol. 30 (9), pp. 1911-1918.
Langlois, M.A., et al., "Hammerhead Ribozyme-Mediated Destruction of Nuclear Foci in Myotonic Dystrophy Myoblasts," Molecular Therapy, 2003, vol. 7 (5), pp. 670-680.
Laptev, A.V., et al., "Specific Inhibition of Expression of a Human Collagen Gene (COL1A1) with Modified Antisense Oligonucleotides. The Most Effective Target Sites are Clustered in Double Stranded Regions of the Predicted Secondary Structure for the mRNA," Biochemistry, 1994, vol. 33 (36), pp. 11033-11039.

(56) References Cited

OTHER PUBLICATIONS

Lee, J.H., et al., "Receptor Mediated Uptake of Peptides that Bind the Human Transferrin Receptor," European Journal of Biochemistry / FEBS, 2001, vol. 268 (7), pp. 2004-2012.
Lewin, B., "Genes VII," Oxford University Press, 2000, Chapters: 1, 5, 22; pp. 29, 126, 129, 686, 704, 705.
Liu, H.X., et al., "A Mechanism for Exon Skipping Caused by Nonsense or Missense Mutations in BRCA1 and Other Genes," Nature Genetics, Jan. 2001, vol. 27 (1), pp. 55-58.
Liu, H.X., et al., "Identification of Functional Exonic Splicing Enhancer Motifs Recognized by Individual SR Proteins," Genes & Development, 1998, vol. 12 (13), pp. 1998-2012.
Liu, W., et al., "Specific Inhibition of Huntington's Disease Gene Expression by siRNAs in Cultured Cells," Proceedings of the Japan Academy, 2003, vol. 79, pp. 293-298.
Lu, Q.L., et al., "Functional Amounts of Dystrophin Produced by Skipping the Mutated Exon in the mdx Dystrophic Mouse ," Nature Medicine, Aug. 2003, vol. 9 (8), pp. 1009-1014.
Lu, Q.L., et al., "Massive Idiosyncratic Exon Skipping Corrects the Nonsense Mutation in Dystrophic Mouse Muscle and Produces Functional Revertant Fibers by Clonal Expansion," The Journal of Cell Biology, 2000, vol. 148 (5), pp. 985-995.
Lu, Q.L., et al., "Non-Viral Gene Delivery in Skeletal Muscle: A Protein Factory," Gene Therapy, 2003, vol. 10 (2), pp. 131-142.
Lu, Q.L., et al., "Systemic Delivery of Antisense Oligoribonucleotide Restores Dystrophin Expression in Body-Wide Skeletal Muscles," Proceedings of the National Academy of Sciences of the United States of America, Jan. 2005, vol. 102 (1), pp. 198-203.
Mann, C.J., et al., "Antisense-Induced Exon Skipping and Synthesis of Dystrophin in the mdx Mouse," Proceedings of the National Academy of Sciences of the United States of America, Jan. 2001, vol. 98 (1), pp. 42-47.
Mann, C.J., et al., "Improved Antisense Oligonucleotide Induced Exon Skipping in the mdx Mouse Model of Muscular Dystrophy," The Journal of Gene Medicine, 2002, vol. 4 (6), pp. 644-654.
Martin, F.H., et al., "Base Pairing Involving Deoxyinosine: Implications for Probe Design," Nucleic Acids Research, vol. 13 (24), pp. 8927-8938, 1985.
Martiniuk, F., et al., "Correction of Glycogen Storage Disease Type II by Enzyme Replacement with a Recombinant Human Acid Maltase Produced by Over-Expression in a CHO-DHFR(Neg) Cell Line," Biochemical and Biophysical Research Communications, Oct. 2000, vol. 276 (3), pp. 917-923 (Abstract).
Matsuo, M., "Duchenne/Becker Muscular Dystrophy: From Molecular Diagnosis to Gene Therapy," Brain & Development, 1996, vol. 18 (3), pp. 167-172.
Matsuo, M., et al., "Exon Skipping during Splicing of Dystrophin mRNA Precursor due to an Intraexon Deletion in the Dystrophin Gene of Duchenne Muscular Dystrophy Kobe," The Journal of Clinical Investigation, 1991, vol. 87 (6), pp. 2127-2131.
Matsuo, M., et al., "Partial Deletion of a Dystrophin Gene Leads to Exon Skipping and to Loss of an Intra-Exon Hairpin Structure from the Predicted mRNA Precursor," Biochemical and Biophysical Research Communications, 1992, vol. 182 (2), pp. 495-500.
McClorey, G., et al., "Antisense Oligonucleotide-Induced Exon Skipping Restores Dystrophin Expression in Vitro in a Canine Model of DMD," Gene Therapy, vol. 13, pp. 1373-1381, 2006.
McClorey, G., et al., "Induced Dystrophin Exon Skipping in Human Muscle Explants," Neuromuscular Disorders, 2006, vol. 16 (9-10), pp. 583-590.
Miller, K.J., et al., "Antisense Oligonucleotides: Strategies for Delivery," Pharmaceutical Science and Technology Today, Dec. 1998, vol. 1 (9), pp. 377-386.
Monaco, A.P., et al., "An Explanation for the Phenotypic Differences between Patients Bearing Partial Deletions of the DMD Locus," Genomics, 1988, vol. 2 (1), pp. 90-95.
Moon, I.J., et al., "Target Site Search and Effective Inhibition of Leukaemic Cell Growth by a Covalently Closed Multiple Anti-Sense Oligonucleotide to c-myb," The Biochemical Journal, 2000, vol. 346, pp. 295-303.

Munroe, S.H., "Antisense RNA Inhibits Splicing of Pre-mRNA in Vitro," The EMBO Journal, 1988, vol. 7 (8), pp. 2523-2532.
Muntoni, F., et al., "A Mutation in the Dystrophin Gene Selectively Affecting Dystrophin Expression in the Heart," The Journal of Clinical Investigation, Aug. 1995, vol. 96 (2), pp. 693-699.
Nakamura, A., et al., "Exon Skipping Therapy for Duchenne Muscular Dystrophy," Neuropathology, 2009, vol. 29 (4), pp. 494-501.
Nederlandsch Octrooibureau, "Comparative Analysis of AONs for inducing the skipping of exon 53 from the dystrophin gene in human control muscle cells," EP1619249, 3 pages, Jan. 8, 2014.
Nederlandsch Octrooibureau, Exon 45 Alignment—EP1619249, 1 page, Aug. 23, 2013.
Nederlandsch Octrooibureau, Exon 46 Alignment—EP1619249, 1 page, Aug. 23, 2013.
Nederlandsch Octrooibureau, Exon 53 Alignment—EP1619249, 1 page, Aug. 23, 2013.
Nederlandsch Octrooibureau, Grounds of Appeal—EP1619249, 16 pages, Aug. 23, 2013.
Nederlandsch Octrooibureau, List of all submitted documents—EP1619249, 4 pages, Jan. 8, 2014.
Nederlandsch Octrooibureau, List of all submitted documents—EP1619249, 4 pages, Aug. 23, 2013.
Nederlandsch Octrooibureau, Patentee Letter in EP1619249 Opposition Appeal Proceedings, 25 pages, Jun. 10, 2014.
Nederlandsch Octrooibureau, Patentee's response to communication dated Jul. 29, 2009 from the Opposition Division of EPO in relation to European Patent Application (EP 05 076 770.6), Jan. 27, 2010, 41 pages.
Nederlandsch Octrooibureau, Reply to the Grounds of Appeal—EP1619249, 35 pages, Jan. 8, 2014.
Nederlandsch Octrooibureau, Response to Communication pursuant to Article 94(3) EPC, European Patent Application No. 10718717.1, Apr. 14, 2014, 3 pages.
Nederlandsch Octrooibureau, Response to Communication pursuant to Rule 161(2) and Rule 162 EPC, European Patent Application No. 10718717.1, Jun. 4, 2012, 3 pages.
Nederlandsch Octrooibureau, Sequence of Exon 53, putative SES fragments and oligonucleotides further comprising oligonucleotides of WO 2006/000057, EP1619249, 1 page, Jan. 8, 2014.
Nishio, H., et al., "Identification of a Novel First Exon in the Human Dystrophin Gene and of a New Promoter Located More Than 500 Kb Upstream of the Nearest Known Promoter," The Journal of Clinical Investigation, 1994, vol. 94 (3), pp. 1037-1042.
O'Shaughnessy, J., et al., "Superior Survival With Capecitabine Plus Docetaxel Combination Therapy in Anthracycline-Pretreated Patients With Advanced Breast Cancer: Phase III Trial Results," Journal of Clinical Oncology, 2002, vol. 20 (12), pp. 2812-2823.
Opalinska, J.B., et al., "Nucleic-Acid Therapeutics: Basic Principles and Recent Applications," Nature Reviews. Drug Discovery, Jul. 2002, vol. 1 (7), pp. 503-514.
Patel, K., et al., "The Function of Myostatin and Strategies of Myostatin Blockade-New Hope for Therapies Aimed at Promoting Growth of Skeletal Muscle," Neuromuscular Disorders, 2005, vol. 15 (2), pp. 117-126.
Patent Trial and Appeal Board, Declaration—37 C.F.R., §41.203(b), 7 pages, entered Jul. 18, 2014.
Patent Trial and Appeal Board, Standing Order, Entered Mar. 8, 2011, 81 pages.
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a), 53 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a) (Substitute), 53 pages, entered May 12, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Errata, filed May 23, 2016, 2 pages [Patent Interference No. 106,007 (RES)].

(56) References Cited

OTHER PUBLICATIONS

Patent Trial and Appeal Board, *University of Western Australia* (U.S. Pat. No. 8,455,636) v. *Academisch Ziekenhuis Leiden* (U.S. Appl. No. 11/233,495), Judgment—Motions—37 C.F.R. § 41.127, 3 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Redeclaration—37 C.F.R. § 41.203(c), 2 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495); *University of Western Australia* (U.S. Pat. Nos. 7,960,541 and 7,807,816) v. *Academisch Ziekenhuis Leiden* (U.S. Appl. No. 13/550,210), Order—Oral Argument—37 C.F.R. § 41.124, 2 pages, entered Mar. 29, 2016 [Patent Interference Nos. 106,007 (RES) and 106,008 (RES)].
Patent Trial and Appeal Board, *University of Western Australia* (U.S. Pat. No. 8,455,636) v. *Academisch Ziekenhuis Leiden* (U.S. Appl. No. 11/233,495), Withdrawal and Reissue of Decision on Motions, 2 pages, entered May 12, 2016 [Patent Interference No. 106,007 (RES)].
Patent Trial and Appeal Board, *University of Western Australia* (U.S. Pat. No. 8,486,907) v. *Academisch Ziekenhuis Leiden* (U.S. Appl. No. 14/198,992), Decision—Priority—37 CFR § 41.125(a), 18 pages, entered Sep. 29, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Judgment—37 CFR § 41.127, 2 pages, entered Sep. 29, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Order to Show Cause—37 C.F.R. § 41.104(a), 3 pages, Jun. 22, 2015 [Patent Interference No. 106,013 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Declaration 37 C.F.R. § 41.203(b), entered Jul. 24, 2014, 7 pages [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Order—Motion Times—37 CFR §41.104(C), entered Jul. 24, 2014, 6 pages [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Decision—Motions—37 C.F.R. § 41.125(a), 20 pages, Sep. 20, 2016 [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Judgment—Motions—37 C.F.R. § 41.127, entered Sep. 20, 2016, 3 pages [Patent Interference No. 106,008 (RES)].
Patent Trial and Appeal Board,*University of Western Australia* (U.S. Pat. No. 8,486,907) v. *Academisch Ziekenhuis Leiden* (U.S. Appl. No. 14/198,992), Decision—Motions—37 C.F.R. § 41.125(a), 12 pages, Jun. 22, 2015 [Patent Interference No. 106,013 (RES)].
Politano, L., et al., "Gentamicin Administration in Duchenne Patients With Premature Stop Codon. Preliminary Results," Acta Myologica, 2003, vol. 22 (1), pp. 15-21.
Popplewell, L.J., et al., "Design of Phosphorodiamidate Morpholino Oligomers (PMOs) for the Induction of Exon Skipping of the Human DMD Gene," Molecular Therapy, Mar. 2009, vol. 17 (3), pp. 554-561.
Pramono, Z.A., et al., "Induction of Exon Skipping of the Dystrophin Transcript in Lymphoblastoid Cells by Transfecting an Antisense Oligodeoxynucleotide Complementary to an Exon Recognition Sequence," Biochemical and Biophysical Research Communications, 1996, vol. 226 (2), pp. 445-449.
Radley, H.G., et al., "Duchenne Muscular Dystrophy: Focus on Pharmaceutical and Nutritional Interventions," The International Journal of Biochemistry & Cell Biology, 2007, vol. 39 (3), pp. 469-477.
Rando, T.A., "Oligonucleotide-Mediated Gene Therapy for Muscular Dystrophies," Neuromuscular Disorders, 2002, vol. 12 (Suppl 1), pp. S55-S60.
Redorbit News, "LUMC and Prosensa Report Positive Results of DMD Study," Dec. 28, 2007, 1 page.
Reitter, B., "Deflazacort vs. Prednisone in Duchenne Muscular Dystrophy: Trends of an Ongoing Study," Brain & Development, 1995, vol. 17 Suppl, pp. 39-43.
Reuser, A.J., et al., "Uptake and Stability of Human and Bovine Acid α-Glucosidase in Cultured Fibroblasts and Skeletal Muscle Cells from Glycogenosis Type II Patients," Experimental Cell Research, 1984, vol. 155 (1), pp. 178-189.
Roberts, R.G., et al., "Direct Detection of Dystrophin Gene Rearrangements by Analysis of Dystrophin mRNA in Peripheral Blood Lymphocytes," American Journal of Human Genetics, 1991, vol. 49 (2), pp. 298-310.
Roberts, R.G., et al., "Direct Diagnosis of Carriers of Duchenne and Becker Muscular Dystrophy by Amplification of Lymphocyte RNA," Lancet, 1990, vol. 336 (8730), pp. 1523-1526.
Roberts, R.G., et al., "Searching for the 1 in 2,400,000: A Review of Dystrophin Gene Point Mutations," Human Mutation, 1994, vol. 4 (1), pp. 1-11.
Roberts, R.G., et al., "Exon Structure of the Human Dystrophin Gene," Genomics, 1993, vol. 16 (2), pp. 536-538.
Rolland, J.F., et al., "Overactivity of Exercise-Sensitive Cation Channels and their Impaired Modulation by IGF-1 in mdx Native Muscle Fibers: Beneficial Effect of Pentoxifylline," Neurobiology of Disease, 2006, vol. 24 (3), pp. 466-474.
Rosen, G., et al., "Combination Chemotherapy and Radiation Therapy in the Treatment of Metastatic Osteogenic Sarcoma," Cancer, 1975, vol. 35 (3), pp. 622-630.
Samoylova, T., et al., "Elucidation of Muscle-Binding Peptides by Phage Display Screening," Muscle & Nerve, Apr. 1999, vol. 22 (4), pp. 460-466.
Sarepta Therapeutics, Inc., "Sarepta Therapeutics and University of Western Australia Announce Exclusive Worldwide Licensing Agreement for Exon-Skipping Program in Duchenne Muscular Dystrophy," News Release, EP1619249, 3 pages, Apr. 2013.
Sarepta Therapeutics, Inc., Third party observations pursuant to Article 115 EPC and Rule 114 EPC against European patent application EP 10718717.1, Oct. 16, 2015, 19 pages.
Scanlon, K.J., "Anti-Genes: siRNA, Ribozymes and Antisense," Current Pharmaceutical Biotechnology, 2004, vol. 5 (5), pp. 415-420.
Schnell, F., "Declaration of Dr. Fred Schnell in Support of Appeal of the Opposition Division's Decision to Maintain EP-1619249 in amended form," 6 pages, Jan. 8, 2014.
Segalat, L., et al., "CAPON Expression in Skeletal Muscle is Regulated by Position, Repair, NOS Activity, and Dystrophy," Experimental Cell Research, 2005, vol. 302 (2), pp. 170-179.
Sertic, J., et al., "Deletion Screening of the Duchenne/Becker Muscular Dystrophy Gene in Croatian Population," Collegium Antropologicum, 1997, vol. 21 (1), pp. 151-156.
Shapiro, M.B., et al., "RNA Splice Junctions of Different Classes of Eukaryotes: Sequence Statistics and Functional Implications in Gene Expression," Nucleic Acids Research, 1987, vol. 15 (17), pp. 7155-7174.
Sherratt, T.G., et al., "Exon Skipping and Translation in Patients with Frameshift Deletions in the Dystrophin Gene," American Journal of Human Genetics, 1993, vol. 53 (5), pp. 1007-1015.
Shiga, N., et al., "Disruption of the Splicing Enhancer Sequence within Exon 27 of the Dystrophin Gene by a Nonsense Mutation Induces Partial Skipping of the Exon and is Responsible for Becker Muscular Dystrophy," The Journal of Clinical Investigation, Nov. 1997, vol. 100 (9), pp. 2204-2210.

(56) References Cited

OTHER PUBLICATIONS

Simoes-Wust, A.P., et al., "bcl-xL Antisense Treatment Induces Apoptosis in Breast Carcinoma Cells," International Journal of Cancer, 2000, vol. 87 (4), pp. 582-590.

Singh, V., et al., "Proportion and Pattern of Dystrophin Gene Deletions in North Indian Duchenne and Becker Muscular Dystrophy Patients," Human Genetics, vol. 99 (2), pp. 206-208, 1997.

Sironi, M., et al., "The Dystrophin Gene is Alternatively Spliced Throughout its Coding Sequence," FEBS Letters, 2002, vol. 517 (1-3), pp. 163-166.

Smith, B.F., et al., "Muscle-specific Peptide #5," XP-002442550, 1 pages, Mar. 23, 1999.

Sontheimer, E.J., *University of Western Australia* (U.S. Pat. Nos. 7,960,541 and 7,807,816) v. *Academisch Ziekenhuis Leiden* (U.S. Appl. No. 13/550,210), 3rd Declaration of Erik J. Sontheimer, Ph.D. 123 pages, filed Feb. 17, 2015 [Patent Interference No. 106,007 (RES)].

Sontheimer, Erik, *University of Western Australia* (U.S. Pat. Nos. 7,960,541 and 7,807,816) v. *Academisch Ziekenhuis Leiden* (U.S. Appl. No. 13/550,210), Declaration of Erik Sontheimer, Ph.D., 112 pages, Nov. 17, 2014 [Patent Interference No. 106,008 (RES)].

Spitali, P., et al., "Exon Skipping-Mediated Dystrophin Reading Frame Restoration for Small Mutations," Human Mutation, vol. 30 (11), pp. 1527-1534, 2009.

Squires, K.E., "An Introduction to Nucleoside and Nucleotide Analogues," Antiviral Therapy, 6 (Suppl. 3), pp. 1-14, 2001.

Sterrenburg, E., et al., "Gene Expression Profiling Highlights Defective Myogenesis in DMD Patients and a Possible Role for Bone Morphogenetic Protein 4," Neurobiology of Disease, vol. 23 (1), pp. 228-236, 2006.

Summerton, J., "Morpholino Antisense Oligomers: The Case for an RNase H-Independent Structural Type," 1999, vol. 1489 (1), pp. 141-158.

Surono, A., et al., "Chimeric RNA/Ethylene-Bridged Nucleic Acids Promote Dystrophin Expression in Myocytes of Duchenne Muscular Dystrophy by Inducing Skipping of the Nonsense Mutation-Encoding Exon," Human Gene Therapy, 2004, vol. 15 (8), pp. 749-757.

Surono, A., et al., "Six Novel Transcripts that Remove a Huge Intron Ranging from 250 to 800 kb are Produced by Alternative Splicing of the 5' Region of the Dystrophin Gene in Human Skeletal Muscle," Biochemical and Biophysical Research Communications, 1997, vol. 239 (3), pp. 895-899.

Suter, D., et al., "Double-Target Antisense U7 snRNAs Promote Efficient Skipping of an Aberrant Exon in Three Human β-Thalassemic Mutations," Human Molecular Genetics, 1999, vol. 8 (13), pp. 2415-2423.

Suwanmanee, T., et al., "Restoration of Human β-Globin Gene Expression in Murine and Human IVS2-654 Thalassemic Erythroid Cells by Free Uptake of Antisense Oligonucleotides," Molecular Pharmacology, 2002, vol. 62 (3), pp. 545-553.

Takeshima, Y., et al., "Intravenous Infusion of an Antisense Oligonucleotide Results in Exon Skipping in Muscle Dystrophin mRNA of Duchenne Muscular Dystrophy," Pediatric Research, 2006, vol. 59 (5), pp. 690-694.

Takeshima, Y., et al., "Modulation of In Vitro Splicing of the Upstream Intron by Modifying an Intra-Exon Sequence Which is Deleted from the Dystrophin Gene in Dystrophin Kobe," The Journal of Clinical Investigation, Feb. 1995, vol. 95 (2), pp. 515-520.

Takeshima, Y., et al., "Oligonucleotides Against a Splicing Enhancer Sequence Led to Dystrophin Production in Muscle Cells from a Duchenne Muscular Dystrophy Patient," Brain& Development, 2001, vol. 23 (8), pp. 788-790.

Tanaka, K., et al., "Polypurine Sequences within a Downstream Exon Function as a Splicing Enhancer," Molecular and Cellular Biology, 1994, vol. 14 (2), pp. 1347-1354.

Tennyson, C.N., et al., "The Human Dystrophin Gene Requires 16 Hours to be Transcribed and is Cotranscriptionally Spliced," Nature Genetics, vol. 9 (2), pp. 184-190, 1995.

Thanh, L.T., et al., "Characterization of Revertant Muscle Fibers in Duchenne Muscular Dystrophy, Using Exon-Specific Monoclonal Antibodies against Dystrophin," American Journal of Human Genetics, 1995, vol. 56 (3), pp. 725-731.

Thomson Reuters Integrity, "Dystrophin gene (DMD) expression inhibitor PR0-051," Prous Integrity, XP002677703, Mar. 8, 2012.

Tian, H., et al., "Selection of Novel Exon Recognition Elements from a Pool of Random Sequences," Molecular and Cellular Biology, Nov. 1995, vol. 15 (11), pp. 6291-6298.

Tsuchida, K., "The Role of Myostatin and Bone Morphogenetic Proteins in Muscular Disorders," Expert Opinion of Biological Therapy, 2006, vol. 6 (2), pp. 147-154.

United States Court of Appeals for the Federal Circuit, *Academisch Ziekenhuis Leiden* v. *University of Western Australia*, Notice Forwarding Certified List, Appeal No. 2016-2262, Aug. 5, 2016, 18 pages [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 10, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Exhibit List as of Feb. 17, 2015, 8 pages, filed Feb. 17, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Miscellaneous Motion 4 (to exclude evidence), 21 pages, filed Apr. 10, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Motion 1 (for Judgment Under 35 U.S.C. §112(a)), 40 pages, filed Nov. 18, 2014 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Motion 2 (for Judgment Under 35 U.S.C. §112(b)), 34 pages, filed Nov. 18, 2014 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Motion 3 (Requesting an Additional Interference Between UWA U.S. Pat. No. 8,455,636 and Academisch Ziekenhuis Leiden's U.S. Appl. No. 14/248,279), 36 pages, filed Nov. 18, 2014 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Reply 1 (to AZL Opposition 1), 28 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Reply 2 (to AZL Opposition 2), 22 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Reply 3 (to Institute an Interference), 17 pages, filed Apr. 3, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Request for Oral Argument, 4 pages, filed Apr. 10, 2015 [Patent Interference No. 106,007 (RES)].

(56) References Cited

OTHER PUBLICATIONS

University of Western Australia, *University of Western Australia* (U.S. Pat. No. 8,455,636) v. *Acadernisch Ziekenhuis Leiden* (U.S. Appl. No. 11/233,495), University of Western Australia List of Proposed Motions, 7 pages, filed Sep. 10, 2014 [Patent Interference No. 106,007 (RES)].

University of Western Australia, *University of Western Australia* (U.S. Pat. No. 8,486,907) v. *Academisch Ziekenhuis Leiden* (U.S. Appl. No. 14/198,992), University of Western Australia Motion 1 (to Maintain Interference Between UWA U.S. Pat. No. 8,486,907 and Academisch Ziekenhuis Leiden's U.S. Appl. No. 14/198,992), 45 pages, filed Nov. 18, 2014 [Patent Interference No. 106,013 (RES)].

University of Western Australia, *University of Western Australia* (U.S. Pat. No. 8,486,907) v. *Academisch Ziekenhuis Leiden* (U.S. Appl. No. 14/198,992), University of Western Australia Response to Order to Show Cause, 28 pages, filed Jul. 20, 2015 [Patent Interference No. 106,013 (RES)].

University of Western Australia, *University of Western Australia* (U.S. Pat. No. 8,455,636) v. *Academisch Ziekenhuis Leiden* (U.S. Appl. No. 11/233,495), University of Western Australia Objections (to Opposition Evidence), 15 pages, filed Feb. 24, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Opposition 1 (Regarding Patentability Under 35 U.S.C. § 102/103), 38 pages, filed Feb. 17, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Opposition 2 (to Retain UWA's Benefit of AU 2004903474), 37 pages, filed Feb. 17, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Opposition 3 (Regarding Patentability Under 35 U.S. C.§ 101), 22 pages, filed Feb. 17, 2015 [Patent Interference No. 106,007 (RES)].

University of Western Australia, *University of Western Australia* (U.S. Pat. No. 8,455,636) v. *Academisch Ziekenhuis Leiden* (U.S. Appl. No. 11/233,495), University of Western Australia Opposition 4 (to deny entry of AZL's Proposed New Claims 104 and 105), 36 pages, filed Feb. 17, 2015 [Patent Interference No. 106,007 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List as of Apr. 10, 2015, 10 pages, filed Apr. 10, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List as of Apr. 3, 2015, 10 pages, filed Apr. 3, 2015 [Patent Interference No. 106,008 (RES)].

University of Western Australia, *University of Western Australia* (U.S. Pat. No. 7,960,541 and 7,807,816) v. *Academisch Ziekenhuis Leiden* (U.S. Appl. No. 13/550,210), University of Western Australia Exhibit List as of Feb. 17, 2015, 8 pages, filed Feb. 17, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Miscellaneous Motion 4 (to exclude evidence), 21 pages, filed Apr. 10, 2015 [Patent Interference No. 106,008 (RES)].

University of Western Australia, *University of Western Australia,* (U.S. Pat. Nos. 7,960,541 and 7,807,816) v. *Academisch Ziekenhuis Leiden* (U.S. Appl. No. 13/550,210), University of Western Australia Objections (to Opposition Evidence), 15 pages, filed Feb. 24, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Opposition 1 (Regarding Patentability Under 35 U.S.C. § 102/103), 39 pages, filed Feb. 17, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Opposition 2 (to Retain UWA's Benefit of AU 2004903474), 31 pages, filed Feb. 17, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Opposition 3 (Regarding Patentability Under 35 U.S.C. § 101), 22 pages, filed Feb. 17, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Opposition 4 (To deny entry of AZL's Proposed New Claims 30 and 31), 36 pages, filed Feb. 17, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 1 (to AZL Opposition 1), 28 pages, filed Apr. 3, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 2 (to AZL Opposition 2), 22 pages, filed Apr. 3, 2015 [Patent Interference No. 106,008 (RES)].

University of Western Australia, *University of Western Australia* (U.S. Pat. No. 7,960,541 and 7,807,816) v. *Academisch Ziekenhuis Leiden* (U.S. Appl. No. 13/550,210), University of Western Australia Reply 3 (for judgment under 35 U.S.C. §135(b)), 19 pages, filed Apr. 3, 2015 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Request for Oral Argument, 4 pages, filed Apr. 10, 2015 [Patent Interference No. 106,008 (RES)].

University of Western Australia, *University of Western Australia* (U.S. Pat. Nos. 7,960,541, 7,807,816) v. *Academisch Ziekenhuis Leiden* (U.S. Appl. No. 13/550,210), University of Western Australia List of Proposed Motions, 6 pages, filed Sep. 10, 2014 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 1 (for Judgment Under 35 U.S.C. §112(a)), 38 pages, filed Nov. 18, 2014 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 2 (for Judgment Under 35 U.S.C. §112(b)), 32 pages, filed Nov. 18, 2014 [Patent Interference No. 106,008 (RES)].

University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 3 (for judgment that Claims 11-12, 14-15, and 17-29 of U.S. Appl. No. 13/550,210 are barred under 35 U.S.C. §135(b)); 25 pages, filed Nov. 18, 2014 [Patent Interference No. 106,008].

University of Western Australia, *University of Western Australia* v. *Academisch Ziekenhuis Leiden*, Motion of Appellant University of Western Australia to Stay Appeal Pending Appeals in Two Related Interferences, Document 4-1, 7 pages, entered May 6, 2016 [Patent Interference No. 106,013] [Civil Action No. 2016-1937].

USPTO Board of Patent Appeals and Interferences. Order—Motion Times—37 C.F.R., §41.104(c) 6 pages, entered Jul. 18, 2014.

USPTO Board of Patent Appeals and Interferences Standing Order, 81 pages, entered Jul. 18, 2014.

Van Deutekom, J.C., "Declaration of Dr. JCT van Deutekom," EP1619249, 2 pages, Aug. 1, 2013.

(56) References Cited

OTHER PUBLICATIONS

Van Deutekom, J.C., Declaration of Dr. Judith van Deutekom, 8 pages, EP 1 619 249, Jun. 10, 2014.
Van Deutekom, J.C., "Declaration of JCT van Deutekom," EP1619249, 6 pages, Jan. 7, 2014.
Van Deutekom, J.C., et al., "Advances in Duchenne Muscular Dystrophy Gene Therapy," Nature Reviews Genetics, Oct. 2003, vol. 4 (10), pp. 774-783.
Van Deutekom, J.C., et al., "Antisense-induced exon skipping restores dystrophin expression in DMD patient derived muscle cells," Human Molecular Genetics, vol. 10, No. 15, pp. 1547-1554, 2001.
Van Deutekom, J.C., et al., "Local Dystrophin Restoration with Antisense Oligonucleotide PRO051," The New England Journal of Medicine, 2007, vol. 357 (26), pp. 2677-2686.
Van Ommen, G.J., et al., "The Therapeutic Potential of Antisense-Mediated Exon Skipping," Current Opinion in Molecular Therapeutics, 2008, vol. 10 (2), pp. 140-149.
Van Vliet, L., et al., "Assessment of the Feasibility of Exon 45-55 Multiexon Skipping for Duchenne Muscular Dystrophy," BMC Medical Genetics, 2008, vol. 9 (105), 7 pages.
Varani, G., et al., "The G•U Wobble Base Pair. A Fundamental Building Block of RNA Structure Crucial to RNA Function in Diverse Biological Systems," EMBO Reports, 2000, vol. 1 (1), pp. 18-23.
Verhaart, I.E., et al., "Prednisolone Treatment Does Not Interfere with 2'-O-Methyl Phosphorothioate Antisense-Mediated Exon Skipping in Duchenne Muscular Dystrophy," Human Gene Therapy, Mar. 2012, vol. 23 (3), pp. 262-273.
Verreault, M., et al., "Gene Silencing in the Development of Personalized Cancer Treatment: The Targets, the Agents and the Delivery Systems," Current Gene Therapy, 2006, vol. 6 (4), pp. 505-533.
Vickers, T.A., et al., "Efficient Reduction of Target RNAs by Small Interfering RNA and RNase H-dependent Antisense Agents. A Comparative Analysis," The Journal of Biological Chemistry, Feb. 2003, vol. 278 (9), pp. 7108-7118.
Wang, B., et al., "Adeno-Associated Virus Vector Carrying Human Minidystrophin Genes Effectively Ameliorates Muscular Dystrophy in mdx Mouse Model," Proceedings of the National Academy of Sciences of the United States of America, 2000, vol. 97 (25), pp. 13714-13719.
Wang, Z., et al., "Sustained AAV-Mediated Dystrophin Expression in a Canine Model of Duchenne Muscular Dystrophy with a Brief Course of Immunosuppression," Molecular Therapy, vol. 15 (6), pp. 1160-1166, Jun. 2007.
Watakabe, A., et al., "The Role of Exon Sequences in Splice Site Selection," Genes & Development, 1993, vol. 7 (3), pp. 407-418.
Watkins, N.E., et al., "Nearest-Neighbor Thermodynamics of Deoxyinosine Pairs in DNA Duplexes," Nucleic Acids Research, vol. 33 (19), pp. 6258-6267, 2005.
Weisbart, R.H., et al., "Cell Type Specific Targeted Intracellular Delivery Into Muscle of a Monoclonal Antibody that Binds Myosin IIb," Molecular Immunology, 2003, vol. 39 (13), pp. 783-789 (Abstract).
Wenk, J., et al., "Quantitation of Mr 46000 and Mr 300000 Mannose 6-Phosphate Receptors in Human Cells and Tissues," Biochemistry International, 1991, vol. 23 (4), pp. 723-731 (Abstract).
Wheway, J.M., et al., "The Dystrophin Lymphocyte Promoter Revisited: 4.5-Megabase Intron, or Artefact?," Neuromuscular Disorders, 2003, vol. 13 (1), pp. 17-20.
Wilton, S.D., et al., "Antisense Oligonucleotide-induced Exon Skipping Across the Human Dystrophin Gene Transcript," Molecular Therapy: The Journal of the American Society of Gene Therapy, Jul. 2007, vol. 15 (7), pp. 1288-1296.
Wilton, S.D., et al., "Antisense Oligonucleotides, Exon Skipping and the Dystrophin Gene Transcript.," Acta Myologica, 2005, vol. 24, pp. 222-229.
Wilton, S.D., et al., "Specific Removal of the Nonsense Mutation from the mdx Dystrophin mRNA Using Antisense Oligonucleotides," Neuromuscular Disorders, 1999, vol. 9 (5), pp. 330-338.
Wood, Matthew J.A., *University of Western Australia* (U.S. Pat. No. 8,455,636) v. *Academisch Ziekenhuis Leiden* (U.S. Appl. No. 11/233,495) [Patent Interference No. 106,007 (RES)] and *University of Western Australia* (U.S. Pat. Nos. 7,960,541 and 7,807,816) v. *Academisch Ziekenhuis Leiden* (U.S. Appl. No. 13/550,210) [Patent Interference No. 106,008 (RES)], *University of Western Australia* (U.S. Pat. No. 8,486,907) v. *Academisch Ziekenhuis Leiden* (U.S. Appl. No. 14/198,992) [Patent Interference No. 106,013 (RES)], Second Declaration of Matthew J.A. Wood, M.D., D. Phil., 78 pages, filed Feb. 17, 2015.
Wood, Matthew J.A., *University of Western Australia* (U.S. Pat. Nos. 8,455,636, 7,960,541, 7,807,816, 8,486,907) v. *Academisch Ziekenhuis Leiden* (U.S. Appl. Nos. 11/233,495, 13/550,210, 14/198,992), Declaration of Matthew J.A. Wood, M.D., D. Phil.—UWA Exhibit 2081, 184 pages, filed Sep. 19, 2014 [Patent Interference Nos. 106,007, 106,008, 106,113 (RES)].
Wu, B., et al., "Targeted Skipping of Human Dystrophin Exons in Transgenic Mouse Model Systemically for Antisense Drug Development," PLoS One, vol. 6 (5), 11 pages, 2011.
Xu, L., et al., "Potential for Pharmacology of Ryanodine Receptor/Calcium Release Channels," Annals of the New York Academy of Sciences, vol. 853, pp. 130-148, Sep. 16, 1998.
Yen, L., et al., "Sequence-specific Cleavage of Huntingtin mRNA by Catalytic DNA," Annals of Neurology, 1999, vol. 46 (3), pp. 366-373.
Yin, H., et al., "Effective Exon Skipping and Restoration of Dystrophin Expression by Peptide Nucleic Acid Antisense Oligonucleotides in mdx Mice," Molecular Therapy, Jan. 2008, vol. 16 (1), pp. 38-45.
Yokota, T., et al., "Antisense Oligo-Mediated Multiple Exon Skipping in a Dog Model of Duchenne Muscular Dystrophy," Methods in Molecular Biology, vol. 709, pp. 299-312, 2011.
Yokota, T., et al., "Efficacy of Systemic Morpholino Exon-Skipping in Duchenne Dystrophy Dogs," American Neurological Association, 2009, vol. 65 (6), pp. 667-676.
Yu, R.Z., et al., "Development of an Ultrasensitive Noncompetitive Hybridization-Ligation Enzyme-Linked Immunosorbent Assay for the Determination of Phosphorothioate Oligodeoxynucleotide in Plasma," Analytical Biochemistry, vol. 304 (1), pp. 19-25, 2002.
Zhang, G., et al., "Efficient Expression of Naked DNA Delivered Intraarterially to Limb Muscles of Nonhuman Primates," Human Gene Therapy, 2001, vol. 12 (4), pp. 427-438 (Abstract).
Zhou, G.Q., et al., "Current Understanding of Dystrophin-Related Muscular Dystrophy and Therapeutic Challenges Ahead," Chinese Medical Journal, 2006, vol. 119 (16), pp. 1381-1391.
U.S. Appl. No. 15/468,239, filed Mar. 24, 2017.
U.S. Appl. No. 15/479,639, filed Apr. 5, 2017.
U.S. Appl. No. 15/479,646, filed Apr. 5, 2017.
Academisch Ziekenhuis Leiden, "Comparative analysis of AONs for inducing the skipping of exon 45 from the dystrophin gene in human control muscle cells," 2 pages, Oct. 23, 2014.
Academisch Ziekenhuis Leiden, Letter in Response to Article 94(3) EPC relating to EP2594641, 7 pages, Oct. 23, 2014.
Academisch Ziekenhuis Leiden, Patentee's letter to European Patent Office in the examination of EP 2602322, 4 pages, dated Dec. 9, 2013.
Academisch Ziekenhuis Leiden, Patentee's Response to Office Action to European Patent Office in the examination of EP 2602322, 6 pages, dated Oct. 21, 2014.
Academisch Ziekenhuis Leiden, Reply Brief of Appellant Academisch Ziekenhuis Leiden, US Court of Appeals for the Federal Circuit, Case: 16-2262, 40 pages, Apr. 25, 2017.
Axelrod et al., "Intestinal Transport of Gentamicin with a Novel, Glycosteroid Drug Transport Agent," Pharmaceutical Research, vol. 15, No. 12, pp. 1876-1881, 1998.
Itoh et al., "Allergic Contact Dermatitis Due to Topical Drugs Contaiing Corticosteroids," Skin Research, 24(2), pp. 270-271, 1982.
Nakamura, et al., "The Latest Finding on Muscular Dystrophy," Medical Online, vol. 42, No. 4, pp. 382-386, 2008 (English translation attached 5 pgs.).

(56) References Cited

OTHER PUBLICATIONS

Nederlandsch Octrooibureau, Patentee's Letter in Response to EPO Communication regarding EP 13170245.8, 4 pages, Apr. 15, 2015.
Nederlandsch Octrooibureau, Patentee's Letter in Response to EPO Communication regarding EP 13170245.8, 5 pages, Oct. 20, 2014.
Nelson et al., "The Properties of Nucleotide Bases Affect the Three-Dimensional Structure of Nucleic Acids," Lehninger Principles of Biochemistry, Third Edition, p. 331, 2000.
Sarepta Therapeutics Inc., Notice of Opposition to European patent EP 2636741 B1, 72 pages, Jan. 27, 2017.
University of Western Australia, Reply Brief of Appellant University of Western Australia, US Court of Appeals for the Federal Circuit, Case: 16-1937, 16-2086, 40 pages, Apr. 25, 2017.
Arai et al., "Synthesis and properties of novel 2'-O-alkoxymethyl-modified nucleic acids," Bioorg. Med. Chem. Lett. 21(21):6285-6287 (2011) (Epub Sep. 8, 2011).
Bruno, "Using drug-excipient interactions for siRNA delivery," Adv. Drug Deliv. Rev. 63(13):1210-1226 (2011) (Epub Sep. 17, 2011).
Cartegni et al., "ESEfinder: A web resource to identify exonic splicing enhancers," Nucleic Acids Res. 31(13):3568-3571 (2003).
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378(9791):595-605 (2011) (Epub Jul. 23, 2011).
Diebold et al., "Nucleic acid agonists for Toll-like receptor 7 are defined by the presence of uridine ribonucleotides," Eur. J. Immunol. 36(12):3256-3267 (2006).
Ehmsen et al., "The dystrophin-associated protein complex," J. Cell Sci. 115(Pt 14):2801-2803 (2002).
Hanessian et al., "Structure-based design of a highly constrained nucleic acid analogue: improved duplex stabilization by restricting sugar pucker and torsion angle $\gamma$," Angew. Chem. Int. Ed. Engl. 51(45):11242-11245 (2012) (Epub Aug. 22, 2012).
Hari et al., "Synthesis and duplex-forming ability of oligonucleotides containing 4'-carboxythymidine analogs," Org. Biomol. Chem. 10(48):9639-9649 (2012) (Epub Nov. 8, 2012).
Hodgetts et al., "Reduced necrosis of dystrophic muscle by depletion of host neutrophils, or blocking TNFalpha function with Etanercept in mdx mice," Neuromuscul. Disord. 16(9-10):591-602 (2006) (Epub Aug. 28, 2006).
Krieg et al., "CpG motifs in bacterial DNA trigger direct B-cell activation," Nature 374(6522):546-549 (1995).
Krieg, "The role of CpG motifs in innate immunity," Curr. Opin. Immunol. 12(1):35-43 (2000).
Kumar et al., "Salt selection in drug development," Pharm. Technol. 3:128-146 (2008).
Peacock et al., "Nucleobase and ribose modifications control immunostimulation by a microRNA-122-mimetic RNA," J. Am. Chem. Soc. 133(24):9200-9203 (2011) (Epub Jun. 1, 2011).
Popovic et al., "High mobility group B1 protein suppresses the human plasmacytoid dendritic cell response to TLR9 agonists," J. Immunol. 177(12):8701-8707 (2006).
Wagner, "Bacterial CpG DNA activates immune cells to signal infectious danger," Adv. Immunol. 73:329-368 (1999).
Yokota et al., "Optimizing exon skipping therapies for DMD," Acta Myol. 26(3):179-184 (2007).
Zucker, "Mfold web server for nucleic acid folding and hybridization prediction," Nucleic Acids Res. 31(13):3406-3415 (2003).

\* cited by examiner

| AON | Conc. (nM) | Sequence (5'-3') |
|---|---|---|
| PS524 | 400 | GUUGCCUCCGGUUCUGAAGGUGUUC |
| PS1317 | 400 | GUUGCCUCCGGUUCUGAAGGUGUUC |
| PS1318 | 400 | GUUGCCUCCGGUUCUGAAGGUGUUC |
| PS1319 | 400 | GUUGCCUCCGGUUCUGAAGGUGUUC |

Fig. 2A

| Compound | mdx vs control (avg muscle) | Concentration AON (μg/g tissue) at day 14 | | | | | Muscle/ liver | Muscle/ kidney | Half-life (tric) |
|---|---|---|---|---|---|---|---|---|---|
| | | heart | dia | gastroc | quadr | tric | | | |
| PS229L | 1.8 | 37.8 | 62.8 | 46.1 | 66.9 | 45.5 | 0.14 | 0.10 | 7 |
| PS524 | 2.3 | 119.8 | 191.2 | 94.2 | 192.7 | 101.4 | 0.22 | 0.16 | 20+ |
| PS631 | 1.8 | 52.7 | 85.0 | 64.6 | 76.6 | 56.5 | 0.11 | 0.12 | 10 |
| PS652 | 2.0 | 149.5 | 169.7 | 274.7 | 171.3 | 122.8 | 0.10 | 0.10 | 25 |

Fig. 2B

| Compound | Dose (mg/kg) | Tmax (min) | Cmax/ dose (μg/ml) | AUC 0-24/ dose (μg.h/mL) | Cl 24h (L/kg/h) |
|---|---|---|---|---|---|
| PS229L | 100 | 15 | 0.98 | 2.05 | 0.49 |
| PS524 | 100 | 15 | 0.87 | 4.67 | 0.21 |
| PS631 | 100 | 60 | 0.73 | 1.81 | 0.55 |
| PS652 | 100 | 15 | 0.76 | 2.71 | 0.37 |

| AON | Sequence (5'-3') |
|---|---|
| PS49 | GGCCAAACCUCGGCUUACCU |
| PS959 | GGCCAAACCUCGGCUUACCU |

| AON | Conc. (nM) | Sequence (5'-3') |
|---|---|---|
| PS43 | 200 | UCAAGGAAGAUGGCAUUUCU |
| PS403 | 200 | UCAAGGAAGAUGGCAUUUCU |
| PS235 | 200 | GGUAAUGAGUUCUUCCAACUGG |
| PS897 | 200 | GGUAAUGAGUUCUUCCAACUGG |
| PS188 | 200 | UCAGCUUCUGUUAGCCACUG |
| PS733 | 200 | UCAGCUUCUGUUAGCCACUG |

SEQUENCE LISTING

```
<160> NUMBER OF SEQ ID NOS: 219

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300
```

```
Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
```

-continued

```
              725                 730                 735
Arg Ser Glu Ala Val Leu Gln Ser Pro Glu Phe Ala Ile Phe Arg Lys
              740                 745                 750
Glu Gly Asn Phe Ser Asp Leu Lys Glu Lys Val Asn Ala Ile Glu Arg
              755                 760                 765
Glu Lys Ala Glu Lys Phe Arg Lys Leu Gln Asp Ala Ser Arg Ser Ala
        770                 775                 780
Gln Ala Leu Val Glu Gln Met Val Asn Glu Gly Val Asn Ala Asp Ser
785                 790                 795                 800
Ile Lys Gln Ala Ser Glu Gln Leu Asn Ser Arg Trp Ile Glu Phe Cys
              805                 810                 815
Gln Leu Leu Ser Glu Arg Leu Asn Trp Leu Glu Tyr Gln Asn Asn Ile
              820                 825                 830
Ile Ala Phe Tyr Asn Gln Leu Gln Gln Leu Glu Gln Met Thr Thr Thr
              835                 840                 845
Ala Glu Asn Trp Leu Lys Ile Gln Pro Thr Thr Pro Ser Glu Pro Thr
850                 855                 860
Ala Ile Lys Ser Gln Leu Lys Ile Cys Lys Asp Glu Val Asn Arg Leu
865                 870                 875                 880
Ser Gly Leu Gln Pro Gln Ile Glu Arg Leu Lys Ile Gln Ser Ile Ala
              885                 890                 895
Leu Lys Glu Lys Gly Gln Gly Pro Met Phe Leu Asp Ala Asp Phe Val
              900                 905                 910
Ala Phe Thr Asn His Phe Lys Gln Val Phe Ser Asp Val Gln Ala Arg
              915                 920                 925
Glu Lys Glu Leu Gln Thr Ile Phe Asp Thr Leu Pro Pro Met Arg Tyr
        930                 935                 940
Gln Glu Thr Met Ser Ala Ile Arg Thr Trp Val Gln Gln Ser Glu Thr
945                 950                 955                 960
Lys Leu Ser Ile Pro Gln Leu Ser Val Thr Asp Tyr Glu Ile Met Glu
              965                 970                 975
Gln Arg Leu Gly Glu Leu Gln Ala Leu Gln Ser Ser Leu Gln Glu Gln
              980                 985                 990
Gln Ser Gly Leu Tyr Tyr Leu Ser Thr Thr Val Lys Glu Met Ser Lys
        995                 1000                1005
Lys Ala Pro Ser Glu Ile Ser Arg Lys Tyr Gln Ser Glu Phe Glu
        1010                1015                1020
Glu Ile Glu Gly Arg Trp Lys Lys Leu Ser Ser Gln Leu Val Glu
        1025                1030                1035
His Cys Gln Lys Leu Glu Glu Gln Met Asn Lys Leu Arg Lys Ile
        1040                1045                1050
Gln Asn His Ile Gln Thr Leu Lys Lys Trp Met Ala Glu Val Asp
        1055                1060                1065
Val Phe Leu Lys Glu Glu Trp Pro Ala Leu Gly Asp Ser Glu Ile
        1070                1075                1080
Leu Lys Lys Gln Leu Lys Gln Cys Arg Leu Leu Val Ser Asp Ile
        1085                1090                1095
Gln Thr Ile Gln Pro Ser Leu Asn Ser Val Asn Glu Gly Gly Gln
        1100                1105                1110
Lys Ile Lys Asn Glu Ala Glu Pro Glu Phe Ala Ser Arg Leu Glu
        1115                1120                1125
Thr Glu Leu Lys Glu Leu Asn Thr Gln Trp Asp His Met Cys Gln
        1130                1135                1140
```

```
-continued

Gln Val Tyr Ala Arg Lys Glu Ala Leu Lys Gly Gly Leu Glu Lys
1145                1150                1155

Thr Val Ser Leu Gln Lys Asp Leu Ser Glu Met His Glu Trp Met
1160                1165                1170

Thr Gln Ala Glu Glu Tyr Leu Glu Arg Asp Phe Glu Tyr Lys
1175                1180                1185

Thr Pro Asp Glu Leu Gln Lys Ala Val Glu Glu Met Lys Arg Ala
1190                1195                1200

Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Gln Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
1490                1495                1500

His Cys Val Asn Leu Tyr Lys Ser Leu Ser Glu Val Lys Ser Glu
1505                1510                1515

Val Glu Met Val Ile Lys Thr Gly Arg Gln Ile Val Gln Lys Lys
1520                1525                1530
```

```
Gln Thr Glu Asn Pro Lys Glu Leu Asp Glu Arg Val Thr Ala Leu
    1535                1540                1545
Lys Leu His Tyr Asn Glu Leu Gly Ala Lys Val Thr Glu Arg Lys
    1550                1555                1560
Gln Gln Leu Glu Lys Cys Leu Lys Leu Ser Arg Lys Met Arg Lys
    1565                1570                1575
Glu Met Asn Val Leu Thr Glu Trp Leu Ala Ala Thr Asp Met Glu
    1580                1585                1590
Leu Thr Lys Arg Ser Ala Val Glu Gly Met Pro Ser Asn Leu Asp
    1595                1600                1605
Ser Glu Val Ala Trp Gly Lys Ala Thr Gln Lys Glu Ile Glu Lys
    1610                1615                1620
Gln Lys Val His Leu Lys Ser Ile Thr Glu Val Gly Glu Ala Leu
    1625                1630                1635
Lys Thr Val Leu Gly Lys Lys Glu Thr Leu Val Glu Asp Lys Leu
    1640                1645                1650
Ser Leu Leu Asn Ser Asn Trp Ile Ala Val Thr Ser Arg Ala Glu
    1655                1660                1665
Glu Trp Leu Asn Leu Leu Leu Glu Tyr Gln Lys His Met Glu Thr
    1670                1675                1680
Phe Asp Gln Asn Val Asp His Ile Thr Lys Trp Ile Ile Gln Ala
    1685                1690                1695
Asp Thr Leu Leu Asp Glu Ser Glu Lys Lys Lys Pro Gln Gln Lys
    1700                1705                1710
Glu Asp Val Leu Lys Arg Leu Lys Ala Glu Leu Asn Asp Ile Arg
    1715                1720                1725
Pro Lys Val Asp Ser Thr Arg Asp Gln Ala Ala Asn Leu Met Ala
    1730                1735                1740
Asn Arg Gly Asp His Cys Arg Lys Leu Val Glu Pro Gln Ile Ser
    1745                1750                1755
Glu Leu Asn His Arg Phe Ala Ala Ile Ser His Arg Ile Lys Thr
    1760                1765                1770
Gly Lys Ala Ser Ile Pro Leu Lys Glu Leu Glu Gln Phe Asn Ser
    1775                1780                1785
Asp Ile Gln Lys Leu Leu Glu Pro Leu Glu Ala Glu Ile Gln Gln
    1790                1795                1800
Gly Val Asn Leu Lys Glu Glu Asp Phe Asn Lys Asp Met Asn Glu
    1805                1810                1815
Asp Asn Glu Gly Thr Val Lys Glu Leu Leu Gln Arg Gly Asp Asn
    1820                1825                1830
Leu Gln Gln Arg Ile Thr Asp Glu Arg Lys Arg Glu Glu Ile Lys
    1835                1840                1845
Ile Lys Gln Gln Leu Leu Gln Thr Lys His Asn Ala Leu Lys Asp
    1850                1855                1860
Leu Arg Ser Gln Arg Arg Lys Lys Ala Leu Glu Ile Ser His Gln
    1865                1870                1875
Trp Tyr Gln Tyr Lys Arg Gln Ala Asp Asp Leu Leu Lys Cys Leu
    1880                1885                1890
Asp Asp Ile Glu Lys Lys Leu Ala Ser Leu Pro Glu Pro Arg Asp
    1895                1900                1905
Glu Arg Lys Ile Lys Glu Ile Asp Arg Glu Leu Gln Lys Lys Lys
    1910                1915                1920
Glu Glu Leu Asn Ala Val Arg Arg Gln Ala Glu Gly Leu Ser Glu
```

-continued

```
            1925                1930                1935

Asp Gly Ala Ala Met Ala Val Glu Pro Thr Gln Ile Gln Leu Ser
            1940                1945                1950

Lys Arg Trp Arg Glu Ile Glu Ser Lys Phe Ala Gln Phe Arg Arg
            1955                1960                1965

Leu Asn Phe Ala Gln Ile His Thr Val Arg Glu Glu Thr Met Met
            1970                1975                1980

Val Met Thr Glu Asp Met Pro Leu Glu Ile Ser Tyr Val Pro Ser
            1985                1990                1995

Thr Tyr Leu Thr Glu Ile Thr His Val Ser Gln Ala Leu Leu Glu
            2000                2005                2010

Val Glu Gln Leu Leu Asn Ala Pro Asp Leu Cys Ala Lys Asp Phe
            2015                2020                2025

Glu Asp Leu Phe Lys Gln Glu Ser Leu Lys Asn Ile Lys Asp
            2030                2035                2040

Ser Leu Gln Gln Ser Ser Gly Arg Ile Asp Ile Ile His Ser Lys
            2045                2050                2055

Lys Thr Ala Ala Leu Gln Ser Ala Thr Pro Val Glu Arg Val Lys
            2060                2065                2070

Leu Gln Glu Ala Leu Ser Gln Leu Asp Phe Gln Trp Glu Lys Val
            2075                2080                2085

Asn Lys Met Tyr Lys Asp Arg Gln Gly Arg Phe Asp Arg Ser Val
            2090                2095                2100

Glu Lys Trp Arg Arg Phe His Tyr Asp Ile Lys Ile Phe Asn Gln
            2105                2110                2115

Trp Leu Thr Glu Ala Glu Gln Phe Leu Arg Lys Thr Gln Ile Pro
            2120                2125                2130

Glu Asn Trp Glu His Ala Lys Tyr Lys Trp Tyr Leu Lys Glu Leu
            2135                2140                2145

Gln Asp Gly Ile Gly Gln Arg Gln Thr Val Val Arg Thr Leu Asn
            2150                2155                2160

Ala Thr Gly Glu Glu Ile Ile Gln Gln Ser Ser Lys Thr Asp Ala
            2165                2170                2175

Ser Ile Leu Gln Glu Lys Leu Gly Ser Leu Asn Leu Arg Trp Gln
            2180                2185                2190

Glu Val Cys Lys Gln Leu Ser Asp Arg Lys Lys Arg Leu Glu Glu
            2195                2200                2205

Gln Lys Asn Ile Leu Ser Glu Phe Gln Arg Asp Leu Asn Glu Phe
            2210                2215                2220

Val Leu Trp Leu Glu Glu Ala Asp Asn Ile Ala Ser Ile Pro Leu
            2225                2230                2235

Glu Pro Gly Lys Glu Gln Gln Leu Lys Glu Lys Leu Glu Gln Val
            2240                2245                2250

Lys Leu Leu Val Glu Glu Leu Pro Leu Arg Gln Gly Ile Leu Lys
            2255                2260                2265

Gln Leu Asn Glu Thr Gly Gly Pro Val Leu Val Ser Ala Pro Ile
            2270                2275                2280

Ser Pro Glu Glu Gln Asp Lys Leu Glu Asn Lys Leu Lys Gln Thr
            2285                2290                2295

Asn Leu Gln Trp Ile Lys Val Ser Arg Ala Leu Pro Glu Lys Gln
            2300                2305                2310

Gly Glu Ile Glu Ala Gln Ile Lys Asp Leu Gly Gln Leu Glu Lys
            2315                2320                2325
```

-continued

Lys Leu Glu Asp Leu Glu Glu Gln Leu Asn His Leu Leu Leu Trp
    2330            2335                 2340

Leu Ser Pro Ile Arg Asn Gln Leu Glu Ile Tyr Asn Gln Pro Asn
    2345            2350                 2355

Gln Glu Gly Pro Phe Asp Val Gln Glu Thr Glu Ile Ala Val Gln
    2360            2365                 2370

Ala Lys Gln Pro Asp Val Glu Glu Ile Leu Ser Lys Gly Gln His
    2375            2380                 2385

Leu Tyr Lys Glu Lys Pro Ala Thr Gln Pro Val Lys Arg Lys Leu
    2390            2395                 2400

Glu Asp Leu Ser Ser Glu Trp Lys Ala Val Asn Arg Leu Leu Gln
    2405            2410                 2415

Glu Leu Arg Ala Lys Gln Pro Asp Leu Ala Pro Gly Leu Thr Thr
    2420            2425                 2430

Ile Gly Ala Ser Pro Thr Gln Thr Val Thr Leu Val Thr Gln Pro
    2435            2440                 2445

Val Val Thr Lys Glu Thr Ala Ile Ser Lys Leu Glu Met Pro Ser
    2450            2455                 2460

Ser Leu Met Leu Glu Val Pro Ala Leu Ala Asp Phe Asn Arg Ala
    2465            2470                 2475

Trp Thr Glu Leu Thr Asp Trp Leu Ser Leu Leu Asp Gln Val Ile
    2480            2485                 2490

Lys Ser Gln Arg Val Met Val Gly Asp Leu Glu Asp Ile Asn Glu
    2495            2500                 2505

Met Ile Ile Lys Gln Lys Ala Thr Met Gln Asp Leu Glu Gln Arg
    2510            2515                 2520

Arg Pro Gln Leu Glu Glu Leu Ile Thr Ala Ala Gln Asn Leu Lys
    2525            2530                 2535

Asn Lys Thr Ser Asn Gln Glu Ala Arg Thr Ile Ile Thr Asp Arg
    2540            2545                 2550

Ile Glu Arg Ile Gln Asn Gln Trp Asp Glu Val Gln Glu His Leu
    2555            2560                 2565

Gln Asn Arg Arg Gln Gln Leu Asn Glu Met Leu Lys Asp Ser Thr
    2570            2575                 2580

Gln Trp Leu Glu Ala Lys Glu Ala Glu Gln Val Leu Gly Gln
    2585            2590                 2595

Ala Arg Ala Lys Leu Glu Ser Trp Lys Glu Gly Pro Tyr Thr Val
    2600            2605                 2610

Asp Ala Ile Gln Lys Lys Ile Thr Glu Thr Lys Gln Leu Ala Lys
    2615            2620                 2625

Asp Leu Arg Gln Trp Gln Thr Asn Val Asp Val Ala Asn Asp Leu
    2630            2635                 2640

Ala Leu Lys Leu Leu Arg Asp Tyr Ser Ala Asp Asp Thr Arg Lys
    2645            2650                 2655

Val His Met Ile Thr Glu Asn Ile Asn Ala Ser Trp Arg Ser Ile
    2660            2665                 2670

His Lys Arg Val Ser Glu Arg Glu Ala Ala Leu Glu Glu Thr His
    2675            2680                 2685

Arg Leu Leu Gln Gln Phe Pro Leu Asp Leu Glu Lys Phe Leu Ala
    2690            2695                 2700

Trp Leu Thr Glu Ala Glu Thr Thr Ala Asn Val Leu Gln Asp Ala
    2705            2710                 2715

-continued

```
Thr Arg Lys Glu Arg Leu Leu Glu Asp Ser Lys Gly Val Lys Glu
2720            2725                2730
Leu Met Lys Gln Trp Gln Asp Leu Gln Gly Glu Ile Glu Ala His
2735            2740                2745
Thr Asp Val Tyr His Asn Leu Asp Glu Asn Ser Gln Lys Ile Leu
2750            2755                2760
Arg Ser Leu Glu Gly Ser Asp Asp Ala Val Leu Leu Gln Arg Arg
2765            2770                2775
Leu Asp Asn Met Asn Phe Lys Trp Ser Glu Leu Arg Lys Lys Ser
2780            2785                2790
Leu Asn Ile Arg Ser His Leu Glu Ala Ser Ser Asp Gln Trp Lys
2795            2800                2805
Arg Leu His Leu Ser Leu Gln Glu Leu Leu Val Trp Leu Gln Leu
2810            2815                2820
Lys Asp Asp Glu Leu Ser Arg Gln Ala Pro Ile Gly Gly Asp Phe
2825            2830                2835
Pro Ala Val Gln Lys Gln Asn Asp Val His Arg Ala Phe Lys Arg
2840            2845                2850
Glu Leu Lys Thr Lys Glu Pro Val Ile Met Ser Thr Leu Glu Thr
2855            2860                2865
Val Arg Ile Phe Leu Thr Glu Gln Pro Leu Glu Gly Leu Glu Lys
2870            2875                2880
Leu Tyr Gln Glu Pro Arg Glu Leu Pro Pro Glu Glu Arg Ala Gln
2885            2890                2895
Asn Val Thr Arg Leu Leu Arg Lys Gln Ala Glu Glu Val Asn Thr
2900            2905                2910
Glu Trp Glu Lys Leu Asn Leu His Ser Ala Asp Trp Gln Arg Lys
2915            2920                2925
Ile Asp Glu Thr Leu Glu Arg Leu Gln Glu Leu Gln Glu Ala Thr
2930            2935                2940
Asp Glu Leu Asp Leu Lys Leu Arg Gln Ala Glu Val Ile Lys Gly
2945            2950                2955
Ser Trp Gln Pro Val Gly Asp Leu Leu Ile Asp Ser Leu Gln Asp
2960            2965                2970
His Leu Glu Lys Val Lys Ala Leu Arg Gly Glu Ile Ala Pro Leu
2975            2980                2985
Lys Glu Asn Val Ser His Val Asn Asp Leu Ala Arg Gln Leu Thr
2990            2995                3000
Thr Leu Gly Ile Gln Leu Ser Pro Tyr Asn Leu Ser Thr Leu Glu
3005            3010                3015
Asp Leu Asn Thr Arg Trp Lys Leu Leu Gln Val Ala Val Glu Asp
3020            3025                3030
Arg Val Arg Gln Leu His Glu Ala His Arg Asp Phe Gly Pro Ala
3035            3040                3045
Ser Gln His Phe Leu Ser Thr Ser Val Gln Gly Pro Trp Glu Arg
3050            3055                3060
Ala Ile Ser Pro Asn Lys Val Pro Tyr Tyr Ile Asn His Glu Thr
3065            3070                3075
Gln Thr Thr Cys Trp Asp His Pro Lys Met Thr Glu Leu Tyr Gln
3080            3085                3090
Ser Leu Ala Asp Leu Asn Asn Val Arg Phe Ser Ala Tyr Arg Thr
3095            3100                3105
Ala Met Lys Leu Arg Arg Leu Gln Lys Ala Leu Cys Leu Asp Leu
```

```
                3110              3115              3120
Leu Ser Leu Ser Ala Ala Cys Asp Ala Leu Asp Gln His Asn Leu
    3125              3130              3135
Lys Gln Asn Asp Gln Pro Met Asp Ile Leu Gln Ile Ile Asn Cys
    3140              3145              3150
Leu Thr Thr Ile Tyr Asp Arg Leu Glu Gln Glu His Asn Asn Leu
    3155              3160              3165
Val Asn Val Pro Leu Cys Val Asp Met Cys Leu Asn Trp Leu Leu
    3170              3175              3180
Asn Val Tyr Asp Thr Gly Arg Thr Gly Arg Ile Arg Val Leu Ser
    3185              3190              3195
Phe Lys Thr Gly Ile Ile Ser Leu Cys Lys Ala His Leu Glu Asp
    3200              3205              3210
Lys Tyr Arg Tyr Leu Phe Lys Gln Val Ala Ser Ser Thr Gly Phe
    3215              3220              3225
Cys Asp Gln Arg Arg Leu Gly Leu Leu Leu His Asp Ser Ile Gln
    3230              3235              3240
Ile Pro Arg Gln Leu Gly Glu Val Ala Ser Phe Gly Gly Ser Asn
    3245              3250              3255
Ile Glu Pro Ser Val Arg Ser Cys Phe Gln Phe Ala Asn Asn Lys
    3260              3265              3270
Pro Glu Ile Glu Ala Ala Leu Phe Leu Asp Trp Met Arg Leu Glu
    3275              3280              3285
Pro Gln Ser Met Val Trp Leu Pro Val Leu His Arg Val Ala Ala
    3290              3295              3300
Ala Glu Thr Ala Lys His Gln Ala Lys Cys Asn Ile Cys Lys Glu
    3305              3310              3315
Cys Pro Ile Ile Gly Phe Arg Tyr Arg Ser Leu Lys His Phe Asn
    3320              3325              3330
Tyr Asp Ile Cys Gln Ser Cys Phe Phe Ser Gly Arg Val Ala Lys
    3335              3340              3345
Gly His Lys Met His Tyr Pro Met Val Glu Tyr Cys Thr Pro Thr
    3350              3355              3360
Thr Ser Gly Glu Asp Val Arg Asp Phe Ala Lys Val Leu Lys Asn
    3365              3370              3375
Lys Phe Arg Thr Lys Arg Tyr Phe Ala Lys His Pro Arg Met Gly
    3380              3385              3390
Tyr Leu Pro Val Gln Thr Val Leu Glu Gly Asp Asn Met Glu Thr
    3395              3400              3405
Pro Val Thr Leu Ile Asn Phe Trp Pro Val Asp Ser Ala Pro Ala
    3410              3415              3420
Ser Ser Pro Gln Leu Ser His Asp Asp Thr His Ser Arg Ile Glu
    3425              3430              3435
His Tyr Ala Ser Arg Leu Ala Glu Met Glu Asn Ser Asn Gly Ser
    3440              3445              3450
Tyr Leu Asn Asp Ser Ile Ser Pro Asn Glu Ser Ile Asp Asp Glu
    3455              3460              3465
His Leu Leu Ile Gln His Tyr Cys Gln Ser Leu Asn Gln Asp Ser
    3470              3475              3480
Pro Leu Ser Gln Pro Arg Ser Pro Ala Gln Ile Leu Ile Ser Leu
    3485              3490              3495
Glu Ser Glu Glu Arg Gly Glu Leu Glu Arg Ile Leu Ala Asp Leu
    3500              3505              3510
```

Glu Glu Glu Asn Arg Asn Leu Gln Ala Glu Tyr Asp Arg Leu Lys
3515            3520                3525

Gln Gln His Glu His Lys Gly Leu Ser Pro Leu Pro Ser Pro Pro
    3530            3535                3540

Glu Met Met Pro Thr Ser Pro Gln Ser Pro Arg Asp Ala Glu Leu
3545            3550                3555

Ile Ala Glu Ala Lys Leu Leu Arg Gln His Lys Gly Arg Leu Glu
3560            3565                3570

Ala Arg Met Gln Ile Leu Glu Asp His Asn Lys Gln Leu Glu Ser
3575            3580                3585

Gln Leu His Arg Leu Arg Gln Leu Leu Glu Gln Pro Gln Ala Glu
3590            3595                3600

Ala Lys Val Asn Gly Thr Thr Val Ser Ser Pro Ser Thr Ser Leu
3605            3610                3615

Gln Arg Ser Asp Ser Ser Gln Pro Met Leu Leu Arg Val Val Gly
3620            3625                3630

Ser Gln Thr Ser Asp Ser Met Gly Glu Glu Asp Leu Leu Ser Pro
3635            3640                3645

Pro Gln Asp Thr Ser Thr Gly Leu Glu Glu Val Met Glu Gln Leu
3650            3655                3660

Asn Asn Ser Phe Pro Ser Ser Arg Gly Arg Asn Thr Pro Gly Lys
3665            3670                3675

Pro Met Arg Glu Asp Thr Met
3680            3685

<210> SEQ ID NO 2
<211> LENGTH: 148
<212> TYPE: RNA
<213> ORGANISM: Homo sapiens

<400> SEQUENCE: 2
gcgauuugac agaucuguug agaaauggcg gcguuuucau uaugauauaa agauauuuaa      60
ucaguggcua acagaagcug aacaguuucu cagaaagaca caaauuccug agaauuggga     120
acaugcuaaa uacaaauggu aucuuaag                                        148

<210> SEQ ID NO 3
<211> LENGTH: 176
<212> TYPE: RNA
<213> ORGANISM: Homo sapiens

<400> SEQUENCE: 3
gaacuccagg auggcauugg gcagcggcaa acuguuguca gaacauugaa ugcaacuggg      60
gaagaaauaa uucagcaauc cucaaaaaca gaugccagua uucuacagga aaaauuggga     120
agccugaauc ugcgguggca ggaggucugc aaacagcugu cagacagaaa aaagag         176

<210> SEQ ID NO 4
<211> LENGTH: 148
<212> TYPE: RNA
<213> ORGANISM: Homo sapiens

<400> SEQUENCE: 4
gcuagaagaa caaaagaaua ucuugucaga auucaaaga gauuuaaaug aauuuguuuu      60
augguuggag gaagcagaua acauugcuag uauccacuu gaaccuggaa aagagcagca     120
acuaaaagaa aagcuugagc aagucaag                                        148

<210> SEQ ID NO 5
<211> LENGTH: 150
<212> TYPE: RNA
<213> ORGANISM: Homo sapiens

<400> SEQUENCE: 5
uuacuggugg aagaguugcc ccugcgccag ggaauucuca aacaauuaaa ugaaacugga      60
ggacccgugc uuguaagugc ucccauaagc ccagaagagc aagauaaacu ugaaaauaag     120
cucaagcaga caaaucucca guggauaaag                                      150

<210> SEQ ID NO 6
<211> LENGTH: 186
<212> TYPE: RNA
<213> ORGANISM: Homo sapiens

<400> SEQUENCE: 6
guuuccagag cuuuaccuga gaaacaagga gaaauugaag cucaaauaaa agaccuuggg      60
cagcuugaaa aaaagcuuga agaccuugaa gagcaguuaa aucaucugcu gcugugguua    120
ucuccuauua ggaaucaguu ggaaauuuau aaccaaccaa accaagaagg accauuugac    180
guucag                                                                186

<210> SEQ ID NO 7
<211> LENGTH: 102
<212> TYPE: RNA
<213> ORGANISM: Homo sapiens

<400> SEQUENCE: 7
gaaacugaaa uagcaguuca agcuaaacaa ccggaugugg aagagauuuu gucuaaaggg      60
cagcauuugu acaaggaaaa accagccacu cagccaguga ag                        102

<210> SEQ ID NO 8
<211> LENGTH: 109
<212> TYPE: RNA
<213> ORGANISM: Homo sapiens

<400> SEQUENCE: 8
aggaaguuag aagaucugag cucugagugg aaggcgguaa accguuuacu ucaagagcug      60
agggcaaagc agccugaccu agcuccugga cugaccacua uuggagccu                 109

<210> SEQ ID NO 9
<211> LENGTH: 233
<212> TYPE: RNA
<213> ORGANISM: Homo sapiens

<400> SEQUENCE: 9
cuccuacuca gacuguuacu cuggugacac aaccuguggu uacuaaggaa acugccaucu      60
ccaaacuaga aaugccaucu uccuugaugu uggaaggucuacc ugcucuggca gauuucaacc   120
gggcuuggac agaacuuacc gacuggcuuu cucgcuuga ucaaguuaua aaaucacaga    180
gggugauggu gggugacccuu gaggauauca acgagaugau caucaagcag aag           233

<210> SEQ ID NO 10
<211> LENGTH: 118
<212> TYPE: RNA
<213> ORGANISM: Homo sapiens

<400> SEQUENCE: 10
gcaacaaugc aggauuugga acagaggcgu ccccaguugg aagaacucau uaccgcugcc      60

```
caaaauuuga aaaacaagac cagcaaucaa gaggcuagaa caaucauuac ggaucgaa      118
```

<210> SEQ ID NO 11
<211> LENGTH: 212
<212> TYPE: RNA
<213> ORGANISM: Homo sapiens

<400> SEQUENCE: 11

```
uugaaagaau ucagaaucag ugggaugaag uacaagaaca ccuucagaac cggaggcaac      60
aguugaauga aauguuaaag gauucaacac aauggcugga agcuaaggaa gaagcugagc     120
aggucuuagg acaggccaga gccaagcuug agucauggaa ggagggcccc uauacaguag     180
augcaaucca aagaaaauc acagaaacca ag                                   212
```

<210> SEQ ID NO 12
<211> LENGTH: 155
<212> TYPE: RNA
<213> ORGANISM: Homo sapiens

<400> SEQUENCE: 12

```
caguuggcca aagaccuccg ccaguggcag acaaauguag auguggcaaa ugacuuggcc      60
cugaaacuuc uccgggauua uucugcagau gauaccagaa aaguccacau gauaacagag     120
aauaucaaug ccucuuggag aagcauucau aaaag                                155
```

<210> SEQ ID NO 13
<211> LENGTH: 190
<212> TYPE: RNA
<213> ORGANISM: Homo sapiens

<400> SEQUENCE: 13

```
ggugagugag cgagaggcug cuuuggaaga aacucauaga uuacugcaac aguuccccu       60
ggaccuggaa aaguuucuug ccuggcuuac agaagcugaa acaacugcca auguccuaca     120
ggaugcuacc cguaaggaaa ggcuccuaga agacuccaag ggaguaaaag agcugaugaa     180
acaauggcaa                                                            190
```

<210> SEQ ID NO 14
<211> LENGTH: 19
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)

```
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is uracil or 5-methyluracil

<400> SEQUENCE: 14
gnnnnnnnnn nnnngnnnn                                                  19

<210> SEQ ID NO 15
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
```

```
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is uracil or 5-methyluracil

<400> SEQUENCE: 15
nnngnnnnng nnngnnnnng                                              20

<210> SEQ ID NO 16
<211> LENGTH: 20
<212> TYPE: RNA
<213> ORGANISM: artificial
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is uracil or 5-methyluracil
<220> FEATURE:
```

<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is cytosine or 5-methylcytosine

<400> SEQUENCE: 16
nnngnnnnnn gnnngnnnnn        20

<210> SEQ ID NO 17
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine

```
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is cytosine or 5-methylcytosine

<400> SEQUENCE: 17
nnnnnnnggn nnnngngnnn nnn                                         23

<210> SEQ ID NO 18
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
```

```
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is cytosine or 5-methylcytosine

<400> SEQUENCE: 18
nnnnnngnnn nnngnnngnn nnn                                          23

<210> SEQ ID NO 19
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine

<400> SEQUENCE: 19
nnnnnggnnn nngngnnnnn n                                          21

<210> SEQ ID NO 20
<211> LENGTH: 23
<212> TYPE: RNA
<213> ORGANISM: Artificial
<220> FEATURE:
<223> OTHER INFORMATION: Oligonucleotide
<220> FEATURE:
```

```
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is adenine or 2,6-diaminopurine
```

<400> SEQUENCE: 20
gnnnnnnnnn nnnngnnnng nnn                                        23

<210> SEQ ID NO 21
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (21)..(21)

```
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is cytosine or 5-methylcytosine
<220> FEATURE:
<221> NAME/KEY: misc_feature
<222> LOCATION: (24)..(24)
<223> OTHER INFORMATION: n is uracil or 5-methyluracil

<400> SEQUENCE: 21
nnngnngnng nnnnnngnnn nnnng                                          25

<210> SEQ ID NO 22
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
```

<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is uracil or 5-methyluracil

<400> SEQUENCE: 22
nngnngnngn nnnnngnnnn nnng                                              24

<210> SEQ ID NO 23
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is adenine or 2,6-diaminopurine
<220> FEATURE:

```
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is uracil or 5-methyluracil

<400> SEQUENCE: 23
nngnngnngn nnnnngnnnn nnngg                                           25

<210> SEQ ID NO 24
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine
```

```
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is cytosine or 5-methylcytosine
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is uracil or 5-methyluracil

<400> SEQUENCE: 24
ngnngnngnn nnnngnnnnn nng                                             23

<210> SEQ ID NO 25
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
```

```
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is cytosine or 5-methylcytosine
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is uracil or 5-methyluracil

<400> SEQUENCE: 25
ngnngnngnn nnnngnnnnn nngg                                      24

<210> SEQ ID NO 26
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
```

<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is cytosine or 5-methylcytosine
<220> FEATURE:
<221> NAME/KEY: misc_feature
<222> LOCATION: (21)..(21)
<223> OTHER INFORMATION: n is uracil or 5-methyluracil

<400> SEQUENCE: 26
gnngnngnnn nnngnnnnnn ng                                            22

<210> SEQ ID NO 27
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:

```
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil

<400> SEQUENCE: 27
nngnngnnnn nngnnnnnnn gg                                              22

<210> SEQ ID NO 28
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is inosine
```

```
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is cytosine or 5-methylcytosine
<220> FEATURE:
<221> NAME/KEY: misc_feature
<222> LOCATION: (24)..(24)
<223> OTHER INFORMATION: n is uracil or 5-methyluracil

<400> SEQUENCE: 28
nnngnnnnng nnnnnngnnn nnnng                                           25

<210> SEQ ID NO 29
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
```

```
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is adenine or 2,6-diaminopurine
<220> FEATURE:
<221> NAME/KEY: misc_feature
<222> LOCATION: (24)..(24)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is cytosine or 5-methylcytosine

<400> SEQUENCE: 29
nngnnngnng nngnnnnnng nnnnn                                       25
```

```
<210> SEQ ID NO 30
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is adenine or 2,6-diaminopurine
<220> FEATURE:
```

```
<221> NAME/KEY: misc_feature
<222> LOCATION: (24)..(24)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is cytosine or 5-methylcytosine
<220> FEATURE:
<221> NAME/KEY: misc_feature
<222> LOCATION: (26)..(26)
<223> OTHER INFORMATION: n is cytosine or 5-methylcytosine
<220> FEATURE:
<221> NAME/KEY: misc_feature
<222> LOCATION: (27)..(27)
<223> OTHER INFORMATION: n is uracil or 5-methyluracil
<220> FEATURE:
<221> NAME/KEY: misc_feature
<222> LOCATION: (30)..(30)
<223> OTHER INFORMATION: n is adenine or 2,6-diaminopurine

<400> SEQUENCE: 30
nngnnngnng nngnnnnnng nnnnnnnggn                                          30

<210> SEQ ID NO 31
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is uracil or 5-methyluracil
```

```
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil

<400> SEQUENCE: 31
nnnnggnngn nggnnnnnnn                                                   20

<210> SEQ ID NO 32
<211> LENGTH: 17
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil

<400> SEQUENCE: 32
nggnnnnnnn ngnnngg                                                      17

<210> SEQ ID NO 33
```

```
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is uracil or 5-methyluracil

<400> SEQUENCE: 33
nnnnnnggnn gnnggnnnnn nn                                            22
```

-continued

```
<210> SEQ ID NO 34
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil
<220> FEATURE:
```

```
<221> NAME/KEY: misc_feature
<222> LOCATION: (24)..(24)
<223> OTHER INFORMATION: n is cytosine or 5-methylcytosine
<220> FEATURE:
<221> NAME/KEY: misc_feature
<222> LOCATION: (25)..(25)
<223> OTHER INFORMATION: n is uracil or 5-methyluracil

<400> SEQUENCE: 34
nnnnnnnnng gnngnnggnn nnnnn                                          25

<210> SEQ ID NO 35
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is adenine or 2,6-diaminopurine
```

```
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is uracil or 5-methyluracil

<400> SEQUENCE: 35
nnnnngngnn nnnnnnnnnn gnn                                             23

<210> SEQ ID NO 36
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
```

```
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is cytosine or 5-methylcytosine
<220> FEATURE:
<221> NAME/KEY: misc_feature
<222> LOCATION: (21)..(21)
<223> OTHER INFORMATION: n is adenine or 2,6-diaminopurine
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is cytosine or 5-methylcytosine

<400> SEQUENCE: 36
nnngngnngg nnnnnnnnnn nnn                                          23

<210> SEQ ID NO 37
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
```

```
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is adenine or 2,6-diaminopurine
<220> FEATURE:
<221> NAME/KEY: misc_feature
<222> LOCATION: (26)..(26)
<223> OTHER INFORMATION: n is uracil or 5-methyluracil
<220> FEATURE:
<221> NAME/KEY: misc_feature
<222> LOCATION: (27)..(27)
<223> OTHER INFORMATION: n is uracil or 5-methyluracil
<220> FEATURE:
<221> NAME/KEY: misc_feature
<222> LOCATION: (28)..(28)
<223> OTHER INFORMATION: n is uracil or 5-methyluracil

<400> SEQUENCE: 37
nnnnnnnggn ngnnggnnnn nnnngnnngg                                  30

<210> SEQ ID NO 38
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is uracil or 5-methyluracil
<220> FEATURE:
```

```
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is adenine or 2,6-diaminopurine

<400> SEQUENCE: 38
nnnnnnnggn ngnnggnnnn nnnng                                    25

<210> SEQ ID NO 39
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
```

```
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is cytosine or 5-methylcytosine

<400> SEQUENCE: 39
nnnnngnnng nnggnnnngn nnnnn                                           25

<210> SEQ ID NO 40
```

```
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil

<400> SEQUENCE: 40
ggnnnngngn nnnnnnnnnn gg                                              22

<210> SEQ ID NO 41
<211> LENGTH: 25
<212> TYPE: RNA
<213> ORGANISM: Artificial
```

```
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is cytosine or 5-methylcytosine
<220> FEATURE:
```

```
<221> NAME/KEY: misc_feature
<222> LOCATION: (25)..(25)
<223> OTHER INFORMATION: n is adenine or 2,6-diaminopurine

<400> SEQUENCE: 41
nnnngnnngn nggnnnngnn nnnnn                                              25

<210> SEQ ID NO 42
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is uracil or 5-methyluracil
```

```
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is cytosine or 5-methylcytosine
<220> FEATURE:
<221> NAME/KEY: misc_feature
<222> LOCATION: (25)..(25)
<223> OTHER INFORMATION: n is cytosine or 5-methylcytosine

<400> SEQUENCE: 42
nnnnnnnngg ggnngnnnnn gnnnn                                              25

<210> SEQ ID NO 43
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
```

```
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is cytosine or 5-methylcytosine
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is cytosine or 5-methylcytosine

<400> SEQUENCE: 43
ngnnnnngnn nnnngnnngn nggnn                                           25

<210> SEQ ID NO 44
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
```

```
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil

<400> SEQUENCE: 44
nngnngnnnn nggnnnng                                                 18

<210> SEQ ID NO 45
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
```

<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is adenine or 2,6-diaminopurine

<400> SEQUENCE: 45
nnnnngnngn nnnnggnnnn gn                                              22

<210> SEQ ID NO 46
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine

```
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is adenine or 2,6-diaminopurine

<400> SEQUENCE: 46
nnnnngnngn nnnnggnnnn gnn                                              23

<210> SEQ ID NO 47
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
```

```
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is adenine or 2,6-diaminopurine

<400> SEQUENCE: 47
nnnnngnngn nnnnggnnnn gnng                                         24

<210> SEQ ID NO 48
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
```

<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is adenine or 2,6-diaminopurine

<400> SEQUENCE: 48
nngnngnnnn nggnnnngnn gg                                             22

<210> SEQ ID NO 49
<211> LENGTH: 23
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is adenine or 2,6-diaminopurine
<220> FEATURE:

```
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is uracil or 5-methyluracil

<400> SEQUENCE: 49
nngnngnnnn nggnnnngnn ggn                                              23

<210> SEQ ID NO 50
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is adenine or 2,6-diaminopurine
```

```
<220> FEATURE:
<221> NAME/KEY: misc_feature
<222> LOCATION: (23)..(23)
<223> OTHER INFORMATION: n is uracil or 5-methyluracil

<400> SEQUENCE: 50
nngnngnnnn nggnnnngnn ggng                                          24

<210> SEQ ID NO 51
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
```

<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is uracil or 5-methyluracil

<400> SEQUENCE: 51
nngnngnnnn nggnnnngnn ggngn                                    25

<210> SEQ ID NO 52
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature

```
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is cytosine or 5-methylcytosine

<400> SEQUENCE: 52
gnngnnnnng gnnnngnngg ngnnn                                         25

<210> SEQ ID NO 53
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
```

```
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is uracil or 5-methyluracil

<400> SEQUENCE: 53
gnnnnnggnn nngnnggngn nnnng                                       25

<210> SEQ ID NO 54
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is uracil or 5-methyluracil
```

<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is cytosine or 5-methylcytosine
<220> FEATURE:
<221> NAME/KEY: misc_feature
<222> LOCATION: (25)..(25)
<223> OTHER INFORMATION: n is uracil or 5-methyluracil
<220> FEATURE:
<221> NAME/KEY: misc_feature
<222> LOCATION: (26)..(26)
<223> OTHER INFORMATION: n is uracil or 5-methyluracil
<220> FEATURE:
<221> NAME/KEY: misc_feature
<222> LOCATION: (28)..(28)
<223> OTHER INFORMATION: n is uracil or 5-methyluracil
<220> FEATURE:
<221> NAME/KEY: misc_feature
<222> LOCATION: (29)..(29)
<223> OTHER INFORMATION: n is adenine or 2,6-diaminopurine
<220> FEATURE:
<221> NAME/KEY: misc_feature
<222> LOCATION: (30)..(30)
<223> OTHER INFORMATION: n is cytosine or 5-methylcytosine

<400> SEQUENCE: 54
nngnnnnngg nnnngnnggn gnnnnngnnn                               30

<210> SEQ ID NO 55
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)

```
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is uracil or 5-methyluracil
<220> FEATURE:
<221> NAME/KEY: misc_feature
<222> LOCATION: (26)..(26)
<223> OTHER INFORMATION: n is uracil or 5-methyluracil
<220> FEATURE:
<221> NAME/KEY: misc_feature
<222> LOCATION: (27)..(27)
<223> OTHER INFORMATION: n is cytosine or 5-methylcytosine
<220> FEATURE:
<221> NAME/KEY: misc_feature
<222> LOCATION: (28)..(28)
<223> OTHER INFORMATION: n is uracil or 5-methyluracil
<220> FEATURE:
<221> NAME/KEY: misc_feature
<222> LOCATION: (29)..(29)
<223> OTHER INFORMATION: n is uracil or 5-methyluracil

<400> SEQUENCE: 55
nngnngnnnn nggnnnngnn gggngnnnng                                    30

<210> SEQ ID NO 56
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
```

```
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is adenine or 2,6-diaminopurine
<220> FEATURE:
<221> NAME/KEY: misc_feature
<222> LOCATION: (23)..(23)
<223> OTHER INFORMATION: n is adenine or 2,6-diaminopurine
<220> FEATURE:
<221> NAME/KEY: misc_feature
<222> LOCATION: (26)..(26)
<223> OTHER INFORMATION: n is uracil or 5-methyluracil
<220> FEATURE:
<221> NAME/KEY: misc_feature
<222> LOCATION: (28)..(28)
<223> OTHER INFORMATION: n is uracil or 5-methyluracil
<220> FEATURE:
<221> NAME/KEY: misc_feature
<222> LOCATION: (29)..(29)
<223> OTHER INFORMATION: n is uracil or 5-methyluracil
<220> FEATURE:
<221> NAME/KEY: misc_feature
<222> LOCATION: (30)..(30)
<223> OTHER INFORMATION: n is cytosine or 5-methylcytosine
<220> FEATURE:
<221> NAME/KEY: misc_feature
<222> LOCATION: (31)..(31)
<223> OTHER INFORMATION: n is uracil or 5-methyluracil
<220> FEATURE:
<221> NAME/KEY: misc_feature
<222> LOCATION: (32)..(32)
<223> OTHER INFORMATION: n is uracil or 5-methyluracil
```

<400> SEQUENCE: 56
nnnnngnngn nnnnggnnnn gnnggngnnn nng                                33

<210> SEQ ID NO 57
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is cytosine or 5-methylcytosine
<220> FEATURE:
<221> NAME/KEY: misc_feature
<222> LOCATION: (21)..(21)
<223> OTHER INFORMATION: n is uracil or 5-methyluracil

```
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is cytosine or 5-methylcytosine

<400> SEQUENCE: 57
gngnnnnnnn nnnngnngnn nnnn                                              24

<210> SEQ ID NO 58
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
```

```
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (22)..(22)
<223> OTHER INFORMATION: n is cytosine or 5-methylcytosine
<220> FEATURE:
<221> NAME/KEY: misc_feature
<222> LOCATION: (23)..(23)
<223> OTHER INFORMATION: n is cytosine or 5-methylcytosine
<220> FEATURE:
<221> NAME/KEY: misc_feature
<222> LOCATION: (24)..(24)
<223> OTHER INFORMATION: n is uracil or 5-methyluracil
<220> FEATURE:
<221> NAME/KEY: misc_feature
<222> LOCATION: (25)..(25)
<223> OTHER INFORMATION: n is cytosine or 5-methylcytosine

<400> SEQUENCE: 58
nnngngnnnn nnnnnnngnn gnnnn                                       25

<210> SEQ ID NO 59
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
```

```
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is adenine or 2,6-diaminopurine
<220> FEATURE:
<221> NAME/KEY: misc_feature
<222> LOCATION: (24)..(24)
<223> OTHER INFORMATION: n is uracil or 5-methyluracil

<400> SEQUENCE: 59
ngnnnnnngn nggnnnnngg nngn                                          24

<210> SEQ ID NO 60
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
```

```
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil

<400> SEQUENCE: 60
nnnnnngnng gnnnnnggnn gnng                                          24

<210> SEQ ID NO 61
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine
```

```
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is adenine or 2,6-diaminopurine
<220> FEATURE:
<221> NAME/KEY: misc_feature
<222> LOCATION: (20)..(20)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is uracil or 5-methyluracil

<400> SEQUENCE: 61
nnnngnnggn nnnnggnngn ngnn                                      24

<210> SEQ ID NO 62
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
```

```
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is uracil or 5-methyluracil
<220> FEATURE:
<221> NAME/KEY: misc_feature
<222> LOCATION: (22)..(22)
<223> OTHER INFORMATION: n is uracil or 5-methyluracil
<220> FEATURE:
<221> NAME/KEY: misc_feature
<222> LOCATION: (23)..(23)
<223> OTHER INFORMATION: n is uracil or 5-methyluracil
<220> FEATURE:
<221> NAME/KEY: misc_feature
<222> LOCATION: (24)..(24)
<223> OTHER INFORMATION: n is cytosine or 5-methylcytosine

<400> SEQUENCE: 62
nngnnggnnn nnggnngnng nnnn                                        24

<210> SEQ ID NO 63
<211> LENGTH: 13
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
```

```
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine

<400> SEQUENCE: 63
nnnnnnnnnn ngn                                                    13

<210> SEQ ID NO 64
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is adenine or 2,6-diaminopurine

<400> SEQUENCE: 64
ngnnnnngnn ngnnn                                                  15
```

```
<210> SEQ ID NO 65
<211> LENGTH: 11
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is adenine or 2,6-diaminopurine

<400> SEQUENCE: 65
nnnnnnnggn n                                                       11

<210> SEQ ID NO 66
<211> LENGTH: 14
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is adenine or 2,6-diaminopurine
```

```
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine

<400> SEQUENCE: 66
nnnngnnnnn ngnn                                                      14

<210> SEQ ID NO 67
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
```

```
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine

<400> SEQUENCE: 67 nnnnnnnnn ngnnnngnnn                                           20

<210> SEQ ID NO 68
<211> LENGTH: 13
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
```

```
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine

<400> SEQUENCE: 68
nnnnnnnnnn ngn                                                         13

<210> SEQ ID NO 69
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine

<400> SEQUENCE: 69
nnngnnnngn nn                                                          12

<210> SEQ ID NO 70
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is uracil or 5-methyluracil
<220> FEATURE:
```

<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is adenine or 2,6-diaminopurine

<400> SEQUENCE: 70
nnngnngnng nnnnnngnnn                                        20

<210> SEQ ID NO 71
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine

```
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is adenine or 2,6-diaminopurine
<220> FEATURE:
<221> NAME/KEY: misc_feature
<222> LOCATION: (10)..(10)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is cytosine or 5-methylcytosine
<220> FEATURE:
<221> NAME/KEY: misc_feature
<222> LOCATION: (18)..(18)
<223> OTHER INFORMATION: n is cytosine or 5-methylcytosine
<220> FEATURE:
<221> NAME/KEY: misc_feature
<222> LOCATION: (19)..(19)
<223> OTHER INFORMATION: n is uracil or 5-methyluracil

<400> SEQUENCE: 71
ngnngnnnnn ngnnnnnnng                                                   20

<210> SEQ ID NO 72
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (5)..(5)
```

```
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is cytosine or 5-methylcytosine
<220> FEATURE:
<221> NAME/KEY: misc_feature
<222> LOCATION: (17)..(17)
<223> OTHER INFORMATION: n is adenine or 2,6-diaminopurine
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is cytosine or 5-methylcytosine
<220> FEATURE:
<221> NAME/KEY: misc_feature
<222> LOCATION: (20)..(20)
<223> OTHER INFORMATION: n is cytosine or 5-methylcytosine

<400> SEQUENCE: 72
gnngnngnnn nnngnnnnnn                                          20

<210> SEQ ID NO 73
<211> LENGTH: 13
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
```

<222> LOCATION: (6)..(6)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is adenine or 2,6-diaminopurine

<400> SEQUENCE: 73
nnggnngnng gnn                               13

<210> SEQ ID NO 74
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine

<400> SEQUENCE: 74
nggnngnngg nn                                12

<210> SEQ ID NO 75
<211> LENGTH: 10
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is adenine or 2,6-diaminopurine
<220> FEATURE:

```
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is adenine or 2,6-diaminopurine

<400> SEQUENCE: 75 ngngnnggnn                                                            10

<210> SEQ ID NO 76
<211> LENGTH: 14
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine

<400> SEQUENCE: 76
ngnnggnnnn nnnn                                                       14

<210> SEQ ID NO 77
<211> LENGTH: 10
```

```
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is adenine or 2,6-diaminopurine
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is adenine or 2,6-diaminopurine

<400> SEQUENCE: 77 nnnnnnnnnn                                                            10

<210> SEQ ID NO 78
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
```

```
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is cytosine or 5-methylcytosine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is adenine or 2,6-diaminopurine

<400> SEQUENCE: 78
nnngngnnnn nnnnn                                                            15

<210> SEQ ID NO 79
<211> LENGTH: 13
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
```

```
<222> LOCATION: (12)..(12)
<223> OTHER INFORMATION: n is cytosine or 5-methylcytosine
<220> FEATURE:
<221> NAME/KEY: misc_feature
<222> LOCATION: (13)..(13)
<223> OTHER INFORMATION: n is adenine or 2,6-diaminopurine

<400> SEQUENCE: 79
nngngnnnnn nnn                                                        13

<210> SEQ ID NO 80
<211> LENGTH: 10
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is adenine or 2,6-diaminopurine

<400> SEQUENCE: 80 ngnnnnnnnn                                                            10

<210> SEQ ID NO 81
<211> LENGTH: 10
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
```

<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is adenine or 2,6-diaminopurine

<400> SEQUENCE: 81 ngnnnnnngn                                                          10

<210> SEQ ID NO 82
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is cytosine or 5-methylcytosine
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is uracil or 5-methyluracil
<220> FEATURE:
<221> NAME/KEY: misc_feature
<222> LOCATION: (14)..(14)
<223> OTHER INFORMATION: n is cytosine or 5-methylcytosine
<220> FEATURE:
<221> NAME/KEY: misc_feature
<222> LOCATION: (15)..(15)
<223> OTHER INFORMATION: n is uracil or 5-methyluracil
<220> FEATURE:
<221> NAME/KEY: misc_feature
<222> LOCATION: (17)..(17)
<223> OTHER INFORMATION: n is adenine or 2,6-diaminopurine

```
<220> FEATURE:
<221> NAME/KEY: misc_feature
<222> LOCATION: (18)..(18)
<223> OTHER INFORMATION: n is adenine or 2,6-diaminopurine

<400> SEQUENCE: 82
gnngnnnnng gnnnngnngg                                               20

<210> SEQ ID NO 83
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (16)..(16)
<223> OTHER INFORMATION: n is uracil or 5-methyluracil
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (19)..(19)
<223> OTHER INFORMATION: n is uracil or 5-methyluracil
<220> FEATURE:
<221> NAME/KEY: misc_feature
<222> LOCATION: (20)..(20)
<223> OTHER INFORMATION: n is cytosine or 5-methylcytosine

<400> SEQUENCE: 83
nnnnggnnnn gnnggngnnn                                               20

<210> SEQ ID NO 84
```

-continued

```
<211> LENGTH: 17
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is cytosine or 5-methylcytosine
<220> FEATURE:
<221> NAME/KEY: misc_feature
<222> LOCATION: (2)..(2)
<223> OTHER INFORMATION: n is cytosine or 5-methylcytosine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is uracil or 5-methyluracil
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil

<400> SEQUENCE: 84
nnnnnggnnn ngnnggn                                                  17

<210> SEQ ID NO 85
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
```

<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (12)..(12)
<223> OTHER INFORMATION: n is adenine or 2,6-diaminopurine
<220> FEATURE:
<221> NAME/KEY: misc_feature
<222> LOCATION: (13)..(13)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is adenine or 2,6-diaminopurine

<400> SEQUENCE: 85
ngnnnnnnnn nnngnn                                                    16

<210> SEQ ID NO 86
<211> LENGTH: 11
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is uracil or 5-methyluracil
<220> FEATURE:
<221> NAME/KEY: misc_feature
<222> LOCATION: (4)..(4)
<223> OTHER INFORMATION: n is uracil or 5-methyluracil
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is uracil or 5-methyluracil
<220> FEATURE:

```
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (9)..(9)
<223> OTHER INFORMATION: n is cytosine or 5-methylcytosine
<220> FEATURE:
<221> NAME/KEY: misc_feature
<222> LOCATION: (10)..(10)
<223> OTHER INFORMATION: n is cytosine or 5-methylcytosine
<220> FEATURE:
<221> NAME/KEY: misc_feature
<222> LOCATION: (11)..(11)
<223> OTHER INFORMATION: n is adenine or 2,6-diaminopurine

<400> SEQUENCE: 86
ngnnnnnnnn n                                                              11

<210> SEQ ID NO 87
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is adenine or 2,6-diaminopurine
<220> FEATURE:
<221> NAME/KEY: misc_feature
<222> LOCATION: (14)..(14)
<223> OTHER INFORMATION: n is adenine or 2,6-diaminopurine
<220> FEATURE:
<221> NAME/KEY: misc_feature
<222> LOCATION: (15)..(15)
<223> OTHER INFORMATION: n is cytosine or 5-methylcytosine
<220> FEATURE:
<221> NAME/KEY: misc_feature
<222> LOCATION: (16)..(16)
<223> OTHER INFORMATION: n is adenine or 2,6-diaminopurine
<220> FEATURE:
<221> NAME/KEY: misc_feature
<222> LOCATION: (17)..(17)
<223> OTHER INFORMATION: n is uracil or 5-methyluracil
```

```
<220> FEATURE:
<221> NAME/KEY: misc_feature
<222> LOCATION: (18)..(18)
<223> OTHER INFORMATION: n is uracil or 5-methyluracil
<220> FEATURE:
<221> NAME/KEY: misc_feature
<222> LOCATION: (21)..(21)
<223> OTHER INFORMATION: n is cytosine or 5-methylcytosine
<220> FEATURE:
<221> NAME/KEY: misc_feature
<222> LOCATION: (22)..(22)
<223> OTHER INFORMATION: n is adenine or 2,6-diaminopurine

<400> SEQUENCE: 87
ngnnnnnngn nggnnnnnggg nn                                              22

<210> SEQ ID NO 88
<211> LENGTH: 11
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (6)..(6)
<223> OTHER INFORMATION: n is cytosine or 5-methylcytosine
<220> FEATURE:
<221> NAME/KEY: misc_feature
<222> LOCATION: (7)..(7)
<223> OTHER INFORMATION: n is cytosine or 5-methylcytosine
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (10)..(10)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is adenine or 2,6-diaminopurine

<400> SEQUENCE: 88
ngnnnnnngn n                                                           11

<210> SEQ ID NO 89
<211> LENGTH: 11
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (2)..(2)
```

-continued

```
<223> OTHER INFORMATION: n is uracil or 5-methyluracil
<220> FEATURE:
<221> NAME/KEY: misc_feature
<222> LOCATION: (3)..(3)
<223> OTHER INFORMATION: n is cytosine or 5-methylcytosine
<220> FEATURE:
<221> NAME/KEY: misc_feature
<222> LOCATION: (4)..(4)
<223> OTHER INFORMATION: n is cytosine or 5-methylcytosine
<220> FEATURE:
<221> NAME/KEY: misc_feature
<222> LOCATION: (5)..(5)
<223> OTHER INFORMATION: n is uracil or 5-methyluracil
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is adenine or 2,6-diaminopurine
<220> FEATURE:
<221> NAME/KEY: misc_feature
<222> LOCATION: (11)..(11)
<223> OTHER INFORMATION: n is adenine or 2,6-diaminopurine

<400> SEQUENCE: 89
nnnnngnngg n                                                          11

<210> SEQ ID NO 90
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is adenine or 2,6-diaminopurine
<220> FEATURE:
<221> NAME/KEY: misc_feature
<222> LOCATION: (4)..(4)
<223> OTHER INFORMATION: n is adenine or 2,6-diaminopurine
<220> FEATURE:
<221> NAME/KEY: misc_feature
<222> LOCATION: (5)..(5)
<223> OTHER INFORMATION: n is cytosine or 5-methylcytosine
<220> FEATURE:
<221> NAME/KEY: misc_feature
<222> LOCATION: (6)..(6)
<223> OTHER INFORMATION: n is adenine or 2,6-diaminopurine
<220> FEATURE:
<221> NAME/KEY: misc_feature
<222> LOCATION: (7)..(7)
<223> OTHER INFORMATION: n is uracil or 5-methyluracil
<220> FEATURE:
<221> NAME/KEY: misc_feature
<222> LOCATION: (8)..(8)
<223> OTHER INFORMATION: n is uracil or 5-methyluracil
<220> FEATURE:
<221> NAME/KEY: misc_feature
<222> LOCATION: (11)..(11)
<223> OTHER INFORMATION: n is cytosine or 5-methylcytosine
<220> FEATURE:
<221> NAME/KEY: misc_feature
<222> LOCATION: (12)..(12)
<223> OTHER INFORMATION: n is adenine or 2,6-diaminopurine

<400> SEQUENCE: 90
nggnnnnngg nn                                                         12

<210> SEQ ID NO 91
<211> LENGTH: 25
<212> TYPE: RNA
<213> ORGANISM: Artificial
```

```
<220> FEATURE:
<223> OTHER INFORMATION: Oligonucleotide

<400> SEQUENCE: 91
guugccuccg guucugaagg uguuc                                              25

<210> SEQ ID NO 92
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: 5-methylcytosine
<220> FEATURE:
<221> NAME/KEY: misc_feature
<222> LOCATION: (6)..(6)
<223> OTHER INFORMATION: 5-methylcytosine
<220> FEATURE:
<221> NAME/KEY: misc_feature
<222> LOCATION: (8)..(8)
<223> OTHER INFORMATION: 5-methylcytosine
<220> FEATURE:
<221> NAME/KEY: misc_feature
<222> LOCATION: (9)..(9)
<223> OTHER INFORMATION: 5-methylcytosine
<220> FEATURE:
<221> NAME/KEY: misc_feature
<222> LOCATION: (14)..(14)
<223> OTHER INFORMATION: 5-methylcytosine
<220> FEATURE:
<221> NAME/KEY: misc_feature
<222> LOCATION: (25)..(25)
<223> OTHER INFORMATION: 5-methylcytosine

<400> SEQUENCE: 92
guugnnunng guunugaagg uguun                                              25

<210> SEQ ID NO 93
<211> LENGTH: 25
<212> TYPE: RNA
<213> ORGANISM: Artificial
<220> FEATURE:
<223> OTHER INFORMATION: Oligonucleotide

<400> SEQUENCE: 93
caacaucaag gaagauggca uuucu                                              25

<210> SEQ ID NO 94
<211> LENGTH: 19
<212> TYPE: RNA
<213> ORGANISM: Artificial
<220> FEATURE:
<223> OTHER INFORMATION: Oligonucleotide

<400> SEQUENCE: 94
gccauuucuc aacagaucu                                                     19

<210> SEQ ID NO 95
<211> LENGTH: 20
<212> TYPE: RNA
<213> ORGANISM: Artificial
<220> FEATURE:
<223> OTHER INFORMATION: Oligonucleotide

<400> SEQUENCE: 95
ucagcuucug uuagccacug                                                    20
```

<210> SEQ ID NO 96
<211> LENGTH: 20
<212> TYPE: RNA
<213> ORGANISM: Artificial
<220> FEATURE:
<223> OTHER INFORMATION: Oligonucleotide

<400> SEQUENCE: 96
uuuguauuua gcauguuccc                                               20

<210> SEQ ID NO 97
<211> LENGTH: 23
<212> TYPE: RNA
<213> ORGANISM: Artificial
<220> FEATURE:
<223> OTHER INFORMATION: Oligonucleotide

<400> SEQUENCE: 97
auucucagga auugugucu uuc                                            23

<210> SEQ ID NO 98
<211> LENGTH: 23
<212> TYPE: RNA
<213> ORGANISM: Artificial
<220> FEATURE:
<223> OTHER INFORMATION: Oligonucleotide

<400> SEQUENCE: 98
ccauuuguau uuagcauguu ccc                                           23

<210> SEQ ID NO 99
<211> LENGTH: 21
<212> TYPE: RNA
<213> ORGANISM: Artificial
<220> FEATURE:
<223> OTHER INFORMATION: Oligonucleotide

<400> SEQUENCE: 99
ucucaggaau uugugucuuu c                                             21

<210> SEQ ID NO 100
<211> LENGTH: 23
<212> TYPE: RNA
<213> ORGANISM: Artificial
<220> FEATURE:
<223> OTHER INFORMATION: Oligonucleotide

<400> SEQUENCE: 100
gccauuucuc aacagaucug uca                                           23

<210> SEQ ID NO 101
<211> LENGTH: 25
<212> TYPE: RNA
<213> ORGANISM: Artificial
<220> FEATURE:
<223> OTHER INFORMATION: Oligonucleotide

<400> SEQUENCE: 101
uuugccgcug cccaaugcca uccug                                         25

<210> SEQ ID NO 102
<211> LENGTH: 24
<212> TYPE: RNA
<213> ORGANISM: Artificial
<220> FEATURE:
<223> OTHER INFORMATION: Oligonucleotide

```
<400> SEQUENCE: 102
uugccgcugc ccaaugccau ccug                                         24

<210> SEQ ID NO 103
<211> LENGTH: 25
<212> TYPE: RNA
<213> ORGANISM: Artificial
<220> FEATURE:
<223> OTHER INFORMATION: Oligonucleotide

<400> SEQUENCE: 103
uugccgcugc ccaaugccau ccugg                                        25

<210> SEQ ID NO 104
<211> LENGTH: 23
<212> TYPE: RNA
<213> ORGANISM: Artificial
<220> FEATURE:
<223> OTHER INFORMATION: Oligonucleotide

<400> SEQUENCE: 104
ugccgcugcc caaugccauc cug                                          23

<210> SEQ ID NO 105
<211> LENGTH: 24
<212> TYPE: RNA
<213> ORGANISM: Artificial
<220> FEATURE:
<223> OTHER INFORMATION: Oligonucleotide

<400> SEQUENCE: 105
ugccgcugcc caaugccauc cugg                                         24

<210> SEQ ID NO 106
<211> LENGTH: 22
<212> TYPE: RNA
<213> ORGANISM: Artificial
<220> FEATURE:
<223> OTHER INFORMATION: Oligonucleotide

<400> SEQUENCE: 106
gccgcugccc aaugccaucc ug                                           22

<210> SEQ ID NO 107
<211> LENGTH: 22
<212> TYPE: RNA
<213> ORGANISM: Artificial
<220> FEATURE:
<223> OTHER INFORMATION: Oligonucleotide

<400> SEQUENCE: 107
ccgcugccca augccauccu gg                                           22

<210> SEQ ID NO 108
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is inosine

<400> SEQUENCE: 108
```
uuugccncug cccaaugcca uccug                                            25

<210> SEQ ID NO 109
<211> LENGTH: 25
<212> TYPE: RNA
<213> ORGANISM: Artificial
<220> FEATURE:
<223> OTHER INFORMATION: Oligonucleotide

<400> SEQUENCE: 109
caguuugccg cugcccaaug ccauc                                            25

<210> SEQ ID NO 110
<211> LENGTH: 30
<212> TYPE: RNA
<213> ORGANISM: Artificial
<220> FEATURE:
<223> OTHER INFORMATION: Oligonucleotide

<400> SEQUENCE: 110
caguuugccg cugcccaaug ccauccugga                                       30

<210> SEQ ID NO 111
<211> LENGTH: 20
<212> TYPE: RNA
<213> ORGANISM: Artificial
<220> FEATURE:
<223> OTHER INFORMATION: Oligonucleotide

<400> SEQUENCE: 111
ucaaggaaga uggcauuucu                                                  20

<210> SEQ ID NO 112
<211> LENGTH: 17
<212> TYPE: RNA
<213> ORGANISM: Artificial
<220> FEATURE:
<223> OTHER INFORMATION: Oligonucleotide

<400> SEQUENCE: 112
uggcauuucu aguuugg                                                     17

<210> SEQ ID NO 113
<211> LENGTH: 22
<212> TYPE: RNA
<213> ORGANISM: Artificial
<220> FEATURE:
<223> OTHER INFORMATION: Oligonucleotide

<400> SEQUENCE: 113
caucaaggaa gauggcauuu cu                                               22

<210> SEQ ID NO 114
<211> LENGTH: 25
<212> TYPE: RNA
<213> ORGANISM: Artificial
<220> FEATURE:
<223> OTHER INFORMATION: Oligonucleotide

<400> SEQUENCE: 114
caacaucaag gaagauggca uuucu                                            25

<210> SEQ ID NO 115
<211> LENGTH: 23
<212> TYPE: RNA
<213> ORGANISM: Artificial

-continued

```
<220> FEATURE:
<223> OTHER INFORMATION: Oligonucleotide

<400> SEQUENCE: 115
ccucugugau uuuauaacuu gau                                          23

<210> SEQ ID NO 116
<211> LENGTH: 23
<212> TYPE: RNA
<213> ORGANISM: Artificial
<220> FEATURE:
<223> OTHER INFORMATION: Oligonucleotide

<400> SEQUENCE: 116
ccagagcagg uaccuccaac auc                                          23

<210> SEQ ID NO 117
<211> LENGTH: 30
<212> TYPE: RNA
<213> ORGANISM: Artificial
<220> FEATURE:
<223> OTHER INFORMATION: Oligonucleotide

<400> SEQUENCE: 117
acaucaagga agauggcauu ucuaguuugg                                   30

<210> SEQ ID NO 118
<211> LENGTH: 25
<212> TYPE: RNA
<213> ORGANISM: Artificial
<220> FEATURE:
<223> OTHER INFORMATION: Oligonucleotide

<400> SEQUENCE: 118
acaucaagga agauggcauu ucuag                                        25

<210> SEQ ID NO 119
<211> LENGTH: 25
<212> TYPE: RNA
<213> ORGANISM: Artificial
<220> FEATURE:
<223> OTHER INFORMATION: Oligonucleotide

<400> SEQUENCE: 119
cucuugauug cggucuugu uuuuc                                         25

<210> SEQ ID NO 120
<211> LENGTH: 22
<212> TYPE: RNA
<213> ORGANISM: Artificial
<220> FEATURE:
<223> OTHER INFORMATION: Oligonucleotide

<400> SEQUENCE: 120
gguaaugagu ucuuccaacu gg                                           22

<210> SEQ ID NO 121
<211> LENGTH: 25
<212> TYPE: RNA
<213> ORGANISM: Artificial
<220> FEATURE:
<223> OTHER INFORMATION: Oligonucleotide

<400> SEQUENCE: 121
ucuugauugc uggucuuguu uuuca                                        25
```

```
<210> SEQ ID NO 122
<211> LENGTH: 25
<212> TYPE: RNA
<213> ORGANISM: Artificial
<220> FEATURE:
<223> OTHER INFORMATION: Oligonucleotide

<400> SEQUENCE: 122
uuccaacugg ggacgccucu guucc                                             25

<210> SEQ ID NO 123
<211> LENGTH: 25
<212> TYPE: RNA
<213> ORGANISM: Artificial
<220> FEATURE:
<223> OTHER INFORMATION: Oligonucleotide

<400> SEQUENCE: 123
uguucuagcc ucuugauugc ugguc                                             25

<210> SEQ ID NO 124
<211> LENGTH: 18
<212> TYPE: RNA
<213> ORGANISM: Artificial
<220> FEATURE:
<223> OTHER INFORMATION: Oligonucleotide

<400> SEQUENCE: 124
cuguugccuc cgguucug                                                     18

<210> SEQ ID NO 125
<211> LENGTH: 22
<212> TYPE: RNA
<213> ORGANISM: Artificial
<220> FEATURE:
<223> OTHER INFORMATION: Oligonucleotide

<400> SEQUENCE: 125
caacuguugc cuccgguucu ga                                                22

<210> SEQ ID NO 126
<211> LENGTH: 23
<212> TYPE: RNA
<213> ORGANISM: Artificial
<220> FEATURE:
<223> OTHER INFORMATION: Oligonucleotide

<400> SEQUENCE: 126
caacuguugc cuccgguucu gaa                                               23

<210> SEQ ID NO 127
<211> LENGTH: 24
<212> TYPE: RNA
<213> ORGANISM: Artificial
<220> FEATURE:
<223> OTHER INFORMATION: Oligonucleotide

<400> SEQUENCE: 127
caacuguugc cuccgguucu gaag                                              24

<210> SEQ ID NO 128
<211> LENGTH: 22
<212> TYPE: RNA
<213> ORGANISM: Artificial
<220> FEATURE:
<223> OTHER INFORMATION: Oligonucleotide
```

```
<400> SEQUENCE: 128
cuguugccuc cgguucugaa gg                                              22

<210> SEQ ID NO 129
<211> LENGTH: 23
<212> TYPE: RNA
<213> ORGANISM: Artificial
<220> FEATURE:
<223> OTHER INFORMATION: Oligonucleotide

<400> SEQUENCE: 129
cuguugccuc cgguucugaa ggu                                             23

<210> SEQ ID NO 130
<211> LENGTH: 24
<212> TYPE: RNA
<213> ORGANISM: Artificial
<220> FEATURE:
<223> OTHER INFORMATION: Oligonucleotide

<400> SEQUENCE: 130
cuguugccuc cgguucugaa ggug                                            24

<210> SEQ ID NO 131
<211> LENGTH: 25
<212> TYPE: RNA
<213> ORGANISM: Artificial
<220> FEATURE:
<223> OTHER INFORMATION: Oligonucleotide

<400> SEQUENCE: 131
cuguugccuc cgguucugaa ggugu                                           25

<210> SEQ ID NO 132
<211> LENGTH: 25
<212> TYPE: RNA
<213> ORGANISM: Artificial
<220> FEATURE:
<223> OTHER INFORMATION: Oligonucleotide

<400> SEQUENCE: 132
guugccuccg guucugaagg uguuc                                           25

<210> SEQ ID NO 133
<211> LENGTH: 25
<212> TYPE: RNA
<213> ORGANISM: Artificial
<220> FEATURE:
<223> OTHER INFORMATION: Oligonucleotide

<400> SEQUENCE: 133
gccuccgguu cugaaggugu ucuug                                           25

<210> SEQ ID NO 134
<211> LENGTH: 30
<212> TYPE: RNA
<213> ORGANISM: Artificial
<220> FEATURE:
<223> OTHER INFORMATION: Oligonucleotide

<400> SEQUENCE: 134
uugccuccgg uucugaaggu guucuuguac                                      30

<210> SEQ ID NO 135
```

```
<211> LENGTH: 30
<212> TYPE: RNA
<213> ORGANISM: Artificial
<220> FEATURE:
<223> OTHER INFORMATION: Oligonucleotide

<400> SEQUENCE: 135 cguugccuc cgguucugaa ggguguucuug                                30

<210> SEQ ID NO 136
<211> LENGTH: 33
<212> TYPE: RNA
<213> ORGANISM: Artificial
<220> FEATURE:
<223> OTHER INFORMATION: Oligonucleotide

<400> SEQUENCE: 136
caacuguugc cuccgguucu gaagguguuc uug                            33

<210> SEQ ID NO 137
<211> LENGTH: 24
<212> TYPE: RNA
<213> ORGANISM: Artificial
<220> FEATURE:
<223> OTHER INFORMATION: Oligonucleotide

<400> SEQUENCE: 137 gaguucuuc caaagcagcc ucuc                                       24

<210> SEQ ID NO 138
<211> LENGTH: 25
<212> TYPE: RNA
<213> ORGANISM: Artificial
<220> FEATURE:
<223> OTHER INFORMATION: Oligonucleotide

<400> SEQUENCE: 138
uaugaguuuc uuccaaagca gccuc                                     25

<210> SEQ ID NO 139
<211> LENGTH: 24
<212> TYPE: RNA
<213> ORGANISM: Artificial
<220> FEATURE:
<223> OTHER INFORMATION: Oligonucleotide

<400> SEQUENCE: 139
agcauccugu aggacauugg cagu                                      24

<210> SEQ ID NO 140
<211> LENGTH: 24
<212> TYPE: RNA
<213> ORGANISM: Artificial
<220> FEATURE:
<223> OTHER INFORMATION: Oligonucleotide

<400> SEQUENCE: 140
cauccuguag gacauuggca guug                                      24

<210> SEQ ID NO 141
<211> LENGTH: 24
<212> TYPE: RNA
<213> ORGANISM: Artificial
<220> FEATURE:
<223> OTHER INFORMATION: Oligonucleotide

<400> SEQUENCE: 141
```
uccuguagga cauuggcagu uguu                                          24

<210> SEQ ID NO 142
<211> LENGTH: 24
<212> TYPE: RNA
<213> ORGANISM: Artificial
<220> FEATURE:
<223> OTHER INFORMATION: Oligonucleotide

<400> SEQUENCE: 142
cuguaggaca uuggcaguug uuuc                                          24

<210> SEQ ID NO 143
<211> LENGTH: 13
<212> TYPE: RNA
<213> ORGANISM: Artificial
<220> FEATURE:
<223> OTHER INFORMATION: Oligonucleotide

<400> SEQUENCE: 143
auuucucaac aga                                                      13

<210> SEQ ID NO 144
<211> LENGTH: 15
<212> TYPE: RNA
<213> ORGANISM: Artificial
<220> FEATURE:
<223> OTHER INFORMATION: Oligonucleotide

<400> SEQUENCE: 144
agcuucuguu agcca                                                    15

<210> SEQ ID NO 145
<211> LENGTH: 11
<212> TYPE: RNA
<213> ORGANISM: Artificial
<220> FEATURE:
<223> OTHER INFORMATION: Oligonucleotide

<400> SEQUENCE: 145
auucucagga a                                                        11

<210> SEQ ID NO 146
<211> LENGTH: 14
<212> TYPE: RNA
<213> ORGANISM: Artificial
<220> FEATURE:
<223> OTHER INFORMATION: Oligonucleotide

<400> SEQUENCE: 146
auuuguauuu agca                                                     14

<210> SEQ ID NO 147
<211> LENGTH: 20
<212> TYPE: RNA
<213> ORGANISM: Artificial
<220> FEATURE:
<223> OTHER INFORMATION: Oligonucleotide

<400> SEQUENCE: 147
auuucucaac agaucuguca                                               20

<210> SEQ ID NO 148
<211> LENGTH: 13
<212> TYPE: RNA

```
<213> ORGANISM: Artificial
<220> FEATURE:
<223> OTHER INFORMATION: Oligonucleotide

<400> SEQUENCE: 148
auuucucaac aga                                                          13

<210> SEQ ID NO 149
<211> LENGTH: 12
<212> TYPE: RNA
<213> ORGANISM: Artificial
<220> FEATURE:
<223> OTHER INFORMATION: Oligonucleotide

<400> SEQUENCE: 149
acagaucugu ca                                                           12

<210> SEQ ID NO 150
<211> LENGTH: 20
<212> TYPE: RNA
<213> ORGANISM: Artificial
<220> FEATURE:
<223> OTHER INFORMATION: Oligonucleotide

<400> SEQUENCE: 150
uuugccgcug cccaaugcca                                                   20

<210> SEQ ID NO 151
<211> LENGTH: 20
<212> TYPE: RNA
<213> ORGANISM: Artificial
<220> FEATURE:
<223> OTHER INFORMATION: Oligonucleotide

<400> SEQUENCE: 151
cgcugcccaa ugccauccug                                                   20

<210> SEQ ID NO 152
<211> LENGTH: 20
<212> TYPE: RNA
<213> ORGANISM: Artificial
<220> FEATURE:
<223> OTHER INFORMATION: Oligonucleotide

<400> SEQUENCE: 152
gccgcugccc aaugccaucc                                                   20

<210> SEQ ID NO 153
<211> LENGTH: 13
<212> TYPE: RNA
<213> ORGANISM: Artificial
<220> FEATURE:
<223> OTHER INFORMATION: Oligonucleotide

<400> SEQUENCE: 153
aaggaagaug gca                                                          13

<210> SEQ ID NO 154
<211> LENGTH: 12
<212> TYPE: RNA
<213> ORGANISM: Artificial
<220> FEATURE:
<223> OTHER INFORMATION: Oligonucleotide

<400> SEQUENCE: 154
aggaagaugg ca                                                           12
```

```
<210> SEQ ID NO 155
<211> LENGTH: 10
<212> TYPE: RNA
<213> ORGANISM: Artificial
<220> FEATURE:
<223> OTHER INFORMATION: Oligonucleotide

<400> SEQUENCE: 155
agagcaggua                                                            10

<210> SEQ ID NO 156
<211> LENGTH: 14
<212> TYPE: RNA
<213> ORGANISM: Artificial
<220> FEATURE:
<223> OTHER INFORMATION: Oligonucleotide

<400> SEQUENCE: 156
agcagguacc ucca                                                       14

<210> SEQ ID NO 157
<211> LENGTH: 10
<212> TYPE: RNA
<213> ORGANISM: Artificial
<220> FEATURE:
<223> OTHER INFORMATION: Oligonucleotide

<400> SEQUENCE: 157
accuccaaca                                                            10

<210> SEQ ID NO 158
<211> LENGTH: 15
<212> TYPE: RNA
<213> ORGANISM: Artificial
<220> FEATURE:
<223> OTHER INFORMATION: Oligonucleotide

<400> SEQUENCE: 158
aaugaguucu uccaa                                                      15

<210> SEQ ID NO 159
<211> LENGTH: 13
<212> TYPE: RNA
<213> ORGANISM: Artificial
<220> FEATURE:
<223> OTHER INFORMATION: Oligonucleotide

<400> SEQUENCE: 159
augaguucuu cca                                                        13

<210> SEQ ID NO 160
<211> LENGTH: 10
<212> TYPE: RNA
<213> ORGANISM: Artificial
<220> FEATURE:
<223> OTHER INFORMATION: Oligonucleotide

<400> SEQUENCE: 160
aguucuucca                                                            10

<210> SEQ ID NO 161
<211> LENGTH: 10
<212> TYPE: RNA
<213> ORGANISM: Artificial
<220> FEATURE:
```

<223> OTHER INFORMATION: Oligonucleotide

<400> SEQUENCE: 161
agccucuuga                                                              10

<210> SEQ ID NO 162
<211> LENGTH: 20
<212> TYPE: RNA
<213> ORGANISM: Artificial
<220> FEATURE:
<223> OTHER INFORMATION: Oligonucleotide

<400> SEQUENCE: 162
guugccuccg guucugaagg                                                   20

<210> SEQ ID NO 163
<211> LENGTH: 20
<212> TYPE: RNA
<213> ORGANISM: Artificial
<220> FEATURE:
<223> OTHER INFORMATION: Oligonucleotide

<400> SEQUENCE: 163
cuccgguucu gaagguguuc                                                   20

<210> SEQ ID NO 164
<211> LENGTH: 17
<212> TYPE: RNA
<213> ORGANISM: Artificial
<220> FEATURE:
<223> OTHER INFORMATION: Oligonucleotide

<400> SEQUENCE: 164
ccuccgguuc ugaaggu                                                      17

<210> SEQ ID NO 165
<211> LENGTH: 16
<212> TYPE: RNA
<213> ORGANISM: Artificial
<220> FEATURE:
<223> OTHER INFORMATION: Oligonucleotide

<400> SEQUENCE: 165
aguuucuucc aaagca                                                       16

<210> SEQ ID NO 166
<211> LENGTH: 11
<212> TYPE: RNA
<213> ORGANISM: Artificial
<220> FEATURE:
<223> OTHER INFORMATION: Oligonucleotide

<400> SEQUENCE: 166
aguuucuucc a                                                            11

<210> SEQ ID NO 167
<211> LENGTH: 22
<212> TYPE: RNA
<213> ORGANISM: Artificial
<220> FEATURE:
<223> OTHER INFORMATION: Oligonucleotide

<400> SEQUENCE: 167
agcauccugu aggacauugg ca                                                22

```
<210> SEQ ID NO 168
<211> LENGTH: 11
<212> TYPE: RNA
<213> ORGANISM: Artificial
<220> FEATURE:
<223> OTHER INFORMATION: Oligonucleotide

<400> SEQUENCE: 168
agcauccugu a                                                          11

<210> SEQ ID NO 169
<211> LENGTH: 11
<212> TYPE: RNA
<213> ORGANISM: Artificial
<220> FEATURE:
<223> OTHER INFORMATION: Oligonucleotide

<400> SEQUENCE: 169
auccuguagg a                                                          11

<210> SEQ ID NO 170
<211> LENGTH: 12
<212> TYPE: RNA
<213> ORGANISM: Artificial
<220> FEATURE:
<223> OTHER INFORMATION: Oligonucleotide

<400> SEQUENCE: 170
aggacauugg ca                                                         12

<210> SEQ ID NO 171
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 171
gguaaugagu unuunnaanu gg                                              22

<210> SEQ ID NO 172
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
```

```
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 172
ggnaangagn ncnnccaacn gg                                              22

<210> SEQ ID NO 173
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (5)..(5)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine

<400> SEQUENCE: 173
ggunnugngu ucuuccnncu gg                                              22

<210> SEQ ID NO 174
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
```

```
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methyluracil

<400> SEQUENCE: 174
ggnaangagn nnnnnnaann gg                                              22

<210> SEQ ID NO 175
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (5)..(5)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 5-methylcytosine

<400> SEQUENCE: 175
```
ggunnugngu unuunnnnnu gg                                          22

<210> SEQ ID NO 176
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (5)..(5)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (20)..(20)
<223> OTHER INFORMATION: n is 5-methyluracil

<400> SEQUENCE: 176
ggnnnngngn ncnnccnncn gg                                          22

<210> SEQ ID NO 177
<211> LENGTH: 22
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature

```
<222> LOCATION: (4)..(4)
<223> OTHER INFORMATION: n is 2,6-diaminopurine
<220> FEATURE:
<221> NAME/KEY: misc_feature
<222> LOCATION: (5)..(5)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methyluracil

<400> SEQUENCE: 177
ggnnnngngn nnnnnnnnnn gg                                          22

<210> SEQ ID NO 178
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
```

```
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 178
uguunuagnn unuugauugn uggun                                  25

<210> SEQ ID NO 179
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil

<400> SEQUENCE: 179
ngnncnagcc ncnnganngc nggnc                                  25

<210> SEQ ID NO 180
<211> LENGTH: 25
```

```
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine

<400> SEQUENCE: 180
uguucungcc ucuugnuugc ugguc                                         25

<210> SEQ ID NO 181
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (20)..(20)
```

```
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methylcytosine

<400> SEQUENCE: 181
ngnnnnagnn nnnnganngn nggnn                                             25

<210> SEQ ID NO 182
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 182
uguunungnn unuugnuugn uggun                                             25

<210> SEQ ID NO 183
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
```

```
<222> LOCATION: (4)..(4)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (7)..(7)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil

<400> SEQUENCE: 183
ngnncnngcc ncnngnnngc nggnc                                          25

<210> SEQ ID NO 184
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (7)..(7)
<223> OTHER INFORMATION: n is 2,6-diaminopurine
<220> FEATURE:
```

<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methylcytosine

<400> SEQUENCE: 184
ngnnnnngnn nnnngnnngn nggnn                                    25

<210> SEQ ID NO 185
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

```
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 185
gaguuunuun naaagnagnn unun                                          24

<210> SEQ ID NO 186
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil

<400> SEQUENCE: 186
gagnnncnnc caaagcagcc ncnc                                          24

<210> SEQ ID NO 187
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (12)..(12)
<223> OTHER INFORMATION: n is 2,6-diaminopurine
<220> FEATURE:
<221> NAME/KEY: misc_feature
<222> LOCATION: (13)..(13)
```

```
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 2,6-diaminopurine

<400> SEQUENCE: 187
gnguuucuuc cnnngcngcc ucuc                                          24

<210> SEQ ID NO 188
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
```

```
<222> LOCATION: (24)..(24)
<223> OTHER INFORMATION: n is 5-methylcytosine

<400> SEQUENCE: 188
gagnnnnnnn naaagnagnn nnnn                                           24

<210> SEQ ID NO 189
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (12)..(12)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 189
gnguuunuun nnnngnngnn unun                                           24

<210> SEQ ID NO 190
<211> LENGTH: 24
<212> TYPE: RNA
<213> ORGANISM: Artificial
<220> FEATURE:
<223> OTHER INFORMATION: Oligonucleotide
<220> FEATURE:
```

```
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (12)..(12)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil

<400> SEQUENCE: 190
gngnnncnnc cnnngcngcc ncnc                                              24

<210> SEQ ID NO 191
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methylcytosine
```

```
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (12)..(12)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methylcytosine

<400> SEQUENCE: 191
gngnnnnnnn nnnngnngnn nnnn                                      24

<210> SEQ ID NO 192
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
```

<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 192
agnaunnugu agganauugg nagu                                          24

<210> SEQ ID NO 193
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil

<400> SEQUENCE: 193
agcanccngn aggacanngg cagn                                          24

<210> SEQ ID NO 194
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine

<400> SEQUENCE: 194
ngcnuccugu nggncnuugg cngu                                            24

<210> SEQ ID NO 195
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methyluracil

<400> SEQUENCE: 195
agnannnngn aggananngg nagn                                            24

<210> SEQ ID NO 196
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:

<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 2,6-diaminopurine

<400> SEQUENCE: 196
ngnnunnugu nggnnnuugg nngu                                        24

<210> SEQ ID NO 197
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

```
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 5-methyluracil

<400> SEQUENCE: 197
ngcnnccngn nggncnnngg cngn                                              24

<210> SEQ ID NO 198
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
```

```
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 5-methyluracil

<400> SEQUENCE: 198
ngnnnnnngn nggnnnnngg nngn                                    24

<210> SEQ ID NO 199
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 199
guugnnunng guunugaagg uguun                                   25

<210> SEQ ID NO 200
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
```

```
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine

<400> SEQUENCE: 200
uuugnngnug nnnaaugnna unnug                                        25

<210> SEQ ID NO 201
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 201
nunuugauug nuggunuugu uuuun                                        25

<210> SEQ ID NO 202
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
```

```
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 202
ncaaggaaga nggcannncn                                        20

<210> SEQ ID NO 203
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methyluracil

<400> SEQUENCE: 203
nnaaggaaga nggnannnnn                                        20

<210> SEQ ID NO 204
<211> LENGTH: 20
<212> TYPE: RNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil

<400> SEQUENCE: 204
ncagcnncng nnagccacng                                                         20

<210> SEQ ID NO 205
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methyluracil
<220> FEATURE:
<221> NAME/KEY: misc_feature
<222> LOCATION: (15)..(15)
```

```
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil

<400> SEQUENCE: 205
nnagnnnnng nnagnnanng                                         20

<210> SEQ ID NO 206
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (7)..(7)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (15)..(15)
<223> OTHER INFORMATION: n is 2,6-diaminopurine

<400> SEQUENCE: 206
ucnnggnngn uggcnuuucu                                         20

<210> SEQ ID NO 207
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (17)..(17)
<223> OTHER INFORMATION: n is 2,6-diaminopurine

<400> SEQUENCE: 207
ucngcuucug uungccncug                                         20
```

```
<210> SEQ ID NO 208
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 208
unagnuunug uuagnnanug                                          20

<210> SEQ ID NO 209
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
```

```
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methyluracil

<400> SEQUENCE: 209
nnngnngnng nnnaangnna nnnng                                    25

<210> SEQ ID NO 210
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (15)..(15)
<223> OTHER INFORMATION: n is 2,6-diaminopurine
<220> FEATURE:
<221> NAME/KEY: misc_feature
<222> LOCATION: (20)..(20)
<223> OTHER INFORMATION: n is 2,6-diaminopurine

<400> SEQUENCE: 210
uuugccgcug cccnnugccn uccug                                    25

<210> SEQ ID NO 211
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
```

<220> FEATURE:
<221> NAME/KEY: misc_feature
<222> LOCATION: (12)..(12)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil

<400> SEQUENCE: 211
gnngccnccg gnncngaagg ngnnc                                            25

<210> SEQ ID NO 212
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)

```
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (24)..(24)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methylcytosine

<400> SEQUENCE: 212
gnngnnnnng gnnnngaagg ngnnn                                           25

<210> SEQ ID NO 213
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (17)..(17)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine

<400> SEQUENCE: 213
guugccuccg guucugnngg uguuc                                           25

<210> SEQ ID NO 214
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 214
ggccaaaccn cggcnnaccn                                                 20

<210> SEQ ID NO 215
<211> LENGTH: 20
<212> TYPE: RNA
<213> ORGANISM: Artificial
```

```
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 215
unaaggaaga uggnauuunu                                              20

<210> SEQ ID NO 216
<211> LENGTH: 20
<212> TYPE: RNA
<213> ORGANISM: Artificial
<220> FEATURE:
<223> OTHER INFORMATION: Oligonucleotide

<400> SEQUENCE: 216
ggccaaaccu cggcuuaccu                                              20

<210> SEQ ID NO 217
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 217
guugnnuccg guunugaagg uguun                                        25

<210> SEQ ID NO 218
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine

<400> SEQUENCE: 218
guugnnuccg guucugaagg uguuc                                        25
```

```
<210> SEQ ID NO 219
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 219
guugcnuccg guunugaagg uguun                                              25
```

RNA MODULATING OLIGONUCLEOTIDES WITH IMPROVED CHARACTERISTICS FOR THE TREATMENT OF DUCHENNE AND BECKER MUSCULAR DYSTROPHY

CROSS REFERENCE

This application is a continuation of U.S. patent application Ser. No. 14/444,244 filed on Jul. 28, 2014 which is a continuation of international Patent Application No. PCT/NL2013/050045, filed Jan. 28, 2013, which claims the benefit of EP 12152934.1 filed Jan. 27, 2012, and U.S. Provisional Application No. 61/591,354 filed Jan. 27, 2012 and 61/612,467 filed Mar. 19, 2012, all of which are incorporated by reference in their entirety.

FIELD

The invention relates to the field of human genetics, more specifically neuromuscular disorders. The invention in particular relates to the use of an oligonucleotide with improved characteristics enhancing clinical applicability as further defined herein.

BACKGROUND OF THE INVENTION

Neuromuscular diseases are characterized by impaired functioning of the muscles due to either muscle or nerve pathology (myopathies and neuropathies). The myopathies include genetic muscular dystrophies that are characterized by progressive weakness and degeneration of skeletal, heart and/or smooth muscle. Duchenne muscular dystrophy (DMD) and Becker muscular dystrophy (BMD) are the most common childhood forms of muscular dystrophy. DMD is a severe, lethal neuromuscular disorder resulting in a dependency on wheelchair support before the age of 12 and patients often die before the age of thirty due to respiratory- or heart failure. It is caused by reading frame-shifting deletions (~67%) or duplications (~7%) of one or more exons, or by point mutations (~25%) in the 2.24 Mb DMD gene, resulting in the absence of functional dystrophin. BMD is also caused by mutations in the DMD gene, but these maintain the open reading frame, yield semi-functional dystrophin proteins, and result in a typically much milder phenotype and longer lifespan. During the last decade, specific modification of splicing in order to restore the disrupted reading frame of the transcript has emerged as a promising therapy for DMD (van Ommen et al., 2008; Yokota et al., 2007; van Deutekom et al., 2007; Goemans et al., 2011; Cirak et al., 2011). Using highly sequence-specific antisense oligonucleotides (AONs) which bind to the exon flanking or containing the mutation and which interfere with its splicing signals, the skipping of that exon can be induced during the processing of the DMD pre-mRNA. Despite the resulting truncated transcript, the open reading frame is restored and a protein is introduced which is similar to those found in BMD patients. AON-induced exon skipping provides a mutation-specific, and thus personalized, therapeutic approach for DMD patients. Several oligonucleotides are currently being developed for skipping most relevant exons of the dystrophin pre-mRNA such as exons 2, 8, 9, 17, 29, 43, 44, 45, 46, 47, 48, 50, 51, 52, 53, 54, 55, 56, 57, 58, 59, 60-63, 71-78 as described in WO 02/024906, WO2004/083446, WO2006/112705, WO2007/135105, WO 2009/139630, WO 2010/050801 or WO 2010/050802.

As the majority of the mutations cluster around exons 45 to 55, the skipping of one specific exon may be therapeutic for many patients with different mutations. The skipping of exon 51 applies to the largest subset of patients (~13%), including those with deletions of exons 45 to 50, 48 to 50, 50, or 52. The AONs applied are chemically modified to resist endonucleases, exonucleases and RNaseH, and to promote RNA binding and duplex stability. Two different AON chemistries are currently being developed for exon 51 skipping in DMD: 2'-O-methyl phosphorothioate RNA AONs (2OMePS, GSK2402968/PRO051) and phosphorodiamidate morpholino oligomers (PMO, AVI-4658) (Goemans et al., 2011; Cirak et al., 2011). In two independent phase I/II studies, both were shown to specifically induce exon 51 skipping and at least partly restore dystrophin expression at the muscle fiber membranes after systemic administration. Although AONs are typically not well taken up by healthy muscle fibers, the dystrophin deficiency in DMD, resulting in damaged and thus more permeable fiber membranes, actually promotes uptake. In studies in the dystrophin-deficient mdx mouse model, 2'-O-methyl phosphorothioate RNA oligonucleotides have demonstrated an up to 10 times higher uptake in different muscle groups when compared to that in wild type mice (Heemskerk et al., 2010). Although the recent phase I/II results with both 2'-O-methyl phosphorothioate RNA and phosphorodiamidate morpholino AONs in DMD patients confirm this enhanced uptake in dystrophic muscle, the different chemical modifications seemed to result in a differential uptake by and distribution through muscle. The levels of novel dystrophin in both studies after 3 months of treatment were promising but still moderate and challenges the field to investigate next generation oligochemistry.

The particular characteristics of a chosen chemistry at least in part affects the delivery of an AON to the target transcript: administration route, biostability, biodistribution, intra-tissue distribution, and cellular uptake and trafficking. In addition, further optimization of oligonucleotide chemistry is conceived to enhance binding affinity and stability, enhance activity, improve safety, and/or to reduce cost of goods by reducing length or improving synthesis and/or purification procedures. Multiple chemical modifications have become generally and/or commercially available to the research community (such as 2'-O-methyl RNA and 5-substituted pyrimidines and 2,6-diaminopurines), whereas most others still present significant synthetic effort to obtain. Especially preliminary encouraging results have been obtained using 2'-O-methyl phosphorothioate RNA containing modifications on the pyrimidine and purine bases as identified herein.

In conclusion, to enhance the therapeutic applicability of AONs for DMD, there is a need for AONs with further improved characteristics.

DESCRIPTION OF THE INVENTION

Oligonucleotide

In a first aspect, the invention provides an oligonucleotide comprising a 2'-O-methyl RNA monomer and a phosphorothioate backbone or consisting of 2'-O-methyl RNA monomers linked by phosphorothioate backbones, and comprising a 5-methylpyrimidine and/or a 2,6-diaminopurine base preferably for use as a medicament for treating Duchenne Muscular Dystrophy or Becker Muscular Dystrophy. Therefore, the invention provides an oligonucleotide comprising a 2'-O-methyl RNA monomer, a phosphorothioate backbone and a 5-methylpyrimidine and/or a 2,6-diaminopurine base preferably for use as a medicament for treating Duchenne Muscular Dystrophy or Becker Muscular Dystrophy.

Accordingly the invention also provides an oligonucleotide consisting of 2'-O-methyl RNA monomers and a phosphorothioate backbone and comprises a 5-methylpyrimidine and/or a 2,6-diaminopurine base preferably for use as a medicament for treating Duchenne Muscular Dystrophy or Becker Muscular Dystrophy.

It is clear for the skilled person that "an RNA monomer" as present in an oligonucleotide of the invention may also be identified as being "an RNA nucleotide residue". Both terms may be used interchangeably throughout the application.

Within the context of the invention, "a" in each of the following expressions means "at least one": a 2'-O-methyl RNA monomer, a 2'-O-methyl RNA nucleotide residue, a 2'-O-methyl phosphorothioate RNA monomer, a 5-methylpyrimidine base, a 2,6-diaminopurine base.

Within the context of the invention, it is clear for the skilled person that "an oligonucleotide comprising a 2'-O-methyl RNA monomer, a phosphorothioate backbone" could be replaced by "an oligonucleotide comprising a 2'-O-methyl RNA monomer linked by phosphorothioate backbones". The same holds for "an oligonucleotide consisting of 2'-O-methyl RNA monomers and a phosphorothioate backbone" that could be replaced by "an oligonucleotide consisting of 2'-O-methyl RNA monomer linked by phosphorothioate backbones".

In the context of the invention, the expression "for use as a medicament for treating Duchenne Muscular Dystrophy or Becker Muscular Dystrophy" could be replaced by the expression "for use in the treatment of Duchenne Muscular Dystrophy or Becker Muscular Dystrophy."

Preferably, an oligonucleotide is an oligonucleotide with less than 34 nucleotides. Said oligonucleotide may have 10, 11, 12, 13, 14, 15, 16, 17, 18, 19, 20, 21, 22, 23, 24, 25, 26, 27, 28, 29, 30, 31, 32, or 33 nucleotides. Such oligonucleotide may also be identified as an oligonucleotide having from 10 to 33 nucleotides.

Accordingly, an oligonucleotide of the invention comprises a 2'-O-methyl RNA monomer and a phosphorothioate backbone and comprises less than 34 nucleotides (i.e. it comprises 10, 11, 12, 13, 14, 15, 16, 17, 18, 19, 20, 21, 22, 23, 24, 25, 26, 27, 28, 29, 30, 31, 32, or 33 nucleotides).

Accordingly, an oligonucleotide of the invention consists of 2'-O-methyl RNA monomers linked by phosphorothioate backbone and comprises less than 34 nucleotides (i.e. it comprises 10, 11, 12, 13, 14, 15, 16, 17, 18, 19, 20, 21, 22, 23, 24, 25, 26, 27, 28, 29, 30, 31, 32, or 33 nucleotides)

Accordingly, an oligonucleotide of the invention comprises a 2'-O-methyl RNA monomer, a phosphorothioate backbone, comprises less than 34 nucleotides (i.e. it comprises 10, 11, 12, 13, 14, 15, 16, 17, 18, 19, 20, 21, 22, 23, 24, 25, 26, 27, 28, 29, 30, 31, 32, or 33 nucleotides) and a 5-methylpyrimidine and/or a 2,6-diaminopurine base.

Accordingly, an oligonucleotide of the invention consists of 2'-O-methyl RNA monomers linked by phosphorothioate backbone, and comprises less than 34 nucleotides (i.e. it comprises 10, 11, 12, 13, 14, 15, 16, 17, 18, 19, 20, 21, 22, 23, 24, 25, 26, 27, 28, 29, 30, 31, 32, or 33 nucleotides) and a 5-methylpyrimidine and/or a 2,6-diaminopurine base.

Each of these oligonucleotides is for use or may be for use as a medicament for treating Duchenne Muscular Dystrophy or Becker Muscular Dystrophy.

An oligonucleotide of the invention comprises or consists of a 2'-O-methyl phosphorothioate RNA monomer. Such oligonucleotide comprises a 2'-O-methyl RNA monomer connected through or linked by a phosphorothioate backbone or consists of 2'-O-methyl phosphorothioate RNA. Preferably, such oligonucleotide consists of a 2'-O-methyl phosphorothioate RNA. Such chemistry is known to the skilled person. Throughout the application, an oligonucleotide comprising a 2'-O-methyl RNA monomer and a phosphorothioate backbone may be replaced by an oligonucleotide comprising a 2'-O-methyl phosphorothioate RNA. Throughout the application, an oligonucleotide consisting of 2'-O-methyl RNA monomers linked by or connected through phosphorothioate backbones may be replaced by an oligonucleotide consisting of 2'-O-methyl phosphorothioate RNA.

In the context of the invention, "backbone" is used to identify the linkage between two sugar units or modified versions of a sugar unit or moiety as later defined herein (i.e. internucleoside linkage). Throughout the description, the words "backbone", "internucleoside linkage" and "linkage" may be used interchangeably. Thus, an oligonucleotide having 10 nucleotides contains 9 backbones, linking the 10 sugar units or modified versions of a sugar unit or moiety as later defined herein together. At least one of the backbones of the oligonucleotide according to the invention consists of a phosphorothioate moiety, linking two sugar units or modified versions of a sugar unit or moiety as later defined herein. Thus, at least one phosphodiester backbones present in RNA is replaced by phosphorothioate moiety. A naturally occurring internucleoside linkage or backbone is the 3' to 5' phosphodiester linkage.

In addition, an oligonucleotide of the invention may comprise a base modification that increases binding affinity to target strands, increases melting temperature of the resulting duplex of said oligonucleotide with its target, and/or decreases immunostimulatory effects, and/or increases biostability, and/or improves biodistribution and/or intra-tissue distribution, and/or cellular uptake and trafficking. In a more preferred embodiment, an oligonucleotide of the invention comprises a 5-methylpyrimidine and/or a 2,6-diaminopurine base. A 5-methylpyrimidine base is selected from a 5-methylcytosine and/or a 5-methyluracil and/or a thymine, in which thymine is identical to 5-methyluracil.

Accordingly, the expression "comprises a 5-methylcytosine and/or a 5-methyluracil and/or a 2,6-diaminopurine base" in the context of the modified oligonucleotide of the invention may be replaced by "comprises a base modification selected from the group consisting of: a 5-methylcytosine, a 5-methyluracil and a 2,6-diaminopurine base".

Where an oligonucleotide of the invention has two or more such base modifications, said base modifications may be identical, for example all such modified bases in the oligonucleotide are 5-methylcytosine, or said base modifications may be combinations of different base modifications, for example the oligonucleotide may have one or more 5-methylcytosines and one or more 5-methyluracils.

'Thymine' and '5-methyluracil' may be interchanged throughout the document. In analogy, 2,6-diaminopurine is identical to 2-aminoadenine and these terms may be interchanged throughout the document. The use of 2,6-diaminopurine has been disclosed in another context in U.S. Pat. No. 7,745,420.

The term "base modification" or "modified base" as identified herein refers to the modification of an existing base (i.e. pyrimidine or purine base) or to the de novo synthesis of a base. This de novo synthesized base could be qualified as "modified" by comparison to an existing base. An oligonucleotide of the invention comprising a 5-methylcytosine and/or a 5-methyluracil and/or a 2,6-diaminopurine base means that at least one of the cytosine nucleobases of said oligonucleotide has been modified by substitution of the proton at the 5-position of the pyrimidine ring with a methyl group, i.e. a 5-substituted cytosine, and/or that at least one of the uracil nucleobases of said oligonucleotide has been modified by substitution of the proton at the 5-position of the pyrimidine ring with a methyl group (i.e. a 5-methyluracil), and/or that at least one of the adenine nucleobases of said oligonucleotide has been modified by substitution of the proton at the 2-position with an amino group (i.e. a 2,6-diaminopurine), respectively. Within the context of the invention, the expression "the substitution of a proton with a methyl group in position 5 of the pyrimidine ring" may be replaced by the expression "the substitution of a pyrimidine with a 5-methylpyrimidine," with pyrimidine referring to only uracil, only cytosine or both. Likewise, within the context of the invention, the expression "the substitution of a proton with an amino group in position 2 of adenine" may be replaced by the expression "the substitution of an adenine with a 2,6-diaminopurine." If said oligonucleotide comprises 1, 2, 3, 4, 5, 6, 7, 8, 9 or more cytosines, uracils, and/or adenines, at least one, 2, 3, 4, 5, 6, 7, 8, 9 or more cytosines, uracils and/or adenines respectively have been modified this way. Preferably all cytosines, uracils and/or adenines have been modified this way or substituted by 5-methylcytosine, 5-methyluracil and/or 2,6-diaminopurine, respectively. No need to say that this aspect of the invention could only be applied to oligonucleotides comprising at least one cytosine, uracil, or adenine, respectively, in their sequence. An oligonucleotide comprising at least one 5-methylcytosine, 5-methyluracil and/or 2,6-diaminopurine may be called a modified oligonucleotide by reference to its non-modified counterpart comprising no 5-methylcytosine, no 5-methyluracil and no 2,6-diaminopurine. A non-modified counterpart may also be identified as being an oliognucleotide comprising unmodified cytosines, unmodified uraciles and unmodified adenines. Preferred non-modified sequences are represented by one of the following base or nucleotide sequences comprising or consisting of SEQ ID NO:91, 93-170.

We discovered that the presence of a 5-methylcytosine, 5-methyluracil and/or a 2,6-diaminopurine in an oligonucleotide of the invention has a positive effect on at least one of the parameters of said oligonucleotides. In this context, parameters may include: binding affinity and/or kinetics, exon skipping activity, biostability, (intra-tissue) distribution, cellular uptake and/or trafficking, and/or immunogenicity of said oligonucleotide, as explained below. Said positive effect may be correlated with the number or percentage of base modifications incorporated. For the parameter of exon skipping activity, we found for some oligonucleotides that modification of nucleobases is not needed per se to obtain relatively high levels of exon skipping. This may be related to the specific role (and strength) of the specifically targeted sequence within the exon in its splicing process.

Binding affinity and kinetics depend on the AON's thermodynamic properties. These are at least in part determined by the melting temperature of said oligonucleotide (Tm; calculated with e.g. the oligonucleotide properties calculator (unc.edu/~cail/biotool/oligo/index.html or eu.idtdna.com/analyzer/Applications/OligoAnalyzer/) for single stranded RNA using the basic Tm and the nearest neighbor model), and/or the free energy of the oligonucleotide-target exon complex (using RNA structure version 4.5 or RNA mfold version 3.5). If a Tm is increased, the exon skipping activity typically increases, but when a Tm is too high, the AON is expected to become less sequence-specific. An acceptable Tm and free energy depend on the sequence of the oligonucleotide. Therefore, it is difficult to give preferred ranges for each of these parameters.

Exon skipping activity is preferably measured by analysing total RNA isolated from AON-treated muscle cell cultures or muscle tissue by reverse transcriptase polymerase chain reaction (RT-PCR) using DMD gene-specific primers flanking the targeted exon as described (Aartsma-Rus et al., 2003). RT-PCR products are analyzed on 1-2% agarose gels or with the Agilent 2100 bioanalyzer (Agilent Technologies, The Netherlands). The ratio of shorter transcript fragments, representing transcripts in which the targeted exon is skipped, to the total of transcript products is assessed (calculated as percentage of exon skipping induced by an AON). Shorter fragments may also be sequenced to determine the correctness and specificity of the targeted exon skipping. An increase in percentage of exon skipping may be detected for a modified oligonucleotide of the invention (i.e. an oligonucleotide comprising a 2'-O-methyl RNA monomer, a phosphorothioate backbone and a 5-methylpyrimidine and/or a 2,6-diaminopurine base) compared to its non-modified counterpart (i.e. an oligonucleotide comprising a 2'-O-methyl RNA monomer, a phosphorothioate backbone and not comprising any 5-methylpyrimidine and any 2,6-diaminopurine base). Said increase is preferably a detectable increase assessed as explained above using RT-PCR. Said increase is preferably an increase of at least 5%, 10%, 20%, 30%, 40%, 50%, 60%, 70%, 80%, 90%, 100%, 110%, 120%, 130%, 140%, 150%, 160%, 170%, 180%, 190%, 200%, 210%, 300%, 400%, 500%, 600%, 700%, 800%, 900%, 1000%, or at least 2, 3, 4, 5, 6, 7, 8, 9, or 10 times higher, or even 11, 12, 13, 14, 15, 16, 17, 18, 19 or 20 times higher or more.

Biodistribution and biostability are preferably at least in part determined by a validated hybridization ligation assay adapted from Yu et al., 2002. In an embodiment, plasma or homogenized tissue samples are incubated with a specific capture oligonucleotide probe. After separation, a DIG-labeled oligonucleotide is ligated to the complex and detection followed using an anti-DIG antibody-linked peroxidase. Non-compartmental pharmacokinetic analysis is performed using WINNONLIN software package (model 200, version 5.2, Pharsight, Mountainview, Calif.). Levels of AON (ug) per mL plasma or mg tissue are monitored over time to assess area under the curve (AUC), peak concentration ($C_{max}$), time to peak concentration ($T_{max}$), terminal half life and absorption lag time ($t_{lag}$). Such a preferred assay has been disclosed in the experimental part.

AONs may stimulate an innate immune response by activating the Toll-like receptors (TLR), including TLR9 and TLR7 (Krieg et al., 1995). The activation of TLR9 typically occurs due to the presence of non-methylated CG sequences present in oligodeoxynucleotides (ODNs), by mimicking bacterial DNA which activates the innate immune system through TLR9-mediated cytokine release. The 2'-O-methyl modification is however suggested to markedly reduce such possible effect. TLR7 has been described to recognize uracil repeats in RNA (Diebold et al., 2006).

Activation of TLR9 and TLR7 result in a set of coordinated immune responses that include innate immunity (macrophages, dendritic cells (DC), and NK cells)(Krieg et al., 1995; Krieg, 2000). Several chemo- and cytokines, such as IP-10, TNFα, IL-6, MCP-1 and IFNα (Wagner, 1999; Popovic et al., 2006) have been implicated in this process. The inflammatory cytokines attract additional defensive cells from the blood, such as T and B cells. The levels of these cytokines can be investigated by in vitro testing. In short, human whole blood is incubated with increasing concentrations of AONs after which the levels of the cytokines are determined by standard commercially available ELISA kits. Such a preferred assay has been described in the experimental part. A decrease in immunogenicity preferably corresponds to a detectable decrease of concentration of at least one of the cytokines mentioned above by comparison to the concentration of corresponding cytokine in an assay in a cell treated with an oligonucleotide comprising at least one 5-methylcytosine compared to a cell treated with a corresponding oligonucleotide having no 5-methylcytosines.

Accordingly, a preferred oligonucleotide of the invention has an improved parameter, such as an acceptable or a decreased immunogenicity and/or a better biodistribution and/or acceptable or improved RNA binding kinetics and/or thermodynamic properties by comparison to a corresponding oligonucleotide consisting of a 2'-O-methyl phosphorothioate RNA without a 5-methylcytosine, a 5-methyluracil and a 2,6-diaminopurine (i.e. so called non-modified oligonucleotide). Said non-modified oligonucleotide may also be identified as being an oliognucleotide comprising unmodified cytosines, unmodified uraciles and unmodified adenines. Each of these parameters could be assessed using assays known to the skilled person or preferably as disclosed herein.

Below other chemistries and modifications of the oligonucleotide of the invention are defined. These additional chemistries and modifications may be present in combination with the chemistry already defined for said oligonucleotide, i.e. the presence of a 5-methylcytosine, a 5-methyluracil and/or a 2,6-diaminopurine, and the oligonucleotide comprising or consisting of a 2'-O-methyl phosphorothioate RNA.

A preferred oligonucleotide of the invention comprises or consists of an RNA molecule or a modified RNA molecule. In a preferred embodiment, an oligonucleotide is single stranded. The skilled person will understand that it is however possible that a single stranded oligonucleotide may form an internal double stranded structure. However, this oligonucleotide is still named a single stranded oligonucleotide in the context of this invention.

In addition to the modifications described above, the oligonucleotide of the invention may comprise further modifications such as different types of nucleic acid monomers or nucleotides as described below. Different types of nucleic acid monomers may be used to generate an oligonucleotide of the invention. Said oligonucleotide may have at least one backbone, and/or sugar modification and/or at least one base modification compared to an RNA-based oligonucleotide.

A base modification includes a modified version of the natural purine and pyrimidine bases (e.g. adenine, uracil, guanine, cytosine, and thymine), such as hypoxanthine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof, $N^2$-cyclopentylguanine (cPent-G), $N^2$-cyclopentyl-2-aminopurine (cPent-AP), and $N^2$-propyl-2-aminopurine (Pr-AP), pseudouracil or derivatives thereof, and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173 (Epoch Biosciences), which is incorporated here entirely by reference. cPent-G, cPent-AP and Pr-AP were shown to reduce immunostimulatory effects when incorporated in siRNA (Peacock H. et al. J. Am. Chem. Soc. 2011, 133, 9200).

A pseudouracil is a naturally occurring isomerized version of uracil, with a C-glycoside rather than the regular N-glycoside as in uridine. Pseudouridine-containing synthetic mRNA may have an improved safety profile compared to uridine-containing mRNA (WO 2009127230, incorporated here in its entirety by reference).

In an embodiment, an oligonucleotide of the invention comprises an abasic site or an abasic monomer. Within the context of the invention, such monomer may be called an abasic site or an abasic monomer. An abasic monomer or abasic site is a monomer or building block that lacks a nucleobase by comparison to a corresponding monomer comprising a nucleobase. Within the invention, an abasic monomer is thus a building block part of an oligonucleotide but lacking a nucleobase. Such abasic monomer may be present or linked or attached or conjugated to a free terminus of an oligonucleotide. In a more preferred embodiment, an oligonucleotide of the invention comprises 1-20 or more abasic monomers. Therefore, 1, 2, 3, 4, 5, 6, 7, 8, 9, 10, 11, 12, 13, 14, 15, 16, 17, 18, 19, 20 or more abasic monomers may be present in an oligonucleotide of the invention.

An abasic monomer may be of any type known and conceivable by the skilled person, non-limiting examples of which are depicted below:

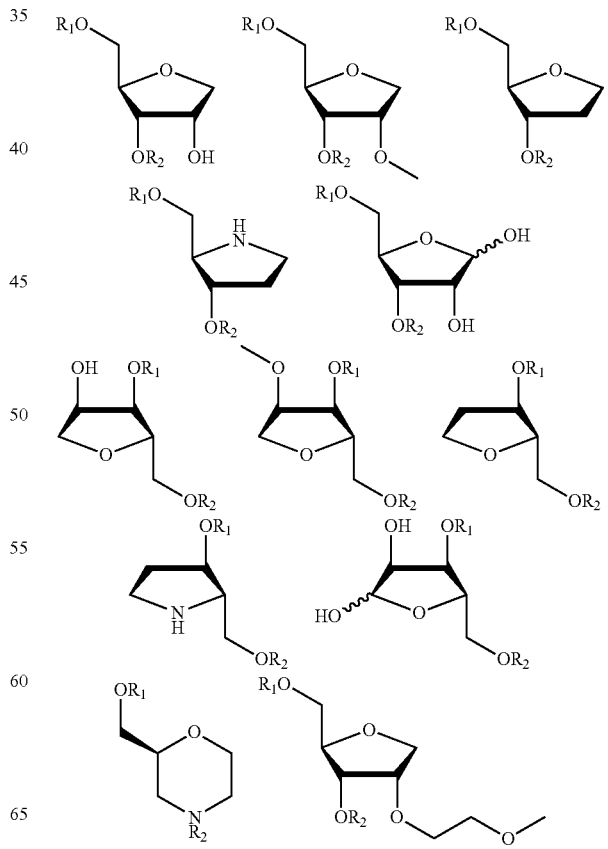

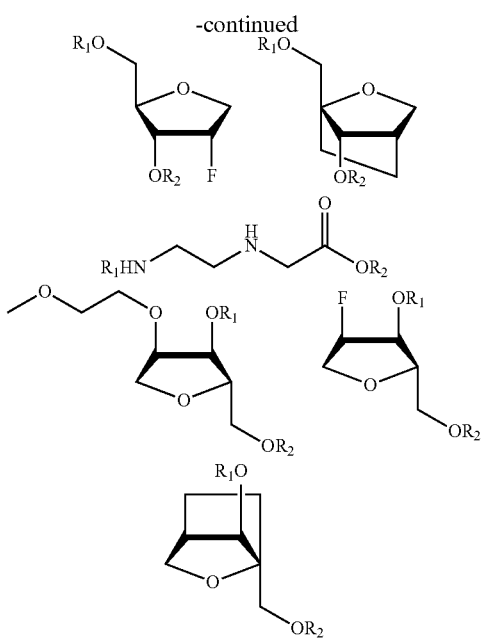

Herein, $R_1$ and $R_2$ are independently H, an oligonucleotide or other abasic site(s), provided that not both $R_1$ and $R_2$ are H and $R_1$ and $R_2$ are not both an oligonucleotide. An abasic monomer(s) can be attached to either or both termini of the oligonucleotide as specified before. It should be noted that an oligonucleotide attached to one or two an abasic site(s) or abasic monomer(s) may comprise less than 10 nucleotides. In this respect, the oligonucleotide according to the invention may comprise at least 10 nucleotides, optionally including one or more abasic sites or abasic monomers at one or both termini.

Depending on its length an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 base modifications. It is also encompassed by the invention to introduce more than one distinct base modification in said oligonucleotide.

A sugar modification includes a modified version of the ribosyl moiety, such as 2'-O-modified RNA such as 2'-O-alkyl or 2'-O-(substituted)alkyl e.g. 2'-O-methyl, 2'-O-(2-cyanoethyl), 2'-O-(2-methoxy)ethyl (2'-MOE), 2'-O-(2-thiomethyl)ethyl, 2'-O-butyryl, 2'-O-propargyl, 2'-O-allyl, 2'-O-(3-amino)propyl, 2'-O-(3-(dimethylamino)propyl), 2'-O-(2-amino)ethyl, 2'-O-(2-(dimethylamino)ethyl); 2'-deoxy (DNA); 2'-O-(haloalkoxy)methyl (Arai K. et al. *Bioorg. Med. Chem.* 2011, 21, 6285) e.g. 2'-O-(2-chloroethoxy)methyl (MCEM), 2'-O-(2,2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl](DCME); 2'-halo e.g. 2'-F, FANA (2'-F arabinosyl nucleic acid); carbasugar, sulfa and sulfosugar and azasugar modifications; 3'-O-alkyl e.g. 3'-O-methyl, 3'-O-butyryl, 3'-O-propargyl; 4'-carboxy e.g. 4'-carboxythymidine (Hari et al.); and their derivatives.

Other sugar modification includes "bridged" or "bicylic" nucleic acid (BNA), e.g. locked nucleic acid (LNA), xylo-LNA, α-L-LNA, β-D-LNA, cEt (2'-O,4'-C constrained ethyl) LNA, cMOEt (2'-O,4'-C constrained methoxyethyl) LNA, ethylene-bridged nucleic acid (ENA), tricyclo DNA (tcDNA, tc-PS-DNA e.g. US patent application 20120149756); 3'-S-phosphorothiolate DNA (e.g. *Org. Biol. Chem.* 2013, 11, 966); doubly constrained nucleic acid (tri-NA, e.g. Hanessian et al.); unlocked nucleic acid (UNA); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PPMO, PMOPlus, PMO-X); and their derivatives. Depending on its length, an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 sugar modifications. It is also encompassed by the invention to introduce more than one distinct sugar modification in said oligonucleotide. In an embodiment, an oligonucleotide as defined herein comprises or consists of an LNA or a derivative thereof. BNA derivatives are for example described in WO 2011/097641, which is incorporated in its entirety by reference. In a more preferred embodiment, an oligonucleotide of the invention is fully 2'-O-methyl modified. Examples of PMO-X are described in WO2011150408, which is incorporated here in its entirety by reference.

A backbone modification includes a modified version of the phosphodiester present in RNA, such as phosphorothioate (PS), chirally pure phosphorothioate, phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methyl boranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, triazole, oxalyl, carbamate, methyleneimino (MMI), 3'-S-phosphorothiolate (*Org. Biol. Chem.* 2013, 11, 966) and thioacetamido nucleic acid (TANA); and their derivatives. Depending on its length, an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 backbone modifications. It is also encompassed by the invention to introduce more than one distinct backbone modification in said oligonucleotide.

In a preferred embodiment, an oligonucleotide of the invention comprises at least one phosphorothioate modification. In a more preferred embodiment, an oligonucleotide of the invention is fully phosphorothioate modified.

Other chemical modifications of an oligonucleotide of the invention include peptide-base nucleic acid (PNA), boron-cluster modified PNA, pyrrolidine-based oxy-peptide nucleic acid (POPNA), glycol- or glycerol-based nucleic acid (GNA), threose-based nucleic acid (TNA), acyclic threoninol-based nucleic acid (aTNA), morpholino-based oligonucleotide (PMO, PPMO, PMO-X), cationic morpholino-based oligomers (PMOPlus), oligonucleotides with integrated bases and backbones (ONIBs), pyrrolidine-amide oligonucleotides (POMs); and their derivatives.

In another embodiment, an oligonucleotide comprises a peptide nucleic acid and/or a morpholino phosphorodiamidate or a derivative thereof.

In another embodiment, an oligonucleotide comprises a monothiophosphate moiety at the 5' position of the 5' terminal residue and/or a monothiophosphate moiety at the 3' position of the 3' terminal residue. These monothiophosphate groups have been shown to improve oligonucleotide stability (e.g. US patent application 20120148664-miRagen).

With the advent of nucleic acid mimicking technology it has become possible to generate molecules that have a similar, preferably the same hybridization characteristics in kind not necessarily in amount as nucleic acid itself. Such functional equivalents are of course also suitable for use in the invention.

The skilled person will understand that not each sugar, base, and/or backbone may be modified the same way. Several distinct modified sugars, bases and/or backbones may be combined into one single oligonucleotide of the invention.

A person skilled in the art will also recognize that there are many synthetic derivatives of oligonucleotides. A backbone modification includes a modified version of the phosphodiester present in RNA, such as phosphorothioate (PS), chirally pure phosphorothioate, phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methyl boranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, and thioacetamido nucleic acid (TANA); and their derivatives.

Preferably, said oligonucleotide comprises RNA, as RNA/RNA duplexes are very stable. It is preferred that an RNA oligonucleotide comprises a modification providing the RNA with an additional property, for instance resistance to endonucleases, exonucleases, and RNaseH, additional hybridisation strength, increased stability (for instance in a bodily fluid), increased or decreased flexibility, increased activity, reduced toxicity, increased intracellular transport, tissue-specificity, etc. In addition, the mRNA complexed with the oligonucleotide of the invention is preferably not susceptible to RNaseH cleavage. Preferred modifications have been identified above.

Accordingly, the invention provides an oligonucleotide comprising a 2'-O-methyl phosphorothioate RNA monomer or consisting of 2'-O-methyl phosphorothioate RNA and comprising a 5-methylpyrimidine and/or a 2,6-diaminopurine base. Most preferably, this oligonucleotide consists of 2'-O-methyl RNA monomers connected through a phosphorothioate backbone and all of its cytosines and/or all of its uracils and/or all of its adenines, independently, have been substituted by 5-methylcytosine, 5-methyluracil and/or 2,6-diaminopurine, respectively. Preferred modified and non-modified oligonucleotides encompassed by the invention and disclosed herein comprises or consists of one of a base or nucleotide sequence selected from one of SEQ ID NO: 14-90 as identified in table 1. The expression "oligonucleotide represented by a nucleotide or base sequence selected from SEQ ID NO: 14-90" could be replaced by the expression "oligonucleotide represented by a nucleotide or base sequence selected from one of SEQ ID NO:14-90" or by the expression "oligonucleotide represented by a nucleotide or base sequence selected from the list of SEQ ID NO:14-90". The same holds for other groups of SEQ ID NO referred herein. Preferred non-modified oligonucleotides are derived from one of SEQ ID NO: 14-90 and encompassed by the present invention and disclosed herein comprises or consists of one of a base or nucleotide sequences selected from SEQ ID NO: 91, 93-170.

Modified oligonucleotides are preferably derived from one of SEQ ID NO:14-90 and encompassed by the present invention and disclosed herein comprises or consists of one of a base or nucleotide sequences selected from SEQ ID NO: 92, 171-213, 215.

Please note that two SEQ ID NO present in the sequence listing are identical: SEQ ID NO:91 is identical with SEQ ID NO: 132. SEQ ID NO: 92 is identical with SEQ ID NO:199.

The sequence representing each of these oligonucleotides is disclosed in Tables 1-3 and in the sequence listing. Later on in the description, most preferred oligonucleotides are described in more detail.

Thus, an oligonucleotide of the invention may have:

At least one and preferably all cytosines substituted with 5-methylcytosines,

At least one and preferably all cytosines substituted with 5-methylcytosines and at least one and preferably all uracils substituted with 5-methyluracils, At least one and preferably all cytosines substituted with 5-methylcytosines and at least one and preferably all adenines substituted with 2,6-diaminopurines, At least one and preferably all cytosines substituted with 5-methylcytosines and at least one and preferably all uracils substituted with 5-methyluracils and at least one and preferably all adenines substituted with 2,6-diaminopurines, At least one and preferably all uracils substituted with 5-methyluracils, At least one and preferably all uracils substituted with 5-methyluracils and at least one and preferably all adenines substituted with 2,6-diaminopurines, or At least one and preferably all adenines substituted with 2,6-diaminopurines.

However, an oligonucleotide may also have at least one or at least two or at least half or all its cytosines substituted with 5-methylcytosines. If a non-modified oligonucleotide of the invention preferably based on SEQ ID NO:14-90 has x cytosines, x being an integer ranged from 1 to 33, a corresponding modified oligonucleotide of the invention may have 1, 2, 3, . . . (x-2), (x-1), x 5-methylcytosines.

If x is 3 in such a non-modified oligonucleotide, the number of 5-methylcytosines in a corresponding modified oligonucleotide is 1, 2 or 3.

If x is 4 in such a non-modified oligonucleotide, the number of 5-methylcytosines in a corresponding modified oligonucleotide is 1, 2, 3 or 4.

If x is 5 in such a non-modified oligonucleotide, the number of 5-methylcytosines in a corresponding modified oligonucleotide is 1, 2, 3, 4 or 5.

If x is 6 in such a non-modified oligonucleotide, the number of 5-methylcytosines in a corresponding modified oligonucleotide is 1, 2, 3, 4, 5 or 6.

If x is 7 in such a non-modified oligonucleotide, the number of 5-methylcytosines in a corresponding modified oligonucleotide is 1, 2, 3, 4, 5, 6 or 7.

If x is 8 in such a non-modified oligonucleotide, the number of 5-methylcytosines in a corresponding modified oligonucleotide is 1, 2, 3, 4, 5, 6, 7, or 8.

The same holds for uracils substituted with 5-methyluracils and adenines substituted with 2,6-diaminopurines.

Preferably, an oligonucleotide of the invention is for use as a medicament for DMD, more preferably said oligonucleotide is for use in therapeutic RNA modulation. Therefore, an oligonucleotide is an antisense oligonucleotide (AON). An antisense oligonucleotide is an oligonucleotide which is reverse complementary to a specific sequence of the DMD or dystrophin pre-mRNA derived from the coding sense strand of a DNA of an individual. This oligonucleotide binds to and/or targets and/or hybridizes and/or is able to bind to and/or is able to target and/or is able to hybridize said sequence of said pre-mRNA. The objective of RNA modulation for DMD is to skip one or more specific exons in the DMD or dystrophin pre-mRNA in order to restore the open reading frame of the transcript and to induce the expression of a shorter but (more) functional dystrophin protein, with the ultimate goal to be able to interfere with the course of the disease In a preferred embodiment, an oligonucleotide of the invention is thus used for inducing exon-skipping in the DMD or dystrophin pre-mRNA in a cell, in an organ, in a tissue and/or in an individual. Exon-skipping results in a mature DMD or dystrophin mRNA that does not contain a skipped exon and thus, when said exon codes for amino acids, can lead to the expression of a shorter protein product. The skipping of an exon is preferably induced by the binding of an AON to specific exon-internal sequences comprising splicing regulatory elements, the splice sites and/or intronic branchpoint sequences.

As defined herein a DMD pre-mRNA preferably means a pre-mRNA of a DMD gene coding for a dystrophin protein. A mutated DMD pre-mRNA corresponds to a pre-mRNA of a BMD or DMD patient with a mutation when compared to a wild type DMD pre-mRNA of a non-affected person, resulting in (reduced levels of) an aberrant protein (BMD), or the absence of functional dystrophin (DMD). A DMD pre-mRNA is also named a dystrophin pre-mRNA. A DMD gene may also be named a dystrophin gene. Dystrophin and DMD may be used interchangeably throughout the application.

A patient is preferably intended to mean a patient having DMD or BMD as later defined herein or a patient susceptible to develop DMD or BMD due to his or her genetic background. In the case of a DMD patient, an oligonucleotide used will preferably correct one mutation as present in the DMD gene of said patient and create a protein that will look like a BMD protein: said protein will preferably be a functional or semi-functional dystrophin as later defined herein. In the case of a BMD patient, an oligonucleotide as used will preferably correct one mutation as present in the BMD gene of said patient and create a dystrophin which will be more functional than the dystrophin which was originally present in said BMD patient.

As defined herein, a functional dystrophin is preferably a wild type dystrophin corresponding to a protein having the amino acid sequence as identified in SEQ ID NO: 1. As defined herein, a semi-functional dystrophin is preferably a BMD-like dystrophin corresponding to a protein having an acting binding domain in its N terminal part (first 240 amino acids at the N terminus), a cysteine-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO: 1. In other words, a functional or a semi-functional dystrophin is a dystrophin which exhibits at least to some extent an activity of a wild type dystrophin. "At least to some extent" preferably means at least 10%, 20%, 30%, 40%, 50%, 60%, 70%, 80%, 90%, 95% or 100% of a corresponding activity of a wild type functional dystrophin. In this context, an activity of a functional dystrophin is preferably binding to actin and to the dystrophin-associated glycoprotein complex (DGC or DAPC) (Ehmsen J et al, 2002).

Binding of dystrophin to actin and to the DGC or DAPC complex may be visualized by either co-immunoprecipitation using total protein extracts or immunofluorescence analysis of cross-sections using various antibodies reacting with the different members of the complex, from a control (non-DMD) biopsy of one from a muscle suspected to be dystrophic, pre- and/or post-treatment, as known to the skilled person.

Individuals or patients suffering from Duchenne muscular dystrophy typically have a mutation in the gene encoding dystrophin (the DMD or dystrophin gene) that prevents synthesis of the complete protein, i.e a premature stop codon prevents the synthesis of the C-terminus. In Becker muscular dystrophy the dystrophin gene also comprises a mutation compared to the wild type but the mutation does typically not result in a premature stop codon and the C-terminus is typically synthesized. As a result a functional or semi-functional dystrophin protein is synthesized that has at least the same activity in kind as the wild type protein, although not necessarily the same amount of activity. The genome of a BMD patient typically encodes a dystrophin protein comprising the N terminal part (first 240 amino acids at the N terminus), a cysteine-rich domain (amino acid 3361 till 3685) and a C-terminal domain (last 325 amino acids at the C-terminus) but in the majority of cases its central rod shaped domain is shorter than the one of a wild type dystrophin (Monaco et al., 1988). Antisense oligonucleotide-induced exon skipping for the treatment of DMD is typically directed to overcome a premature stop in the pre-mRNA by skipping an exon, preferably in the central rod-domain shaped domain, to correct the open reading frame and allow synthesis of remainder of the dystrophin protein including the C-terminus, albeit that the protein is somewhat smaller as a result of a smaller rod domain. In a preferred embodiment, an individual having DMD and being treated by an oligonucleotide as defined herein will be provided a dystrophin which exhibits at least to some extent an activity of a wild type dystrophin. More preferably, if said individual is a Duchenne patient or is suspected to be a Duchenne patient, a functional or a semi-functional dystrophin is a dystrophin of an individual having BMD: typically said dystrophin is able to interact with both actin and the DGC or DAPC, but its central rod shaped domain may be shorter than the one of a wild type dystrophin (Monaco et al., 1988). The central rod domain of wild type dystrophin comprises 24 spectrin-like repeats. For example, a central rod shaped domain of a dystrophin as provided herein may comprise 5 to 23, 10 to 22 or 12 to 18 spectrin-like repeats as long as it can bind to actin and to DGC.

Alleviating one or more symptom(s) of Duchenne Muscular Dystrophy or Becker Muscular Dystrophy in an individual using an oligonucleotide of the invention may be assessed by any of the following assays: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur et al (2008) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using an oligonucleotide of the invention. Detectable improvement or prolongation is preferably a statistically significant improvement or prolongation as described in Hodgetts et al. (2006). Alternatively, the alleviation of one or more symptom(s) of Duchenne Muscular Dystrophy or Becker Muscular Dystrophy may be assessed by measuring an improvement of a muscle fiber function, integrity and/or survival. In a preferred method, one or more symptom(s) of a DMD or a BMD patient is/are alleviated and/or one or more characteristic(s) of one or more muscle cells from a DMD or a BMD patient is/are improved. Such symptoms or characteristics may be assessed at the cellular, tissue level or on the patient self.

An alleviation of one or more characteristics of a muscle cell from a patient may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

The improvement of muscle fiber function, integrity and/or survival may be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in Hodgetts et al. (2006). A detectable decrease in creatine kinase may mean a decrease of 5%, 10%, 20%, 30%, 40%, 50%, 60%, 70%, 80%, 90% or more compared to the concentration of creatine kinase in a same DMD or BMD patient before treatment.

A detectable decrease of necrosis of muscle fibers is preferably assessed in a muscle biopsy, more preferably as described in Hodgetts et al. (2006), using biopsy cross-sections. A detectable decrease of necrosis may be a decrease of 5%, 10%, 20%, 30%, 40%, 50%, 60%, 70%, 80%, 90% or more of the area wherein necrosis has been identified using biopsy cross-sections. The decrease is measured by comparison to the necrosis as assessed in a same DMD or BMD patient before treatment.

A detectable increase of the homogeneity of the diameter of a muscle fiber is preferably assessed in a muscle biopsy cross-section, more preferably as described in Hodgetts et al. (2006). The increase is measured by comparison to the homogeneity of the diameter of a muscle fiber in a same DMD or BMD patient before treatment Preferably, an oligonucleotide of the invention provides said individual with a functional or a semi-functional dystrophin protein (typically in the case of DMD) and is able to, for at least in part decrease the production of an aberrant dystrophin protein in said individual (typically in the case of BMD).

Decreasing the production of an aberrant dystrophin mRNA, or aberrant dystrophin protein, preferably means that 90%, 80%, 70%, 60%, 50%, 40%, 30%, 20%, 10%, 5% or less of the initial amount of aberrant dystrophin mRNA, or aberrant dystrophin protein, is still detectable by RT PCR (mRNA) or immunofluorescence or western blot analysis (protein). An aberrant dystrophin mRNA or protein is also referred to herein as a less functional (compared to a wild type functional dystrophin protein as earlier defined herein) or a non-functional dystrophin mRNA or protein. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein. The detection of a functional or semi-functional dystrophin mRNA or protein may be done as for an aberrant dystrophin mRNA or protein.

Once a DMD patient is provided with a functional or a semi-functional dystrophin protein, at least part of the cause of DMD is taken away. Hence, it would then be expected that the symptoms of DMD are at least partly alleviated. The enhanced skipping frequency also increases the level of functional or a semi-functional dystrophin protein produced in a muscle cell of a DMD or BMD individual.

Exons contain one or more specific sequences comprising splicing regulatory elements which have shown to be effective targets for antisense oligonucleotides (Aartsma-Rus et al, 2010). One embodiment therefore provides an oligonucleotide for providing said individual with a functional or semi-functional dystrophin protein wherein said oligonucleotide comprises a sequence which is specifically binding, targeting and/or hybridizing with and/or blocking these splicing regulatory elements in a dystrophin pre-mRNA exon. Such oligonucleotide is also able to bind and/or target and/or hybridize with and/or block these splicing regulatory elements in a dystrophin pre-mRNA. In addition, since an exon will only be included into the resulting mRNA when both the splice sites are recognized by the spliceosome complex, splice sites are other targets for an oligonucleotide of the invention. One embodiment therefore provides an oligonucleotide for providing said individual with a functional or semi-functional dystrophin protein wherein said oligonucleotide comprises a sequence which is specifically binding and/or targeting and/or hybridizing with, and/or blocking one of or both the splice sites of an exon of a dystrophin pre-mRNA. Such oligonucleotide is also able to bind and/or target, hybridize with and/or block one or both of these splice sites of an exon of a dystrophin pre-mRNA. Usually a splice site of an exon comprises 1, 2, 3, or more nucleotides present in said exon and 1, 2, 3, or more nucleotides present in an adjacent or neighboring intron. In one embodiment an oligonucleotide is used which is solely binding to and/or targeting and/or hybridizing with an intron region of a dystrophin pre-mRNA. Such oligonucleotide is able to bind and/or able to target and/or able to hybridize with said intron region. This is however not necessary: it is also possible to use an oligonucleotide which targets and/or binds and/or hybridizes with and/or is able to target and/or is able to binds and/or is able to hybridizes with an intron-specific sequence as well as exon-specific sequence. Of course, an oligonucleotide is not necessarily binding to and/or targeting and/or hybridizing with the entire sequence of a dystrophin exon or intron. Such oligonucleotide is also not necessary able to bind to and/or able to target and/or able to hybridize with the entire sequence of a dystrophin exon or intron. Oligonucleotides which are specifically binding, targeting and/or hybridizing with and/or which are specifically able to bind and/or able to target and/or able to hybridize part of such exon or intron are preferred. An oligonucleotide is used, said oligonucleotide is preferably reverse complementary to, and/or binds to, and/or targets and/or hybridizes with and/or is able to bind to and/or is able to target and/or is able to hybridize with at least part of a dystrophin exon and/or intron, said part having at least 10, 11, 12, 13, 14, 15, 16, 17, 18, 19, 20, 21, 22, 23, 24, 25, 26, 27, 28, 29, 30, 31, 32, or 33 nucleotides.

Splicing of a dystrophin pre-mRNA occurs via two sequential transesterification reactions involving an intronic branch point and a splice site of an adjacent intron. Hence, an oligonucleotide is used for exon skipping, wherein said oligonucleotide comprises a sequence which is binding to and/or targeting and/or hybridizing with or is able to bind to and/or is able to target and/or is able to hybridize with such branch point and/or splice site. Preferably said splice site and/or branch point is present in a dystrophin pre-mRNA.

Since splice sites contain consensus sequences, the use of an oligonucleotide part or a functional equivalent thereof comprising a sequence which is capable of binding to and/or able to bind to and/or able to target and/or able to hybridize and/or binds to and/or target and/or hybridizes with a splice site involves the risk of promiscuous hybridization. Hybridization of said oligonucleotide to other splice sites than the sites of the exon to be skipped could easily interfere with the accuracy of the splicing process. To overcome these and other potential problems related to the use of an oligonucleotide which is binding and/or hybridizing and/or targeting and/or is able to bind to and/or is able to target and/or is able to hybridize a splice site, most preferred embodiment provides an oligonucleotide for providing said individual with a functional or a semi-functional dystrophin protein, wherein said oligonucleotide or a functional equivalent thereof, binding to and/or hybridizing with and/or targeting and/or is able to bind to and/or is able to hybridize and/or is able to target a specific part of a dystrophin pre-mRNA exon. Exons contain coding sequences which are typically more specific that the non-coding intron sequences. Preferably, said oligonucleotide binding to and/or hybridizing with and/or targeting and/or able to bind to and/or able to hybridize with and/or able to target a specific part of a dystrophin pre-mRNA exon is capable of specifically blocking, interfering and/or inhibiting a splicing regulatory sequence and/or structure of the anticipated exon(s) in said dystrophin pre-mRNA. Interfering with such splicing regulatory sequence and/or structure has the advantage that such elements are located within the exon. The risk for sequence-related off-target effects is therefore limited. By providing an oligonucleotide for the interior of the exon to be skipped, it is possible to mask the exon from the splicing apparatus. The failure of the splicing apparatus to recognize the exon to be skipped thus leads to exclusion of the exon from the final mRNA. This embodiment does not interfere directly with the enzymatic process of the splicing machinery (the joining of the exons). It is thought that this allows the method to be more specific and/or reliable. It has been found that an oligonucleotide capable of binding to and/or able to bind to and/or able to target and/or able to hybridize and/or binding to and/or hybridizing with and/or targeting an exon at any point may be able to induce the skipping of said exon.

Within the context of the invention, an oligonucleotide of the invention may comprise a functional equivalent or an equivalent of an oligonucleotide. A functional equivalent or an equivalent of an oligonucleotide preferably means an oligonucleotide as defined herein wherein one or more nucleotides have been substituted and wherein an activity of said functional equivalent or equivalent is retained to at least some extent. Preferably, an activity of said oligonucleotide comprising a functional equivalent or equivalent of an oligonucleotide is providing a functional or a semi-functional dystrophin protein. Said activity of said oligonucleotide comprising a functional equivalent or an equivalent of an oligonucleotide is therefore preferably assessed by quantifying the amount of a functional or a semi-functional dystrophin protein. A functional or semi-functional dystrophin is herein preferably defined as being a dystrophin able to bind actin and members of the DGC (or DAPC) protein complex. The assessment of said activity of said functional equivalent of an oligonucleotide is preferably done by RT-PCR and sequencing (on RNA level; for detection of specific exon skipping), or by immunofluorescence and Western blot analyses (on protein level: for detection of protein restoration). Said activity is preferably retained to at least some extent when it represents at least 50%, or at least 60%, or at least 70% or at least 80% or at least 90% or at least 95% or more of corresponding activity of said oligonucleotide the functional equivalent or equivalent derives from. Throughout this application, when the word oligonucleotide is used it may be replaced by a functional equivalent thereof or an equivalent thereof as defined herein. In an embodiment, an equivalent or a functional equivalent of an oligonucleotide of the invention comprises a modification. Throughout this application, when the word oligonucleotide is used it may be replaced by an antisense oligonucleotide as defined herein unless otherwise indicated.

Hence, the use of an oligonucleotide or a functional equivalent thereof, or an equivalent thereof comprising a 2'-O-methyl phosphorothioate RNA monomer or consisting of 2'-O-methyl phosphorothioate RNA and comprising a 5-methylpyrimidine (i.e. a 5-methylcytosine and/or a 5-methyluracil) and/or a 2,6-diaminopurine base and being represented by a nucleotide sequence comprising or consisting of a sequence which is reverse complementary to, and/or binds to and/or targets and/or hybridizes and/or is able to bind to and/or is able to target and/or is able to hybridize with a dystrophin pre-mRNA exon is assumed to have a positive effect on at least one of the parameters of said oligonucleotide, as has already been defined herein, when compared to their counterparts which do not comprise any 5-methylcytosine, 5-methyluracil and 2,6-diaminopurine (i.e. so called non-modified oligonucleotide) as indicated earlier herein, and is therefore assumed to exhibit an improved therapeutic result in a DMD or a BMD cell of a patient and/or in a DMD or a BMD patient. Such a therapeutic result may be characterized by:

alleviating one or more symptom(s) of DMD or BMD and/or alleviating one or more characteristics of a muscle cell from a patient and/or providing said individual with a functional or semi-functional dystrophin protein and/or at least in part decreasing the production of an aberrant dystrophin protein in said individual.

Each of these features has already been defined herein.

Preferably, an oligonucleotide is represented by a nucleotide sequence which comprises or consists of a sequence which is binding to and/or targeting and/or being reverse complementary to and/or is hybridizing with and/or which is able to bind to and/or is able to target and/or is able to hybridize with and/or is reverse complementary to at least a part of dystrophin pre-mRNA exons 44 to 55, said oligonucleotide having a length of at least 10 nucleotides. However, the length of said oligonucleotide may be at least 11, 12, 13, 14, 15, 16, 17, 18, 19, 20, 21, 22, 23, 24, 25, 26, 27, 28, 29, 30, 31, 32, or 33 nucleotides. Throughout the invention, said sequence representing the oligonucleotide may also be called a base or a nucleotide sequence.

Preferably, an oligonucleotide of the invention is represented by a nucleotide sequence or a base sequence comprising or consisting of a sequence that is capable of binding to, and/or targeting and/or being reverse complementary to and/or hybridizing with and/or being able to bind to and/or being able to hybridize with and/or being able to target a part of an exon of dystrophin pre-mRNA. Said binding or targeted part may be at least 50% of the length of the oligonucleotide of the invention, or at least 60%, or at least 70%, or at least 80%, or at least 90% or at least 95%, or 98% and up to 100%. An oligonucleotide may be represented by a nucleotide or a base sequence, said nucleotide or base sequence comprising a sequence that binds and/or targets and/or is reverse complementary to and/or hybridizes with and/or is able to bind to and/or is able to hybridize with and/or is able to target at least a part of an exon selected from the group consisting of exons 44 to 55 of dystrophin pre-mRNA as defined herein and additional flanking sequences. In a more preferred embodiment, the length of said binding or targeted part of said oligonucleotide is of at least 10, 11, 12, 13, 14, 15, 16, 17, 18, 19, 20, 21, 22, 23, 24, 25, 26, 27, 28, 29, 30, 31, 32, or 33 nucleotides. Several types of flanking sequences may be used. Preferably, flanking sequences are used to modify the binding of a protein to said oligonucleotide, or to modify a thermodynamic property of said oligonucleotide, more preferably to modify target RNA binding affinity. In another preferred embodiment, additional flanking sequences are reverse complementary to sequences of the dystrophin pre-mRNA which are not present in said exon. Such flanking sequences are preferably capable of binding to and/or targeting sequences comprising or consisting of the branchpoint and/or the splice site acceptor or donor consensus sequences of said exon. In a preferred embodiment, such flanking sequences are capable of binding to and/or targeting sequences comprising or consisting of sequences of an intron of the dystrophin pre-mRNA which is adjacent to said exon.

One preferred embodiment provides an oligonucleotide for providing said individual with a functional or a semi-functional dystrophin protein, said oligonucleotide or a functional equivalent thereof or an equivalent thereof, being represented by a sequence or a base sequence which comprises:

a sequence which binds, is able to bind, targets, hybridizes or is reverse complementary to a region of a dystrophin pre-mRNA exon that is hybridized to another part of a dystrophin pre-mRNA exon (closed structure), and a sequence which binds and/or targets and/or hybridizes and/or is reverse complementary to and/or is able to bind and/or is able to target and/or is able to hybridize with a region of a dystrophin pre-mRNA exon that is not hybridized in said dystrophin pre-mRNA (open structure).

For this embodiment, reference is made to the WO 2004/083446 patent application. RNA molecules exhibit strong secondary structures, mostly due to base pairing of complementary or partly complementary stretches within the same RNA. It has long since been thought that structures in the RNA play a role in the function of the RNA. Without being bound by theory, it is believed that the secondary structure of the RNA of an exon plays a role in structuring the splicing process. Through its structure, an exon is recognized as a part that needs to be included in the mRNA. In an embodiment, an oligonucleotide is capable of interfering with the structure of the exon and therefore capable of interfering with the splicing apparatus of said exon, masking the exon from the splicing apparatus and thereby inducing the skipping of said exon. It has been found that many oligonucleotides indeed comprise this capacity, some more efficient than others. Without being bound by theory it is thought that the overlap with an open structure improves the invasion efficiency of the oligonucleotide (i.e. increases the efficiency with which the oligonucleotide can enter the structure), whereas the overlap with the closed structure subsequently increases the efficiency of interfering with the secondary structure of the RNA of the exon. It is found that the length of the partial reverse complementarity to both the closed and the open structure is not extremely restricted. We have observed high efficiencies with compounds comprising oligonucleotides with variable lengths of reverse complementarity in either structure. The term (reverse) complementarity is used herein to refer to a stretch of nucleic acids that can hybridise to another stretch of nucleic acids under physiological conditions. Hybridization conditions are later defined herein. It is thus not absolutely required that all the bases in the region of complementarity are capable of pairing with bases in the opposing strand. For instance, when designing an antisense oligonucleotide, one may want to incorporate for instance a residue that does not base pair with the base on the complementary strand. Mismatches may to some extent be allowed, if under the circumstances in the cell, the stretch of nucleotides is capable of hybridizing to the complementary part.

In a preferred embodiment a reverse complementary part of an antisense oligonucleotide (either to said open or to said closed structure) comprises at least 3, and more preferably at least 4 consecutive nucleotides. The reverse complementary regions are preferably designed such that, when combined, they are specific for an exon in a pre-mRNA. Such specificity may be created with various lengths of reverse complementary regions as this depends on the actual sequences in other (pre-)mRNA in the system. The risk that also one or more other pre-mRNA will be able to hybridise to an oligonucleotide decreases with increasing size of said oligonucleotide.

It is clear that an antisense oligonucleotide comprising mismatches in the region of reverse complementarity but that retain the capacity to hybridise to the targeted region(s) in the pre-mRNA, can be used in the present invention. However, preferably at least the reverse complementary parts do not comprise such mismatches as these typically have a higher efficiency and a higher specificity than oligonucleotide having such mismatches in one or more reverse complementary regions. It is thought that higher hybridisation strengths, (i.e. increasing number of interactions with the opposing strand) are favourable in increasing the efficiency of the process of interfering with the splicing machinery of the system. Preferably, the reverse complementarity is from 90 to 100%. In general this allows for 1 or 2 mismatch(es) in an oligonucleotide of 20 nucleotides or 1 to 4 mismatches in an oligonucleotide of 40 nucleotides. Therefore, we may have 1, 2, 3, 4, 5 mismatches in an oligonucleotide of 10 to 50 nucleotides. Preferably, 0, 1 or 2 mismatches are present in an oligonucleotide of 10 to 50 nucleotides.

The structure (i.e. open and closed structures) is best analyzed in the context of the pre-mRNA wherein the exon resides. Such structure may be analyzed in the actual RNA. However, it is currently possible to predict the secondary structure of an RNA molecule (at lowest energy costs) quite well using structure-modeling programs. Non-limiting examples of a suitable program are RNA structure version 4.5 or RNA mfold version 3.5 (Zuker et al., 2003). A person skilled in the art will be able to predict, with suitable reproducibility, a likely structure of an exon, given a nucleotide sequence.

Best predictions are obtained when providing such modeling programs with both said exon and flanking intron sequences. It is typically not necessary to model the structure of the entire pre-mRNA.

The open and closed structure to which the oligonucleotide of an oligonucleotide is directed, are preferably adjacent to one another. It is thought that in this way the annealing of the oligonucleotide to the open structure induces opening of the closed structure whereupon annealing progresses into this closed structure. Through this action the previously closed structure assumes a different conformation. However, when potential (cryptic) splice acceptor and/or donor sequences are present within the targeted exon, occasionally a new exon inclusion signal or splicing regulatory sequence, element, structure, or signal is generated defining a different (neo) exon, i.e. with a different 5' end, a different 3' end, or both. This type of activity is within the scope of the present invention as the targeted exon is excluded from the mRNA. The presence of a new exon, containing part of the targeted exon, in the mRNA does not alter the fact that the targeted exon, as such, is excluded. The inclusion of a neo-exon can be seen as a side effect which occurs only occasionally. There are two possibilities when exon skipping is used to restore (part of) an open reading frame of dystrophin that is disrupted as a result of a mutation. One is that the neo-exon is functional in the restoration of the reading frame, whereas in the other case the reading frame is not restored. When selecting a compound comprising an oligonucleotide for restoring dystrophin reading frames by means of exon-skipping it is of course clear that under these conditions only those compounds comprising those oligonucleotide are selected that indeed result in exon-skipping that restores the dystrophin open reading frame, with or without a neo-exon.

Further provided is an oligonucleotide for providing said individual with a functional or a semi-functional dystrophin protein, wherein said oligonucleotide or a functional equivalent thereof or an equivalent thereof comprises a 2'-O-methyl phosphorothioate RNA monomer or consists of 2'-O-methyl phosphorothioate RNA and comprises a 5-methylpyrimidine (i.e. a 5-methylcytosine, and/or a 5-methyluracil) and/or a 2,6-diaminopurine base and is represented by a nucleotide or a base sequence comprising a sequence that is reverse complementary to and/or binds to and/or targets and/or hybridizes with and/or is able to bind to and/or is able to target and/or is able to hybridize with a binding site for a serine-arginine (SR) protein in RNA of an exon of a dystrophin pre-mRNA. In WO 2006/112705 patent application we have disclosed the presence of a correlation between the affectivity of an exon-internal antisense oligonucleotide in inducing exon skipping and the presence of a (for example by ESEfinder) predicted SR binding site in the target pre-mRNA site of said AON. Therefore, in one embodiment an oligonucleotide is generated comprising determining a (putative) binding site for an SR (Ser-Arg) protein in RNA of a dystrophin exon and producing a corresponding compound comprising oligonucleotide that is reverse complementary to and/or binds to and/or targets and/or hybridizes with and/or is able to bind and/or is able to target and/or is able to hybridize with said RNA and that at least partly overlaps said (putative) binding site. The term "at least partly overlaps" is defined herein as to comprise an overlap of only a single nucleotide of an SR binding site as well as multiple nucleotides of said binding site as well as a complete overlap of said binding site. This embodiment preferably further comprises determining from a secondary structure of said RNA, a region that is hybridized to another part of said RNA (closed structure) and a region that is not hybridized in said structure (open structure), and subsequently generating an oligonucleotide that at least partly overlaps said (putative) binding site and that overlaps at least part of said closed structure and overlaps at least part of said open structure. In this way we increase the chance of obtaining an oligonucleotide that is capable of interfering with the exon inclusion from the pre-mRNA into mRNA. It is possible that a first selected SR-binding region does not have the requested open-closed structure in which case another (second) SR protein binding site is selected which is then subsequently tested for the presence of an open-closed structure. This process is continued until a sequence is identified which contains an SR protein binding site as well as a(n) (partly overlapping) open-closed structure. This sequence is then used to design an oligonucleotide which is reverse complementary to said sequence.

Such a method for generating an antisense oligonucleotide is also performed by reversing the described order, i.e. first generating an oligonucleotide comprising determining, from a secondary structure of RNA from a dystrophin exon, a region that assumes a structure that is hybridised to another part of said RNA (closed structure) and a region that is not hybridised in said structure (open structure), and subsequently generating an oligonucleotide, of which at least a part of said oligonucleotide is reverse complementary to said closed structure and of which at least another part of said oligonucleotide is reverse complementary to said open structure. This is then followed by determining whether an SR protein binding site at least overlaps with said open/closed structure. In this way the method of WO 2004/083446 is improved. In yet another embodiment the selections are performed simultaneously.

Without wishing to be bound by any theory it is currently thought that use of an oligonucleotide directed to or targeting an SR protein binding site results in (at least partly) impairing the binding of an SR protein to the binding site of an SR protein which results in disrupted or impaired splicing.

Preferably, an open/closed structure and an SR protein binding site partly overlap and even more preferred an open/closed structure completely overlaps an SR protein binding site or an SR protein binding site completely overlaps an open/closed structure. This allows for an improved disruption of exon inclusion.

Besides consensus splice site and branchpoint intronic sequences, many (if not all) exons contain splicing regulatory sequences such as but not limited to exonic splicing enhancer (ESE) sequences to facilitate the recognition of genuine splice sites by the spliceosome (Cartegni et al., 2002; and Cartegni et al., 2003). A subgroup of splicing factors, called the SR proteins, can bind to these ESEs and recruit other splicing factors, such as U1 and U2AF to (weakly defined) splice sites. The binding sites of the four most abundant SR proteins (SF2/ASF, SC35, SRp40 and SRp55) have been analyzed in detail and these results are implemented in ESEfinder, a web source that predicts potential binding sites for these SR proteins (Cartegni et al., 2002; and Cartegni et al., 2003). There is a correlation between the effectiveness of an oligonucleotide and the presence/absence of an SF2/ASF, SC35 and SRp40 binding site in the site targeted by said oligonucleotide. In a preferred embodiment, the invention thus provides an oligonucleotide as described above, which is reverse complementary to and/or targets and/or binds to and/or hybridizes with and/or is able to target and/or is able to bind and/or is able to hybridize with a binding site for a SR protein. Preferably, said SR protein is SF2/ASF or SC35 or SRp40.

In one embodiment a DMD patient is provided with a functional or a semi-functional dystrophin protein by using an oligonucleotide or a functional equivalent thereof or an equivalent thereof comprising a 2'-O-methyl phosphorothioate RNA monomer or consisting of 2'-O-methyl phosphorothioate RNA and comprising a 5-methylpyrimidine (i.e. a 5-methylcytosine, and/or a 5-methyluracil) and/or a 2,6-diaminopurine base and being capable of specifically binding or targeting and/or being able to bind and/or being able to target and/or being able to hybridize a regulatory RNA sequence which is required for the correct splicing of a dystrophin exon in a transcript. Several cis-acting RNA sequences are required for the correct splicing of exons in a transcript. In particular, elements such as an exonic splicing enhancer (ESE), an exon recognition sequence (ERS), and/or an exonic splicing silencer (ESS) are identified to regulate specific and efficient splicing of constitutive and alternative exons. Using a sequence-specific antisense oligonucleotide or a base-specific antisense oligonucleotide (AON) that binds to and/or targets and/or is reverse complementary to and/or hybridizes with and/or is able to bind and/or is able to hybridize with and/or is able to target the elements, their regulatory function is disturbed so that the exon is skipped, as shown for DMD. Hence, in one preferred embodiment, an oligonucleotide or a functional equivalent thereof or an equivalent thereof is used which is reverse complementary to and/or binds to and/or targets and/or hybridizes with and/or is able to bind to and/or is able to target and/or is able to hybridize with an exonic splicing enhancer (ESE), an exon recognition sequence (ERS), and/or an exonic splicing silencer (ESS).

In a preferred embodiment, an oligonucleotide of the invention comprises or consists of a sequence or a base sequence that is reverse complementary to and/or binds to and/or targets and/or hybridizes with and/or is able to bind to and/or is able to target and/or is able to hybridize with at least a part of dystrophin pre-mRNA exon 44, 45, 46, 47, 48, 49, 50, 51, 52, 53, 54, or 55, said part having at least 10 nucleotides. However, said part may also have at least 11, 12, 13, 14, 15, 16, 17, 18, 19, 20, 21, 22, 23, 24, 25, 26, 27, 28, 29, 30, 31, 32, or, 33 nucleotides. For the dystrophin exons identified above, we provide the stretch of nucleotides (SEQ ID NO: 2 to 13 identified below) of said exon to which an oligonucleotide binds to and/or is reverse complementary to and/or targets and/or hybridizes with and/or is able to bind to and/or is able to target and/or is able to hybridize with.

(SEQ ID NO: 2)
5'-GCGAUUUGACAGAUCUGUUGAGAAAUGGCGGCGUUUUCAUUAUGAU

AUAAAGAUAUUUAAUCAGUGGCUAACAGAAGCUGAACAGUUUCUCAGAA

AGACACAAAUUCCUGAGAAUUGGGAACAUGCUAAAUACAAAUGGUAUCU

UAAG-3' for skipping of exon 44;

(SEQ ID NO: 3)
5'-GAACUCCAGGAUGGCAUUGGGCAGCGGCAAACUGUUGUCAGAACAU

UGAAUGCAACUGGGGAAGAAAUAAUUCAGCAAUCCUCAAAAACAGAUGC

CAGUAUUCUACAGGAAAAAUUGGGAAGCCUGAAUCUGCGGUGGCAGGAG

GUCUGCAAACAGCUGUCAGACAGAAAAAAGAG-3' for skipping of exon 45;

(SEQ ID NO: 4)
5'-GCUAGAAGAACAAAAGAAUAUCUUGUCAGAAUUUCAAAGAGAUUUA

AAUGAAUUUGUUUUAUGGUUGGAGGAAGCAGAUAACAUUGCUAGUAUCC

CACUUGAACCUGGAAAAGAGCAGCAACUAAAAGAAAAGCUUGAGCAAGU

CAAG-3' for skipping of exon 46;

(SEQ ID NO: 5)
5'-UUACUGGUGGAAGAGUUGCCCCUGCGCCAGGGAAUUCUCAAACAAU

UAAAUGAAACUGGAGGACCCGUGCUUGUAAGUGCUCCCAUAAGCCCAGA

AGAGCAAGAUAAACUUGAAAAUAAGCUCAAGCAGACAAAUCUCCAGUGG

AUAAAG-3' for skipping of exon 47

(SEQ ID NO: 6)
5'-GUUUCCAGAGCUUUACCUGAGAAACAAGGAGAAAUUGAAGCUCAAA

UAAAAGACCUUGGGCAGCUUGAAAAAAAGCUUGAAGACCUUGAAGAGCA

GUUAAAUCAUCUGCUGCUGUGGUUAUCUCCUAUUAGGAAUCAGUUGGAA

AUUUAUAACCAACCAAACCAAGAAGGACCAUUUGACGUUCAG-3' for skipping of exon 48

(SEQ ID NO: 7)
5'-GAAACUGAAAUAGCAGUUCAAGCUAAACAACCGGAUGUGGAAGAGA

UUUUGUCUAAAGGGCAGCAUUUGUACAAGGAAAAACCAGCCACUCAGCC

AGUGAAG-3' for skipping of exon 49

(SEQ ID NO: 8)
5'-AGGAAGUUAGAAGAUCUGAGCUCUGAGUGGAAGGCGGUAAACCGUU

UACUUCAAGAGCUGAGGGCAAAGCAGCCUGACCUAGCUCCUGGACUGAC

CACUAUUGGAGCCU-3' for skipping of exon 50;

(SEQ ID NO: 9)
5'-CUCCUACUCAGACUGUUACUCUGGUGACACAACCUGUGGUUACUAA

GGAAACUGCCAUCUCCAAACUAGAAAUGCCAUCUUCCUUGAUGUUGGAG

GUACCUGCUCUGGCAGAUUUCAACCGGGCUUGGACAGAACUUACCGACU

GGCUUUCUCUGCUUGAUCAAGUUAUAAAAUCACAGAGGGUGAUGGUGGG

UGACCUUGAGGAUAUCAACGAGAUGAUCAUCAAGCAGAAG-3' for skippthg of exon 51;

(SEQ ID NO: 10)
5'-GCAACAAUGCAGGAUUUGGAACAGAGGCGUCCCCAGUUGGAAGAAC

UCAUUACCGCUGCCCAAAAUUUGAAAAACAAGACCAGCAAUCAAGAGGC

UAGAACAAUCAUUACGGAUCGAA-3'

-continued for skipping of exon 52;

(SEQ ID NO: 11)
5'-UUGAAAGAAUUCAGAAUCAGUGGGAUGAAGUACAAGAACACCUUCA

GAACCGGAGGCAACAGUUGAAUGAAAUGUUAAAGGAUUCAACACAAUGG

CUGGAAGCUAAGGAAGAAGCUGAGCAGGUCUUAGGACAGGCCAGAGCCA

AGCUUGAGUCAUGGAAGGAGGGUCCCUAUACAGUAGAUGCAAUCCAAAA

GAAAAUCACAGAAACCAAG-3' for skipping of exon 53;

(SEQ ID NO: 12)
5'-CAGUUGGCCAAAGACCUCCGCCAGUGGCAGACAAAUGUAGAUGUGG

CAAAUGACUUGGCCCUGAAACUUCUCCGGGAUUAUUCUGCAGAUGAUAC

CAGAAAAGUCCACAUGAUAACAGAGAAUAUCAAUGCCUCUUGGAGAAGC

AUUCAUAAAAG-3' for skipping of exon 54;

(SEQ ID NO: 13)
5'-GGUGAGUGAGCGAGAGGCUGCUUUGGAAGAAACUCAUAGAUUACUG

CAACAGUUCCCCUGGACCUGGAAAAGUUUCUUGCCUGGCUUACAGAAG

CUGAAACAACUGCCAAUGUCCUACAGGAUGCUACCCGUAAGGAAAGGCU

CCUAGAAGACUCCAAGGGAGUAAAAGAGCUGAUGAAACAAUGGCAA-3' for skipping of exon 55.

Therefore, a preferred oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base and binds to and/or is reverse complementary to and/or targets and/or hybridizes with and/or is able to bind and/or is able to target and/or is able to hybridize with a continuous stretch of at least 10 and up to 33 nucleotides within one of the following exon nucleotide sequences selected from SEQ ID NO: 2 to 13.

Preferred oligonucleotides are also defined as follows:
comprise a 2'-O-methyl phosphorothioate RNA monomer or consist of 2'-O-methyl phosphorothioate RNA and
bind to and/or are reverse complementary to and/or target and/or hybridize with and/or is able to bind to and/or is able to target and/or is able to hybridize with a continuous stretch of at least 10 and up to 33 nucleotides within one of the following exon nucleotide sequences selected from SEQ ID NO: 2 to 13 as identified above.

More preferably, such oligonucleotides comprise a 5-methylpyrimidine (i.e. a 5-methylcytosine, and/or a 5-methyluracil) and/or a 2,6-diaminopurine base as earlier defined herein.

More preferred oligonucleotides comprise a 2'-O-methyl phosphorothioate RNA monomer or consist of 2'-O-methyl phosphorothioate RNA and more preferably comprise a 5-methylpyrimidine (i.e. a 5-methylcytosine, and/or a 5-methyluracil) and/or a 2,6-diaminopurine base and are represented by a nucleotide or a base sequence comprising or consisting of SEQ ID NO: 14-90 or by a nucleotide or a base sequence comprising or consisting of a fragment of SEQ ID NO: 14-90. SEQ ID NO:14-90 are identified in Table 1. In this context, "a 5-methylpyrimidine" means at least one 5-methylpyrimidine. Accordingly "at least one 5-methylpyrimindine" means at least one 5-methylcytosine and/or at least one 5-methyluracile.

Accordingly, preferred non-modified oligonucleotides are preferably derived from one of the nucleotide or base sequences SEQ ID NO:14-90 with X=C, Y=U, Z=A), and/or are represented by SEQ ID NO:91, 93, 94-170. Each of these non-modified oligonucleotides comprises no 5-methylpyrimidine (i.e. a 5-methylcytosine, and/or a 5-methyluracil) and no 2,6-diaminopurine. Please note that SEQ ID NO:91 is identical with SEQ ID NO: 132.

Accordingly, preferred modified oligonucleotides are derived from one of the nucleotide or base sequences SEQ ID NO: 14-90 and comprise at least one 5-methylpyrimidine (i.e. a 5-methylcytosine, and/or a 5-methyluracil) and/or at least one 2,6-diaminopurine (i.e. at least one X is $m^5C=X_1$ and/or at least one Y is $m^5U=Y_1$ and/or at least one Z is $a^2A=Z_1$). Please note that SEQ ID NO: 92 is identical with SEQ ID NO: 199. More preferred modified oligonucleotides are represented by a nucleotide or a base sequence comprising or consisting of SEQ ID NO: 92, 171-213, 215, 217, 218, 219. Even more preferred modified oligonucleotides (all $X=m^5C=X_1$ and/or all $Y=m^5U=Y_1$ and/or all $Z=a^2A=Z_1$) are derived from the most preferred nucleotide or base sequences (SEQ ID NO:15, 21, 31, 40, 52, and 57) and are represented by SEQ ID NO: 92, 171-174, 185-188, 199, 200, 202-215, 217, 218, 219. The most preferred modified oligonucleotides are disclosed in Table 3.

Within the context of the invention, a fragment of SEQ ID NO: 14-90, or a fragment of SEQ ID NO:91-219, preferably means a nucleotide or a base sequence comprising or consisting of at least 10 contiguous nucleotides from said SEQ ID NO:14-90 or from said SEQ ID NO:91-219.

Such more preferred oligonucleotides are also defined as follows:
comprise a 2'-O-methyl phosphorothioate RNA monomer or consist of 2'-O-methyl phosphorothioate RNA and
are represented by a nucleotide or base sequence comprising or consisting of SEQ ID NO: 14-90, 91, 93-170 or by a nucleotide or a base sequence comprising or consisting of a fragment of SEQ ID NO: 14-90, 91, 93-170.

More preferably, such oligonucleotides comprise a 5-methylpyrimidine (i.e. a 5-methylcytosine, and/or a 5-methyluracil) and/or a 2,6-diaminopurine base as earlier defined herein.

Even more preferred oligonucleotides comprise a 2'-O-methyl phosphorothioate RNA monomer or consist of 2'-O-methyl phosphorothioate RNA and more preferably comprise a 5-methylpyrimidine (i.e. a 5-methylcytosine, and/or a 5-methyluracil) and/or a 2,6-diaminopurine base, are represented by a nucleotide or a base sequence comprising or consisting of SEQ ID NO: 14-90, 92, 171-215, 217, 218, 219 or by a nucleotide or a base sequence comprising or consisting of a fragment of SEQ ID NO:14-90, 92, 171-215, 217, 218, 219 and having a length of 10, 11, 12, 13, 14, 15, 16, 17, 18, 19, 20, 21, 22, 23, 24, 25, 26, 27, 28, 29, 30, 31, 32 or 33 nucleotides. Preferred sequences (i.e. preferred nucleotide or base sequences) among SEQ ID NO:14-90, 92, and 171-215, 217, 218, 219 include SEQ ID NO: 15, 21, 31, 40, 43, 52, 57, 59, 171-174, 185-188, 199, 200, 202-213, 215, 217, 218, 219 more preferably SEQ ID NO: 40, 43, 52, 57, 59, 208, 207, 200, 210, 206, 171, 173, 199, 213, 185, 187.

Such even more preferred oligonucleotides are also defined as follows:
comprise a 2'-O-methyl phosphorothioate RNA monomer or consist of 2'-O-methyl phosphorothioate RNA and are represented by a nucleotide or a base sequence comprising or consisting of SEQ ID NO: 14-90, 91, 93-170, 216 or by a nucleotide or a base sequence comprising or consisting of a fragment of SEQ ID NO: 14-90, 91, 93-170 and have a length of 10, 11, 12, 13, 14, 15, 16, 17, 18, 19, 20, 21, 22, 23, 24, 25, 26, 27, 28, 29, 30, 31, 32 or 33 nucleotides. More preferably, such oligonucleotides comprise a 5-methylpyrimidine (i.e. a 5-methylcytosine, and/or a 5-methyluracil) and/or a 2,6-diaminopurine base as earlier defined herein.

Even more preferably, such modified oligonucleotides are represented by a nucleotide or a base sequence comprising or consisting of SEQ ID NO: 92, 171-213, 215 217, 218, 219 or by a nucleotide or a base sequence comprising or consisting of a fragment of SEQ ID NO: 92, 171-213, 215, 217, 218, 219 and have a length of 10, 11, 12, 13, 14, 15, 16, 17, 18, 19, 20, 21, 22, 23, 24, 25, 26, 27, 28, 29, 30, 31, 32 or 33 nucleotides. Even more preferred modified oligonucleotides are derived from the most preferred nucleotide or base sequences (SEQ ID NO:15, 21, 31, 40, 52, and 57) and are represented by a nucleotide or a base sequence comprising or consisting of SEQ ID NO: 92, 171-174, 185-188, 199, 200, 202-213, 215, 217, 218, 219 or by a nucleotide or a base sequence comprising or consisting of a fragment of SEQ ID NO: 92, 171-174, 185-188, 199, 200, 202-213, 215, 217, 218, 219 and having a length of 10, 11, 12, 13, 14, 15, 16, 17, 18, 19, 20, 21, 22, 23, 24, 25, 26, 27, 28, 29, 30, 31, 32 or 33 nucleotides.

Preferred oligonucleotides for inducing the skipping of exon 44 from the dystrophin pre-mRNA are as follows below.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 14 and has a length of 19, 20, 21, 22, 23, 24, 25, 26, 27, 28, 29, 30, 31, 32, or 33 nucleotides or by a fragment of SEQ ID NO:14 comprising or consisting of at least 10 contiguous nucleotides or bases of SEQ ID NO:14.

Accordingly a non-modified oligonucleotide derived from SEQ ID NO:14 is represented by SEQ ID NO:94 and a preferred fragment of SEQ ID NO:94 is represented by SEQ ID NO:143.

Accordingly, in a preferred embodiment, an oligonucleotide comprises a 2'-O-methyl phosphorothioate RNA monomer or consists of 2'-O-methyl phosphorothioate RNA and is represented by a nucleotide or a base sequence comprising SEQ ID NO: 94 and has a length of 19, 20, 21, 22, 23, 24, 25, 26, 27, 28, 29, 30, 31, 32, or 33 nucleotides or by a fragment of SEQ ID NO:94 comprising or consisting of at least 10 contiguous nucleotides or bases of SEQ ID NO:94.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:14 comprises SEQ ID NO: 63 and a preferred fragment of SEQ ID NO:94 comprises SEQ ID NO: 143, and each of said preferred fragments has a length of 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 15 and has a length of 20, 21, 22, 23, 24, 25, 26, 27, 28, 29, 30, 31, 32, or 33 nucleotides or by a fragment of SEQ ID NO:15 comprising or consisting of at least 10 contiguous nucleotides or bases of SEQ ID NO:15.

Accordingly a non-modified oligonucleotide derived from SEQ ID NO:15 is represented by SEQ ID NO:95.

Accordingly, in a preferred embodiment, an oligonucleotide comprises a 2'-O-methyl phosphorothioate RNA monomer or consists of 2'-O-methyl phosphorothioate RNA is represented by a nucleotide or base sequence comprising SEQ ID NO: 95 and has a length of 20, 21, 22, 23, 24, 25, 26, 27, 28, 29, 30, 31, 32, or 33 nucleotides or by a fragment of SEQ ID NO:95 comprising or consisting of at least 10 contiguous nucleotides or bases of SEQ ID NO:95.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:15 comprises SEQ ID NO: 64 and a preferred fragment of SEQ ID NO:95 comprises SEQ ID NO:144 and each of said fragments has a length of 15, 16, 17, 18, 19, 20, 21, 22, 23, 24, 25, 26, 27, 28, 29, 30, 31, 32 or 33 nucleotides. Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such preferred oligonucleotide is also defined as follows:
comprises a 2'-O-methyl phosphorothioate RNA monomer or consists of 2'-O-methyl phosphorothioate RNA and
is represented by a nucleotide or base sequence comprising or consisting of SEQ ID NO: 15 or 95 or 64 or 144 and has a length of 20, 21, 22, 23, 24, 25, 26, 27, 28, 29, 30, 31, 32, or 33 nucleotides or by a nucleotide or base sequence comprising or consisting of a fragment of SEQ ID NO: 15 or 95 or 64 or 144, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:15 or 95 or 64 or 144.

More preferably, such oligonucleotide comprises a 5-methylpyrimidine (i.e. a 5-methylcytosine, and/or a 5-methyluracil) and/or a 2,6-diaminopurine base as earlier defined herein More preferably, an oligonucleotide:
consists of 2'-O-methyl phosphorothioate RNA,
all its cytosines have been replaced by 5-methylcytosines,
such oligonucleotide is represented by a nucleotide or base sequence comprising SEQ ID NO: 15 and has a length of 20, 21, 22, 23, 24, 25, 26, 27, 28, 29, 30, 31, 32, or 33 nucleotides or by a fragment of SEQ ID NO:15 comprising or consisting of at least 10 contiguous nucleotides or bases of SEQ ID NO:15. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles,
such oligonucleotide is represented by a nucleotide or base sequence comprising SEQ ID NO: 204 and has a length of 20, 21, 22, 23, 24, 25, 26, 27, 28, 29, 30, 31, 32, or 33 nucleotides or by a fragment of SEQ ID NO:204 comprising or consisting of at least 10 contiguous nucleotides or bases of SEQ ID NO:204. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its cytosines have been replaced by 5-methylcytosines,
such oligonucleotide is represented by a nucleotide or base sequence comprising SEQ ID NO: 208 and has a length of 20, 21, 22, 23, 24, 25, 26, 27, 28, 29, 30, 31, 32, or 33 nucleotides or by a fragment of SEQ ID NO:208 comprising or consisting of at least 10 contiguous nucleotides or bases of SEQ ID NO:208. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles and all its cytosines have been replaced by 5-methylcytosines,
such oligonucleotide is represented by a nucleotide or base sequence comprising SEQ ID NO: 205 and has a length of 20, 21, 22, 23, 24, 25, 26, 27, 28, 29, 30, 31, 32, or 33 nucleotides or by a fragment of SEQ ID NO:205 comprising or consisting of at least 10 contiguous nucleotides or bases of SEQ ID NO:205. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its adenines have been replaced by 2,6-diaminopurines,
such oligonucleotide is represented by a nucleotide or base sequence comprising SEQ ID NO: 207 and has a length of 20, 21, 22, 23, 24, 25, 26, 27, 28, 29, 30, 31, 32, or 33 nucleotides or by a fragment of SEQ ID NO:207 comprising or consisting of at least 10 contiguous nucleotides or bases of SEQ ID NO:207. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or base sequence comprising SEQ ID NO: 16 and has a length of 20, 21, 22, 23, 24, 25, 26, 27, 28, 29, 30, 31, 32, or 33 nucleotides or by a fragment of SEQ ID NO:16 comprising or consisting of at least 10 contiguous nucleotides or bases of SEQ ID NO:16.

Accordingly a non-modified oligonucleotide derived from SEQ ID NO:16 is represented by SEQ ID NO:96.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 96 and has a length of 20, 21, 22, 23, 24, 25, 26, 27, 28, 29, 30, 31, 32, or 33 nucleotides or by a fragment of SEQ ID NO:96 comprising or consisting of at least 10 contiguous nucleotides or bases of SEQ ID NO:96.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 17 and has a length of 23, 24, 25, 26, 27, 28, 29, 30, 31, 32, or 33 nucleotides or by a fragment of SEQ ID NO:17 comprising or consisting of at least 10 contiguous nucleotides or bases of SEQ ID NO:17.

Accordingly a non-modified oligonucleotide derived from SEQ ID NO:17 is represented by SEQ ID NO:97 and a preferred fragment of SEQ ID NO:97 is represented by SEQ ID NO:145.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 97 and has a length of 23, 24, 25, 26, 27, 28, 29, 30, 31, 32, or 33 nucleotides or by a fragment of SEQ ID NO:97 comprising or consisting of at least 10 contiguous nucleotides or bases of SEQ ID NO:97.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:17 comprises SEQ ID NO: 65 and a preferred fragment of SEQ ID NO: 97 comprises SEQ ID NO: 145, each of said fragments has a length of 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 18 and has a length of 23, 24, 25, 26, 27, 28, 29, 30, 31, 32, or 33 nucleotides or by a fragment of SEQ ID NO:18 comprising or consisting of at least 10 contiguous nucleotides or bases of SEQ ID NO:18.

Accordingly a non-modified oligonucleotide derived from SEQ ID NO:18 is represented by SEQ ID NO:98 and a preferred fragment of SEQ ID NO:98 is represented by SEQ ID NO:146.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:18 comprises SEQ ID NO: 66 and a preferred fragment of SEQ ID NO: 98 comprises SEQ ID NO: 146, each of said fragments has a length of 14, 15, 16, 17, 18, 19, 20, 21, 22, 23, 24, 25, 26, 27, 28, 29, 30, 31, 32 or 33 nucleotides.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 98 and has a length of 23, 24, 25, 26, 27, 28, 29, 30, 31, 32, or 33 nucleotides or by a fragment of SEQ ID NO:98 comprising or consisting of at least 10 contiguous nucleotides or bases of SEQ ID NO:98.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 19 and has a length of 21, 22, 23, 24, 25, 26, 27, 28, 29, 30, 31, 32, or 33 nucleotides or by a fragment of SEQ ID NO:19 comprising or consisting of at least 10 contiguous nucleotides or bases of SEQ ID NO:19.

Accordingly a non-modified oligonucleotide derived from SEQ ID NO:19 is represented by SEQ ID NO:99.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 99 and has a length of 21, 22, 23, 24, 25, 26, 27, 28, 29, 30, 31, 32, or 33 nucleotides or by a fragment of SEQ ID NO:99 comprising or consisting of at least 10 contiguous nucleotides or bases of SEQ ID NO:99.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 20 and has a length of 23, 24, 25, 26, 27, 28, 29, 30, 31, 32, or 33 nucleotides or by a fragment of SEQ ID NO:20 comprising or consisting of at least 10 contiguous nucleotides or bases of SEQ ID NO:20.

Accordingly a non-modified oligonucleotide derived from SEQ ID NO:20 is represented by SEQ ID NO:100 and a preferred fragment of SEQ ID NO:100 is represented by SEQ ID NO:147, 148 or 149.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 100 and has a length of 23, 24, 25, 26, 27, 28, 29, 30, 31, 32, or 33 nucleotides or by a fragment of SEQ ID NO:100 comprising or consisting of at least 10 contiguous nucleotides or bases of SEQ ID NO:100.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:20 comprises SEQ ID NO: 67 and a preferred fragment of SEQ ID NO:100 comprises SEQ ID NO:147, each of said fragments has a length of 20, 21, 22, 23, 24, 25, 26, 27, 28, 29, 30, 31, 32 or 33 nucleotides. Another preferred fragment of SEQ ID NO:20 comprises SEQ ID NO: 68 and another preferred fragment of SEQ ID NO:100 comprises SEQ ID NO: 148, each of said fragments has a length of 13, 14, 15, 16, 17, 18, 19, 20, 21, 22, 23, 24, 25, 26, 27, 28, 29, 30, 31, 32 or 33 nucleotides. Another preferred fragment of SEQ ID NO:20 comprises SEQ ID NO: 69 and another preferred fragment of SEQ ID NO:100 comprises SEQ ID NO: 149, each of said fragments has a length of 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Preferred oligonucleotides for inducing the skipping of exon 45 from the dystrophin pre-mRNA are as follows below.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 21 and has a length of 25, 26, 27, 28, 29, 30, 31, 32, or 33 nucleotides or by a fragment of SEQ ID NO:21 comprising or consisting of at least 10 contiguous nucleotides or bases of SEQ ID NO:21.

Accordingly a non-modified oligonucleotide derived from SEQ ID NO:21 is represented by SEQ ID NO:101 and a preferred fragment of SEQ ID NO:101 is represented by SEQ ID NO:150, 151 or 152.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 101 and has a length 25, 26, 27, 28, 29, 30, 31, 32, or 33 nucleotides or by a fragment of SEQ ID NO:101 comprising or consisting of at least 10 contiguous nucleotides or bases of SEQ ID NO:101.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:21 comprises SEQ ID NO: 70 and a preferred fragment of SEQ ID NO:101 comprises SEQ ID NO:150, each of said fragments has a length of 20, 21, 22, 23, 24, 25, 26, 27, 28, 29, 30, 31, 32 or 33 nucleotides. Another preferred fragment of SEQ ID NO:21 comprises SEQ ID NO: 71 and another preferred fragment of SEQ ID NO:101 comprises SEQ ID NO:151, each of said fragments has a length of 20, 21, 22, 23, 24, 25, 26, 27, 28, 29, 30, 31, 32 or 33 nucleotides. Another preferred fragment of SEQ ID NO:21 comprises SEQ ID NO: 72 and a preferred fragment of SEQ ID NO:101 comprises SEQ ID NO:152, each of said fragments has a length of 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 21 and has a length of 25, 26, 27, 28, 29, 30, 31, 32, or 33 nucleotides or by a nucleotide or a base sequence comprising or consisting of a fragment of SEQ ID NO: 21, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:21.

More preferably, such oligonucleotide comprises a 5-methylpyrimidine (i.e. a 5-methylcytosine, and/or a 5-methyluracil) and/or a 2,6-diaminopurine base as earlier defined herein.

More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 21 and has a length of 25, 26, 27, 28, 29, 30, 31, 32, or 33 nucleotides or by a fragment of SEQ ID NO:21 comprising or consisting of at least 10 contiguous nucleotides or bases of SEQ ID NO:21.

Accordingly, said oligonucleotide is particularly represented by a nucleotide or a base sequence comprising SEQ ID NO: 200 and has a length of 25, 26, 27, 28, 29, 30, 31, 32, or 33 nucleotides or by a fragment of SEQ ID NO:200 comprising or consisting of at least 10 contiguous nucleotides or bases of SEQ ID NO:200.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles and
all its cytosines have been replaced by 5-methylcytosines,
such oligonucleotide is represented by a nucleotide or a base sequence comprising SEQ ID NO: 21 or SEQ ID NO:209 in particular, and has a length of 20, 21, 22, 23, 24, 25, 26, 27, 28, 29, 30, 31, 32, or 33 nucleotides, or by a fragment of SEQ ID NO:21 or 209 comprising or consisting of at least 10 contiguous nucleotides or bases of SEQ ID NO: 21 or 209. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its adenines have been replaced by 2,6-diaminopurines,
such oligonucleotide is represented by a nucleotide or a base sequence comprising SEQ ID NO: 21 or SEQ ID NO: 210 in particular, and has a length of 20, 21, 22, 23, 24, 25, 26, 27, 28, 29, 30, 31, 32, or 33 nucleotides, or by a fragment of SEQ ID NO:21 or 210 comprising or consisting of at least 10 contiguous nucleotides or bases of SEQ ID NO:21 or 210. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 22 and has a length of 24, 25, 26, 27, 28, 29, 30, 31, 32, or 33 nucleotides or by a fragment of SEQ ID NO:22 comprising or consisting of at least 10 contiguous nucleotides or bases of SEQ ID NO:22.

Accordingly a non-modified oligonucleotide derived from SEQ ID NO:22 is represented by SEQ ID NO:102.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 102 and has a length 24, 25, 26, 27, 28, 29, 30, 31, 32, or 33 nucleotides or by a fragment of SEQ ID NO:102 comprising or consisting of at least 10 contiguous nucleotides or bases of SEQ ID NO:102.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 23 and has a length of 25, 26, 27, 28, 29, 30, 31, 32, or 33 nucleotides or by a fragment of SEQ ID NO:23 comprising or consisting of at least 10 contiguous nucleotides or bases of SEQ ID NO:23.

Accordingly a non-modified oligonucleotide derived from SEQ ID NO:23 is represented by SEQ ID NO:103.

Accordingly, in a preferred embodiment, an oligonucleotide comprises a 2'-O-methyl phosphorothioate RNA monomer or consists of 2'-O-methyl phosphorothioate RNA is represented by a nucleotide or base sequence comprising SEQ ID NO: 103 and has a length 25, 26, 27, 28, 29, 30, 31, 32, or 33 nucleotides or by a fragment of SEQ ID NO:103 comprising or consisting of at least 10 contiguous nucleotides or bases of SEQ ID NO:103.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 24 and has a length of 23, 24, 25, 26, 27, 28, 29, 30, 31, 32, or 33 nucleotides or by a fragment of SEQ ID NO:24 comprising or consisting of at least 10 contiguous nucleotides or bases of SEQ ID NO:24.

Accordingly a non-modified oligonucleotide derived from SEQ ID NO:24 is represented by SEQ ID NO:104.

Accordingly, in a preferred embodiment, an oligonucleotide comprises a 2'-O-methyl phosphorothioate RNA monomer or consists of 2'-O-methyl phosphorothioate RNA is represented by a nucleotide or base sequence comprising SEQ ID NO: 104 and has a length 23, 24, 25, 26, 27, 28, 29, 30, 31, 32, or 33 nucleotides or by a fragment of SEQ ID NO:104 comprising or consisting of at least 10 contiguous nucleotides or bases of SEQ ID NO:104.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 25 and has a length of 24, 25, 26, 27, 28, 29, 30, 31, 32, or 33 nucleotides or by a fragment of SEQ ID NO:25 comprising or consisting of at least 10 contiguous nucleotides or bases of SEQ ID NO:25.

Accordingly a non-modified oligonucleotide derived from SEQ ID NO:25 is represented by SEQ ID NO:105.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 105 and has a length 24, 25, 26, 27, 28, 29, 30, 31, 32, or 33 nucleotides or by a fragment of SEQ ID NO:105 comprising or consisting of at least 10 contiguous nucleotides or bases of SEQ ID NO:105.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 26 and has a length of 22, 23, 24, 25, 26, 27, 28, 29, 30, 31, 32, or 33 nucleotides or by a fragment of SEQ ID NO:26 comprising or consisting of at least 10 contiguous nucleotides or bases of SEQ ID NO:26.

Accordingly a non-modified oligonucleotide derived from SEQ ID NO:26 is represented by SEQ ID NO:106.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 106 and has a length 22, 23, 24, 25, 26, 27, 28, 29, 30, 31, 32, or 33 nucleotides or by a fragment of SEQ ID NO:106 comprising or consisting of at least 10 contiguous nucleotides or bases of SEQ ID NO:106.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 27 and has a length of 22, 23, 24, 25, 26, 27, 28, 29, 30, 31, 32, or 33 nucleotides or by a fragment of SEQ ID NO:27 comprising or consisting of at least 10 contiguous nucleotides or bases of SEQ ID NO:27.

Accordingly a non-modified oligonucleotide derived from SEQ ID NO:27 is represented by SEQ ID NO:107.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 107 and has a length 22, 23, 24, 25, 26, 27, 28, 29, 30, 31, 32, or 33 nucleotides or by a fragment of SEQ ID NO:107 comprising or consisting of at least 10 contiguous nucleotides or bases of SEQ ID NO:107.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 28 and has a length of 25, 26, 27, 28, 29, 30, 31, 32, or 33 nucleotides or by a fragment of SEQ ID NO:28 comprising or consisting of at least 10 contiguous nucleotides or bases of SEQ ID NO:28.

Accordingly a non-modified oligonucleotide derived from SEQ ID NO:28 is represented by SEQ ID NO:108. Each of SEQ ID NO:28 and SEQ ID NO:108 identified in table 1 comprises an hypoxanthine base at position 7.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 108 and has a length 25, 26, 27, 28, 29, 30, 31, 32, or 33 nucleotides or by a fragment of SEQ ID NO: 108 comprising or consisting of at least 10 contiguous nucleotides or bases of SEQ ID NO:108.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 29 and has a length of 25, 26, 27, 28, 29, 30, 31, 32, or 33 nucleotides or by a fragment of SEQ ID NO:29 comprising or consisting of at least 10 contiguous nucleotides or bases of SEQ ID NO:29.

Accordingly a non-modified oligonucleotide derived from SEQ ID NO:29 is represented by SEQ ID NO:109.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 109 and has a length 25, 26, 27, 28, 29, 30, 31, 32, or 33 nucleotides or by a fragment of SEQ ID NO: 109 comprising or consisting of at least 10 contiguous nucleotides or bases of SEQ ID NO:109.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 30 and has a length of 30, 31, 32 or 33 nucleotides or by a fragment of SEQ ID NO:30 comprising or consisting of at least 10 contiguous nucleotides or bases of SEQ ID NO:30.

Accordingly a non-modified oligonucleotide derived from SEQ ID NO:30 is represented by SEQ ID NO:110.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 110 and has a length 30, 31, 32, or 33 nucleotides or by a fragment of SEQ ID NO:110 comprising or consisting of at least 10 contiguous nucleotides or bases of SEQ ID NO:110.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Preferred oligonucleotides for inducing the skipping of exon 51 from the dystrophin pre-mRNA are as follows below.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 31 and has a length of 20, 21, 22, 23, 24, 25, 26, 27, 28, 29, 30, 31, 32, or 33 nucleotides or by a fragment of SEQ ID NO:31 comprising or consisting of at least 10 contiguous nucleotides or bases of SEQ ID NO:31.

Accordingly a non-modified oligonucleotide derived from SEQ ID NO:31 is represented by SEQ ID NO:111 and a preferred fragment of SEQ ID NO:111 is represented by SEQ ID NO:153 or 154.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 111 and has a length 20, 21, 22, 23, 24, 25, 26, 27, 28, 29, 30, 31, 32, or 33 nucleotides or by a fragment of SEQ ID NO:111 comprising or consisting of at least 10 contiguous nucleotides or bases of SEQ ID NO:111.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:31 comprises SEQ ID NO: 73 and a preferred fragment of SEQ ID NO: 111 comprises SEQ ID NO: 153, and each of said fragments has a length of 13, 14, 15, 16, 17, 18, 19, 20, 21, 22, 23, 24, 25, 26, 27, 28, 29, 30, 31, 32 or 33 nucleotides. Another preferred fragment of SEQ ID NO:31 comprises SEQ ID NO: 74 and another preferred fragment of SEQ ID NO: 111 comprises SEQ ID NO: 154, and each of said fragments has a length of 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such preferred oligonucleotide is also defined as follows:
  comprises a 2'-O-methyl phosphorothioate RNA monomer or consists of 2'-O-methyl phosphorothioate RNA and
  is represented by a nucleotide or a base sequence comprising or consisting of SEQ ID NO: 31 and has a length of 20, 21, 22, 23, 24, 25, 26, 27, 28, 29, 30, 31, 32, or 33 nucleotides or by a nucleotide or a base sequence comprising or consisting of a fragment of SEQ ID NO: 31, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:31.

More preferably, such oligonucleotide comprises a 5-methylpyrimidine (i.e. a 5-methylcytosine, and/or a 5-methyluracil) and/or a 2,6-diaminopurine base as earlier defined herein.

More preferably, an oligonucleotide:
  consists of 2'-O-methyl phosphorothioate RNA,
  all its cytosines have been replaced by 5-methylcytosines,
  such oligonucleotide is represented by a nucleotide or a base sequence comprising SEQ ID NO: 31 or SEQ ID NO: 215 and has a length of 20, 21, 22, 23, 24, 25, 26, 27, 28, 29, 30, 31, 32, or 33 nucleotides, or by a fragment of SEQ ID NO:31 or SEQ ID NO:215 comprising or consisting of at least 10 contiguous nucleotides of SEQ ID NO:31 or of SEQ ID NO: 215. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:

consists of 2'-O-methyl phosphorothioate RNA, all its uraciles have been replaced by 5-methyluraciles, such oligonucleotide is represented by a nucleotide or a base sequence comprising SEQ ID NO: 202 and has a length of 20, 21, 22, 23, 24, 25, 26, 27, 28, 29, 30, 31, 32, or 33 nucleotides, or by a fragment of SEQ ID NO:202 comprising or consisting of at least 10 contiguous nucleotides or bases of SEQ ID NO:202. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:

consists of 2'-O-methyl phosphorothioate RNA, all its cytosines have been replaced by 5-methylcytosines and all its uraciles have been replaced by 5-methyluraciles, such oligonucleotide is represented by a nucleotide or a base sequence comprising SEQ ID NO: 203 and has a length of 20, 21, 22, 23, 24, 25, 26, 27, 28, 29, 30, 31, 32, or 33 nucleotides, or by a fragment of SEQ ID NO:203 comprising or consisting of at least 10 contiguous nucleotides or bases of SEQ ID NO:203. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:

consists of 2'-O-methyl phosphorothioate RNA, all its adenines have been replaced by 2,6-diaminopurines, such oligonucleotide is represented by a nucleotide or a base sequence comprising SEQ ID NO: 206 and has a length of 20, 21, 22, 23, 24, 25, 26, 27, 28, 29, 30, 31, 32, or 33 nucleotides, or by a fragment of SEQ ID NO:206 comprising or consisting of at least 10 contiguous nucleotides or bases of SEQ ID NO:206. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 32 and has a length of 17, 18, 19, 20, 21, 22, 23, 24, 25, 26, 27, 28, 29, 30, 31, 32, or 33 nucleotides, or by a fragment of SEQ ID NO:32 comprising or consisting of at least 10 contiguous nucleotides or bases of SEQ ID NO:32.

Accordingly a non-modified oligonucleotide derived from SEQ ID NO:32 is represented by SEQ ID NO:112.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 112 and has a length 17, 18, 19, 20, 21, 22, 23, 24, 25, 26, 27, 28, 29, 30, 31, 32, or 33 nucleotides or by a fragment of SEQ ID NO:112 comprising or consisting of at least 10 contiguous nucleotides or bases of SEQ ID NO:112.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 33 and has a length of 22, 23, 24, 25, 26, 27, 28, 29, 30, 31, 32, or 33 nucleotides or by a fragment of SEQ ID NO:33 comprising or consisting of at least 10 contiguous nucleotides or bases of SEQ ID NO:33.

Accordingly a non-modified oligonucleotide derived from SEQ ID NO:33 is represented by SEQ ID NO:113.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 113 and has a length 22, 23, 24, 25, 26, 27, 28, 29, 30, 31, 32, or 33 nucleotides or by a fragment of SEQ ID NO:113 comprising or consisting of at least 10 contiguous nucleotides or bases of SEQ ID NO:113.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In another embodiment, an oligonucleotide comprises a 2'-O-methyl phosphorothioate RNA monomer or consists of 2'-O-methyl phosphorothioate RNA and is represented by a nucleotide or a base sequence comprising SEQ ID NO: 34 and has a length of 25, 26, 27, 28, 29, 30, 31, 32, or 33 nucleotides or by a fragment of SEQ ID NO:34 comprising or consisting of at least 10 contiguous nucleotides or bases of SEQ ID NO:34.

Accordingly a non-modified oligonucleotide derived from SEQ ID NO:34 is represented by SEQ ID NO:114.

Accordingly, in a preferred embodiment, an oligonucleotide comprises a 2'-O-methyl phosphorothioate RNA monomer or consist of 2'-O-methyl phosphorothioate RNA is represented by a nucleotide sequence comprising SEQ ID NO: 114 and has a length 25, 26, 27, 28, 29, 30, 31, 32, or 33 nucleotides or by a fragment of SEQ ID NO:114 comprising or consisting of at least 10 contiguous nucleotides of SEQ ID NO:114.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO: 34 comprises or consists of SEQ ID NO: 93 (PS1116: 5'-CAACAUCAAGGAAGAUGGCAUUUCU-3').

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 34 or 93 or 114 and has a length of 25, 26, 27, 28, 29, 30, 31, 32, or 33 nucleotides or by a nucleotide sequence comprising or consisting of a fragment of SEQ ID NO: 34 or 93 or 114, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:34 or 93 or 114.

More preferably, such oligonucleotide comprises a 5-methylpyrimidine (i.e. a 5-methylcytosine, and/or a 5-methyluracil) and/or a 2,6-diaminopurine base as earlier defined herein More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 34 and has a length of 25, 26, 27, 28, 29, 30, 31, 32, or 33 nucleotides, or by a fragment of SEQ ID NO:34 comprising or consisting of at least 10 contiguous nucleotides or bases of SEQ ID NO:34. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its adenines have been replaced by 2,6-diaminopurines
such oligonucleotide is represented by a nucleotide or a base sequence comprising SEQ ID NO: 34 and has a length of 25, 26, 27, 28, 29, 30, 31, 32, or 33 nucleotides, or by a fragment of SEQ ID NO:34 comprising or consisting of at least 10 contiguous nucleotides or bases of SEQ ID NO:34. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 35 and has a length of 23, 24, 25, 26, 27, 28, 29, 30, 31, 32, or 33 nucleotides or by a fragment of SEQ ID NO:35 comprising or consisting of at least 10 contiguous nucleotides or bases of SEQ ID NO:35.

Accordingly a non-modified oligonucleotide derived from SEQ ID NO:35 is represented by SEQ ID NO:115.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 115 and has a length 23, 24, 25, 26, 27, 28, 29, 30, 31, 32, or 33 nucleotides, or by a fragment of SEQ ID NO:115 comprising or consisting of at least 10 contiguous nucleotides or bases of SEQ ID NO:115.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 36 and has a length of 23, 24, 25, 26, 27, 28, 29, 30, 31, 32, or 33 nucleotides or by a fragment of SEQ ID NO:36 comprising or consisting of at least 10 contiguous nucleotides or bases of SEQ ID NO:36.

Accordingly a non-modified oligonucleotide derived from SEQ ID NO:36 is represented by SEQ ID NO:116 and a preferred fragment of SEQ ID NO:116 is represented by SEQ ID NO:155 or 156 or 157.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 116 and has a length 23, 24, 25, 26, 27, 28, 29, 30, 31, 32, or 33 nucleotides, or by a fragment of SEQ ID NO:116 comprising or consisting of at least 10 contiguous nucleotides or bases of SEQ ID NO:116.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. A preferred fragment of SEQ ID NO:36 comprises SEQ ID NO: 75 or a preferred fragment of SEQ ID NO: 116 comprises SEQ ID NO: 155, and each of said fragments has a length of 10, 11, 12, 13, 14, 15, 16, 17, 18, 19, 20, 21, 22, 23, 24, 25, 26, 27, 28, 29, 30, 31, 32 or 33 nucleotides. Another preferred fragment of SEQ ID NO:36 comprises SEQ ID NO: 76 or another preferred fragment of SEQ ID NO: 116 comprises SEQ ID NO: 156, and each of said fragments has a length of 14, 15, 16, 17, 18, 19, 20, 21, 22, 23, 24, 25, 26, 27, 28, 29, 30, 31, 32 or 33 nucleotides. Another preferred fragment of SEQ ID NO:36 comprises SEQ ID NO: 77 or another preferred fragment of SEQ ID NO: 116 comprises SEQ ID NO: 157, and each of said fragments has a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 37 and has a length of 30, 31, 32 or 33 nucleotides or by a fragment of SEQ ID NO:37 comprising or consisting of at least 10 contiguous nucleotides or bases of SEQ ID NO:37.

Accordingly a non-modified oligonucleotide derived from SEQ ID NO:37 is represented by SEQ ID NO:117.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 117 and has a length 30, 31, 32, or 33 nucleotides or by a fragment of SEQ ID NO:117 comprising or consisting of at least 10 contiguous nucleotides or bases of SEQ ID NO:117.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 38 and has a length of 25, 26, 27, 28, 29, 30, 31, 32, or 33 nucleotides or by a fragment of SEQ ID NO:38 comprising or consisting of at least 10 contiguous nucleotides or bases of SEQ ID NO:38.

Accordingly a non-modified oligonucleotide derived from SEQ ID NO:38 is represented by SEQ ID NO: 118.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 118 and has a length 25, 26, 27, 28, 29, 30, 31, 32, or 33 nucleotides, or by a fragment of SEQ ID NO:118 comprising or consisting of at least 10 contiguous nucleotides or bases of SEQ ID NO:118.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Preferred oligonucleotides for inducing the skipping of exon 52 from the dystrophin pre-mRNA are as follows below.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 39 and has a length of 25, 26, 27, 28, 29, 30, 31, 32, or 33 nucleotides or by a fragment of SEQ ID NO:39 comprising or consisting of at least 10 contiguous nucleotides or bases of SEQ ID NO:39.

Accordingly a non-modified oligonucleotide derived from SEQ ID NO:39 is represented by SEQ ID NO:119.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 119 and has a length 25, 26, 27, 28, 29, 30, 31, 32, or 33 nucleotides or by a fragment of SEQ ID NO:119 comprising or consisting of at least 10 contiguous nucleotides or bases of SEQ ID NO:119.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 201 and has a length of 25, 26, 27, 28, 29, 30, 31, 32, or 33 nucleotides or by a fragment of SEQ ID NO:201 comprising or consisting of at least 10 contiguous nucleotides or bases of SEQ ID NO:201. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 40 and has a length of 22, 23, 24, 25, 26, 27, 28, 29, 30, 31, 32, or 33 nucleotides, or by a fragment of SEQ ID NO:40 comprising or consisting of at least 10 contiguous nucleotides or bases of SEQ ID NO:40. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly a non-modified oligonucleotide derived from SEQ ID NO:40 is represented by SEQ ID NO:120 and a preferred fragment of SEQ ID NO:120 is represented by SEQ ID NO:158 or 159 or 160.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 120 and has a length 22, 23, 24, 25, 26, 27, 28, 29, 30, 31, 32, or 33 nucleotides or by a fragment of SEQ ID NO:120 comprising or consisting of at least 10 contiguous nucleotides or bases of SEQ ID NO:120.

A preferred fragment of SEQ ID NO:40 comprises SEQ ID NO: 78 and a preferred fragment of SEQ ID NO:120 comprises SEQ ID NO:158, and each fragment has a length of 15, 16, 17, 18, 19, 20, 21, 22, 23, 24, 25, 26, 27, 28, 29, 30, 31, 32 or 33 nucleotides. Another preferred fragment of SEQ ID NO:40 comprises SEQ ID NO: 79 and another preferred fragment of SEQ ID NO:120 comprises SEQ ID NO:159, and each fragment has a length of 13, 14, 15, 16, 17, 18, 19, 20, 21, 22, 23, 24, 25, 26, 27, 28, 29, 30, 31, 32 or 33 nucleotides. Another preferred fragment of SEQ ID NO:40 comprises SEQ ID NO: 80 and another preferred fragment of SEQ ID NO:120 comprises SEQ ID NO:160, and each fragment has a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 40 or 120 and has a length of 22, 23, 24, 25, 26, 27, 28, 29, 30, 31, 32, or 33 nucleotides or by a nucleotide sequence comprising or consisting of a fragment of SEQ ID NO: 40 or 120, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:40 or 120.

More preferably, such oligonucleotide comprises a 5-methylpyrimidine (i.e. a 5-methylcytosine, and/or a 5-methyluracil) and/or a 2,6-diaminopurine base as earlier defined herein More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 40 and has a length of 22, 23, 24, 25, 26, 27, 28, 29, 30, 31, 32, or 33 nucleotides or by a fragment of SEQ ID NO:40 comprising or consisting of at least 10 contiguous nucleotides or bases of SEQ ID NO:40. Accordingly, said oligonucleotide is represented by a nucleotide or a base sequence comprising SEQ ID NO: 171 and has a length of 22, 23, 24, 25, 26, 27, 28, 29, 30, 31, 32, or 33 nucleotides or by a fragment of SEQ ID NO:171 comprising or consisting of at least 10 contiguous nucleotides or bases of SEQ ID NO: 171. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 4 cytosines of SEQ ID NO:40 are modified as represented in SEQ ID NO:171. It is encompassed that 1, 2 or 3 of these cytosines are modified.

More preferably, an oligonucleotide:
consists of 2'-O-methyl phosphorothioate RNA,
all its uraciles have been replaced by 5-methyluraciles,
such oligonucleotide is represented by a nucleotide or a base sequence comprising SEQ ID NO:172 and has a length of 22, 23, 24, 25, 26, 27, 28, 29, 30, 31, 32, or 33 nucleotides or by a fragment of SEQ ID NO: 172 comprising or consisting of at least 10 contiguous nucleotides or bases of SEQ ID NO: 172. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 7 uraciles of SEQ ID NO:40 are modified as represented in SEQ ID NO:172. It is encompassed that 1, 2, 3, 4, 5 or 6 of these uraciles are modified.

More preferably, an oligonucleotide:
consists of 2'-O-methyl phosphorothioate RNA,
all its adenines have been replaced by 2,6-diaminopurines,
such oligonucleotide is represented by a nucleotide or a base sequence comprising SEQ ID NO: 173 and has a length of 22, 23, 24, 25, 26, 27, 28, 29, 30, 31, 32, or 33 nucleotides or by a fragment of SEQ ID NO:173 comprising or consisting of at least 10 contiguous nucleotides or bases of SEQ ID NO: 173. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 5 adenines of SEQ ID NO:40 are modified as represented in SEQ ID NO:173. It is encompassed that 1, 2, 3 or 4 of these adenines are modified.

More preferably, an oligonucleotide:
consists of 2'-O-methyl phosphorothioate RNA,
all its cytosines have been replaced by 5-methylcytosines and all its uraciles have been replaced by 5-methyluraciles,
such oligonucleotide is represented by a nucleotide or a base sequence comprising SEQ ID NO: 174 and has a length of 22, 23, 24, 25, 26, 27, 28, 29, 30, 31, 32, or 33 nucleotides or by a fragment of SEQ ID NO:174 comprising or consisting of at least 10 contiguous nucleotides or bases of SEQ ID NO:174. Accordingly, said oligonucleotide is represented by a nucleotide or a base sequence comprising SEQ ID NO: 174 and has a length of 22, 23, 24, 25, 26, 27, 28, 29, 30, 31, 32, or 33 nucleotides, or by a fragment of SEQ ID NO:174 comprising or consisting of at least 10 contiguous nucleotides or bases of SEQ ID NO: 174. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 4 cytosines and not all the 7 uraciles of SEQ ID NO:40 are modified as represented in SEQ ID NO:174. It is encompassed that 1, 2 or 3 of these cytosines and-or 1, 2, 3, 4, 5 or 6 of these uraciles are modified.

More preferably, an oligonucleotide:
consists of 2'-O-methyl phosphorothioate RNA,
all its cytosines have been replaced by 5-methylcytosines and all its adenines have been replaced by 2,6-diaminopurines,
such oligonucleotide is represented by a nucleotide or a base sequence comprising SEQ ID NO: 175 and has a length of 22, 23, 24, 25, 26, 27, 28, 29, 30, 31, 32, or 33 nucleotides or by a fragment of SEQ ID NO:175 comprising or consisting of at least 10 contiguous nucleotides or bases of SEQ ID NO:175. Accordingly, said oligonucleotide is represented by a nucleotide sequence comprising SEQ ID NO: 175 and has a length of 22, 23, 24, 25, 26, 27, 28, 29, 30, 31, 32, or 33 nucleotides, or by a fragment of SEQ ID NO:175 comprising or consisting of at least 10 contiguous nucleotides or bases of SEQ ID NO: 175. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides It is also encompassed that not all the 4 cytosines and not all the 5 adenines of SEQ ID NO:40 are modified as represented in SEQ ID NO:175. It is encompassed that 1, 2 or 3 of these cytosines and-or 1, 2, 3 or 4 of these adenines are modified.

More preferably, an oligonucleotide:
consists of 2'-O-methyl phosphorothioate RNA,
all its adenines have been replaced by 2,6-diaminopurines and all its uraciles have been replaced by 5-methyluraciles,
such oligonucleotide is represented by a nucleotide or a base sequence comprising SEQ ID NO: 176 and has a length of 22, 23, 24, 25, 26, 27, 28, 29, 30, 31, 32, or 33 nucleotides or by a fragment of SEQ ID NO:176 comprising or consisting of at least 10 contiguous nucleotides or bases of SEQ ID NO: 176. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 5 adenines and not all the 7 uraciles of SEQ ID NO: 40 are modified as represented in SEQ ID NO:176.

It is encompassed that 1, 2, 3 or 4 of these adenines and-or 1, 2, 3, 4, 5 or 6 of these uraciles are modified.

More preferably, an oligonucleotide:

consists of 2'-O-methyl phosphorothioate RNA, all its adenines have been replaced by 2,6-diaminopurines, all its cytosines have been replaced by 5-methylcytosines and all its uraciles have been replaced by 5-methyluraciles, such oligonucleotide is represented by a nucleotide or a base sequence comprising SEQ ID NO: 177 and has a length of 22, 23, 24, 25, 26, 27, 28, 29, 30, 31, 32, or 33 nucleotides or by a fragment of SEQ ID NO:177 comprising or consisting of at least 10 contiguous nucleotides or bases of SEQ ID NO: 177. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 4 cytosines and not all the 7 uraciles and not all the 5 adenines of SEQ ID NO:40 are modified as represented in SEQ ID NO:177. It is encompassed that 1, 2 or 3 of these cytosines and-or 1, 2, 3, 4, 5 or 6 of these uraciles and-or 1, 2, 3 or 4 of these adenines are modified.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide sequence or a base comprising SEQ ID NO: 41 and has a length of 25, 26, 27, 28, 29, 30, 31, 32, or 33 nucleotides, or by a fragment of SEQ ID NO:41 comprising or consisting of at least 10 contiguous nucleotides or bases of SEQ ID NO:41.

Accordingly a non-modified oligonucleotide derived from SEQ ID NO:41 is represented by SEQ ID NO:121.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 121 and has a length 25, 26, 27, 28, 29, 30, 31, 32, or 33 nucleotides, or by a fragment of SEQ ID NO:121 comprising or consisting of at least 10 contiguous nucleotides or bases of SEQ ID NO:121.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 42 and has a length of 25, 26, 27, 28, 29, 30, 31, 32, or 33 nucleotides or by a fragment of SEQ ID NO:42 comprising or consisting of at least 10 contiguous nucleotides or bases of SEQ ID NO:42.

Accordingly a non-modified oligonucleotide derived from SEQ ID NO:42 is represented by SEQ ID NO:122.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 122 and has a length 25, 26, 27, 28, 29, 30, 31, 32, or 33 nucleotides, or by a fragment of SEQ ID NO:122 comprising or consisting of at least 10 contiguous nucleotides or bases of SEQ ID NO:122.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 43 and has a length of 25, 26, 27, 28, 29, 30, 31, 32, or 33 nucleotides, or by a fragment of SEQ ID NO:43 comprising or consisting of at least 10 contiguous nucleotides or bases of SEQ ID NO:43.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Such preferred oligonucleotide is also defined as follows:

comprises a 2'-O-methyl phosphorothioate RNA monomer or consists of 2'-O-methyl phosphorothioate RNA and is represented by a nucleotide or a base sequence comprising or consisting of SEQ ID NO: 43 or 123 and has a length of 25, 26, 27, 28, 29, 30, 31, 32, or 33 nucleotides or by a nucleotide sequence comprising or consisting of a fragment of SEQ ID NO: 43 or 123, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:43 or 123. Accordingly a non-modified oligonucleotide derived from SEQ ID NO:43 is represented by SEQ ID NO:123 and a preferred fragment of SEQ ID NO:123 is represented by SEQ ID NO: 161.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 123 and has a length 22, 23, 24, 25, 26, 27, 28, 29, 30, 31, 32, or 33 nucleotides, or by a fragment of SEQ ID NO:123 comprising or consisting of at least 10 contiguous nucleotides or bases of SEQ ID NO:123.

More preferably, such oligonucleotide comprises a 5-methylpyrimidine (i.e. a 5-methylcytosine, and/or a 5-methyluracil) and/or a 2,6-diaminopurine base as earlier defined herein. Even more preferably, said oligonucleotide has all its cytosines and/or all its uracil and/or all its adenines that have been substituted or modified as defined herein.

More preferably, an oligonucleotide:

consists of 2'-O-methyl phosphorothioate RNA, all its cytosines have been replaced by 5-methylcytosines, such oligonucleotide is represented by a nucleotide or a base sequence comprising SEQ ID NO: 43 and has a length of 25, 26, 27, 28, 29, 30, 31, 32, or 33 nucleotides or by a fragment of SEQ ID NO:43 comprising or consisting of at least 10 contiguous nucleotides or bases of SEQ ID NO:43. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. Accordingly, said oligonucleotide is represented by a nucleotide or a base sequence comprising SEQ ID NO: 178 and has a length of 25, 26, 27, 28, 29, 30, 31, 32, or 33 nucleotides, or by a fragment of SEQ ID NO:178 comprising or consisting of at least 10 contiguous nucleotides or bases of SEQ ID NO: 178. It is also encompassed that not all the 6 cytosines of SEQ ID NO:43 are modified as represented in SEQ ID NO:178. It is encompassed that 1, 2, 3, 4 or 5 of these cytosines are modified.

A preferred fragment of SEQ ID NO:43 comprises SEQ ID NO: 81 and a preferred fragment of SEQ ID NO:123 comprises SEQ ID NO:161, each of said fragments has a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles,
such oligonucleotide is represented by a nucleotide or a base sequence comprising SEQ ID NO:179 and has a length of 25, 26, 27, 28, 29, 30, 31, 32, or 33 nucleotides, or by a fragment of SEQ ID NO:179 comprising or consisting of at least 10 contiguous nucleotides or bases of SEQ ID NO:179. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 11 uraciles of SEQ ID NO:43 are modified as represented in SEQ ID NO:179. It is encompassed that 1, 2, 3, 4, 5, 6, 7, 8, 9 or 10 of these uraciles are modified.

More preferably, an oligonucleotide:
consists of 2'-O-methyl phosphorothioate RNA,
all its adenines have been replaced by 2,6-diaminopurines,
such oligonucleotide is represented by a nucleotide or a base sequence comprising SEQ ID NO: 180 and has a length of 25, 26, 27, 28, 29, 30, 31, 32, or 33 nucleotides or by a fragment of SEQ ID NO:180 comprising or consisting of at least 10 contiguous nucleotides or bases of SEQ ID NO: 180. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 2 adenines of SEQ ID NO:43 are modified as represented in SEQ ID NO:180. It is encompassed that 1 of these adenines are modified.

More preferably, an oligonucleotide:
consists of 2'-O-methyl phosphorothioate RNA,
all its cytosines have been replaced by 5-methylcytosines and all its uraciles have been replaced by 5-methyluraciles,
such oligonucleotide is represented by a nucleotide or a base sequence comprising SEQ ID NO: 181 and has a length of 25, 26, 27, 28, 29, 30, 31, 32, or 33 nucleotides or by a fragment of SEQ ID NO:181 comprising or consisting of at least 10 contiguous nucleotides or bases of SEQ ID NO:181. Accordingly, said oligonucleotide is represented by a nucleotide or a base sequence comprising SEQ ID NO: 181 and has a length of 25, 26, 27, 28, 29, 30, 31, 32, or 33 nucleotides or by a fragment of SEQ ID NO:181 comprising or consisting of at least 10 contiguous nucleotides or bases of SEQ ID NO: 181. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 cytosines and not all the 11 uraciles of SEQ ID NO: 43 are modified as represented in SEQ ID NO:181. It is encompassed that 1, 2, 3, 4 or 5 of these cytosines and-or 1, 2, 3, 4, 5, 6, 7, 8, 9 or 10 of these uraciles are modified.

More preferably, an oligonucleotide:
consists of 2'-O-methyl phosphorothioate RNA,
all its cytosines have been replaced by 5-methylcytosines and all its adenines have been replaced by 2,6-diaminopurines,
such oligonucleotide is represented by a nucleotide or a base sequence comprising SEQ ID NO: 182 and has a length of 25, 26, 27, 28, 29, 30, 31, 32, or 33 nucleotides or by a fragment of SEQ ID NO:182 comprising or consisting of at least 10 contiguous nucleotides or bases of SEQ ID NO:182. Accordingly, said oligonucleotide is represented by a nucleotide or a base sequence comprising SEQ ID NO: 182 and has a length of 25, 26, 27, 28, 29, 30, 31, 32, or 33 nucleotides or by a fragment of SEQ ID NO:182 comprising or consisting of at least 10 contiguous nucleotides or bases of SEQ ID NO: 182. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 cytosines and not all the 2 adenines of SEQ ID NO:43 are modified as represented in SEQ ID NO:182. It is encompassed that 1, 2, 3, 4 or 5 of these cytosines and-or 1 of these adenines are modified.

More preferably, an oligonucleotide:
consists of 2'-O-methyl phosphorothioate RNA,
all its adenines have been replaced by 2,6-diaminopurines and all its uraciles have been replaced by 5-methyluraciles,
such oligonucleotide is represented by a nucleotide or a base sequence comprising SEQ ID NO: 183 and has a length of 25, 26, 27, 28, 29, 30, 31, 32, or 33 nucleotides or by a fragment of SEQ ID NO:183 comprising or consisting of at least 10 contiguous nucleotides or bases of SEQ ID NO:183. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 2 adenines and not all the 11 uraciles of SEQ ID NO:43 are modified as represented in SEQ ID NO:183. It is encompassed that 1 of these adenines and/or 1, 2, 3, 4, 5, 6, 7, 8, 9 or 10 of these uraciles are modified.

More preferably, an oligonucleotide:
consists of 2'-O-methyl phosphorothioate RNA,
all its adenines have been replaced by 2,6-diaminopurines, all its cytosines have been replaced by 5-methylcytosines and all its uraciles have been replaced by 5-methyluraciles,
such oligonucleotide is represented by a nucleotide or a base sequence comprising SEQ ID NO: 184 and has a length of 25, 26, 27, 28, 29, 30, 31, 32, or 33 nucleotides or by a fragment of SEQ ID NO:184 comprising or consisting of at least 10 contiguous nucleotides or bases of SEQ ID NO:184. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 cytosines and not all the 11 uraciles and not all the 2 adenines of SEQ ID NO:43 are modified as represented in SEQ ID NO:184. It is encompassed that 1, 2, 3, 4 or 5 of these cytosines and-or 1, 2, 3, 4, 5, 6, 7, 8, 9 or 10 of these uraciles and-or 1 of these adenines are modified.

Preferred oligonucleotides for inducing the skipping of exon 53 from the dystrophin pre-mRNA are as follows below.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 44 and has a length of 18, 19, 20, 21, 22, 23, 24, 25, 26, 27, 28, 29, 30, 31, 32, or 33 nucleotides or by a fragment of SEQ ID NO:44 comprising or consisting of at least 10 contiguous or bases nucleotides of SEQ ID NO:44.

Accordingly a non-modified oligonucleotide derived from SEQ ID NO:44 is represented by SEQ ID NO:124.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 124 and has a length 18, 19, 20, 21, 22, 23, 24, 25, 26, 27, 28, 29, 30, 31, 32, or 33 nucleotides, or by a fragment of SEQ ID NO:124 comprising or consisting of at least 10 contiguous nucleotides or bases of SEQ ID NO:124.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 45 and has a length of 22, 23, 24, 25, 26, 27, 28, 29, 30, 31, 32, or 33 nucleotides, or by a fragment of SEQ ID NO:45 comprising or consisting of at least 10 contiguous nucleotides or bases of SEQ ID NO:45.

Accordingly a non-modified oligonucleotide derived from SEQ ID NO:45 is represented by SEQ ID NO:125.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 125 and has a length 22, 23, 24, 25, 26, 27, 28, 29, 30, 31, 32, or 33 nucleotides or by a fragment of SEQ ID NO:125 comprising or consisting of at least 10 contiguous nucleotides or bases of SEQ ID NO:125.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base.

Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 46 and has a length of 24, 25, 26, 27, 28, 29, 30, 31, 32, or 33 nucleotides, or by a fragment of SEQ ID NO:46 comprising or consisting of at least 10 contiguous nucleotides or bases of SEQ ID NO:46.

Accordingly a non-modified oligonucleotide derived from SEQ ID NO:46 is represented by SEQ ID NO:126.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 126 and has a length 24, 25, 26, 27, 28, 29, 30, 31, 32, or 33 nucleotides or by a fragment of SEQ ID NO:126 comprising or consisting of at least 10 contiguous nucleotides or bases of SEQ ID NO: 126.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 47 and has a length of 24, 25, 26, 27, 28, 29, 30, 31, 32, or 33 nucleotides, or by a fragment of SEQ ID NO:47 comprising or consisting of at least 10 contiguous nucleotides or bases of SEQ ID NO:47.

Accordingly a non-modified oligonucleotide derived from SEQ ID NO:47 is represented by SEQ ID NO:127.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 127 and has a length 24, 25, 26, 27, 28, 29, 30, 31, 32, or 33 nucleotides, or by a fragment of SEQ ID NO:127 comprising or consisting of at least 10 contiguous nucleotides or bases of SEQ ID NO: 127.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 48 and has a length of 22, 23, 24, 25, 26, 27, 28, 29, 30, 31, 32, or 33 nucleotides or by a fragment of SEQ ID NO:48 comprising or consisting of at least 10 contiguous nucleotides or bases of SEQ ID NO:48.

Accordingly a non-modified oligonucleotide derived from SEQ ID NO:48 is represented by SEQ ID NO:128.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 128 and has a length 22, 23, 24, 25, 26, 27, 28, 29, 30, 31, 32, or 33 nucleotides, or by a fragment of SEQ ID NO:128 comprising or consisting of at least 10 contiguous nucleotides or bases of SEQ ID NO:128.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 49 and has a length of 23, 24, 25, 26, 27, 28, 29, 30, 31, 32, or 33 nucleotides, or by a fragment of SEQ ID NO:49 comprising or consisting of at least 10 contiguous nucleotides or bases of SEQ ID NO:49.

Accordingly a non-modified oligonucleotide derived from SEQ ID NO:49 is represented by SEQ ID NO:129.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 129 and has a length 23, 24, 25, 26, 27, 28, 29, 30, 31, 32, or 33 nucleotides, or by a fragment of SEQ ID NO:129 comprising or consisting of at least 10 contiguous nucleotides or bases of SEQ ID NO: 129.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 50 and has a length of 24, 25, 26, 27, 28, 29, 30, 31, 32, or 33 nucleotides, or by a fragment of SEQ ID NO:50 comprising or consisting of at least 10 contiguous nucleotides or bases of SEQ ID NO:50.

Accordingly a non-modified oligonucleotide derived from SEQ ID NO:50 is represented by SEQ ID NO:130.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 130 and has a length 24, 25, 26, 27, 28, 29, 30, 31, 32, or 33 nucleotides, or by a fragment of SEQ ID NO:130 comprising or consisting of at least 10 contiguous nucleotides or bases of SEQ ID NO:130.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 51 and has a length of 25, 26, 27, 28, 29, 30, 31, 32, or 33 nucleotides, or by a fragment of SEQ ID NO:51 comprising or consisting of at least 10 contiguous nucleotides or bases of SEQ ID NO:51.

Accordingly a non-modified oligonucleotide derived from SEQ ID NO:51 is represented by SEQ ID NO:131.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 131 and has a length 25, 26, 27, 28, 29, 30, 31, 32, or 33 nucleotides, or by a fragment of SEQ ID NO:131 comprising or consisting of at least 10 contiguous nucleotides or bases of SEQ ID NO:131.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 52 and has a length of 25, 26, 27, 28, 29, 30, 31, 32, or 33 nucleotides, or by a fragment of SEQ ID NO:52 comprising or consisting of at least 10 contiguous nucleotides or bases of SEQ ID NO:52.

Accordingly a non-modified oligonucleotide derived from SEQ ID NO:52 is represented by SEQ ID NO: 91 and a preferred fragment of SEQ ID NO:91 is represented by SEQ ID NO:162, 163 or 164. SEQ ID NO: 91 is identical with SEQ ID NO: 132.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 91 and has a length 25, 26, 27, 28, 29, 30, 31, 32, or 33 nucleotides, or by a fragment of SEQ ID NO:191 comprising or consisting of at least 10 contiguous nucleotides or bases of SEQ ID NO:91.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such preferred oligonucleotide is also defined as follows:
comprises a 2'-O-methyl phosphorothioate RNA monomer or consists of 2'-O-methyl phosphorothioate RNA and
is represented by a nucleotide or base sequence comprising or consisting of SEQ ID NO: 52 or 91 and has a length of 25, 26, 27, 28, 29, 30, 31, 32, or 33 nucleotides or by a nucleotide sequence comprising or consisting of a fragment of SEQ ID NO: 52 or 91, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:52 or 91.

More preferably, such oligonucleotide comprises a 5-methylpyrimidine (i.e. a 5-methylcytosine, and/or a 5-methyluracil) and/or a 2,6-diaminopurine base as earlier defined herein.

More preferably, an oligonucleotide:
consists of 2'-O-methyl phosphorothioate RNA,
all its cytosines have been replaced by 5-methylcytosines,
such oligonucleotide is represented by a nucleotide or base sequence comprising SEQ ID NO: 52 and has a length of 25, 26, 27, 28, 29, 30, 31, 32, or 33 nucleotides or by a fragment of SEQ ID NO:52 comprising or consisting of at least 10 contiguous nucleotides or bases of SEQ ID NO:52. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

A preferred fragment of SEQ ID NO:52 comprises SEQ ID NO: 82 and a preferred fragment of SEQ ID NO:91 comprises SEQ ID NO:162, each of said fragments has a length of 20, 21, 22, 23, 24, 25, 26, 27, 28, 29, 30, 31, 32 or 33 nucleotides. Another preferred fragment of SEQ ID NO:52 comprises SEQ ID NO: 83 and another preferred fragment of SEQ ID NO:91 comprises SEQ ID NO:163, each of said fragments has a length of 20, 21, 22, 23, 24, 25, 26, 27, 28, 29, 30, 31, 32 or 33 nucleotides. Another preferred fragment of SEQ ID NO:52 comprises SEQ ID NO: 84 and another preferred fragment of SEQ ID NO:91 comprises SEQ ID NO:164, each of said fragments has a length of 17, 18, 19, 20, 21, 22, 23, 24, 25, 26, 27, 28, 29, 30, 31, 32 or 33 nucleotides. A most preferred fragment of SEQ ID NO: 52 comprises or consists of SEQ ID NO: 91 (PS229L: 5'-GUUGCCUCCGGUUCUGAAGGUGUUC-3'). Another most preferred fragment of SEQ ID NO: 52 comprises or consists of SEQ ID NO: 92 (PS524: 5'-GUUGXXUXXGGUUXUGAAGGUGUUX-3'; wherein X is 5-methylcytosine).

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 82, 83, 84, 91 or 92 or 162 or 163 or 164 and has a length of 17, 18, 19, 20, 21, 22, 23, 24, 25, 26, 27, 28, 29, 30, 31, 32, or 33 nucleotides or by a nucleotide or a base sequence comprising or consisting of a fragment of SEQ ID NO: 82, 83, 84, 91 or 92, or 162 or 163 or 164, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:82, 83, 84, 91, or 92 or 162, 163 or 164.

More preferably, such oligonucleotide comprises a 5-methylpyrimidine (i.e. a 5-methylcytosine, and/or a 5-methyluracil) and/or a 2,6-diaminopurine base as earlier defined herein More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 82, 83, 84 or 92 and has a length of 17, 18, 19, 20, 21, 22, 23, 24, 25, 26, 27, 28, 29, 30, 31, 32, or 33 nucleotides, or by a fragment of SEQ ID NO:82, 83, 84, or 92 comprising or consisting of at least 10 contiguous nucleotides or bases of SEQ ID NO:82, 83, 84, or 92. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. SEQ ID NO: 92 is identical with SEQ ID NO: 199. It is also encompassed that not all the 6 cytosines of SEQ ID NO:52 are modified as represented in SEQ ID NO:92. It is encompassed that 1, 2, 3, 4 or 5 of these cytosines are modified.

More preferably, an oligonucleotide:
consists of 2'-O-methyl phosphorothioate RNA,
two of its cytosines have been replaced by 5-methylcytosines,
such oligonucleotide is represented by a nucleotide or a base sequence comprising SEQ ID NO: 218 and has a length of 17, 18, 19, 20, 21, 22, 23, 24, 25, 26, 27, 28, 29, 30, 31, 32, or 33 nucleotides, or by a fragment of SEQ ID NO:218 comprising or consisting of at least 10 contiguous nucleotides or bases of SEQ ID NO:218. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
three of its cytosines have been replaced by 5-methylcytosines,
such oligonucleotide is represented by a nucleotide or a base sequence comprising SEQ ID NO: 219 and has a length of 17, 18, 19, 20, 21, 22, 23, 24, 25, 26, 27, 28, 29, 30, 31, 32, or 33 nucleotides, or by a fragment of SEQ ID NO:219 comprising or consisting of at least 10 contiguous nucleotides or bases of SEQ ID NO:219. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
four of its cytosines have been replaced by 5-methylcytosines,
such oligonucleotide is represented by a nucleotide or a base sequence comprising SEQ ID NO: 217 and has a length of 17, 18, 19, 20, 21, 22, 23, 24, 25, 26, 27, 28, 29, 30, 31, 32, or 33 nucleotides, or by a fragment of SEQ ID NO:217 comprising or consisting of at least 10 contiguous nucleotides or bases of SEQ ID NO:217. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles,
such oligonucleotide is represented by a nucleotide or a base sequence comprising SEQ ID NO: 211 and has a length of 25, 26, 27, 28, 29, 30, 31, 32, or 33 nucleotides, or by a fragment of SEQ ID NO:211 comprising or consisting of at least 10 contiguous nucleotides or bases of SEQ ID NO:211. Accordingly, said oligonucleotide is represented by a nucleotide or a base sequence comprising SEQ ID NO: 211 and has a length of 25, 26, 27, 28, 29, 30, 31, 32, or 33 nucleotides, or by a fragment of SEQ ID NO:211 comprising or consisting of at least 10 contiguous nucleotides or bases of SEQ ID NO:211. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 9 uraciles of SEQ ID NO:52 are modified as represented in SEQ ID NO:211. It is encompassed that 1, 2, 3, 4, 5, 6, 7, or 8 of these uraciles are modified.

More preferably, an oligonucleotide:

consists of 2'-O-methyl phosphorothioate RNA, all its cytosines have been replaced by 5-methylcytosines and all its uraciles have been replaced by 5-methyluraciles, such oligonucleotide is represented by a nucleotide or a base sequence comprising SEQ ID NO: 212 and has a length of 22, 23, 24, 25, 26, 27, 28, 29, 30, 31, 32, or 33 nucleotides, or by a fragment of SEQ ID NO:212 comprising or consisting of at least 10 contiguous nucleotides or bases of SEQ ID NO:212. Accordingly, said oligonucleotide is represented by a nucleotide or a base sequence comprising SEQ ID NO: 212 and has a length of 22, 23, 24, 25, 26, 27, 28, 29, 30, 31, 32, or 33 nucleotides, or by a fragment of SEQ ID NO:212 comprising or consisting of at least 10 contiguous nucleotides or bases of SEQ ID NO:212. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 cytosines and not all the 9 uraciles of SEQ ID NO:52 are modified as represented in SEQ ID NO:212. It is encompassed that 1, 2, 3, 4, or 5 of these cytosines and/or 1, 2, 3, 4, 5, 6, 7, or 8 of these uraciles are modified.

More preferably, an oligonucleotide:

consists of 2'-O-methyl phosphorothioate RNA, all its adenines have been replaced by 2,6-diaminopurines, such oligonucleotide is represented by a nucleotide or a base sequence comprising SEQ ID NO: 213 and has a length of 25, 26, 27, 28, 29, 30, 31, 32, or 33 nucleotides, or by a fragment of SEQ ID NO:213 comprising or consisting of at least 10 contiguous nucleotides or bases of SEQ ID NO:213. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 2 adenines of SEQ ID NO:52 are modified as represented in SEQ ID NO:213. It is encompassed that 1 of these adenines are modified.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 53 and has a length of 25, 26, 27, 28, 29, 30, 31, 32, or 33 nucleotides, or by a fragment of SEQ ID NO:53 comprising or consisting of at least 10 contiguous nucleotides or bases of SEQ ID NO:53.

Accordingly a non-modified oligonucleotide derived from SEQ ID NO:53 is represented by SEQ ID NO:133.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 133 and has a length 25, 26, 27, 28, 29, 30, 31, 32, or 33 nucleotides, or by a fragment of SEQ ID NO: 133 comprising or consisting of at least 10 contiguous nucleotides or bases of SEQ ID NO:133.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 54 and has a length of 30, 31, 32 or 33 nucleotides, or by a fragment of SEQ ID NO:54 comprising or consisting of at least 10 contiguous nucleotides or bases of SEQ ID NO:54.

Accordingly a non-modified oligonucleotide derived from SEQ ID NO:54 is represented by SEQ ID NO:134.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 134 and has a length 30, 31, 32, or 33 nucleotides, or by a fragment of SEQ ID NO:134 comprising or consisting of at least 10 contiguous nucleotides or bases of SEQ ID NO:134.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 55 and has a length of 30, 31, 32 or 33 nucleotides, or by a fragment of SEQ ID NO:55 comprising or consisting of at least 10 contiguous nucleotides or bases of SEQ ID NO:55.

Accordingly a non-modified oligonucleotide derived from SEQ ID NO:55 is represented by SEQ ID NO:135.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 135 and has a length 30, 31, 32, or 33 nucleotides, or by a fragment of SEQ ID NO:135 comprising or consisting of at least 10 contiguous nucleotides or bases of SEQ ID NO:135.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 56 and has a length of 33, 34 or 35 nucleotides or by a fragment of SEQ ID NO:56 comprising or consisting of at least 10 contiguous nucleotides or bases of SEQ ID NO:56.

Accordingly a non-modified oligonucleotide derived from SEQ ID NO:56 is represented by SEQ ID NO:136.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 136 and has a length 33, 34 or 35 nucleotides, or by a fragment of SEQ ID NO: 136 comprising or consisting of at least 10 contiguous nucleotides or bases of SEQ ID NO: 136.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Preferred oligonucleotides for inducing the skipping of exon 55 from the dystrophin pre-mRNA are as follows below.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 57 and has a length of 24, 25, 26, 27, 28, 29, 30, 31, 32, or 33 nucleotides or by a fragment of SEQ ID NO:57 comprising or consisting of at least 10 contiguous nucleotides or bases of SEQ ID NO:57. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 57 and has a length of 24, 25, 26, 27, 28, 29, 30, 31, 32, or 33 nucleotides or by a nucleotide sequence comprising or consisting of a fragment of SEQ ID NO: 57, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:57.

Accordingly a non-modified oligonucleotide derived from SEQ ID NO:57 is represented by SEQ ID NO:137 and a preferred fragment of SEQ ID NO:137 is represented by SEQ ID NO:165 or 166.

Accordingly, in a preferred embodiment, an oligonucleotide comprises a 2'-O-methyl phosphorothioate RNA monomer or consists of 2'-O-methyl phosphorothioate RNA and is represented by a nucleotide or a base sequence comprising SEQ ID NO: 137 and has a length 24, 25, 26, 27, 28, 29, 30, 31, 32, or 33 nucleotides, or by a fragment of SEQ ID NO:137 comprising or consisting of at least 10 contiguous nucleotides or bases of SEQ ID NO:137.

More preferably, such oligonucleotide comprises a 5-methylpyrimidine (i.e. a 5-methylcytosine, and/or a 5-methyluracil) and/or a 2,6-diaminopurine base as earlier defined herein. Even more preferably, said oligonucleotide has all its cytosines and/or all its uracil and/or all its adenines that have been substituted or modified as defined herein.

More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 57 and has a length of 24, 25, 26, 27, 28, 29, 30, 31, 32, or 33 nucleotides or by a fragment of SEQ ID NO:57 comprising or consisting of at least 10 contiguous nucleotides or bases of SEQ ID NO:57.

Accordingly, said oligonucleotide is represented by a nucleotide or a base sequence comprising SEQ ID NO: 185 and has a length of 24, 25, 26, 27, 28, 29, 30, 31, 32, or 33 nucleotides or by a fragment of SEQ ID NO:185 comprising or consisting of at least 10 contiguous nucleotides or bases of SEQ ID NO:185. It is also encompassed that not all the 8 cytosines of SEQ ID NO:57 are modified as represented in SEQ ID NO:185. It is encompassed that 1, 2, 3, 4, 5, 6, or 7 of these cytosines are modified.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

A preferred fragment of SEQ ID NO:57 comprises SEQ ID NO: 85 and a preferred fragment of SEQ ID NO:137 comprises SEQ ID NO: 165, each of said fragments has a length of 16, 17, 18, 19, 20, 21, 22, 23, 24, 25, 26, 27, 28, 29, 30, 31, 32 or 33 nucleotides. Another preferred fragment of SEQ ID NO:57 comprises SEQ ID NO: 86 and another preferred fragment of SEQ ID NO:137 comprises SEQ ID NO: 166, each of said fragments has a length of 11, 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles,
such oligonucleotide is represented by a nucleotide or a base sequence comprising SEQ ID NO:186 and has a length of 24, 25, 26, 27, 28, 29, 30, 31, 32, or 33 nucleotides or by a fragment of SEQ ID NO: 186 comprising or consisting of at least 10 contiguous nucleotides or bases of SEQ ID NO: 186. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 7 uraciles of SEQ ID NO:57 are modified as represented in SEQ ID NO:186. It is encompassed that 1, 2, 3, 4, 5 or 6 of these uraciles are modified.

More preferably, an oligonucleotide:
consists of 2'-O-methyl phosphorothioate RNA,
all its adenines have been replaced by 2,6-diaminopurines,
such oligonucleotide is represented by a nucleotide or a base sequence comprising SEQ ID NO: 187 and has a length of 24, 25, 26, 27, 28, 29, 30, 31, 32, or 33 nucleotides or by a fragment of SEQ ID NO:187 comprising or consisting of at least 10 contiguous nucleotides or bases of SEQ ID NO: 187. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 5 adenines of SEQ ID NO:57 are modified as represented in SEQ ID NO:187. It is encompassed that 1, 2, 3 or 4 of these adenines are modified.

More preferably, an oligonucleotide:
consists of 2'-O-methyl phosphorothioate RNA,
all its cytosines have been replaced by 5-methylcytosines and all its uraciles have been replaced by 5-methyluraciles,
such oligonucleotide is represented by a nucleotide or a base sequence comprising SEQ ID NO: 188 and has a length of 24, 25, 26, 27, 28, 29, 30, 31, 32, or 33 nucleotides, or by a fragment of SEQ ID NO:188 comprising or consisting of at least 10 contiguous nucleotides or bases of SEQ ID NO:188. Accordingly, said oligonucleotide is represented by a nucleotide or a base sequence comprising SEQ ID NO: 188 and has a length of 24, 25, 26, 27, 28, 29, 30, 31, 32, or 33 nucleotides or by a fragment of SEQ ID NO:188 comprising or consisting of at least 10 contiguous nucleotides or bases of SEQ ID NO: 188. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 8 cytosines and not all the 7 uraciles of SEQ ID NO:57 are modified as represented in SEQ ID NO:188. It is encompassed that 1, 2, 3, 4, 5, 6 or 7 of these cytosines and-or 1, 2, 3, 4, 5 or 6 of these uraciles are modified.

More preferably, an oligonucleotide:
consists of 2'-O-methyl phosphorothioate RNA,
all its cytosines have been replaced by 5-methylcytosines and all its adenines have been replaced by 2,6-diaminopurines,
such oligonucleotide is represented by a nucleotide or a base sequence comprising SEQ ID NO: 189 and has a length of 24, 25, 26, 27, 28, 29, 30, 31, 32, or 33 nucleotides, or by a fragment of SEQ ID NO:189 comprising or consisting of at least 10 contiguous nucleotides or bases of SEQ ID NO:189. Accordingly, said oligonucleotide is represented by a nucleotide or a base sequence comprising SEQ ID NO: 189 and has a length of 24, 25, 26, 27, 28, 29, 30, 31, 32, or 33 nucleotides or by a fragment of SEQ ID NO:189 comprising or consisting of at least 10 contiguous nucleotides or bases of SEQ ID NO: 189. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides It is also encompassed that not all the 8 cytosines and not all the 5 adenines of SEQ ID NO:57 are modified as represented in SEQ ID NO:189. It is encompassed that 1, 2, 3, 4, 5, 6 or 7 of these cytosines and-or 1, 2, 3 or 4 of these adenines are modified.

More preferably, an oligonucleotide:
consists of 2'-O-methyl phosphorothioate RNA,
all its adenines have been replaced by 2,6-diaminopurines and all its uraciles have been replaced by 5-methyluraciles,
such oligonucleotide is represented by a nucleotide or a base sequence comprising SEQ ID NO: 190 and has a length of 24, 25, 26, 27, 28, 29, 30, 31, 32, or 33 nucleotides, or by a fragment of SEQ ID NO:190 comprising or consisting of at least 10 contiguous nucleotides or bases of SEQ ID NO: 190. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 5 adenines and not all the 7 uraciles of SEQ ID NO:57 are modified as represented in SEQ ID NO: 190. It is encompassed that 1, 2, 3 or 4 of these adenines and-or 1, 2, 3, 4, 5 or 6 of these uraciles are modified.

More preferably, an oligonucleotide:
consists of 2'-O-methyl phosphorothioate RNA,
all its adenines have been replaced by 2,6-diaminopurines, all its cytosines have been replaced by 5-methylcytosines and all its uraciles have been replaced by 5-methyluraciles,
such oligonucleotide is represented by a nucleotide or a base sequence comprising SEQ ID NO: 191 and has a length of 24, 25, 26, 27, 28, 29, 30, 31, 32, or 33 nucleotides or by a fragment of SEQ ID NO:191 comprising or consisting of at least 10 contiguous nucleotides or bases of SEQ ID NO: 191. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 8 cytosines and not all the 7 uraciles and not all the 5 adenines of SEQ ID NO:57 are modified as represented in SEQ ID NO:191. It is encompassed that 1, 2, 3, 4, 5, 6 or 7 of these cytosines and-or 1, 2, 3, 4, 5 or 6 of these uraciles and-or 1, 2, 3 or 4 of these adenines are modified.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 58 and has a length of 25, 26, 27, 28, 29, 30, 31, 32, or 33 nucleotides, or by a fragment of SEQ ID NO:58 comprising or consisting of at least 10 contiguous nucleotides or bases of SEQ ID NO:58.

Accordingly a non-modified oligonucleotide derived from SEQ ID NO:58 is represented by SEQ ID NO:138.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 138 and has a length 25, 26, 27, 28, 29, 30, 31, 32 or 33 nucleotides, or by a fragment of SEQ ID NO:138 comprising or consisting of at least 10 contiguous nucleotides or bases of SEQ ID NO:138.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 58 or 138 and has a length of 25, 26, 27, 28, 29, 30, 31, 32, or 33 nucleotides, or by a nucleotide or a base sequence comprising or consisting of a fragment of SEQ ID NO: 58 or 138, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:58 or 138.

More preferably, such oligonucleotide comprises a 5-methylpyrimidine (i.e. a 5-methylcytosine, and/or a 5-methyluracil) and/or a 2,6-diaminopurine base as earlier defined herein More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 58 and has a length of 25, 26, 27, 28, 29, 30, 31, 32, or 33 nucleotides or by a fragment of SEQ ID NO:58 comprising or consisting of at least 10 contiguous nucleotides or bases of SEQ ID NO:58. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 59 and has a length of 24, 25, 26, 27, 28, 29, 30, 31, 32, or 33 nucleotides or by a fragment of SEQ ID NO:59 comprising or consisting of at least 10 contiguous nucleotides or bases of SEQ ID NO:59. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Such preferred oligonucleotide is also defined as follows:
comprises a 2'-O-methyl phosphorothioate RNA monomer or consists of 2'-O-methyl phosphorothioate RNA and
is represented by a nucleotide or a base sequence comprising or consisting of SEQ ID NO: 59 and has a length of 24, 25, 26, 27, 28, 29, 30, 31, 32, or 33 nucleotides or by a nucleotide sequence comprising or consisting of a fragment of SEQ ID NO: 59, said fragment comprising or consisting of at least 10, 11, 12, 13, 14, 15, 16, 17, 18, 19, 20, 21, 22, 23, 24, 25, 26, 27, 28, 29, 30, 31, 32 or 33 contiguous nucleotides or bases of SEQ ID NO:59.

Accordingly a non-modified oligonucleotide derived from SEQ ID NO:59 is represented by SEQ ID NO:139 and a preferred fragment of SEQ ID NO:139 is represented by SEQ ID NO: 167 or 168 or 169 or 170.

Accordingly, in a preferred embodiment, an oligonucleotide comprises a 2'-O-methyl phosphorothioate RNA monomer or consists of 2'-O-methyl phosphorothioate RNA and is represented by a nucleotide or a base sequence comprising SEQ ID NO: 139 and has a length 24, 25, 26, 27, 28, 29, 30, 31, 32, or 33 nucleotides, or by a fragment of SEQ ID NO:139 comprising or consisting of at least 10 contiguous nucleotides or bases of SEQ ID NO:139.

More preferably, such oligonucleotide comprises a 5-methylpyrimidine (i.e. a 5-methylcytosine, and/or a 5-methyluracil) and/or a 2,6-diaminopurine base as earlier defined herein. Even more preferably, said oligonucleotide has all its cytosines and/or all its uracil and/or all its adenines that have been substituted or modified as defined herein.

More preferably, an oligonucleotide:
consists of 2'-O-methyl phosphorothioate RNA,
all its cytosines have been replaced by 5-methylcytosines,
such oligonucleotide is represented by a nucleotide or a base sequence comprising SEQ ID NO: 59 and has a length of 24, 25, 26, 27, 28, 29, 30, 31, 32, or 33 nucleotides, or by a fragment of SEQ ID NO:59 comprising or consisting of at least 10 contiguous nucleotides or bases of SEQ ID NO:59.

Accordingly, said oligonucleotide is represented by a nucleotide or a base sequence comprising SEQ ID NO: 192 and has a length of 24, 25, 26, 27, 28, 29, 30, 31, 32, or 33 nucleotides, or by a fragment of SEQ ID NO:192 comprising or consisting of at least 10 contiguous nucleotides or bases of SEQ ID NO:192. It is also encompassed that not all the 5 cytosines of SEQ ID NO:59 are modified as represented in SEQ ID NO:192. It is encompassed that 1, 2, 3 or 4 of these cytosines are modified.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

A preferred fragment of SEQ ID NO:59 comprises SEQ ID NO: 87 and a preferred fragment of SEQ ID NO:139 comprises SEQ ID NO:167, each of said fragments has a length of 22, 23, 24, 25, 26, 27, 28, 29, 30, 31, 32 or 33 nucleotides. Another preferred fragment of SEQ ID NO:59 comprises SEQ ID NO: 88 and another preferred fragment of SEQ ID NO:139 comprises SEQ ID NO:168, each of said fragments has a length of 11, 12, 13, 14, 15, 16, 17, 18, 19, 20, 21, 22, 23, 24, 25, 26, 27, 28, 29, 30, 31, 32 or 33 nucleotides. Another preferred fragment of SEQ ID NO:59 comprises SEQ ID NO: 89 and another preferred fragment of SEQ ID NO:139 comprises SEQ ID NO:169, each of said fragments has a length of 11, 12, 13, 14, 15, 16, 17, 18, 19, 20, 21, 22, 23, 24, 25, 26, 27, 28, 29, 30, 31, 32 or 33 nucleotides. Another preferred fragment of SEQ ID NO:59 comprises SEQ ID NO: 90 and another preferred fragment of SEQ ID NO:139 comprises SEQ ID NO:170, each of said fragmentshas a length of 12, 13, 14, 15, 16, 17, 18, 19, 20, 21, 22, 23, 24, 25, 26, 27, 28, 29, 30, 31, 32 or 33 nucleotides.

More preferably, an oligonucleotide:
consists of 2'-O-methyl phosphorothioate RNA,
all its uraciles have been replaced by 5-methyluraciles,
such oligonucleotide is represented by a nucleotide or a base sequence comprising SEQ ID NO:193 and has a length of 22, 23, 24, 25, 26, 27, 28, 29, 30, 31, 32, or 33 nucleotides or by a fragment of SEQ ID NO:193 comprising or consisting of at least 10 contiguous nucleotides or bases of SEQ ID NO: 193. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 uraciles of SEQ ID NO:59 are modified as represented in SEQ ID NO:193. It is encompassed that 1, 2, 3, 4 or 5 of these uraciles are modified.

More preferably, an oligonucleotide:
consists of 2'-O-methyl phosphorothioate RNA,
all its adenines have been replaced by 2,6-diaminopurines, such oligonucleotide is represented by a nucleotide or a base sequence comprising SEQ ID NO: 194 and has a length of 22, 23, 24, 25, 26, 27, 28, 29, 30, 31, 32, or 33 nucleotides or by a fragment of SEQ ID NO:194 comprising or consisting of at least 10 contiguous nucleotides or bases of SEQ ID NO: 194. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 adenines of SEQ ID NO:59 are modified as represented in SEQ ID NO:194. It is encompassed that 1, 2, 3, 4 or 5 of these adenines are modified.

More preferably, an oligonucleotide:
consists of 2'-O-methyl phosphorothioate RNA,
all its cytosines have been replaced by 5-methylcytosines and all its uraciles have been replaced by 5-methyluraciles,
such oligonucleotide is represented by a nucleotide or a base sequence comprising SEQ ID NO: 195 and has a length of 22, 23, 24, 25, 26, 27, 28, 29, 30, 31, 32, or 33 nucleotides, or by a fragment of SEQ ID NO:195 comprising or consisting of at least 10 contiguous nucleotides or bases of SEQ ID NO:195. Accordingly, said oligonucleotide is represented by a nucleotide or a base sequence comprising SEQ ID NO: 195 and has a length of 22, 23, 24, 25, 26, 27, 28, 29, 30, 31, 32, or 33 nucleotides, or by a fragment of SEQ ID NO:195 comprising or consisting of at least 10 contiguous nucleotides or bases of SEQ ID NO: 195. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 5 cytosines and not all the 6 uraciles of SEQ ID NO:59 are modified as represented in SEQ ID NO: 195. It is encompassed that 1, 2, 3 or 4 of these cytosines and-or 1, 2, 3, 4 or 5 of these uraciles are modified.

More preferably, an oligonucleotide:
consists of 2'-O-methyl phosphorothioate RNA,
all its cytosines have been replaced by 5-methylcytosines and all its adenines have been replaced by 2,6-diaminopurines,
such oligonucleotide is represented by a nucleotide or a base sequence comprising SEQ ID NO: 196 and has a length of 22, 23, 24, 25, 26, 27, 28, 29, 30, 31, 32, or 33 nucleotides, or by a fragment of SEQ ID NO:196 comprising or consisting of at least 10 contiguous nucleotides or bases of SEQ ID NO:196. Accordingly, said oligonucleotide is represented by a nucleotide or a base sequence comprising SEQ ID NO: 196 and has a length of 22, 23, 24, 25, 26, 27, 28, 29, 30, 31, 32, or 33 nucleotides, or by a fragment of SEQ ID NO:196 comprising or consisting of at least 10 contiguous nucleotides or bases of SEQ ID NO: 196. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides It is also encompassed that not all the 5 cytosines and not all the 6 adenines of SEQ ID NO:59 are modified as represented in SEQ ID NO:196. It is encompassed that 1, 2, 3 or 4 of these cytosines and/or 1, 2, 3, 4 or 5 of these adenines are modified.

More preferably, an oligonucleotide:
consists of 2'-O-methyl phosphorothioate RNA,
all its adenines have been replaced by 2,6-diaminopurines and all its uraciles have been replaced by 5-methyluraciles,
such oligonucleotide is represented by a nucleotide or a base sequence comprising SEQ ID NO: 197 and has a length of 22, 23, 24, 25, 26, 27, 28, 29, 30, 31, 32, or 33 nucleotides, or by a fragment of SEQ ID NO:197 comprising or consisting of at least 10 contiguous nucleotides or bases of SEQ ID NO: 197. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 6 adenines and not all the 6 uraciles of SEQ ID NO:59 are modified as represented in SEQ ID NO: 197. It is encompassed that 1, 2, 3, 4 or 5 of these adenines and/or 1, 2, 3, 4 or 5 of these uraciles are modified.

More preferably, an oligonucleotide:
consists of 2'-O-methyl phosphorothioate RNA,
all its adenines have been replaced by 2,6-diaminopurines, all its cytosines have been replaced by 5-methylcytosines and all its uraciles have been replaced by 5-methyluraciles,
such oligonucleotide is represented by a nucleotide or a base sequence comprising SEQ ID NO: 198 and has a length of 22, 23, 24, 25, 26, 27, 28, 29, 30, 31, 32, or 33 nucleotides, or by a fragment of SEQ ID NO:198 comprising or consisting of at least 10 contiguous nucleotides or bases of SEQ ID NO: 198. Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides. It is also encompassed that not all the 5 cytosines and not all the 6 uraciles and not all the 6 adenines of SEQ ID NO:59 are modified as represented in SEQ ID NO:198. It is encompassed that 1, 2, 3 or 4 of these cytosines and/or 1, 2, 3, 4 or 5 of these uraciles and/or 1, 2, 3, 4 or 5 of these adenines are modified.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 60 and has a length of 24, 25, 26, 27, 28, 29, 30, 31, 32, or 33 nucleotides, or by a fragment of SEQ ID NO:60 comprising or consisting of at least 10 contiguous nucleotides or bases of SEQ ID NO:60.

Accordingly a non-modified oligonucleotide derived from SEQ ID NO:60 is represented by SEQ ID NO:140.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 140 and has a length 24, 25, 26, 27, 28, 29, 30, 31, 32 or 33 nucleotides, or by a fragment of SEQ ID NO:140 comprising or consisting of at least 10 contiguous nucleotides or bases of SEQ ID NO: 140.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 61 and has a length of 24, 25, 26, 27, 28, 29, 30, 31, 32, or 33 nucleotides or by a fragment of SEQ ID NO:61 comprising or consisting of at least 10 contiguous nucleotides or bases of SEQ ID NO:61.

Accordingly a non-modified oligonucleotide derived from SEQ ID NO:61 is represented by SEQ ID NO:141.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 141 and has a length 24, 25, 26, 27, 28, 29, 30, 31, 32 or 33 nucleotides or by a fragment of SEQ ID NO:141 comprising or consisting of at least 10 contiguous nucleotides or bases of SEQ ID NO:141.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

In a preferred embodiment, an oligonucleotide comprises a 2'-O-methyl phosphorothioate RNA monomer or consists of 2'-O-methyl phosphorothioate RNA and more preferably comprises a 5-methylpyrimidine (i.e. a 5-methylcytosine, and/or a 5-methyluracil) and/or a 2,6-diaminopurine base, is represented by a nucleotide or a base sequence comprising SEQ ID NO: 62 and has a length of 24, 25, 26, 27, 28, 29, 30, 31, 32, or 33 nucleotides or by a fragment of SEQ ID NO:62 comprising or consisting of at least 10 contiguous nucleotides or bases of SEQ ID NO:62.

Accordingly a non-modified oligonucleotide derived from SEQ ID NO:62 is represented by SEQ ID NO:142.

Accordingly, in a preferred embodiment, an oligonucleotide comprises a 2'-O-methyl phosphorothioate RNA monomer or consists of 2'-O-methyl phosphorothioate RNA is represented by a nucleotide or a base sequence comprising SEQ ID NO: 142 and has a length 24, 25, 26, 27, 28, 29, 30, 31, 32 or 33 nucleotides or by a fragment of SEQ ID NO:142 comprising or consisting of at least 10 contiguous nucleotides or bases of SEQ ID NO: 142.

Such fragment has preferably a length of 10, 11, 12, 13, 14, 15, 16, 17, 18, 19, 20, 21, 22, 23, 24, 25, 26, 27, 28, 29, 30, 31, 32 or 33 nucleotides.

Accordingly, more preferably, said oligonucleotide comprises a 5-methylpyrimidine (i.e. a 5-methylcytosine, and/or a 5-methyluracil) and/or a 2,6-diaminopurine base. Accordingly, even more preferably, said oligonucleotide has all its cytosines and/or all its uracil and/or all its adenines that have been substituted or modified as defined herein.

Composition

In a second aspect, there is provided a composition comprising an oligonucleotide as described in the previous section entitled "Oligonucleotide". This composition preferably comprises or consists of an oligonucleotide as described above.

In a preferred embodiment, said composition is for use as a medicament. Said composition is therefore a pharmaceutical composition. A pharmaceutical composition usually comprises a pharmaceutically accepted carrier, diluent and/or excipient. In a preferred embodiment, a composition of the current invention comprises a compound as defined herein and optionally further comprises a pharmaceutically acceptable formulation, filler, preservative, solubilizer, carrier, diluent, excipient, salt, adjuvant and/or solvent. Such pharmaceutically acceptable carrier, filler, preservative, solubilizer, diluent, salt, adjuvant, solvent and/or excipient may for instance be found in Remington: The Science and Practice of Pharmacy, 20th Edition. Baltimore, Md.: Lippincott Williams & Wilkins, 2000. The compound as described in the invention may possess at least one ionizable group. An ionizable group may be a base or acid, and may be charged or neutral. An ionizable group may be present as ion pair with an appropriate counterion that carries opposite charge(s). Examples of cationic counterions are sodium, potassium, cesium, Tris, lithium, calcium, magnesium, trialkylammonium, triethylammonium, and tetraalkylammonium. Examples of anionic counterions are chloride, bromide, iodide, lactate, mesylate, acetate, trifluoroacetate, dichloroacetate, and citrate. Examples of counterions have been described [e.g. Kumar, 2008, which is incorporated here in its entirety by reference].

In a preferred embodiment, a composition comprises the oligonucleotide of the invention and sodium as counterion. Said oligonucleotide present in said composition may also be named as an oligonucleotide in its sodium form.

In another preferred embodiment, a composition comprises the oligonucleotide of the invention and calcium and/or magnesium as counterion. Siad oligonucleotide present in said composition may also be named as an oligonucleotide in its calcium or magnesium or mixed calcium/magnesium form.

Such type of composition comprising an oligonucleotide of the invention and a counterion may be obtained through either formulating the counterion salt of the oligonucleotide or by adding appropriate amounts of said salt to an oligonucleotide. A positive effect of calcium salts present in composition comprising an oligonucleotide with respect to immunostimulatory effects of said oligonucleotides has been described (e.g. patent application WO 2012021985 (Replicor), incorporated here in its entirety by reference).

A pharmaceutical composition may comprise an aid in enhancing the stability, solubility, absorption, bioavailability, activity, pharmacokinetics, pharmacodynamics and cellular uptake of said compound, in particular an excipient capable of forming complexes, nanoparticles, microparticles, nanotubes, nanogels, hydrogels, poloxamers or pluronics, polymersomes, colloids, microbubbles, vesicles, micelles, lipoplexes, and/or liposomes. Examples of nanoparticles include polymeric nanoparticles, gold nanoparticles, magnetic nanoparticles, silica nanoparticles, lipid nanoparticles, sugar particles, protein nanoparticles and peptide nanoparticles.

A preferred composition comprises at least one excipient that may further aid in enhancing the targeting and/or delivery of said composition and/or said oligonucleotide to a tissue and/or a cell and/or into a tissue and/or a cell. A preferred tissue or cell is a muscle tissue or cell.

Many of these excipients are known in the art (e.g. see Bruno, 2011) and may be categorized as a first type of excipient. Examples of first type of excipients include polymers (e.g. polyethyleneimine (PEI), poly-2-hydroxypropyleneimine (pHP), polypropyleneimine (PPI), dextran derivatives, butylcyanoacrylate (PBCA), hexylcyanoacrylate (PHCA), poly(lactic-co-glycolic acid) (PLGA), polyamines (e.g. spermine, spermidine, putrescine, cadaverine), chitosan, poly(amido amines) (PAMAM), poly(ester amine), polyvinyl ether, polyvinyl pyrrolidone (PVP), polyethylene glycol (PEG) cyclodextrins, hyaluronic acid, colominic acid, and derivatives thereof), dendrimers (e.g. poly(amidoamine)), lipids {e.g. 1,2-dioleoyl-3-dimethylammonium propane (DODAP), dioleoyldimethylammonium chloride (DO- DAC), phosphatidylcholine derivatives [e.g 1,2-distearoyl-sn-glycero-3-phosphocholine (DSPC)], lyso-phosphatidylcholine derivatives [e.g. 1-stearoyl-2-lyso-sn-glycero-3-phosphocholine (S-LysoPC)], sphingomyeline, 2-{3-[Bis-(3-amino-propyl)-amino]-propylamino}-N-ditetracedyl carbamoyl methylacetamide (RPR209120), phosphoglycerol derivatives [e.g. 1,2-dipalmitoyl-sn-glycero-3-phosphoglycerol, sodium salt (DPPG-Na), phosphaticid acid derivatives [1,2-distearoyl-sn-glycero-3-phosphaticid acid, sodium salt (DSPA), phosphatidylethanolamine derivatives [e.g. dioleoyl-L-R-phosphatidylethanolamine (DOPE), 1,2-distearoyl-sn-glycero-3-phosphoethanolamine (DSPE),2-diphytanoyl-sn-glycero-3-phosphoethanolamine (DP-hyPE),], N-[1-(2,3-dioleoyloxy)propyl]-N,N,N-trimethylammonium (DOTAP), N-[1-(2,3-dioleyloxy)propyl]-N,N,N-trimethylammonium (DOTMA), 1,3-di-oleyloxy-2-(6-carboxy-spermyl)-propylamid (DOSPER), (1,2-dimyristyolxypropyl-3-dimethylhydroxy ethyl ammonium (DMRIE), (N1-cholesteryloxycarbonyl-3,7-diazanonane-1,9-diamine (CDAN), dimethyldioctadecylammonium bromide (DDAB), 1-palmitoyl-2-oleoyl-sn-glycerol-3-phosphocholine (POPC), (b-L-Arginyl-2,3-L-diaminopropionic acid-N-palmityl-N-olelyl-amide trihydrochloride (AtuFECT01), 1, N,N-dimethyl-3-amino-propane derivatives [e.g. 1,2-distearoyloxy-N,N-dimethyl-3-aminopropane (DSDMA), 1,2-dioleyloxy-N,N-dimethyl-3-aminopropane (DoDMA), 1,2-Dilinoleyloxy-N,N-3-dimethylaminopropane (DLinDMA), 2,2-dilinoleyl-4-dimethylaminomethyl [1,3]-dioxolane (DLin-K-DMA), phosphatidylserine derivatives [1,2-dioleyl-sn-glycero-3-phospho-L-serine, sodium salt (DOPS)], cholesterol}proteins (e.g. albumin, gelatins, atellocollagen), and peptides (e.g. protamine, PepFects, NickFects, polyarginine, polylysine, CADY, MPG).

Another preferred composition may comprise at least one excipient categorized as a second type of excipient. A second type of excipient may comprise or contain a conjugate group as described herein to enhance targeting and/or delivery of the composition and/or of the oligonucleotide of the invention to a tissue and/or cell and/or into a tissue and/or cell, as for example muscle tissue or cell. Both types of excipients may be combined together into one single composition as identified herein.

The skilled person may select, combine and/or adapt one or more of the above or other alternative excipients and delivery systems to formulate and deliver a compound for use in the present invention.

Such a pharmaceutical composition of the invention may be administered in an effective concentration at set times to an animal, preferably a mammal. More preferred mammal is a human being. An oligonucleotide or a composition as defined herein for use according to the invention may be suitable for direct administration to a cell, tissue and/or an organ in vivo of individuals affected by or at risk of developing a disease or condition as identified herein, and may be administered directly in vivo, ex vivo or in vitro. Administration may be via topical, systemic and/or parenteral routes, for example intravenous, subcutaneous, intraperitoneal, intrathecal, intramuscular, ocular, nasal, urogenital, intradermal, dermal, enteral, intravitreal, intracavernous, intracerebral, intrathecal, epidural or oral route.

Preferably, such a pharmaceutical composition of the invention may be encapsulated in the form of an emulsion, suspension, pill, tablet, capsule or soft-gel for oral delivery, or in the form of aerosol or dry powder for delivery to the respiratory tract and lungs.

In an embodiment an oligonucleotide of the invention may be used together with another compound already known to be used for the treatment of said disease. Such other compounds may be used for reducing inflammation, preferably for reducing muscle tissue inflammation, and/or an adjunct compound for improving muscle fiber function, integrity and/or survival and/or improve, increase or restore cardiac function. Examples are, but not limited to, a steroid, preferably a (gluco)corticosteroid, an ACE inhibitor (preferably perindopril), an angiotensin II type 1 receptor blocker (preferably losartan), a tumor necrosis factor-alpha (TNFα) inhibitor, a TGFβ inhibitor (preferably decorin), human recombinant biglycan, a source of mIGF-1, a myostatin inhibitor, mannose-6-phosphate, an antioxidant, an ion channel inhibitor, a protease inhibitor, a phosphodiesterase inhibitor (preferably a PDE5 inhibitor, such as sildenafil or tadalafil), a histone deacetylase inhibitor (HDAC inhibitor, androgen receptor modulator, creatine, creatine phosphate, and/or L-arginine. Such combined use may be a sequential use: each component is administered in a distinct composition. Alternatively each compound may be used together in a single composition.

Use

In a further aspect, there is provided the use of a composition or an oligonucleotide as described in the previous sections for use as a medicament or part of therapy, or applications in which said oligonucleotide exerts its activity intracellularly.

Preferably, an oligonucleotide or composition of the invention is for use as a medicament or part of a therapy for preventing, delaying, curing, ameliorating and/or treating DMD or BMD.

Method

In a further aspect, there is provided a method for preventing, treating, curing, ameliorating and/or delaying a condition or disease as defined in the previous section in an individual, in a cell, tissue or organ of said individual. The method comprising administering an oligonucleotide or a composition of the invention to said individual or a subject in the need thereof.

The method according to the invention wherein an oligonucleotide or a composition as defined herein may be suitable for administration to a cell, tissue and/or an organ in vivo of individuals affected by any of the herein defined diseases, and may be administered in vivo, ex vivo or in vitro. An individual or a subject in need is preferably a mammal, more preferably a human being.

In a further aspect, there is provided a method for diagnosis wherein the oligonucleotide of the invention is provided with a radioactive label or fluorescent label.

In an embodiment, in a method of the invention, a concentration of an oligonucleotide or composition is ranged from 0.01 nM to 1 μM. More preferably, the concentration used is from 0.05 to 500 nM, or from 0.1 to 500 nM, or from 0.02 to 500 nM, or from 0.05 to 500 nM, even more preferably from 1 to 200 nM.

Dose ranges of an oligonucleotide or composition according to the invention are preferably designed on the basis of rising dose studies in clinical trials (in vivo use) for which rigorous protocol requirements exist. An oligonucleotide as defined herein may be used at a dose which is ranged from 0.01 to 200 mg/kg or 0.05 to 100 mg/kg or 0.1 to 50 mg/kg or 0.1 to 20 mg/kg, preferably from 0.5 to 10 mg/kg.

The ranges of concentration or dose of oligonucleotide or composition as given above are preferred concentrations or doses for in vitro or ex vivo uses. The skilled person will understand that depending on the identity of the oligonucleotide used, the target cell to be treated, the gene target and its expression levels, the medium used and the transfection and incubation conditions, the concentration or dose of oligonucleotide used may further vary and may need to be optimised any further.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that an oligonucleotide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each embodiment as identified herein may be combined together unless otherwise indicated. All patent and literature references cited in the present specification are hereby incorporated by reference in their entirety.

Definitions

Throughout the application, the word "binds", "targets", "hybridizes" could be used interchangeably when used in the context of an antisense oligonucleotide which is reverse complementary to a part of a pre-mRNA as identified herein.

In addition, throughout the application, the expression "able to bind", "able to target", "able to hybridize" could be used interchangeably when used in the context of an antisense oligonucleotide which is reverse complementary to a part of a pre-mRNA as identified herein and for which conditions could be found wherein said oligonucleotide could bind, target or hybridize with said part of said pre-mRNA.

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymine and uracil which pair through the formation of hydrogen bonds. The natural base guanine is nucleobase complementary to the natural bases cytosine and 5-methylcytosine. Hybridization can occur under varying circumstances.

As used herein, "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

In the context of the invention, "hybridizes" is used under physiological conditions in a cell, preferably a muscular cell unless otherwise indicated.

As used herein, "nucleoside" refers to a compound comprising a heterocyclic base moiety and a sugar moiety. Nucleosides include, but are not limited to, naturally occurring nucleosides (as found in DNA and RNA), abasic nucleosides, modified nucleosides, and sugar-modified nucleosides. Nucleosides may be modified with any of a variety of substituents.

As used herein, "sugar moiety" means a natural (furanosyl), a modified sugar moiety or a sugar surrogate.

As used herein, "modified sugar moiety" means a chemically-modified furanosyl sugar or a non-furanosyl sugar moiety. Also, embraced by this term are furanosyl sugar analogs and derivatives including tricyclic sugars, bicyclic sugars, tetrahydropyrans, morpholinos, 2'-modified sugars, 4'-modified sugars, 5'-modified sugars, and 4'-substituted sugars.

As used herein, "sugar-modified nucleoside" means a nucleoside comprising a modified sugar moiety.

As used herein the term "sugar surrogate" refers to a structure that is capable of replacing the furanose ring of a naturally occurring nucleoside. In certain embodiments, sugar surrogates are non-furanose (or 4'-substituted furanose) rings or ring systems or open systems. Such structures include simple changes relative to the natural furanose ring, such as a six membered ring or may be more complicated as is the case with the non-ring system used in peptide nucleic acid. Sugar surrogates includes without limitation morpholinos and cyclohexenyls and cyclohexitols. In most nucleosides having a sugar surrogate group the heterocyclic base moiety is generally maintained to permit hybridization.

As used herein, "nucleotide" refers to a nucleoside further comprising a modified or unmodified phosphate linking group or a non-phosphate internucleoside linkage.

As used herein, "linked nucleosides" may or may not be linked by phosphate linkages and thus includes "linked nucleotides".

As used herein, "nucleobase" refers to the heterocyclic base portion of a nucleoside. Nucleobases may be naturally occurring or may be modified and therefore include, but are not limited to adenine, cytosine, guanine, uracil, thymine and analogues thereof such as 5-methylcytosine. In certain embodiments, a nucleobase may comprise any atom or group of atoms capable of hydrogen bonding to a base of another nucleic acid.

As used herein, "modified nucleoside" refers to a nucleoside comprising at least one modification compared to naturally occurring RNA or DNA nucleosides. Such modification may be at the sugar moiety and/or at the nucleobases.

As used herein, "$T_m$" means melting temperature which is the temperature at which the two strands of a duplex nucleic acid separate. $T_m$ is often used as a measure of duplex stability or the binding affinity of an antisense compound toward a complementary RNA molecule.

As used herein, "2'-modified" or "2'-substituted" refers to a nucleoside comprising a sugar comprising a substituent at the 2' position other than H or OH. 2'-modified nucleosides include, but are not limited to, bicyclic nucleosides wherein the bridge connecting two carbon atoms of the sugar ring connects the 2' carbon and another carbon of the sugar ring; and nucleosides with non-bridging 2'-substituents, such as allyl, amino, azido, thio, O-allyl, O—$C_1$-$C_{10}$ alkyl, —$OCF_3$, O—$(CH_2)_2$—O—$CH_3$, 2'—O$(CH_2)_2SCH_3$, O—$(CH_2)_2$—O—N$(R_m)(R_n)$, or O—$CH_2$—C(=O)—N$(R_m)(R_n)$, wherein each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-OMe" or "2'-OCH$_3$" or "2'-O-methyl" each refers to a nucleoside comprising a sugar comprising an —$OCH_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, the term "adenine analogue" means a chemically-modified purine nucleobase that, when incorporated into an oligomer, is capable with forming a Watson-Crick base pair with either a thymine or uracil of a complementary strand of RNA or DNA.

As used herein, the term "uracil analogue" means a chemically-modified pyrimidine nucleobase that, when incorporated into an oligomer, is capable with forming a Watson-Crick base pair with either a adenine of a complementary strand of RNA or DNA.

As used herein, the term "thymine analogue" means a chemically-modified pyrimidine nucleobase that, when incorporated into an oligomer, is capable with forming a Watson-Crick base pair with an adenine of a complementary strand of RNA or DNA.

As used herein, the term "cytosine analogue" means a chemically-modified pyrimidine nucleobase that, when incorporated into an oligomer, is capable with forming a Watson-Crick base pair with a guanine of a complementary strand of RNA or DNA. For example, cytosine analogue can be a 5-methylcytosine.

As used herein, the term "guanine analogue" means a chemically-modified purine nucleobase that, when incorporated into an oligomer, is capable with forming a Watson-Crick base pair with a cytosine of a complementary strand of RNA or DNA.

As used herein, the term "guanosine" refers to a nucleoside or sugar-modified nucleoside comprising a guanine or guanine analog nucleobase.

As used herein, the term "uridine" refers to a nucleoside or sugar-modified nucleoside comprising a uracil or uracil analog nucleobase.

As used herein, the term "thymidine" refers to a nucleoside or sugar-modified nucleoside comprising a thymine or thymine analog nucleobase.

As used herein, the term "cytidine" refers to a nucleoside or sugar-modified nucleoside comprising a cytosine or cytosine analog nucleobase.

As used herein, the term "adenosine" refers to a nucleoside or sugar-modified nucleoside comprising an adenine or adenine analog nucleobase.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

As used herein "oligonucleoside" refers to an oligonucleotide in which none of the internucleoside linkages contains a phosphorus atom. As used herein, oligonucleotides include oligonucleosides.

As used herein, "modified oligonucleotide" or "chemically-modified oligonucleotide" refers to an oligonucleotide comprising at least one modified sugar, a modified nucleobase and/or a modified internucleoside linkage or backbone.

As used herein, "internucleoside linkage" or "backbone" refers to a covalent linkage between adjacent nucleosides.

As used herein "naturally occurring internucleoside linkage" refers to a 3' to 5' phosphodiester linkage.

As used herein, "modified internucleoside linkage" refers to any internucleoside linkage other than a naturally occurring internucleoside linkage.

As used herein, "oligomeric compound" refers to a polymeric structure comprising two or more sub-structures. In certain embodiments, an oligomeric compound is an oligonucleotide. In certain embodiments, an oligomeric compound is a single-stranded oligonucleotide. In certain embodiments, an oligomeric compound is a double-stranded duplex comprising two oligonucleotides. In certain embodiments, an oligomeric compound is a single-stranded or double-stranded oligonucleotide comprising one or more conjugate groups and/or terminal groups.

As used herein, "conjugate" refers to an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to the parent compound such as an oligomeric compound. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are terminal groups. In certain embodiments, conjugates are attached to a 3' or 5' terminal nucleoside or to an internal nucleosides of an oligonucleotide.

As used herein, "conjugate linking group" refers to any atom or group of atoms used to attach a conjugate to an oligonucleotide or oligomeric compound. Linking groups or bifunctional linking moieties such as those known in the art are amenable to the present invention.

As used herein, "antisense compound" refers to an oligomeric compound, at least a portion of which is at least partially complementary to a target nucleic acid to which it hybridizes and modulates the activity, processing or expression of said target nucleic acid.

As used herein, "expression" refers to the process by which a gene ultimately results in a protein. Expression includes, but is not limited to, transcription, splicing, post-transcriptional modification, and translation.

As used herein, "antisense oligonucleotide" refers to an antisense compound that is an oligonucleotide.

As used herein, "antisense activity" refers to any detectable and/or measurable activity attributable to the hybridization of an anti sense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. In certain embodiments, antisense activity is assessed by observing a phenotypic change in a cell or animal.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

As used herein, "target mRNA" refers to a pre-selected RNA molecule that encodes a protein.

As used herein, "targeting" or "targeted to" refers to the association of an antisense compound to a particular target nucleic acid molecule or a particular region of nucleotides within a target nucleic acid molecule. An anti sense compound targets a target nucleic acid if it is sufficiently complementary to the target nucleic acid to allow hybridization under physiological conditions.

As used herein, "target site" refers to a region of a target nucleic acid that is bound by an antisense compound. In certain embodiments, a target site is at least partially within the 3' untranslated region of an RNA molecule. In certain embodiments, a target site is at least partially within the 5' untranslated region of an RNA molecule. In certain embodiments, a target site is at least partially within the coding region of an RNA molecule. In certain embodiments, a target site is at least partially within an exon of an RNA molecule. In certain embodiments, a target site is at least partially within an intron of an RNA molecule. In certain embodiments, a target site is at least partially within a microRNA target site of an RNA molecule. In certain embodiments, a target site is at least partially within a repeat region of an RNA molecule.

As used herein, "target protein" refers to a protein, the expression of which is modulated by an antisense compound. In certain embodiments, a target protein is encoded by a target nucleic acid. In certain embodiments, expression of a target protein is otherwise influenced by a target nucleic acid.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, or nucleic acids, refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the anti sense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" refers to a pattern of modifications in an oligomeric compound or a region thereof. Motifs may be defined by modifications at certain nucleosides and/or at certain linking groups of an oligomeric compound.

As used herein, "nucleoside motif" refers to a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "linkage motif" refers to a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "the same modifications" refer to modifications relative to naturally occurring molecules that are the same as one another, including absence of modifications. Thus, for example, two unmodified DNA nucleoside have "the same modification," even though the DNA nucleoside is unmodified.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "separate regions" refers to a portion of an oligomeric compound wherein the nucleosides and internucleoside linkages within the region all comprise the same modifications; and the nucleosides and/or the internucleoside linkages of any neighboring portions include at least one different modification.

As used herein, "pharmaceutically acceptable salts" refers to salts of active compounds that retain the desired biological activity of the active compound and do not impart undesired toxicological effects thereto.

As used herein, "cap structure" or "terminal cap moiety" refers to chemical modifications incorporated at either terminus of an anti sense compound.

As used herein, the term "independently" means that each occurrence of a repetitive variable within a claimed oligonucleotide is selected independent of one another. For example, each repetitive variable can be selected so that (i)

each of the repetitive variables are the same, (ii) two or more are the same, or (iii) each of the repetitive variables can be different.

General Chemistry Definitions

As used herein, "alkyl" refers to a saturated straight or branched hydrocarbon substituent or radical, typically containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to 24 carbon atoms, more typically from 1 to 12 carbon atoms ($C_1$-$C_{12}$ alkyl) with from 1 to 6 carbon atoms ($C_1$-$C_6$ alkyl) being more preferred. The term "lower alkyl" as used herein includes from 1 to 6 carbon atoms ($C_1$-$C_6$ alkyl). Alkyl groups as used herein may optionally include one or more further substituent groups.

As used herein, "alkenyl" refers to a straight or branched hydrocarbon chain radical or substituent, typically containing up to twenty four carbon atoms, and having at least one carbon-carbon double bond. Examples of alkenyl groups include, but are not limited to, ethenyl, propenyl, butenyl, 1-methyl-2-buten-1-yl, dienes such as 1,3-butadienyl and the like. Alkenyl groups typically include from 2 to 24 carbon atoms, more typically from 2 to 12 carbon atoms with from 2 to 6 carbon atoms being more preferred. Alkenyl groups as used herein may optionally include one or more further substituent groups.

As used herein, "alkynyl" refers to a straight or branched hydrocarbon radical or substituent, typically containing up to twenty four carbon atoms, and having at least one carbon-carbon triple bond. Examples of alkynyl groups include, but are not limited to, ethynyl, 1-propynyl, 1-butynyl, and the like. Alkynyl groups typically include from 2 to 24 carbon atoms, more typically from 2 to 12 carbon atoms with from 2 to 6 carbon atoms being more preferred. Alkynyl groups as used herein may optionally include one or more further substituent groups.

As used herein, "aminoalkyl" refers to an amino substituted alkyl radical or substituent. This term is meant to include $C_1$-$C_{12}$ alkyl groups having an amino substituent at any position and wherein the aminoalkyl group is attached to the parent molecule via its alkyl moiety. The alkyl and/or amino portions of the aminoalkyl group can be further substituted with substituent groups.

As used herein, "aliphatic" refers to a straight or branched hydrocarbon radical or substituent, typically containing up to twenty four carbon atoms, wherein the saturation between any two carbon atoms is a single, double or triple bond. An aliphatic group preferably contains from 1 to 24 carbon atoms, more typically from 1 to 12 carbon atoms with from 1 to 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

As used herein, "alicyclic" or "alicyclyl" refers to a cyclic radical or substituent, wherein the ring system is aliphatic. The ring system can comprise one or more rings wherein at least one ring is aliphatic. Preferred alicyclic moieties include rings having from 5 to 9 carbon atoms in the ring. Alicyclic groups as used herein may optionally include further substituent groups.

As used herein, "alkoxy" refers to a radical or substituent comprising an alkyl group and an oxygen atom, wherein the alkoxy group is attached to a parent molecule via its oxygen atom. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "halo", "halide" and "halogen" refer to an atom, radical or substituent selected from fluorine, chlorine, bromine and iodine.

As used herein, "aryl" and "aromatic" refer to a radical or substituent comprising a mono- or polycyclic carbocyclic ring system having one or more aromatic rings. Examples of aryl groups include, but are not limited to, phenyl, naphthyl, tetrahydronaphthyl, indanyl, idenyl and the like. Preferred aryl ring systems have from 5 to 20 carbon atoms in one or more rings. Aryl groups as used herein may optionally include further substituent groups.

As used herein, "aralkyl" and "arylalkyl" refer to a radical or substituent comprising an alkyl group and an aryl group, wherein the aralkyl or arylalkyl group is attached to a parent molecule via its alkyl moiety. Examples include, but are not limited to, benzyl, phenethyl and the like. Aralkyl groups as used herein may optionally include further substituent groups attached to the alkyl, the aryl or both groups that form the radical or substituent.

As used herein, "heterocyclyl" refers to a radical or substituent comprising a mono- or polycyclic ring system that includes at least one heteroatom and is unsaturated, partially saturated or fully saturated, thereby including heteroaryl groups. Heterocyclyl is also meant to include fused ring system moieties wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein, "heteroaryl" and "heteroaromatic" refer to a radical or substituent comprising a mono- or polycyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals or substituents can be attached to a parent molecule directly or through a linking moiety such as an aliphatic group or a heteroatom. Heteroaryl groups as used herein may optionally include further substituent groups.

As used herein, "heteroarylalkyl" refers to a radical or substituent comprising a heteroaryl group as previously defined and an alkyl moiety, wherein the heteroarylalkyl group is attached to a parent molecule via its alkyl moiety. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

As used herein, "mono or polycyclic" refers to any ring systems, such as a single ring or a polycyclic system having rings that are fused or linked, and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and polycyclic structures can contain rings that have a uniform or varying degree of saturation, including fully saturated, partially saturated or fully unsaturated rings. Each ring can comprise ring atoms selected from C, N, O and S to give rise to heterocyclic rings as well as rings comprising only C ring atoms. Heterocyclic and all-carbon rings can be present in a mixed motif, such as for example benzimidazole wherein one ring of the fused ring system has only carbon ring atoms and the other ring has two nitrogen atoms. The mono or polycyclic structures can be further substituted with substituent groups such as for example phthalimide which has two oxo groups (=O) attached to one of the rings. In another aspect, mono or polycyclic structures can be attached to a parent molecule directly through a ring atom, through a substituent group or a bifunctional linking moiety.

As used herein, "acyl" refers to a radical or substituent comprising a carbonyl moiety (C=O or —C(O)—) and a further substituent X, wherein the acyl group is attached to a parent molecule via its carbonyl moiety. As such, an acyl group is formally obtained by removal of a hydroxyl group from an organic acid and has the general formula —C(O)—X, wherein X is typically aliphatic, alicyclic or aromatic. The term "acyl" is also meant to include heteroacyl radicals or substituents with general formula —Y(O)$_n$—X, wherein X is as defined above and Y(O)$_n$ is typically sulfonyl, sulfinyl or phosphate. Examples of acyl groups include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "substituent" and "substituent group" include groups that are typically added to other substituents or parent compounds to enhance desired properties or give desired effects. Substituent groups can be protected or unprotected and can be attached to one available site or to many available sites in a parent compound. Substituent groups may also be further substituted with other substituent groups and may be attached directly or via a linking group such as an alkyl or hydrocarbyl group to a parent compound. Herein, "hydrocarbyl" refers to any group comprising C, O and H. Included are straight, branched and cyclic groups having any degree of saturation. Such hydrocarbyl groups can include one or more heteroatoms selected from N, O and S and can be further substituted with one or more substituent groups.

Unless otherwise indicated, the term substituted or "optionally substituted" refers to the optional presence of any of the following substituents: halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxo (—O—R$_{aa}$), aryl, aralkyl, heterocyclic, heteroaryl, heteroarylalkyl, amino (—NR$_{bb}$R$_{cc}$), imino (=NR$_{bb}$), amido (—C(O)NR$_{bb}$R$_{cc}$ or —N(R$_{bb}$)C(O)R$_{aa}$), azido (—N$_3$), nitro (—NO$_2$), cyano (—CN), carbamido (—OC(O)NR$_{bb}$R$_{cc}$ or —N(R$_{bb}$)C(O)OR$_{aa}$), ureido (—N(R$_{bb}$)C(O)NR$_{bb}$R$_{cc}$), thioureido (—N(R$_{bb}$)C(S)NR$_{bb}$R$_{cc}$), guanidinyl (—N(R$_{bb}$)C(=NR$_{bb}$)NR$_{bb}$R$_{cc}$), amidinyl (—C(=NR$_{bb}$)NR$_{bb}$R$_{cc}$ or —N(R$_{bb}$)C(NR$_{bb}$)R$_{aa}$), thiol (—SR$_{bb}$), sulfinyl (—S(O)R$_{bb}$), sulfonyl (—S(O)$_2$R$_{bb}$), sulfonamidyl (—S(O)$_2$NR$_{bb}$R$_{cc}$ or —N(R$_{bb}$)S(O)$_2$R$_{bb}$) and conjugate groups. Herein, each R$_{aa}$, R$_{bb}$ and R$_{cc}$ is, independently, H, an optionally linked chemical functional group or a further substituent group, preferably but without limitation chosen from the group consisting of H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein, a zero (0) in a range indicating number of a particular unit means that the unit may be absent. For example, an oligomeric compound comprising 0-2 regions of a particular motif means that the oligomeric compound may comprise one or two such regions having the particular motif, or the oligomeric compound may not have any regions having the particular motif. In instances where an internal portion of a molecule is absent, the portions flanking the absent portion are bound directly to one another. Likewise, the term "none" as used herein, indicates that a certain feature is not present.

As used herein, "analogue" or "derivative" means either a compound or moiety similar in structure but different in respect to elemental composition from the parent compound regardless of how the compound is made. For example, an analogue or derivative compound does not need to be made from the parent compound as a chemical starting material.

The following examples are offered for illustrative purposes only, and are not intended to limit the scope of the present invention in any way.

LEGENDS TO THE FIGURE

FIG. 1.

Comparison of AONs with or without cytosine to 5-methylcytosine substitution in differentiated healthy muscle cells in vitro after transfection with (A) PS229L/PS524, SEQ ID NO:52 (corresponding to SEQ ID NO: 91 for the non-modified sequence, corresponding to SEQ ID NO: 92 wherein all cytosines are modified) or (B) PS220/PS339 (SEQ ID NO:21, corresponding to SEQ ID NO:101 for the non-modified sequence, corresponding to SEQ ID NO:200 wherein all cytosines are modified) or (C) PS524/PS1317/PS1318/PS1319, SEQ ID NO:52 (corresponding to SEQ ID NO: 92 (PS524) wherein all 6 cytosines are modified, to SEQ ID NO: 217 (PS1317) wherein 4 of the 6 cytosines are modified, to SEQ ID NO: 218 (PS1318) wherein 2 of the 6 cytosines are modified and to SEQ ID NO:219 (PS1319) wherein 3 of the 6 cytosines are modified SEQ ID NO:217). Average skipping percentages were calculated from triplo (n=3) (A,B) or duplo (n=2) (C) transfections per concentration. Solid lines refer to AONs with 5-methylcytosines, dotted lines to AONs with non-substituted cytosines (A,B).

FIG. 2.

Summary of the pharmacokinetic study in wild type (control) and mdx mice, comparing plasma and muscle tissue profiles of AONs with 5-methylcytosines (PS524, SEQ ID NO:52 (i.e. corresponding to SEQ ID NO: 92 wherein all cytosines are modified) and PS652, SEQ ID NO:57 (i.e. corresponding to SEQ ID NO: 185 wherein all cytosines are modified) and AONs with unmodified (non-methylated) cytosines (PS229L, SEQ ID NO:52 corresponding to SEQ ID NO: 91 for the non-modified sequence, and PS531, SEQ ID NO:57 corresponding to SEQ ID NO: 137 for the non-modified sequence). (A) Pharmacokinetic tissue analysis of: 1) the ratio between the average levels of AON in muscle in mdx mice versus control mice after one single sc injection; 2) the levels of the AONs (μg/g) in several mdx muscles (dia=diaphragm, gastroc=gastrocnemius, quadr=quadriceps, tric=triceps) at 14 days; 3) the relative muscle/kidney and muscle/liver levels at day 14, and 4) the estimated half-life of the different AONs in triceps. B) Pharmacokinetic plasma analysis of 1) Tmax (time at which Cmax was reached, only two time points of analysis included (15 or 60 min), 2) Cmax (highest plasma concentration reached), 3) AUC (area under curve; indicative for bioavailability) an 4) Cl (plasma clearance at 24 h.

FIG. 3.

Analysis of cytokine levels in human whole blood upon incubation with 0, 10, 25, or 50 μg/ml of AONs with unmodified cytosines PS232 (SEQ ID NO: 39, corresponding to SEQ ID NO: 119 for the non-modified sequence) and PS534 (SEQ ID NO:59, corresponding to SEQ ID NO: 139 for the non-modified sequence) (black bars) or AONs with 5-methylcytosines PS648 (SEQ ID NO: 39, corresponding to SEQ ID NO: 201 wherein all cytosines are modified) and PS653 (SEQ ID NO:59, to SEQ ID NO: 192 wherein all cytosines are modified) (grey bars). The levels of TNFα(A, B), MCP-1 (C, D), IP-10 (E, F), and IL6 (G, H) were determined using commercially available ELISA kits. Each experiment was repeated four times (n=4). Data is shown for the most pronounced response of each cytokine.

FIG. 4.

Activity comparisons of AONs with 5-methylcytosines and/or 5-methyluracils with corresponding AONs without these base modifications, (A) Transfection of 200 nM, in duplo, into differentiated healthy muscle cells in vitro. Activity was expressed as average percentage exon 51 (PS43, non-modified sequence represented by SEQ ID NO: 111, PS559 corresponding to SEQ ID NO: 202, wherein all uraciles are modified, PS1106 corresponding to SEQ ID NO:203, wherein all cytosines and all uraciles are modified. All sequences are derived from SEQ ID NO: 31), exon 44 (PS188, non-modified sequence represented by SEQ ID NO: 95, PS785, corresponding to SEQ ID NO: 204, wherein all uraciles are modified, PS1107: corresponding to SEQ ID NO:205, wherein all cytosines and all uraciles are modified. All sequences are derived from SEQ ID NO 15); or exon 52 (PS235, non-modified sequence represented by SEQ ID NO: 120, PS786: corresponding to SEQ ID NO: 172, wherein all uraciles are modified. All sequences are derived from SEQ ID NO 40) skipping (n=2). AON sequences (5' to 3') and base modifications (bold, underlined nucleotides) are shown in the table underneath. (B) Intramuscular injection of 20 μg of PS49 (non-modified sequence, SEQ ID NO: 216) or PS959 (modified sequence wherein all uracils are modified, SEQ ID NO:214) in the gastrocnemius muscles of mdx mice. Activity was expressed as average percentage murine exon 23 skipping (n=4). AON sequences (5' to 3') and base modifications (bold, underlined nucleotides) are shown in the table underneath.

FIG. 5.

Activity comparisons of AONs with 2,6-diaminopurines with corresponding AONs without this base modification. (A), Transfection of 200 nM, in duplo, into differentiated healthy muscle cells in vitro. Activity was expressed as average percentage exon 51 (PS43, non-modified sequence represented by SEQ ID NO: 111, PS403, corresponding to SEQ ID NO: 206, wherein all adenines have been modified. All sequences are derived from SEQ ID NO: 31), exon 52 (PS235, non-modified sequence represented by SEQ ID NO: 120, PS897: corresponding to SEQ ID NO: 173, wherein all adenines have been modified. All sequences are derived from SEQ ID NO: 40), or exon 44 (PS188, non-modified sequence represented by SEQ ID NO: 95, PS733: corresponding to SEQ ID NO: 207, wherein all adenines have been modified. All sequences are derived from SEQ ID NO: 15) skipping (n=2). AON sequences (5' to 3') and base modifications (bold, underlined nucleotides) are shown in the table underneath. (B) and (C) The effect of substituting all unmodified adenines (PS188; SEQ ID NO: 95) with 2,6-diaminopurines (PS733; SEQ ID NO:207) on in vitro safety. As markers for activation of the alternative complement pathway, split factors C3a (B) and Bb (C) were measured in monkey plasma.

EXAMPLES

TABLE 1

General structures of AONs. X = C or $m^5C$, Y = U or $m^5U$, Z = A or $a^2A$; I = inosine (hypoxanthine base), $X_1$ = $m^5C$, $Y_1$ = $m^5U$, $Z_1$ = $a^2A$

| DMD Exon | AON Sequence (5'→3') | SEQ ID NO |
|---|---|---|
| 44 | GXXZYYYXYXZZXZGZYXY | 14 |
|    | GCCAUUUCUCAACAGAUCU | 94 |
| 44 | YXZGXYYXYGYYZGXXZXYG | 15 |
|    | UCAGCUUCUGUUAGCCACUG | 95 |
|    | $Y_1$CAGCY$_1Y_1$CY$_1$GY$_1Y_1$AGCCACY$_1$G | 204 |
|    | UX$_1$AGX$_1$UUX$_1$UGUUAGX$_1X_1$AX$_1$UG | 208 |
|    | $Y_1X_1$AGX$_1Y_1Y_1X_1Y_1$GY$_1Y_1$AGX$_1X_1$AX$_1Y_1$G | 205 |
|    | UCZ$_1$GCUUCUGUUZ$_1$GCCZ$_1$CUG | 207 |
| 44 | YYYGYZYYYZGXZYGYYXXX | 16 |
|    | UUUGUAUUUAGCAUGUUCCC | 96 |
| 44 | ZYYXYXZGGZZYYYGYGYXYYYX | 17 |
|    | AUUCUCAGGAAUUUGUGUCUUUC | 97 |
| 44 | XXZYYYGYZYYYZGXZYGYYXXX | 18 |
|    | CCAUUUGUAUUUAGCAUGUUCCC | 98 |
| 44 | YXYXZGGZZYYYGYGYXYYYX | 19 |
|    | UCUCAGGAAUUUGUGUCUUUC | 99 |

TABLE 1-continued

General structures of AONs. X = C or $m^5C$, Y = U or $m^5U$, Z = A or $a^2A$; I = inosine (hypoxanthine base), $X_1 = m^5C$, $Y_1 = m^5U$, $Z_1 = a^2A$

| DMD Exon | AON Sequence (5'→3') | SEQ ID NO |
|---|---|---|
| 44 | GXXZYYYXYXZZXZGZYXYGYXZ | 20 |
|  | GCCAUUUCUCAACAGAUCUGUCA | 100 |
| 45 | YYYGXXGXYGXXXZZYGXXZYXXYG | 21 |
|  | UUUGCCGCUGCCCAAUGCCAUCCUG | 101 |
|  | UUUGX$_1$X$_1$GX$_1$UGX$_1$X$_1$AAUGX$_1$X$_1$AUX$_1$X$_1$UG | 200 |
|  | Y$_1$Y$_1$Y$_1$GX$_1$X$_1$GX$_1$Y$_1$GX$_1$X$_1$AAY$_1$GX$_1$X$_1$AY$_1$X$_1$X$_1$G | 209 |
|  | UUUGCCGCUGCCCZ$_1$Z$_1$UGCCZ$_1$UCCUG | 210 |
| 45 | YYGXXGXYGXXXZZYGXXZYXXYG | 22 |
|  | UUGCCGCUGCCCAAUGCCAUCCUG | 102 |
| 45 | YGXXGXYGXXXZZYGXXZYXXYGG | 23 |
|  | UUGCCGCUGCCCAAUGCCAUCCUGG | 103 |
| 45 | YGXXGXYGXXXZZYGXXZYXXYG | 24 |
|  | UGCCGCUGCCCAAUGCCAUCCUG | 104 |
| 45 | YGXXGXYGXXXZZYGXXZYXXYGG | 25 |
|  | UGCCGCUGCCCAAUGCCAUCCUGG | 105 |
| 45 | GXXGXYGXXXZZYGXXZYXXYG | 26 |
|  | GCCGCUGCCCAAUGCCAUCCUG | 106 |
| 45 | XXGXYGXXXZZYGXXZYXXYGG | 27 |
|  | CCGCUGCCCAAUGCCAUCCUGG | 107 |
| 45 | YYYGXXIXYGXXXZZYGXXZYXXYG | 28 |
|  | UUUGCCICUGCCCAAUGCCAUCCUG | 108 |
| 45 | XZGYYYGXXGXYGXXXZZYGXXZYX | 29 |
|  | CAGUUUGCCGCUGCCCAAUGCCAUC | 109 |
| 45 | XZGYYYGXXGXYGXXXZZYGXXZYXXYGGZ | 30 |
|  | CAGUUUGCCGCUGCCCAAUGCCAUCCUGGA | 110 |
| 51 | YXZZGGZGZYGGXZYYYXY | 31 |
|  | UCAAGGAAGAUGGCAUUUCU | 111 |
|  | Y$_1$CAAGGAAGAY$_1$GGCAY$_1$Y$_1$Y$_1$CY$_1$ | 202 |
|  | Y$_1$X$_1$AAGGAAGAY$_1$GGX$_1$AY$_1$Y$_1$Y$_1$X$_1$Y$_1$ | 203 |
|  | UCZ$_1$Z$_1$GGZ$_1$GZ$_1$UGGCZ$_1$UUUCU | 206 |
|  | UX$_1$AAGGAAGAUGGX$_1$AUUUX$_1$U | 215 |
| 51 | YGGXZYYYXYZGYYYGG | 32 |
|  | UGGCAUUUCUAGUUUGG | 112 |
| 51 | XZYXZZGGZGZYGGXZYYYXY | 33 |
|  | CAUCAAGGAAGAUGGCAUUUCU | 113 |
| 51 | XZZXZYXZZGGZGZYGGXZYYYXY | 34 |
|  | CAACAUCAAGGAAGAUGGCAUUUCU | 114 |
| 51 | XXYXYGYGZYYYYZYZZXYYGZY | 35 |
|  | CCUCUGUGAUUUAUAACUUGAU | 115 |
| 51 | XXZGZGXZGGYZXXYXXZZXZYX | 36 |
|  | CCAGAGCAGGUACCUCCAACAUC | 116 |
| 51 | ZXZYXZZGGZZGZYGGXZYYYXYZGYYYGG | 37 |
|  | ACAUCAAGGAAGAUGGCAUUUCUAGUUUGG | 117 |
| 51 | ZXZYXZZGGZZGZYGGXZYYYXYZG | 38 |
|  | ACAUCAAGGAAGAUGGCAUUUCUAG | 118 |
| 52 | XYXYYGZYYGXYGGYXYYGYYYYYX | 39 |
|  | CUCUUGAUUGCUGGUCUUGUUUUUC | 119 |
|  | X$_1$UX$_1$UUGAUUGX$_1$UGGUX$_1$UUGUUUUUX$_1$ | 201 |
| 52 | GGYZZYGZGYXYYXXZZXYGG | 40 |
|  | GGUAAUGAGUUCUUCCAACUGG | 120 |
|  | GGUAAUGAGUUX$_1$UUX$_1$X$_1$AAX$_1$UGG | 171 |
|  | GGY$_1$AAY$_1$GAGY$_1$Y$_1$CY$_1$Y$_1$CCAACY$_1$GG | 172 |
|  | GGUZ$_1$Z$_1$UGZ$_1$GUUCUUCCZ$_1$Z$_1$CUGG | 173 |
|  | GGY$_1$AAY$_1$GAGY$_1$Y$_1$X$_1$Y$_1$Y$_1$X$_1$X$_1$AAX$_1$Y$_1$GG | 174 |
|  | GGUZ$_1$Z$_1$UGZ$_1$GUUX$_1$UUX$_1$X$_1$Z$_1$Z$_1$X$_1$UGG | 175 |
|  | GGY$_1$Z$_1$Z$_1$Y$_1$GZ$_1$GY$_1$Y$_1$CY$_1$Y$_1$CCZ$_1$Z$_1$CY$_1$GG | 176 |
|  | GGY$_1$Z$_1$Z$_1$Y$_1$GZ$_1$GY$_1$Y$_1$X$_1$Y$_1$Y$_1$X$_1$X$_1$Z$_1$Z$_1$X$_1$Y$_1$GG | 177 |
| 52 | YXYYGZYYGXYGGYXYYGYYYYXZ | 41 |
|  | UCUUGAUUGCUGGUCUUGUUUUCA | 121 |
| 52 | YYXXZZXYGGGGZXGXXYXYGYYXX | 42 |
|  | UUCCAACUGGGGACGCCUCUGUUCC | 122 |
| 52 | YGYYXYZGXXYXYYGZYYGXYGGYX | 43 |
|  | UGUUCUAGCCUCUUGAUUGCUGGUC | 123 |
|  | UGUUX$_1$UAGX$_1$X$_1$UX$_1$UUGAUUGX$_1$UGGUX$_1$ | 178 |
|  | Y$_1$GY$_1$Y$_1$CY$_1$Y$_1$AGCCY$_1$CY$_1$Y$_1$GAY$_1$Y$_1$GCY$_1$GGY$_1$C | 179 |
|  | UGUUCUZ$_1$GCCUCUGZ$_1$UUGCUGGUC | 180 |
|  | Y$_1$GY$_1$Y$_1$X$_1$Y$_1$AGX$_1$X$_1$Y$_1$Y$_1$Y$_1$GAY$_1$Y$_1$GX$_1$Y$_1$GGY$_1$X$_1$ | 181 |
|  | UGUUX$_1$UZ$_1$GX$_1$X$_1$UX$_1$UUGZ$_1$UUGX$_1$UGGUX$_1$ | 182 |
|  | Y$_1$GY$_1$Y$_1$CY$_1$Z$_1$GCCCY$_1$CY$_1$GZ$_1$Y$_1$Y$_1$GCY$_1$GGY$_1$C | 183 |
|  | Y$_1$GY$_1$YAN$_1$Z$_1$GX$_1$X$_1$Y$_1$Y$_1$Y$_1$GZ$_1$Y$_1$Y$_1$GX$_1$Y$_1$GGY$_1$X$_1$ | 184 |
| 53 | XYGYYGXXYXXGGYYXYG | 44 |
|  | CUGUUGCCUCCGGUUCUG | 124 |
| 53 | XZZXYGYYGXXYXXGGYYXYGZ | 45 |
|  | CAACUGUUGCCUCCGGUUCUGA | 125 |
| 53 | XZZXYGYYGXXYXXGGYYXYGZZ | 46 |
|  | CAACUGUUGCCUCCGGUUCUGAA | 126 |
| 53 | XZZXYGYYGXXYXXGGYYXYGZZG | 47 |
|  | CAACUGUUGCCUCCGGUUCUGAAG | 127 |
| 53 | XYGYYGXXYXXGGYYXYGZZGG | 48 |
|  | CUGUUGCCUCCGGUUCUGAAGG | 128 |
| 53 | XYGYYGXXYXXGGYYXYGZZGGY | 49 |
|  | CUGUUGCCUCCGGUUCUGAAGGU | 129 |
| 53 | XYGYYGXXYXXGGYYXYGZZGGYG | 50 |
|  | CUGUUGCCUCCGGUUCUGAAGGUG | 130 |
| 53 | XYGYYGXXYXXGGYYXYGZZGGYGY | 51 |
|  | CUGUUGCCUCCGGUUCUGAAGGUGU | 131 |
| 53 | GYYGXXYXXGGYYXYGZZGGYGYYX | 52 |
|  | GUUGCCUCCGGUUCUGAAGGUGUUC | 91 |
|  | GUUGX$_1$X$_1$UX$_1$X$_1$GGUUX$_1$UGAAGGUGUUX$_1$ | 92 |
|  | GUUGX$_1$X$_1$UCCGGUUX$_1$UGAAGGUGUUX$_1$ | 217 |
|  | GUUGX$_1$X$_1$UCCGGUUCUGAAGGUGUUC | 218 |
|  | GUUGCX$_1$UCCGGUUX$_1$UGAAGGUGUUX$_1$ | 219 |
|  | GY$_1$Y$_1$GCCY$_1$CCGGY$_1$CY$_1$GAAGGY$_1$GY$_1$Y$_1$C | 211 |
|  | GY$_1$Y$_1$GX$_1$XY$_1$X$_1$X$_1$GGY$_1$Y$_1$X$_1$Y$_1$GAAGGY$_1$GY$_1$Y$_1$X$_1$ | 212 |
|  | GUUGCCUCCGGUUCUGZ$_1$Z$_1$GGUGUUC | 213 |
| 53 | GXXYXXGGYYXYGZZGGYGYYXYYG | 53 |
|  | GCCUCCGGUUCUGAAGGUGUUCUUG | 133 |
| 53 | YYGXXYXXGGYYXYGZZGGYGYYXYYGYZX | 54 |
|  | UUGCCUCCGGUUCUGAAGGUGUUCUUGUAC | 134 |
| 53 | XYGYYGXXYXXGGYYXYGZZGGYGYYXYYG | 55 |
|  | CUGUUGCCUCCGGUUCUGAAGGUGUUCUUG | 135 |
| 53 | XZZXYGYYGXXYXXGGYYXYGZZGGYGYYXYYG | 56 |
|  | CAACUGUUGCCUCCGGUUCUGAAGGUGUUCUUG | 136 |
| 55 | GZGYYYXYYXXZZZGXZGXXYXYX | 57 |
|  | GAGUUUCUUCCAAAGCAGCCUCUC | 137 |
|  | GAGUUUX$_1$UUX$_1$X$_1$AAAGX$_1$AGX$_1$X$_1$UX$_1$UX$_1$ | 185 |
|  | GAGY$_1$Y$_1$Y$_1$CY$_1$Y$_1$CCAAAGCAGCCY$_1$CY$_1$C | 186 |
|  | GZ$_1$GUUUCUUCCZ$_1$Z$_1$Z$_1$GCZ$_1$GCCUCUC | 187 |
|  | GAGY$_1$Y$_1$Y$_1$X$_1$Y$_1$Y$_1$X$_1$X$_1$AAAGX$_1$AGX$_1$X$_1$Y$_1$X$_1$Y$_1$X$_1$ | 188 |

TABLE 1-continued

General structures of AONs. X = C or m⁵C, Y = U or m⁵U, Z = A or a²A; I = inosine (hypoxanthine base), $X_1$ = m⁵C, $Y_1$ = m⁵U, $Z_1$ = a²A

| DMD Exon | AON Sequence (5'→3') | SEQ ID NO |
|---|---|---|
|  | GZ₁GUUUX₁UUX₁X₁Z₁Z₁GX₁Z₁GX₁X₁UX₁UX₁ | 189 |
|  | GZ₁GY₁Y₁Y₁CY₁Y₁CCZ₁Z₁Z₁GCZ₁GCCY₁CY₁C | 190 |
|  | GZ₁GY₁Y₁Y₁Y₁Y₁X₁X₁Z₁Z₁Z₁GX₁Z₁GX₁X₁Y₁Y₁X₁ | 191 |
| 55 | YZYGZGYYYXYYXXZZZGXZGXXYX<br>UAUGAGUUUCUUCCAAAGCAGCCUC | 58<br>138 |
| 55 | ZGXZYXXYGYZGGZXZYYGGXZGY<br>AGCAUCCUGUAGGACAUUGGCAGU<br>AGX₁AUX₁X₁UGUAGGAX₁AUUGGX₁AGU<br>AGCAY₁CCY₁GY₁AGGACAY₁Y₁GGCAGY₁<br>Z₁GCZ₁UCCUGUZ₁GGZ₁CZ₁UUGGCZ₁GU<br>AGX₁AY₁X₁X₁Y₁GY₁AGGAX₁AY₁Y₁GGX₁AGY₁<br>Z₁GX₁Z₁UX₁X₁UGUZ₁GGZ₁X₁Z₁UUGGX₁Z₁GU<br>Z₁GCZ₁Y₁CCY₁GY₁Z₁GGZ₁CZ₁Y₁Y₁GGCZ₁GY₁<br>Z₁GX₁Z₁Y₁X₁Y₁GY₁Z₁GGZ₁X₁Z₁Y₁Y₁GGX₁Z₁GY₁ | 59<br>139<br>192<br>193<br>194<br>195<br>196<br>197<br>198 |
| 55 | XZYXXYGYZGGZXZYYGGXZGYYG<br>CAUCCUGUAGGACAUUGGCAGUUG | 60<br>140 |
| 55 | YXXYGYZGGZXZYYGGXZGYYGYY<br>UCCUGUAGGACAUUGGCAGUUGUU | 61<br>141 |
| 55 | XYGYZGGZXZYYGGXZGYYGYYYX<br>CUGUAGGACAUUGGCAGUUGUUUC | 62<br>142 |

TABLE 2

General structures of AONs. X = C or m⁵C, Y = U or m⁵U, Z = A or a²A; I = inosine (hypoxanthine base), $X_1$ = m⁵C, $Y_1$ = 2 m⁵U, $Z_1$ = a²A

| DMD Exon | AON Sequence (5'→3') | SEQ ID NO |
|---|---|---|
| 44 | ZYYYXYXZZXZGZ<br>AUUUCUCAACAGA | 63<br>143 |
| 44 | ZGXYYXYGYYZGXXZ<br>AGCUUCUGUUAGCCA | 64<br>144 |
| 44 | ZYYXYXZGGZZ<br>AUUCUCAGGAA | 65<br>145 |
| 44 | ZYYYGYZYYYZGXZ<br>AUUUGUAUUUAGCA | 66<br>146 |
| 44 | ZYYYXYXZZXZGZYXYGYXZ<br>AUUUCUCAACAGAUCUGUCA | 67<br>147 |
| 44 | ZYYYXYXZZXZGZ<br>AUUUCUCAACAGA | 68<br>148 |
| 44 | ZXZGZYXYGYXZ<br>ACAGAUCUGUCA | 69<br>149 |
| 45 | YYYGXXGXYGXXXZZYGXXZ<br>UUUGCCGCUGCCCAUGCCA | 70<br>150 |
| 45 | XGXYGXXXZZYGXXZYXXYG<br>CGCUGCCCAUGCCAUCCUG | 71<br>151 |
| 45 | GXXGXYGXXXZZYGXXZYXX<br>GCCGCUGCCCAUGCCAUCC | 72<br>152 |
| 51 | ZZGGZZGZYGGXZ<br>AAGGAAGAUGGCA | 73<br>153 |
| 51 | ZGGZZGZYGGXZ<br>AGGAAGAUGGCA | 74<br>154 |

TABLE 2-continued

General structures of AONs. X = C or m⁵C, Y = U or m⁵U, Z = A or a²A; I = inosine (hypoxanthine base), $X_1$ = m⁵C, $Y_1$ = 2 m⁵U, $Z_1$ = a²A

| DMD Exon | AON Sequence (5'→3') | SEQ ID NO |
|---|---|---|
| 51 | ZGZGXZGGYZ<br>AGAGCAGGUA | 75<br>155 |
| 51 | ZGXZGGYZXXYXXZ<br>AGCAGGUACCUCCA | 76<br>156 |
| 51 | ZXXYXXZZXZ<br>ACCUCCAACA | 77<br>157 |
| 52 | ZZYGZGYYXYYXXZZ<br>AAUGAGUUCUUCCAA | 78<br>158 |
| 52 | ZYGZGYYXYYXXZ<br>AUGAGUUCUUCCA | 79<br>159 |
| 52 | ZGYYXYYXXZ<br>AGUUCUUCCA | 80<br>160 |
| 52 | ZGXXYXYYGZ<br>AGCCUCUUGA | 81<br>161 |
| 53 | GYYGXXYXXGGYYXYGZZGG<br>GUUGCCUCCGGUUCUGAAGG | 82<br>162 |
| 53 | XYXXGGYYXYGZZGGYGYYX<br>CUCCGGUUCUGAAGGUGUUC | 83<br>163 |
| 53 | XXYXXGGYYXYGZZGGY<br>CCUCCGGUUCUGAAGGU | 84<br>164 |
| 55 | ZGYYYXYYXXZZZGXZ<br>AGUUUCUUCCAAAGCA | 85<br>165 |
| 55 | ZGYYYXYYXXZ<br>AGUUUCUUCCA | 86<br>166 |
| 55 | ZGXZYXXYGYZGGZXZYYGGXZ<br>AGCAUCCUGUAGGACAUUGGCA | 87<br>167 |
| 55 | ZGXZYXXYGYZ<br>AGCAUCCUGUA | 88<br>168 |
| 55 | ZYXXYGYZGGZ<br>AUCCUGUAGGA | 89<br>169 |
| 55 | ZGGZXZYYGGXZ<br>AGGACAUUGGCA | 90<br>170 |

TABLE 3

Most preferred AONs
General structures of AONs. X = C or $m^5C$, Y = U or $m^5U$, Z = A or $a^2A$;
I = inosine (hypoxanthine base), $X_1 = m^5C$, $Y_1 = m^5U$, $Z_1 = a^2A$

Figure 1B:
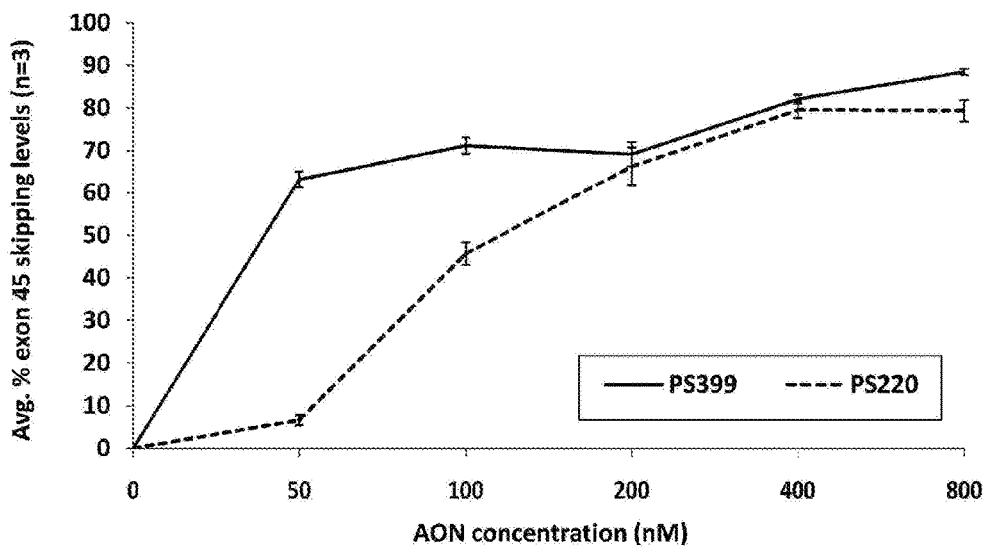
Figure 1C:
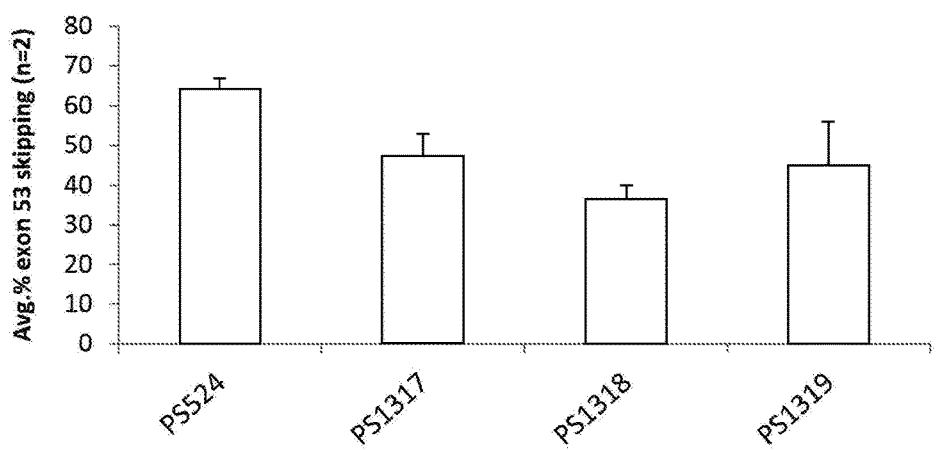
Figure 3A:
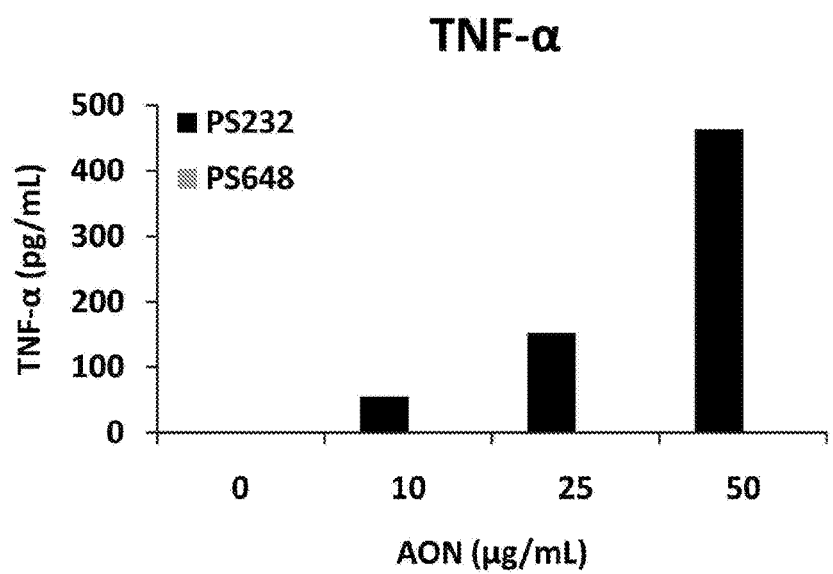
Figure 3B:
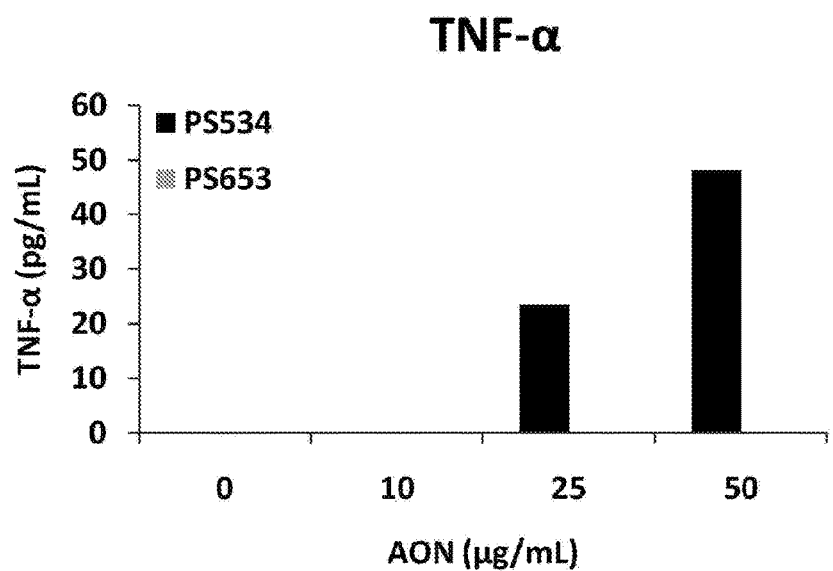
Figure 3C:
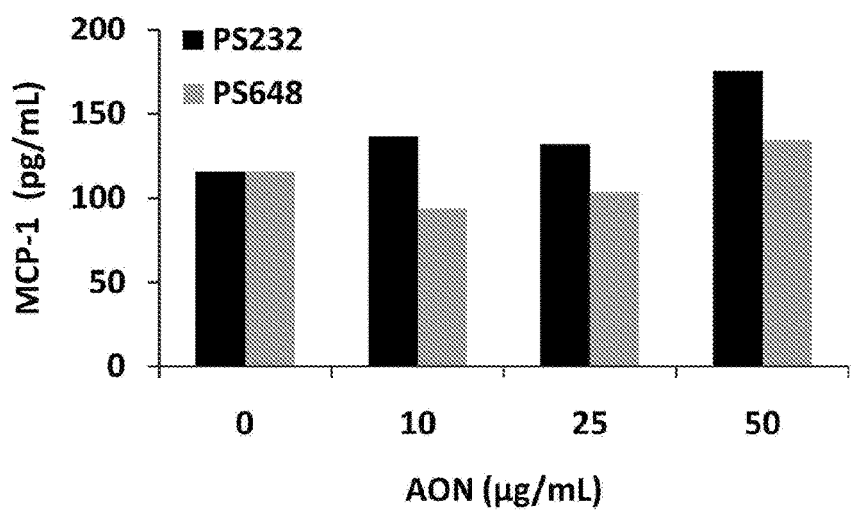
Figure 3D:
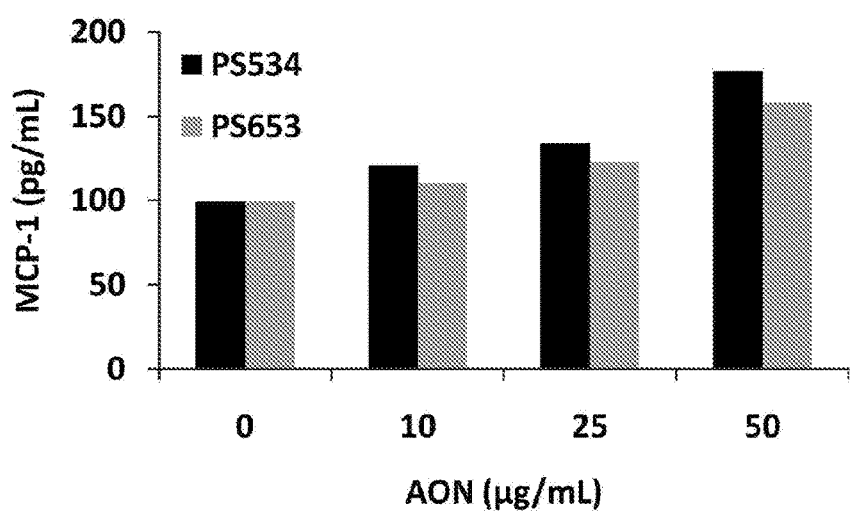
Figure 3E:
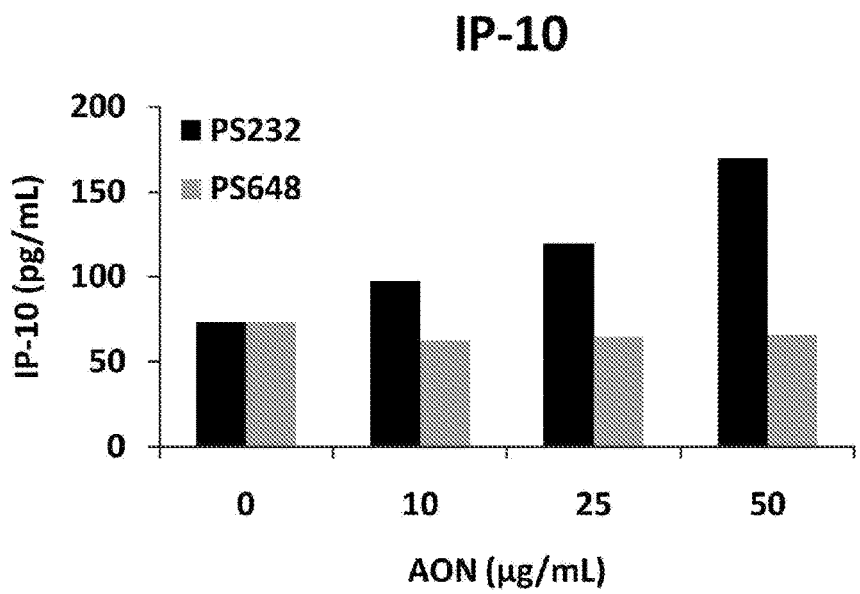
Figure 3F:
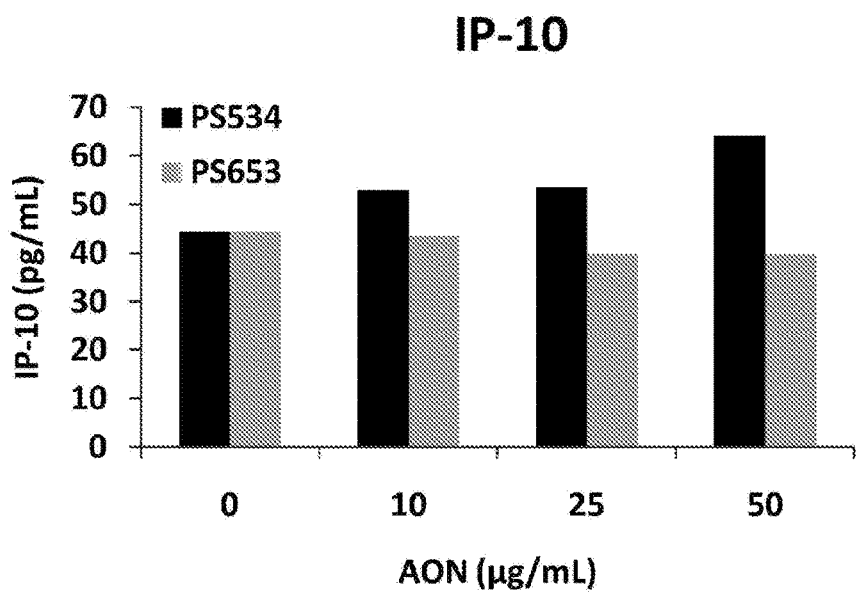
Figure 3G:
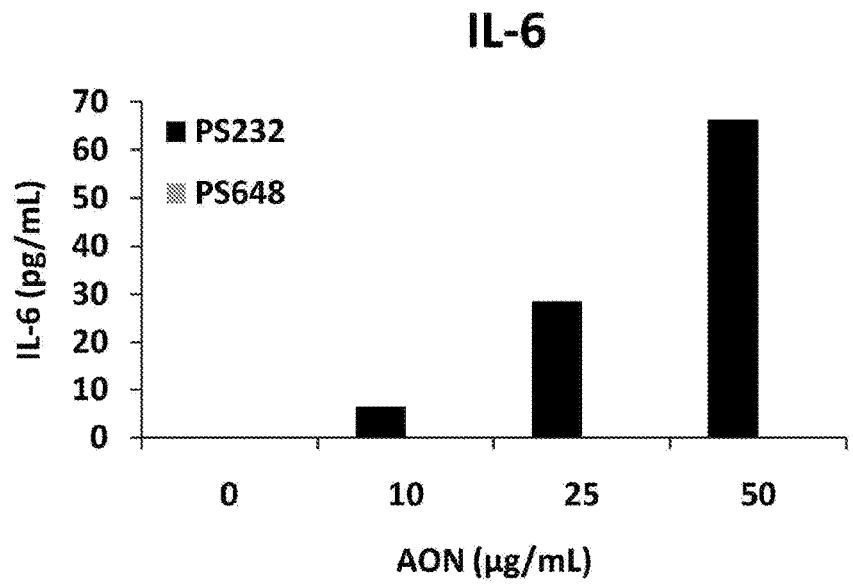
Figure 3H:
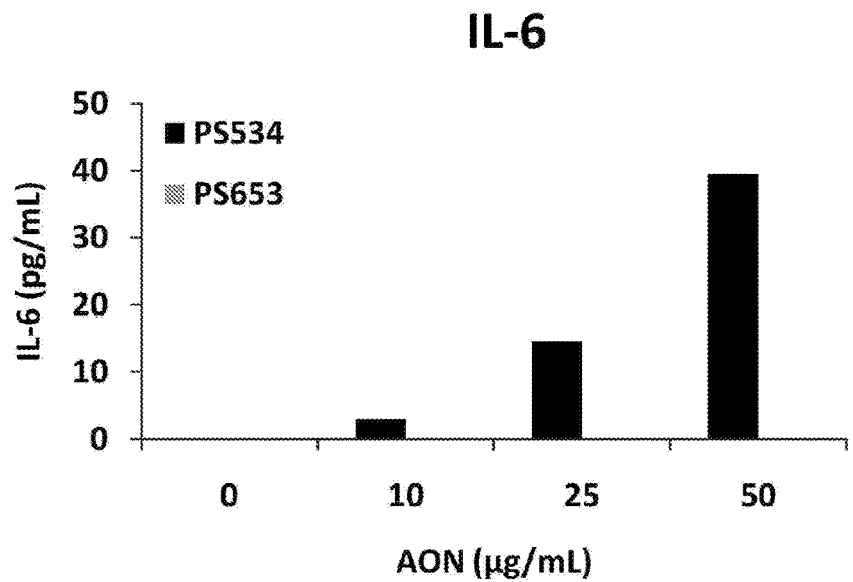
Figure 4A:
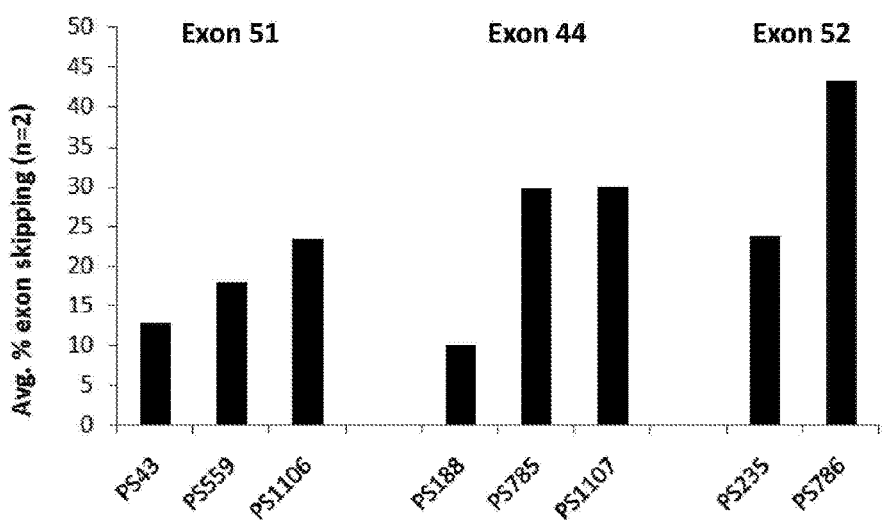
Figure 4B:
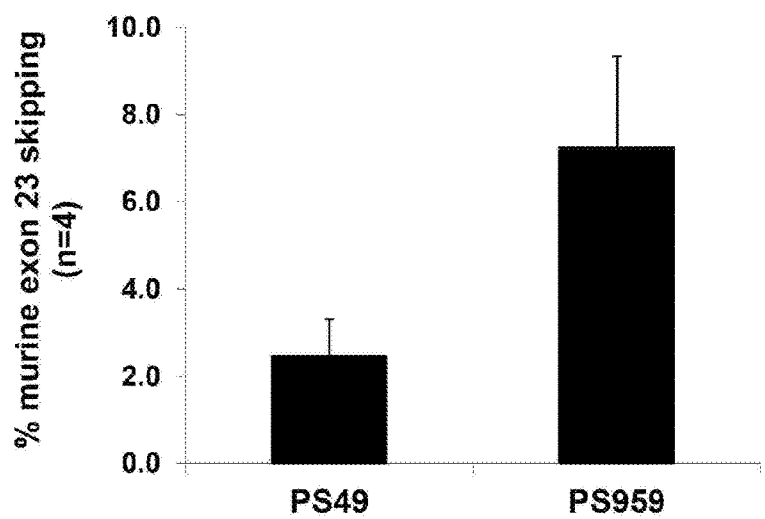
Figure 5A:
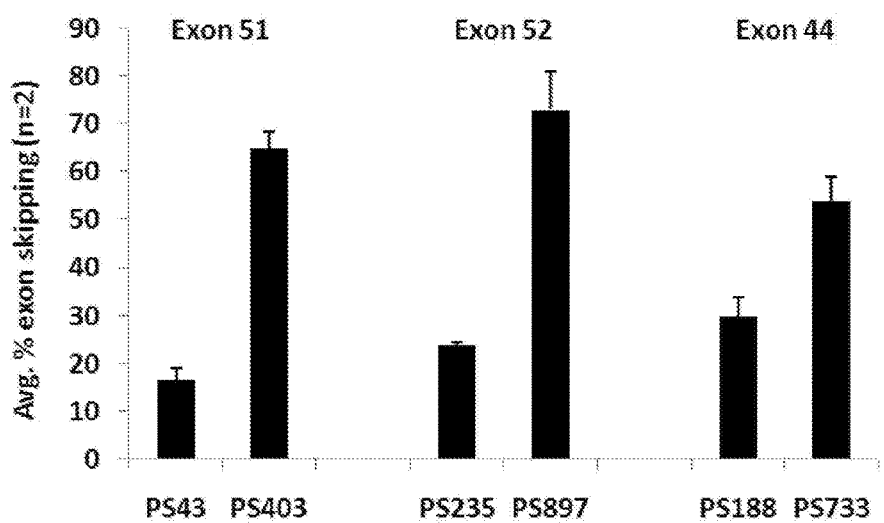
Figure 5B:
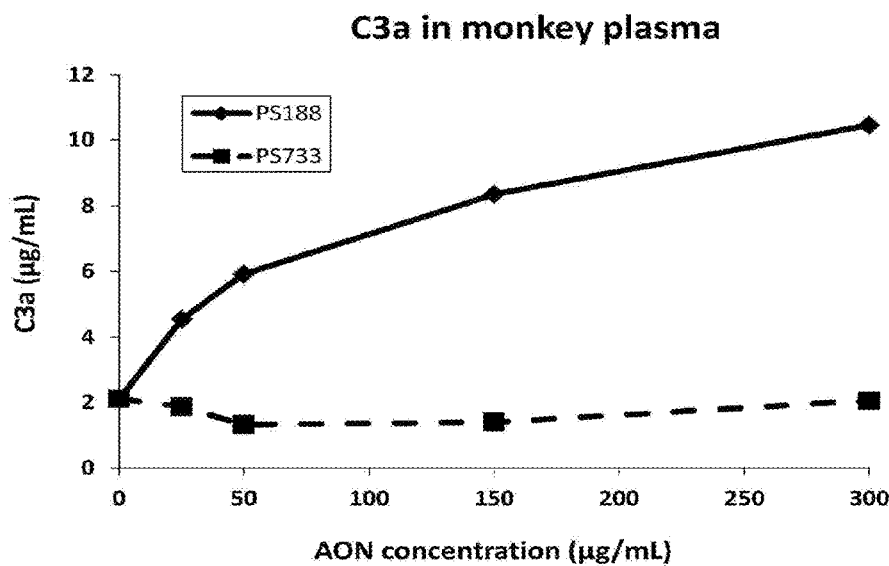
Figure 5C:
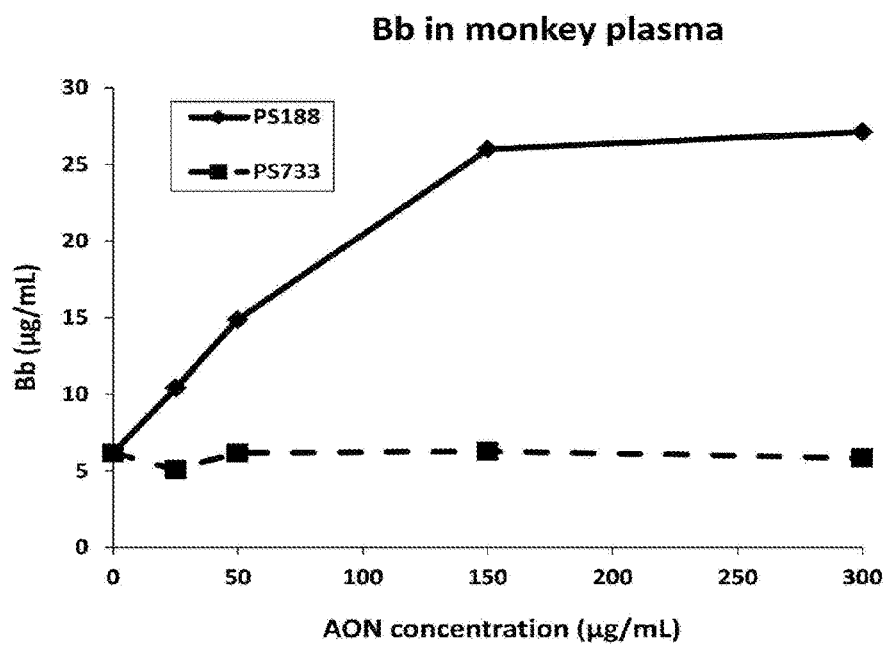

| DMD Exon | AON Sequence (5'→3') | SEQ ID NO | | |
|---|---|---|---|---|
| 44 | YXZGXYYXYGYYZGXXZXYG | 15 | | |
| | UCAGCUUCUGUUAGCCACUG | 95 | PS188 | FIG.4,5 |
| | $Y_1CAGCY_1Y_1CY_1GY_1Y_1AGCCACY_1G$ | 204 | PS785 | FIG.4 |
| | $UX_1AGX_1UUX_1UGUUAGX_1X_1AX_1UG$ | 208 | PS658 | |
| | $Y_1X_1AGX_1Y_1Y_1X_1Y_1GY_1Y_1AGX_1X_1AX_1Y_1G$ | 205 | PS1107 | FIG.4 |
| | $UCZ_1GCUUCUGUUZ_1GCCZ_1CUG$ | 207 | PS733 | FIG.5 |
| 45 | YYYGXXGXYGXXXZZYGXXZYXXYG | 21 | | |
| | UUUGCCGCUGCCCAAUGCCAUCCUG | 101 | PS220 | FIG.1b |
| | $UUUGX_1X_1GX_1UGX_1X_1X_1AAUGX_1X_1AUX_1X_1UG$ | 200 | PS399 | FIG.1b |
| | $Y_1Y_1Y_1GX_1X_1GX_1Y_1GX_1X_1X_1AAY_1GX_1X_1AY_1X_1X_1Y_1G$ | 209 | PS1108 | |
| | $UUUGCCGCUGCCCZ_1Z_1UGCCZ_1UCCUG$ | 210 | PS1229 | |
| | YYYGXXIXYGXXXZZYGXXZYXXYG | 28 | | |
| | UUUGCCICUGCCCAAUGCCAUCCUG | 108 | PS305 | |
| 51 | YXZZGGZZGZYGGXZYYYXY | 31 | | |
| | UCAAGGAAGAUGGCAUUUCU | 111 | PS43 | FIG.4,5 |
| | $Y_1CAAGGAAGAY_1GGCAY_1Y_1Y_1CY_1$ | 202 | PS559 | FIG.4 |
| | $Y_1X_1AAGGAAGAY_1GGX_1AY_1Y_1Y_1X_1Y_1$ | 203 | PS1106 | FIG.4 |
| | $UCZ_1Z_1GGZ_1Z_1GZ_1UGGCZ_1UUUCU$ | 206 | PS403 | FIG.5 |
| | $UX_1AAGGAAGAUGGX_1AUUUX1U$ | 215 | PS401 | |
| 52 | GGYZZYGZGYYXYYXXZZXYGG | 40 | | |
| | GGUAAUGAGUUCUUCCAACUGG | 120 | PS235 | FIG.4,5 |
| | $GGUAAUGAGUUX_1UUX_1X_1AAX_1UGG$ | 171 | PS650 | |
| | $GGY_1AAY_1GAGY_1Y_1CY_1Y_1CCAACY_1GG$ | 172 | PS786 | FIG.4 |
| | $GGUZ_1Z_1UGZ_1GUUCUUCCZ_1Z_1CUGG$ | 173 | PS897 | FIG.5 |
| | $GGY_1AAY_1GAGY_1Y_1X_1Y_1Y_1X_1X_1AAX_1Y_1GG$ | 174 | PS1110 | |
| 53 | GYYGXXYXXGGYYXYGZZGGYGYYX | 52 | | |
| | GUUGCCUCCGGUUCUGAAGGUGUUC | 91 | PS229L | FIG.1a,2 |
| | $GUUGX_1X_1UX_1X_1GGUUX_1UGAAGGUGUUX_1$ | 92 | PS524 | FIG.1a,c,2 |
| | $GUUGX_1X_1UCCGGUUX_1UGAAGGUGUUX_1$ | 217 | PS1317 | FIG.1c |
| | $GUUGX_1X_1UCCGGUUCUGAAGGUGUUC$ | 218 | PS1318 | FIG.1c |
| | $GUUGCX_1UCCGGUUX_1UGAAGGUGUUX_1$ | 219 | PS1319 | FIG.1c |
| | $GY_1Y_1GCCY_1CCGGY_1Y_1CY_1GAAGGY_1GY_1Y_1C$ | 211 | | |
| | $GY_1Y_1GX_1Y_1X_1X_1GGY_1Y_1X_1Y_1GAAGGY_1GY_1Y_1X_1$ | 212 | PS1109 | |
| | $GUUGCCUCCGGUUCUGZ_1Z_1GGUGUUC$ | 213 | | |
| 55 | GZGYYYXYYXXZZZGXZGXXYXYX | 57 | | |
| | GAGUUUCUUCCAAAGCAGCCUCUC | 137 | PS531 | FIG.2 |
| | $GAGUUUX_1UUX_1X_1AAAGX_1AGX_1X_1UX_1UX_1$ | 185 | PS652 | FIG.2 |
| | $GAGY_1Y_1Y_1CY_1Y_1CCAAAGCAGCCY_1CY_1C$ | 186 | | |
| | $GZ_1GUUUCUUCCZ_1Z_1Z_1GCZ_1GCCUCUC$ | 187 | | |
| | $GAGY_1Y_1Y_1X_1Y_1Y_1X_1X_1AAAGX_1AGX_1X_1Y_1X_1Y_1X_1$ | 188 | PS1112 | |

Preferred non modified oligonucleotides (X=C, Y=U, Z=A) are more preferably derived from each of the oligonucleotide basis sequence (SEQ ID NO:14-90) and are represented by a nucleotide or base sequence SEQ ID NO:91, 93-170 Preferred modified oligonucleotides derived from one of the nucleotide or base sequences SEQ ID NO:14-90 and comprising at least one X is $m^5C$ and/or at least one Y is $m^5U$ and/or at least one Z is $a^2A$ are represented by a nucleotide or a base sequence comprising or consisting of SEQ ID NO: 92, 171-213, 215, 217, 218, 219. Even more preferred modified oligonucleotides (all X=$m^5C$=$X_1$ and/or all Y=$m^5U$=$Y_1$ and/or all Z=$a^2A$=$Z_1$) are derived from the most preferred nucleotide or base sequences (SEQ ID NO:15, 21, 31, 40, 52, and 57) and are represented by SEQ ID NO: 92, 171-174, 185-188, 199, 200, 202-213, 215, 217, 218, 219. The most preferred modified oligonucleotides are disclosed in Table 3.

Example 1

Material and Methods

AONs

All oligonucleotides (PS220/PS399, based on SEQ ID NO:21 corresponding to SEQ ID NO:101 for the non-modified sequence (PS220) and to SEQ ID NO:200 wherein all cytosines are modified (PS399); PS229L/PS524/PS1317/PS1318/PS1319, based on SEQ ID NO:52 corresponding to SEQ ID NO:91 for the non-modified sequence (PS229L), to SEQ ID NO:92 (PS524) wherein all 6 cytosines are modified, to SEQ ID NO: 217 (PS1317) wherein 4 of the 6 cytosines are modified, to SEQ ID NO: 218 (PS1318) wherein 2 of the 6 cytosines are modified and to SEQ ID NO:219 (PS1319) wherein 3 of the 6 cytosines are modified; PS232/PS648, based on SEQ ID NO: 39 corresponding to SEQ ID NO:119 for the non-modified sequence (PS232) and to SEQ ID NO:201 wherein all cytosines are modified (PS648); PS531/PS652, based on SEQ ID NO:57 corresponding to SEQ ID NO:137 for the non-modified sequence (PS531) and to SEQ ID NO:185 wherein all cytosines are modified (PS652); PS534/PS653, based on SEQ ID NO:59 corresponding to SEQ ID NO:139 for the non-modified sequence (PS534) and to SEQ ID NO:192 wherein all cytosines are modified (PS653)) were 2'-O-methyl phosphorothioate RNA, and synthesized using an OP-10 synthesizer (GE/ÄKTA Oligopilot), through standard phosphoramidite protocols, or obtained from commercial suppliers, in 40 nmol-4.5 mmol synthesis scale. Prosensa-synthesized oligonucleotides were cleaved and deprotected in a two step sequence (DIEA followed by conc. $NH_4OH$ treatment), purified by HPLC and dissolved in water and an excess of NaCl was added to exchange ions. After evaporation, compounds were redissolved in water, desalted by FPLC or ultrafiltration and lyophilized. Mass spectrometry confirmed the identity of all compounds, and purity (determined by UPLC) was found acceptable for all compounds (>75-80%); compounds obtained from commercial sources were used as received: PS399 (ChemGenes, 1 µmol synthesis scale, used as received), PS1317, PS1318, and PS1319 (ChemGenes, 200 nmol synthesis scale, used as received), PS229L, PS232, PS524, and PS648 (EuroGentec, 40 nmol synthesis scale, used as received), PS229L (Prosensa, 5.9 g obtained material, purity 81%), PS524 (Avecia, 4.5 mmol synthesis scale, purity 93%), PS534 (Prosensa, 2 µmol synthesis scale, purity 86%), PS653 (Prosensa, 40 nmol synthesis scale, purity 77%), PS531 (Avecia, 4.6 g obtained material, purity 85%), PS652 (Avecia, 2.4 g obtained material, purity 84% and 3.8 g obtained material, purity 82%). For the in vitro transfection experiments described herein, 50 µM working solutions of the AONs were prepared in 20 mM phosphate buffer (pH 7.0). For the whole blood cytokine release assays in this example, the concentrations of the stock solutions (prepared in DNase/RNase-free distilled water (Invitrogen)) varied: PS232 (8.75 mg/mL), PS534 (7.02 mg/mL), PS648 (8.55 mg/mL), PS653 (8.12 mg/mL).

Transfection and RT-PCR Analysis

Differentiated human healthy control muscle cells (myotubes) were transfected in 6-wells plates with a triplo AON concentration series of 0-100-200-400 nM (FIG. 1a, PS229L/PS524, SEQ ID NO:91/92) or 0-50-100-200-400-800 nM (FIG. 1b, PS220/PS399, SEQ ID NO: 101/200) or with an in duplo concentration of 400 nM (FIG. 1c, PS524/PS1317/PS1318/PS1319, SEQ ID NO:92/217/218/219), according to non-GLP standard operating procedures. For transfection polyethylenimine (ExGen500, Fermentas) was used (2 µl per µg AON, in 0.15M NaCl). Aforementioned transfection procedures were adapted from previously reported material and methods (Aartsma-Rus et al., 2003). At 24 hrs after transfection, RNA was isolated and analyzed by RT-PCR. Briefly, to generate dystrophin-specific cDNA, a DMD gene specific reverse primer in exon 47 (PS220/PS399) or exon 55 (PS229L/PS524/PS1317/PS1318/PS1319) was used in the reverse transcriptase (RT) reaction on 1000 ng input RNA. The PCR analysis was subsequently done on 3 µl of dystrophin cDNA for each sample, and included a first and nested PCR using DMD gene specific primers in exons flanking exon 45 (PS220/PS399) or 53 (PS229L/PS524/PS1317/PS1318/PS1319). The RNA isolation and RT-PCR analysis were performed according to non-GLP standard operating procedures as described (Aartsma-Rus et al., 2003). RT-PCR products were analyzed by gel electrophoresis (2% agarose gels). The resulting RT-PCR fragments were quantified through DNA Lab-on-a-Chip analysis (Agilent). The data was processed by "Agilent 2100 Bioanalyzer" software and Excel 2007. The ratio of the smaller transcript product (containing the exon 45(PS220/PS399) or 53 skip (PS229L/PS524/PS1317/PS1318/PS1319)) to the total amount of transcript products was assessed (representing the exon 45 or 53 skipping efficiencies in percentages) and directly compared to that in non-transfected cells.

Pharmacokinetic Study in Wild Type and Mdx Mice

Mdx (C57Bl/10ScSn-Dmd$^{mdx}$/J) and wild-type (C57Bl/10ScSnJ) mice at 5 weeks of age were obtained from Jackson Laboratory (Maine USA). The AONs (PS229L/PS524 corresponding to SEQ ID NO: 91/92, PS531/PS652 corresponding to SEQ ID NO: 137/185) were administered in physiological saline at a dose of 100 mg/kg by subcutaneous injections three times per week for two weeks. To determine the plasma profile of the AONs, plasma samples were taken from 2 animals per time-point (per AON group) at the following times for the animals: 15 min, 1 h, 2 h, 6 h and 24 hours after dosing. To obtain plasma, venous whole blood was collected into Li-Heparin tubes, centrifuged and kept at −80° C. until analysis. For distribution analysis 7 organs (heart, kidney cortex, liver, diaphragm, gastrocnemius, quadriceps & triceps) were harvested upon sacrifice of the animals. The tissues were snap frozen and stored at −80° C. until analysis.

AON Hybridisation Assay

To determine the concentration of the AONs (PS229L/PS524 corresponding to SEQ ID NO: 91/92, PS531/PS652 corresponding to SEQ ID NO: 137/185) in plasma and tissue an AON hybridization assay was used, which is based on the assay described by Yu et al., 2002. For the tissue distribution analysis, tissues were homogenized, using a MagNaLyzer (Roche) to a concentration of 60 mg/ml in protK buffer (100 mmol/l Tris-HCl pH8.5, 200 mmol/l NaCl, 5 mmol/l EDTA, 0.2% SDS) containing 2 mg/ml proteinase K, followed by a 2 hours incubation (liver) or 4 hours incubation (all other organs) in a rotating hybridization oven at 55° C. and then stored −20° C. until use. All tissue homogenates and calibration curves were diluted (fit to criteria of the assay) in 60 times diluted pooled mdx control tissue homogenate (kidney, liver, several muscle groups). A template probe specific for each AON (5' gaatagacg-anti-AON-biotin 3', DNA phosphate oligonucleotide) and a ligation probe (p-cgtctattc-DIG DNA phosphate oligonucleotide) were used in the hybridization assay. The homogenates were incubated for 1 h at 37° C. with template probe (50 nmol/1) and the hybridized samples were transferred to streptavidin coated 96-well plates and incubated for 30 min at 37° C. Subsequently, the plate was washed 4 times and the digoxigenin-labeled ligation (2 nmol/l) was added and incubated for 30 min at ambient temperature. The DIG-label was detected using an anti-DIG-POD (1:7,500-1:30,000; Roche Diagnostics), which was visualized with a 3,3', 5,5'-tetramethylbenzidine substrate (Sigma Aldrich, the Netherlands), and the reaction was stopped using an acidic solution (Sigma Aldrich). The absorption was measured at 450 nm using a BioTek Synergy HT plate reader (Beun de Ronde, Abcoude, The Netherlands). Plasma samples were analyzed according to the same protocol, using 100 times diluted pooled mdx plasma.

Whole Blood Cytokine Release Assay

For the detection of possible cytokine stimulation induced by selected AONs (PS232/PS648 corresponding to SEQ ID NO: 119/201 and PS534/PS653 corresponding to SEQ ID NO: 139/192) whole blood (anticoagulant CPD) from healthy human volunteers was used. Varying AON concentrations (ranging from 0 to 50 µg/ml, in a dilution of approximately 1:0.01 (v/v)) were added to the blood and the samples were incubated for 4 hours at 37° C. under 5% $CO_2$ atmosphere. After incubation, the samples were centrifuged at 3200×g for 15 minutes at 4° C. and plasma supernatants were collected and stored at −20° C. until cytokine quantification. MCP-1, IL-6, TNF-α, and IP-10 concentrations were determined by sandwich ELISA (human MCP-1, IL-6, TNF-α, IP-10 ELISA kits (R&D Systems). The experiments with human whole blood were repeated three to four times. FIG. 3 is based on one experiment only, but considered representative.

Results

The effect on AON activity (i.e. inducing exon skipping efficiency) of substituting all cytosines with 5-methylcytosines (m5C) was tested in cultured, differentiated, healthy muscle cells in vitro. In FIGS. 1a and 1b two examples are shown. When comparing PS229L and PS524 (=PS229L–m5C) (i.e. non-modified sequence SEQ ID NO: 91 compared with the modified sequence SEQ ID NO: 92 wherein all cytosines have been modified) in a dose-response transfection experiment using 0-100-200-400 nM, PS524 was clearly more efficient than PS229L at 200 and 400 nM (1.9-fold higher exon 53 skipping levels) (FIG. 1a). Similarly, when comparing PS220 and PS399 (=PS220–m5C) (i.e. non-modified sequence SEQ ID NO: 101 compared with the modified sequence SEQ ID NO: 200 wherein all cytosines have been modified) in a dose-response transfection experiment using 0-50-100-200-400-800 nM, PS399 was clearly more efficient than PS220, especially at lower concentrations (up to 10-fold higher exon 45 skipping levels at 50 nM) (FIG. 1b). These results demonstrate that the presence of 5-methylcytosines has a positive effect on the activity of the AONs. In PS524 (SEQ ID NO:92) all 6 cytosines are substituted with 5-methylcytosines (m5C) which had a positive effect on the exon skipping activity when compared to the non-modified counterpart oligonucleotide PS229L (SEQ ID NO:91) (FIG. 1a). To test whether such positive effect may be correlated with the number or percentage of base modifications incorporated, PS1317, PS1318, and PS1319, with respectively 4, 2, and 3 of the 6 cytosines substituted with 5-methylcytosines (m5C), were tested and directly compared to PS524 in cultured, differentiated, healthy muscle cells in vitro. PS1317, PS1318, and PS1319 were all effective in inducing exon 53 skipping (47%, 37%, and 45% respectively) (FIG. 1c). When compared to the levels obtained with PS524 however (64%), these results indeed suggest that reducing the number of 5-methylcytosines (m5C), from 6 to 4, 3, or 2 5-methylcytosines, leads to a reduced positive effect on exon skipping activity of the AON.

To investigate whether 5-methylcytosines affect bio-stability, -distribution, and/or -availability, a pharmacokinetic study was performed both in wild type (control) and mdx mice. The mdx mouse model for DMD has a natural nonsense mutation in exon 23 and is therefore dystrophin-deficient. The lack of dystrophin at the membranes increases the permeability of the muscle fibers for relatively small molecules as AONs, and has indeed been demonstrated to enhance 2'-O-methyl phosphorothioate RNA AON uptake by muscle up to 10-fold (Heemskerk et al., 2010). The mice were injected subcutaneously with 100 mg/kg of either 5-methylcytosine-containing AONs (PS524, PS652 corresponding to SEQ ID NO: 92, 185) or their counterparts with unmodified cytosines (PS229L, PS531 corresponding to SEQ ID NO: 91, 137), three times per week for two weeks. At different time-points (day 1, 7, 14) after the last injection, the mice were sacrificed and different muscle groups (heart, diaphragm, gastrocnemius, quadriceps, and triceps) and liver and kidney were isolated to determine AON concentrations therein (FIG. 2A). As anticipated, for all compounds the concentrations in mdx muscles (average of all samples) was higher than those in control mice. The ratio mdx to control AON levels appeared relatively higher for the AONs with 5-methylcytosines. More specifically, in the mdx mice, the levels of PS524 and PS652 were 2- to 3-fold higher than that of PS229L and PS531. (FIG. 2A). When monitoring the levels of AON in kidney and liver (known toxicity organs), the ratios between muscle tissue and toxicity tissues remained similar, or were even favorable for PS524. These results suggest that AONs with 5-methylcytosine are taken up better by or more stable in muscle than AONs with unmodified cytosines. Indeed the half life in muscle was longer for PS524 (>20 days) and PS652 (25 days) when compared to PS229L (7 days) and PS531 (10 days). In plasma, the Cmax values of the AONs injected were similar, which confirms that the mice received equal doses (FIG. 2B). Remarkably, the AUC values (as indicator for bioavailability) were 1.5 to 2.3-fold higher for the 5-methylcytosine containing AONs. This was associated with a lower clearance which supports their higher muscle tissue levels. The results from this pharmacokinetic study thus demonstrate that the presence of 5-methylcytosines has a positive effect on the bio-stability, -distribution, and/or -availability of the AONs, while the muscle/toxicity organ ratios were similar to those with the AONs with unmodified cytosines.

The in vitro safety profile of AONs with 5-methylcytosines (PS648, PS653 corresponding to SEQ ID NO: 201, 192) was compared to that of AONs with unmodified cytosines (PS232, PS534, corresponding to SEQ ID NO: 119, 139). AONs may stimulate an innate immune response by activating the Toll-like receptors (including TLR7, TLR8, TLR9), which results in set of coordinated immune responses that include innate immunity. Several chemo- and cytokines, such as IP-10, TNFα, IL-6 and MCP-1 play a role in this process, and were therefore monitored in human whole blood incubated with 0 to 50 µg/ml of each AON (using commercially available ELISA kits). PS232 and PS534 both have unmodified cytosines and induced the release of TNF-α (FIG. 3A, B), MCP-1 (FIG. 3C, D), IP-10 (FIG. 3E, F), and IL-6 (FIG. 3G, H) at increasing doses. In contrast, both PS648 and PS653 (with 5-methylcytosines) did not have any effect on TNF-α, IP-10 and IL-6. PS653, not PS648, seemed to induce a minor release of MCP-1 only. In conclusion, the presence of 5-methylcytosines improved the safety profile of these AONs in vitro.

Example 2

Material and Methods

AONs

All oligonucleotides (PS43/PS559/PS1106, all based on SEQ ID NO:31, and corresponding to SEQ ID NO: 111 (PS43) non modified sequence, SEQ ID NO: 202 (PS559) wherein all uraciles have been modified, and SEQ ID NO: 203 (PS1106) wherein all uraciles and all cytosines have been modified; PS188/PS785/PS1107, all based on SEQ ID NO:15, and corresponding to SEQ ID NO: 95 (PS188) non-modified sequence, SEQ ID NO: 204 (PS785) wherein all uraciles have been modified, and SEQ ID NO: 205 (PS1107) wherein all uraciles and all cytosines have been modified; PS235/PS786, both based on SEQ ID NO:40, and corresponding to SEQ ID NO: 120 (PS235) non-modified sequence and SEQ ID NO: 172 (PS786) wherein all uraciles have been modified), and PS49 (SEQ ID NO:216) non-modified sequence and PS959 (SEQ ID NO:214) wherein all cytosines have been modified, were 2'-O-methyl phosphorothioate RNA, and synthesized using an OP-10 synthesizer (GE/ÄKTA Oligopilot) through standard phosphoramidite protocols, or obtained from commercial suppliers, in 200 nmol-286.1 g scale. Prosensa-synthesized oligonucleotides were cleaved and deprotected in a two step sequence (DIEA followed by conc. NH$_4$OH treatment), purified by HPLC and dissolved in water and an excess of NaCl was added to exchange ions. After evaporation, compounds were redissolved in water, desalted by FPLC or ultrafiltration and lyophilized. Mass spectrometry confirmed the identity of all compounds, and purity (determined by UPLC) was found acceptable for all compounds (>75-80%); compounds obtained from commercial sources were used as received: PS188 (Girindus, 286.1 g obtained product, purity 93%), PS785, PS786, PS1106, and PS1107 (ChemGenes, 200 nmol synthesis scale, used as received), PS43 (Prosensa, 1 μmol synthesis scale, purity 90%), PS559 (ChemGenes, 1 μmol synthesis scale, used as received), PS235 (Prosensa, 1.92 mmol synthesis scale, purity 91%). For the in vitro transfection experiments described herein, 50 μM working solutions of the AONs were prepared in 20 mM phosphate buffer (pH 7.0).

Transfection and RT-PCR Analysis

Differentiated human healthy control muscle cells (myotubes) were transfected in 6-wells plates with a fixed AON concentration of 200 nM, according to non-GLP standard operating procedures. For transfection polyethylenimine (ExGen500, Fermentas) was used (2 μl per μg AON, in 0.15M NaCl). Aforementioned transfection procedures were adapted from previously reported material and methods (Aartsma-Rus et al., 2003). At 24 hrs after transfection, RNA was isolated and analyzed by RT-PCR. Briefly, to generate dystrophin-specific cDNA, a DMD gene specific reverse primer in exon 53 (PS43/PS559/PS1106, SEQ ID NO: 111, 202, 203), exon 46 (PS188/PS785/PS1107 SEQ ID NO: 95, 204, 205) or exon 54 (PS235/PS786, SEQ ID NO: 120, 172) was used in the reverse transcriptase (RT) reaction on 1000 ng input RNA. The PCR analysis was subsequently done on 3 μl of dystrophin cDNA for each sample, and included a first and nested PCR using DMD gene specific primers in exons flanking exon 51 (PS43/PS559/PS1106), exon 44 (PS188/PS785/PS1107) or exon 52 (PS235/PS786). The RNA isolation and RT-PCR analysis were performed according to non-GLP standard operating procedures as described [Aartsma-Rus et al., Hum Mol Genet 2003; 12(8): 907-14]. RT-PCR products were analyzed by gel electrophoresis (2% agarose gels). The resulting RT-PCR fragments were quantified through DNA Lab-on-a-Chip analysis (Agilent). The data was processed by "Agilent 2100 Bioanalyzer" software and Excel 2007. The ratio of the smaller transcript product (containing the exon 51 (PS43/PS559/PS1106), exon 44 (PS188/PS785/PS1107), or exon 52 skip (PS235/PS786) to the total amount of transcript products was assessed (representing the exon 51, 44, or 52 skipping efficiencies in percentages) and directly compared to that in non-transfected cells.

In Vivo Administration and RT-PCR

The experiments with the mdx mouse model (C57Bl/10ScSn-mdx/J; Charles River Laboratories) were approved by the local LUMC Animal Ethics Committee (DEC number 11145). Two mdx mice per group were anaesthetized using isoflurane and then injected intramuscularly in both gastrocnemius muscles, with 20 ug PS49 (SEQ ID NO: 216) or PS959 (SEQ ID NO:214), diluted in sterile saline to a total volume of 50 μl per injection, on two consecutive days. Animals were sacrificed 1 week after the last injection by cervical dislocation and muscles were isolated and snap frozen in magnalyzer greenbead tubes (Roche). Six-hundred μl Tripure (Roche) was added to the tubes and muscles were homogenized using the bullet blender machine, 3×1 min speed 10. The lysate was transferred to a clean tube to which 120 μl of chloroform was added. Samples were vigorously shaken en incubated on ice for 5 minutes, then centrifuged for 15 minutes at maximum speed at 4° C. The supernatant was transferred to another tube and 1 volume of isopropanol was added. Samples were mixed and incubated at 4 degrees for at least 30 minutes. Then samples were centrifuged for 15 minutes at maximum speed at 4° C., washed with 70% ethanol followed by a second centrifugation step of 10 minutes at maximum speed at 4° C. RNA pellets were air dried and solved in DEPC treated water. cDNA was generated using 400 ng total RNA with random hexamer primers using Transcriptor reverse transcriptase (RT) (Roche Diagnostics) according to the manufacturer's instructions. PCRs were performed by 30 cycles of 94 degrees for 30 s, 60 degrees for 30 s and 72 degrees for 30 s in a 50 μl reaction using 1.5 μl cDNA as template using primers specific for mouse exon 22 and exon 24. PCR products were visualized on 2% agarose gels quantified the Agilent 2100 Bioanalyzer (Agilent, Santa Clara, Calif., USA).

Results

The effect on AON activity (i.e. inducing exon skipping efficiency) of substituting all unmodified cytosines with 5-methylcytosines and substituting all unmodified uracils with 5-methyluracils (as in PS1106, PS1107, SEQ ID NO: 203, 205), and of only substituting all unmodified uracils with 5-methyluracils (as in PS559, PS785, PS786, SEQ ID NO: 202, 204, 172), was first tested at a fixed 200 nM AON concentration in cultured, differentiated, healthy muscle cells in vitro (FIG. 4A). The AONs with 5-methyluracils (PS559, PS785, and PS786) increased the exon skipping efficiencies 1.3- to 3-fold when compared to their counterparts with unmodified uracils. When also replacing the unmodified cytosines by 5-methylcytosines, the skipping levels were further increased (PS1106 versus PS559, SEQ ID NO: 203 versus 202) or similar (PS1107 versus PS785, SEQ ID NO: 205 versus 204). The effect on AON activity (i.e. inducing exon skipping efficiency) of substituting all unmodified uracils (as in PS49; SEQ ID NO:216) with 5-methyluracils (as in PS959; SEQ ID NO:214) was then also tested in muscle of the mdx mouse model. PS959 with all 5-methyluracils increased the exon 23 skipping efficiencies approximately 3-fold when compared to PS49 with unmodified uracils (n=4 per AON) (FIG. 4B). These results demonstrate that not only 5-methylcytosines may have a positive effect on exon skipping activity (as also shown in FIG. 1) but also, 5-methyluracils, both in vitro and in vivo. In addition the combined use of these 5-methylpyrimidines may even further increase activity.

Example 3

Material and Methods

AONs

All oligonucleotides (PS43/PS403, based on SEQ ID NO:31, and corresponding to SEQ ID NO: 111 (PS43) for the non-modified and SEQ ID NO: 206 (PS403) for the sequence wherein all adenines have been modified; PS188/PS733, based on SEQ ID NO:15, and corresponding to SEQ ID NO: 95 (PS188) for the non-modified and SEQ ID NO: 207 (PS733) for the sequence wherein all adenines have been modified; PS235/PS897, based on SEQ ID NO:40, and corresponding to SEQ ID NO: 120 (PS235) for the non-modified and SEQ ID NO: 173 (PS897) for the sequence wherein all adenines have been modified) were 2'-O-methyl phosphorothioate RNA, and synthesized using an OP-10 synthesizer (GE/ÄKTA Oligopilot) through standard phosphoramidite protocols, or obtained from commercial suppliers, in 200 nmol-151 g scale. Prosensa-synthesized oligonucleotides were cleaved and deprotected in a two step sequence (DIEA followed by conc. NH$_4$OH treatment), purified by HPLC and dissolved in water and an excess of NaCl was added to exchange ions. After evaporation, compounds were redissolved in water, desalted by FPLC or ultrafiltration and lyophilized. Mass spectrometry confirmed the identity of all compounds, and purity (determined by UPLC) was found acceptable for all compounds (>75-80%); compounds obtained from commercial sources were used as received: PS188 (Girindus, 151 g obtained, purity 92%), PS733 (TriLink or ChemGenes, 200 nmol/1 mg synthesis scale, used as received, PS43 (Prosensa, 10 mol synthesis scale, purity 86%), PS403 (ChemGenes, 1 µmol synthesis scale, used as received), PS235 (Prosensa, 1.92 mmol synthesis scale, purity 91%), PS897 (ChemGenes, 200 nmol synthesis scale, used as received). For the in vitro transfection experiments described herein, 50 µM working solutions of the AONs were prepared in 20 mM phosphate buffer (pH 7.0). For the in vitro complement activation assays described herein, 3 mg/mL stock solutions of PS188 and PS733 were prepared in 20 mM phosphate buffer (pH 7.0).

Transfection and RT-PCR Analysis

Differentiated human healthy control muscle cells (myotubes) were transfected in 6-wells plates with a fixed AON concentration of 200 nM, according to non-GLP standard operating procedures. For transfection polyethylenimine (ExGen500, Fermentas) was used (2 µl per g AON, in 0.15M NaCl). Aforementioned transfection procedures were adapted from previously reported material and methods (Aartsma-Rus et al., 2003). At 24 hrs after transfection, RNA was isolated and analyzed by RT-PCR. Briefly, to generate dystrophin-specific cDNA, a DMD gene specific reverse primer in exon 53 (PS43/PS403, SEQ ID NO: 111/206), exon 46 (PS188/PS733, SEQ ID NO: 95/207) or exon 54 (PS235/PS897, SEQ ID NO: 120/173) was used in the reverse transcriptase (RT) reaction on 1000 ng input RNA. The PCR analysis was subsequently done on 3 µl of dystrophin cDNA for each sample, and included a first and nested PCR using DMD gene specific primers in exons flanking exon 51 (PS43/PS403), exon 44 (PS188/PS733) or exon 52 (PS235/PS897). The RNA isolation and RT-PCR analysis were performed according to non-GLP standard operating procedures as described [Aartsma-Rus et al., Hum Mol Genet 2003; 12(8):907-14]. RT-PCR products were analyzed by gel electrophoresis (2% agarose gels). The resulting RT-PCR fragments were quantified through DNA Lab-on-a-Chip analysis (Agilent). The data was processed by "Agilent 2100 Bioanalyzer" software and Excel 2007. The ratio of the smaller transcript product (containing the exon 51 (PS43/PS403), exon 44 (PS188/PS733), or exon 52 skip (PS235/PS897)) to the total amount of transcript products was assessed (representing the exon 51, 44, or 52 skipping efficiencies in percentages) and directly compared to that in non-transfected cells.

Complement Activation Assay

Antisense oligonucleotides may activate the alternative complement pathway, which contains several split factors, such as C3a and factor Bb (the latter is unique to the alternative pathway). The ability of AONs to possibly activate the complement pathway was assessed in plasma from Cynomolgus monkeys (LiHe plasma, CIT, France). Increasing concentrations (from 0 to 300 µg/mL) of PS188 (SEQ ID NO: 95) and PS733 (PS207), in a dilution of 1:10 (v/v)), were added to the plasma and incubated at 37° C. for 30 min. The reaction was terminated by transferring the samples to ice and making dilutions in ice-cold diluent. Bb and C3a concentrations were determined by ELISA (Quidel, San Diego, Calif.).

Results

The effect on AON activity (i.e. inducing exon skipping efficiency) of substituting all unmodified adenines with 2,6-diaminopurines was tested at a fixed AON concentration (200 nM) in cultured, differentiated, healthy muscle cells in vitro. In FIG. 5A examples for three different AON sequences are shown. The AONs with 2,6-diaminopurines (PS403, PS897, and PS733, SEQ ID NO: 206, 207, 173) increased the exon skipping efficiencies 2- to 4-fold when compared to their counterparts with unmodified adenines (compared to SEQ ID NO: 111, 95, 120). There seemed to be a correlation with the number of 2,6-diaminopurines in each AON.

The effect of substituting all unmodified adenines (as in PS188; SEQ ID NO: 95) with 2,6-diaminopurines (as in PS733; SEQ ID NO:207) on in vitro safety, i.e. possible activation of the alternative complement pathway, was tested in monkey plasma. Whereas PS188 induced relatively high levels of both split factors Bb and C3a, the 2,6-diaminopurines in PS733 completely abolished the effect on the alternative pathway, showing no increase in either Bb or C3a levels (FIG. 5B). Thus the presence of 2,6-diaminopurines seemed to improve the safety profile of PS188 in vitro.

These results demonstrate the positive effect of 2,6-diaminopurines on the exon skipping activity and safety of AONs.

LIST OF REFERENCES van Ommen, van Deutekom, Aartsma-Rus, Curr Opin Mol Ther. 2008; 10(2):140-9.
Yokota, Duddy, Partidge, Acta Myol. 2007; 26(3):179-84.
van Deutekom et al., N Engl J Med. 2007; 357(26):2677-86.
Goemans et al., N Engl J Med. 2011; 364(16):1513-22.
Cirak et al., Lancet 2011; 378: 595-605.
Heemskerk et al., Mol Ther 2010; 18(6):1210-7.
Aartsma-Rus et al., Hum Mol Gen 2003; 12(8):907-14.
Yu R Z., Anal Biochem 2002; 304: 19-25.
Krieg A M. et al., Nature 1995; 374: 546-549.
Diebold S. S., et. al., Eur J Immunol. 2006; December; 36(12):3256-67.
Krieg, A. M., Curr. Opin. Immunol. 2000; 12: 35-43.
Wagner, H., Adv. Immunol. 1999; 73: 329-368.
Popovic P J. et al. J of Immunol 2006; 177: 8701-8707.
Peacock H et al. J. Am. Chem. Soc. 2011, 133, 9200
Arai K et al. Bioorg. Med. Chem. 2011, 21, 6285

Ehmsen J. et al, J. Cell Sci. 2002, 115 (Pt14): 2801-2803.
Monaco A. P., et al., Genomics 1988; 2: 90-95.
Manzur A. Y. et al., Wiley publishers, 2008. The Cochrane collaboration.
Hodgetts S., et al, Neuromuscular Disorders 2006; 16: 591-602.
Aartsma-Rus et al, Oligonucleotides 2010, 20(2): 69-77
Zuker M., et al, Nucleic Acids Res. 2003; 31(13):3406-15.
Cartegni L, et al, Nat Rev Genet 2002; 3(4):285-98.
Cartegni L, et al, Nucleic Acids Res 2003; 31(13):3568-71
Remington: The Science and Practice of Pharmacy, 20th Edition. Baltimore, Md.: Lippincott Williams & Wilkins, 2000
Kumar L, Pharm. Technol. 2008, 3, 128
Bruno, K., Advanced Drug Delivery Reviews 2011; 63: 1210.
Hari et al. *Org. Biomol. Chem.* 2012, 10, 9639);
Hanessian et al. *Angew. Chem. Intl Ed.* 2012, 45, 11242

---

The invention claimed is:

1. An isolated antisense oligonucleotide 16-22 nucleotides in length, wherein the oligonucleotide comprises a sequence which is complementary without mismatches to at least 15 contiguous nucleotides of an exon-internal sequence of exon 51 of a human dystrophin pre-mRNA, wherein the exon-internal sequence is the complement of SEQ ID NO: 111, and wherein all cytosines in the antisense oligonucleotide are 5-methylcytosines and all uracils in the antisense oligonucleotide are 5-methyluracils, and wherein the antisense oligonucleotide is capable of inducing skipping of exon 51 of a human dystrophin pre-mRNA.

2. The isolated antisense oligonucleotide of claim 1, wherein the isolated antisense oligonucleotide comprises a peptide nucleic acid, a locked nucleic acid, or a morpholino phosphorodiamidate modification, or a combination thereof.

3. The isolated antisense oligonucleotide of claim 1, wherein the isolated antisense oligonucleotide comprises a locked nucleic acid modification.

4. The isolated antisense oligonucleotide of claim 1, said oligonucleotide being RNA.

5. The isolated antisense oligonucleotide of claim 1, wherein said oligonucleotide is at least 16 nucleotides in length and comprises a locked nucleic acid modification.

6. A method for inducing skipping of an exon of human dystrophin pre-mRNA in a muscle cell, the method comprising contacting said cell with an oligonucleotide of claim 1 for a time and under conditions which permit exon skipping.

7. A method for inducing skipping of an exon of human dystrophin pre-mRNA in a human subject, the method comprising administering an oligonucleotide of claim 1 to said subject in an amount and for a time which is effective to induce exon skipping.

8. A method for treating one or more symptom(s) of Duchenne Muscular Dystrophy or Becker Muscular Dystrophy in an individual, the method comprising administering to said individual an oligonucleotide of claim 1, wherein said oligonucleotide induces skipping of an exon of a dystrophin pre-mRNA.

9. A method for treating one or more symptom(s) of Duchenne Muscular Dystrophy or Becker Muscular Dystrophy in a cell, the method comprising administering to said cell one or more isolated oligonucleotides of claim 1.

* * * * *